United States Patent [19]

Bodor

[11] Patent Number: 4,540,564
[45] Date of Patent: Sep. 10, 1985

[54] BRAIN-SPECIFIC DRUG DELIVERY

[75] Inventor: Nicholas S. Bodor, Gainesville, Fla.

[73] Assignee: University of Florida, Gainesville, Fla.

[21] Appl. No.: 516,382

[22] Filed: Jul. 22, 1983

Related U.S. Application Data

[63] Continuation-in-part of Ser. No. 379,316, May 18, 1982, Pat. No. 4,479,932, Ser. No. 461,543, Jan. 27, 1983, , and Ser. No. 475,493, Mar. 15, 1983, , said Ser. No. 461,543, and Ser. No. 475,493, each is a continuation-in-part of Ser. No. 379,316.

[30] Foreign Application Priority Data

May 12, 1983 [WO] PCT Int'l Appl. ......... WO83/00725
May 16, 1983 [CA] Canada .................... 428192

[51] Int. Cl.³ .................... A61K 49/00; A61K 31/58; C07J 17/00
[52] U.S. Cl. .................... 424/9; 260/239.5; 514/176
[58] Field of Search .................. 424/9, 241; 260/239.5

[56] References Cited

U.S. PATENT DOCUMENTS 3,962,447  6/1976  Higuchi et al. ............ 424/263
4,035,507  7/1977  Bodor et al. ............... 424/319
4,065,566 12/1977  Bodor et al. ............... 424/266
4,479,932 10/1984  Bodor ......................... 424/9

OTHER PUBLICATIONS

Bodor et al., Science, vol. 214 (1981) 1370-2.
Bodor et al., J. Pharm. Sci., 67 (1978) 685-7.
Bodor et al., J. Med. Chem., 26 (1983) 313-8.
Bodor et al., J. Med. Chem., 26 (1983) 528-34.
Sher et al., J. Med. Chem., 19 (1976) 113-7.
Bodor et al., J. Pharm. Sci. 67 (1978) 1045-50.
Chem. and Eng. News, 12/21/81, 24-25.

*Primary Examiner*—Christine M. Nucker
*Attorney, Agent, or Firm*—Dennis P. Clarke

[57] ABSTRACT

The subject compounds, which are adapted for the site-specific/sustained delivery of centrally acting drug species to the brain, are:

(a) compounds of the formula

[D-DHC]   (I)

wherein [D] is a centrally acting drug species, and [DHC] is the reduced, biooxidizable, blood-brain barrier penetrating lipoidal form of a dihydropyridine ⇌ pyridinium salt redox carrier, with the proviso that when [DHC] is

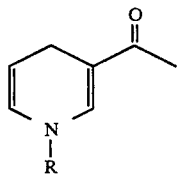

wherein R is lower alkyl or benzyl and [D] is a drug species containing a single NH₂ or OH functional group, the single OH group when present being a primary or secondary OH group, said drug species being linked directly through said NH₂ or OH functional group to the carbonyl function of [DHC], then [D] must be other than a sympathetic stimulant, steroid sex hormone or long chain alkanol; and (b) non-toxic pharmaceutically acceptable salts of compounds of formula (I) wherein [D] is a centrally acting drug species and [DHC] is the reduced, biooxidizable, blood-brain barrier penetrating lipoidal form of a dihydropyridine ⇌ pyridinium salt redox carrier. The corresponding ionic pyridinium salt type drug/carrier entities [D-QC]⁺Y⁻ are also disclosed.

86 Claims, 8 Drawing Figures

BRAIN-SPECIFIC DRUG DELIVERY

CROSS-REFERENCE TO RELATED APPLICATIONS

This application is a continuation-in-part of my earlier copending applications Ser. No. 379,316, filed May 18, 1982, now U.S. Pat. No. 4,479,932 Ser. No. 461,543, filed Jan. 27, 1983, and Ser. No. 475,493, filed Mar. 15, 1983; Ser. No. 461,543 and Ser. No. 475,493 are themselves continuations-in-part of Ser. No. 379,316. All three earlier copending applications are hereby expressly incorporated by reference herein in their entireties and relied upon.

FIELD OF THE INVENTION

The present invention relates to a dihydropyridine/pyridinium salt type of redox system for the site-specific or sustained delivery (or both) of a wide variety of drug species to the brain. More especially, this invention relates to the discovery that a biologically active compound coupled to a lipoidal carrier moiety comprising a dihydropyridine nucleus readily and easily penetrates the blood-brain barrier ("BBB") and attains increased levels of concentration in the brain; oxidation of the dihydropyridine carrier moiety in vivo to the ionic pyridinium salts prevents its elimination from the brain, while elimination from the general circulation is accelerated, resulting in significant and prolongedly sustained brain-specific drug activity, whether ascribable to the cleavage of the [D-QC]+ entity and sustained release of the drug in the brain and/or to [D-QC]+ itself.

BACKGROUND ART

The delivery of drug species to the brain is ofttimes seriously limited by transport and metabolism factors and, more specifically, by the functional barrier of the endothelial brain capillary well deemed the blood-brain barrier, BBB. Site-specific delivery and sustained delivery of drugs to the brain are even more difficult, and to date no useful simple or generic techniques to achieve such phenomena are known to the art.

Indeed, the barriers separating plasma from the brain and cerebrospinal fluid (CSF) are complex systems involving passive and active transport and subserve a number of important functions. The boundary between plasma and the central nervous system (CNS) is much less permeable than that between plasma and other tissue cells to a variety of water soluble substances, such as organic electrolytes, organic acids and bases, as well as to large molecules such as proteins. Such a barrier also provides a path for clearance from the brain of the breakdown products of cellular metabolism. The CNS and its fluids can be considered basically a three-compartment system: the blood or the plasma, CSF and brain tissue. There is a diffusion-controlled exchange between CSF and the extracellular fluid (CF) of the brain. It has also been suggested that the permeabilities of blood-CSF and blood-brain barriers are practically identical with respect to drugs and other foreign substances. Mayer et al, *J. Pharmacol. and Exp. Therap.*, 125, 185 (1959).

The BBB is, moreover, basically the result of the fact that the endothelial cells in the brain capillaries are joined by continuous, tight intercellular junctions, such that material has to pass through the cells rather than between them in order to move from blood to brain. It is interesting that there are areas within the brain, such as the subfornical body and the postremia in which the capillary cells are not closely linked so that they lack the characteristics of the BBB. They provide the entry of small amounts of compounds which would not ordinarily enter the barriers. Hoffmann and Olszewzki, *Neurology (Minneap.)*, 11, 1081 (1961).

Foreign compounds which enter organs other than the central nervous system with ease, may penetrate the CNS slowly or hardly at all. A number of theories concerning the nature of the barrier have been proposed. The widely accepted concept describes the boundary as a fat-like layer interspersed with small pores, although the BBB is not a simple, anatomically well-defined unitary physical entity. Shuttleworth, *Prog. Exp. Tumor Res.*, 17, 279 (1972). Penetration of such a barrier may occur by several processes: lipid soluble substances may passively penetrate into the cells, while small molecules such as water and urea may pass through the pores. In addition to these simple physical processes, carrier-mediated and active transport processes govern the movement of many molecules through the BBB. Thus, it is generally accepted that lipid solubility, degree of ionic dissociation or protonation and the ability of temporary combination with membrane constituents affect delivery through the BBB. It has been shown, for example, that in the class of barbiturates, a quantitative correlation could be established between their ease to pass into the brain (as reflected by the different times of onset of anesthetic action) and their lipid/water partition coefficient. Mark et al, *J. Pharmacol. and Exp. Therap.*, 123, 79 (1957). The role of lipid solubility in drug penetration through the BBB is also exemplified by the better absorption of the sparingly water-soluble thiamine propyl disulfide (TPD) as compared to the water-soluble thiamine hydrochloride (THCl). Thomson et al, *Ann. Int. Med.*, 74, 529 (1971). Some materials such as glucose and amino acids are transported by active mechanism, characterized by saturation, bidirectional molecular specificity, bidirectional competitive inhibition and bidirectional countertransport. Fishman, *Am J. Physiol.*, 206, 836 (1964).

Changes in permeability of the BBB can be caused by several pathological and toxicological processes. Pardridge, Connor and Crawford, *CRC Crit. Rev. Toxicol.*, 179 (1975). A general increase in the barrier permeability, such as a nonspecific breakdown of the barrier has, however, severe consequences, including cerebral edema.

It too is well documented that the BBB is relatively impermeable to the ionized forms of drugs and other molecules. Drugs which are weak organic electrolytes appear to pass from blood to CSF to reach a steady state ratio characteristic of each molecule according to its $pK_a$ and the existence of a normal pH gradient between blood and CSF. It is clear that it is the most difficult for quaternary pyridinium or ammonium salts to penetrate the BBB.

And removal of substances from the brain and CSF is obviously a significant factor in regulating drug concentrations in the CNS. There are several efflux processes: bulk flow via the arachnoid villi, diffusion of lipid soluble substances into brain and blood, active transport and metabolism by adjacent meninges. Once a drug or metabolite enters the CSF from blood or brain by simple diffusion, it may rapidly be removed, either by nonselective bulk flow or by active transport mechanism associated with the choroid plexus or other nondefined structures in the CSF compartment. It is generally accepted that highly lipid-soluble drugs leave the CSF more rapidly than poorly lipid-soluble ones, but the barrier to passage of compounds from CSF has only superficial similarity to the blood-CSF barrier.

Drug elimination processes from the brain are significantly directly related to drug accumulation in the brain. It is generally assumed that efflux in the opposite direction involves almost the same processes as for entry, except that the role of the bulk flow and the metabolic processes in the brain are not to be overlooked.

The two elimination processes studied in the earlier literature and which can be said to have a certain bearing on the present invention involve elimination from the brain of ionic species. Thus, it is found that non-metabolized inonic species, such as the acetate ion, have a three times slower elimination rate from the CSF than from the blood. Freundt, *Arz., Forsch.,* 23, 949 (1973). An even more dramatic change in the elimination rate was found in the case of a quaternary piperidinium salt. The quaternary salt, formed in situ after delivery of a haloalkylamine, which undergoes cyclization to the quaternary salt, in the brain, as well, was found to have an at least ten times slower elimination rate from the brain than from the rest of the body. It was concluded by the authors (Ross and Froden, *Eur. J. Pharmacol.,* 13, 46 [1970]) that the outflow rate of the quaternary salt corresponded to the inflow rate. Similar results were obtained for the erythrocytes: the efflux of the quaternary salt was very slow. Ross, *J. Pharm. Pharmacol.,* 27, 322 (1975).

And while it too has been suggested to deliver a drug species, specifically N-methylpyridinium-2-carbaldoxime chloride (2-PAM), into the brain, the active nucleus of which in and of itself constituting a quaternary pyridinium salt, by way of the dihydropyridine latentiated prodrug form thereof, such approach is conspicuously delimited to relatively small molecule quaternary pyridinium ring-containing drug species and does not provide the overall ideal result of brain-specific, sustained release of the desired drug, with concomitant rapid elimination from the general circulation, enhanced drug efficacy and decreased toxicity. Hence, no "trapping" in the brain of the 2-PAM formed in situ results, and obviously no brain-specific, sustained delivery occurs as any consequence thereof; the 2-PAM is eliminated as fast from the brain as it is from the general circulation and other organs. Compare U.S. Pat. Nos. 3,929,813 and 3,962,447; Bodor et al, *J. Pharm. Sci.,* 67, No. 5, 685 (1978). See also Bodor, "Novel Approaches for the Design of Membrane Transport Properties of Drugs", in *Design of Biopharmaceutical Properties Through Prodrugs and Analogs,* Roche, E. B. (ed.), APhA Academy of Pharmaceutical Sciences, Washington, D.C., 98–135 (1976). It has also been speculated to deliver, e.g., an antitumor agent into the brain by utilizing a dihydropyridine/pyridinium redox carrier moiety therefor, but this particular hypothesis necessarily entails derivatizing the dihydropyridine/pyridinium carrier with a substituent $R_1$ itself critically designed to control the release rate of the active drug species from the quaternary drivative thereof, as well as being critically functionally coordinated with the particular chemical and therapeutic activity/nature of the antitumor drug species itself; Bodor et al, *J. Pharm. Sci.,* supra. Moreover, the hypothesis does not include any indication of what chemical transformations would be needed to link any specific antitumor agent (or indeed any specific drug) to an appropriate carrier moiety.

Accordingly, acutely serious need exists in this art for a truly effective generic but nonetheless flexible method for the site-specific, or sustained delivery, or both, of drug species to the brain, while at the same time avoiding the aforesaid noted and notable disadvantages and drawbacks associated with penetration of the blood-brain barrier, with dihydropyridine latentiated prodrug forms of drug species themselves comprising a pyridinium salt active nucleus, and with the necessity for introducing critically coordinated and designed, release rate-controlling substituents onto any particular drug carrier moiety.

It is also known to this art that Parkinsonism, a striatal dopamine deficiency syndrome [H. Ehringer and O. Hornykiewicz, *Klin. Wsch.,* 38, 1236 (1960)], cannot be treated directly with dopamine, for dopamine and related catecholamines also do not cross the blood-brain barrier [B. E. Roos and G. Steg, *Life Sci.,* 3, 351 (1964)]. L-Dopa, considered as a prodrug for dopamine, was first discovered to be useful in the treatment of Parkinsonism more than twenty years ago [A. Barbeau, *Excepta Medica, Int. Congr. Ser.* 38, 152 (1961); W. Birkmayer and O. Hornykiewicz, *Wien. Klin. Wochnenschr.,* 73, 787 (1961)]. Indeed, L-Dopa is considered to be the best available treatment for Parkinsonism, but, unfortunately, at the expense of a wide variety of undesirable side effects [A. Barbeau, *TIPS,* 2, (11), 297 (1981)]. The peripheral side effects of L-Dopa, which range from nausea and vomiting to cardiac arrythmias and hypotension, appear to be due to one or more of the metabolic products thereof, rather than L-Dopa per se. L-Aromatic amino acid decarboxylase enzyme is responsible for the major metabolism of L-Dopa, whether prior, during or after absorption. Concurrent administration of L-Dopa with an inhibitor of aromatic amino acid decarboxylase, which should not be able to penetrate the BBB, reduces the decarboxylation of L-Dopa in peripheral tissues. Such reduction allows higher proportions of L-Dopa to reach the CNS and at the same time diminishes the peripheral side effects considerably, particularly vomiting and cardiac arrythmias, but a number of serious side effects still persist [A. Barbeau, *TIPS,* supra; A. Barbeau and M. Roy, *Neurology,* 26, 399 [(1976)]. Attempts have also been made to alleviate the well-known dissolution, absorption and metabolism problems of L-Dopa [H. Ninterberger, *Biochem. Med.,* 5, 412 (1971); H. Shindo, T. Komai, K. Tanaka, E. Nakajima and N. Miyakoshi, *Chem. Pharm. Bull.,* 21, 826 (1973); C. O. Rutledge and M. M. Hoehn, *Nature (London),* 244, 447 (1973); R. L. Bronaugh, R. J. McMurty, M. M. Hoehn and C. O. Rutledge, *Biochem. Pharmacol.,* 24, 1317 (1975)], employing prodrug approaches [N. Bodor, K. B. Sloan, T. Higuchi and K. Sasahara, *J. Med. Chem.,* 20, 1435 (1977); A. M. Felix, D. P. Winter, S. S. Wang, I. D. Kulesha, W. R. Pool, D. L. Hane and H. Sheppard, *J. Med. Chem.,* 17, 422 (1974)].

Additionally, dopamine agonists, which are used in the treatment of hyperprolactinemia associated with pituitary adenomas or amenorrhea [R. F. Spark and G. Dickenstein, *Ann. Int. Med.,* 90, 949 (1979)], also induce unwanted side effects.

Thus, especially acutely serious need exists in this art to delivery a dopaminergic agent directly and specifically to the brain, in a sustained manner, and there elicit the desired dopaminergic response, e.g., for the treatment of the Parkinsonism or hyperprolactinemia.

SUMMARY AND OBJECTS OF THE INVENTION

Accordingly, a major object of the present invention is the provision of a generic method for the specific and/or target enhanced delivery to the brain of a wide variety of drug species and to achieve brain-specific drug delivery by effecting the bidirectional transport of the drug species into and out of the brain employing dihydropyridine⇌pyridinium salt carrier type redox systems.

Another object of the invention is to provide for brain specific drug delivery utilizing a dihydropyridine⇌pyridinium salt carrier type redox system, which drug/carrier system is characterized by enhanced drug efficacy and decreased toxicity. Indeed, consistent herewith systemic toxicity is significantly reduced by accelerating the elimination of the drug/quaternary carrier system, and even central toxicity is reduced by providing a low level, sustained release of the active drug species in the brain.

Yet another object of this invention is the provision of a chemical delivery system for the site-specific and sustained release of drug species to the brain, and one in which a special pro-prodrug reduced form of an active drug species is actually delivered to the body of a patient, not a prodrug as such and not a drug/carrier entity necessarily comprised of critically tailored release rate-controlling substituent(s).

Yet another object of this invention is to provide enhanced delivery to the brain of a wide variety of centrally acting agents which are not themselves able to penetrate the blood-brain barrier to any considerable extent.

Briefly, the present invention features a dihydropyridine⇌pyridinium salt carrier redox system for the specific and sustained delivery of drug species to the brain according to the following Scheme 1:

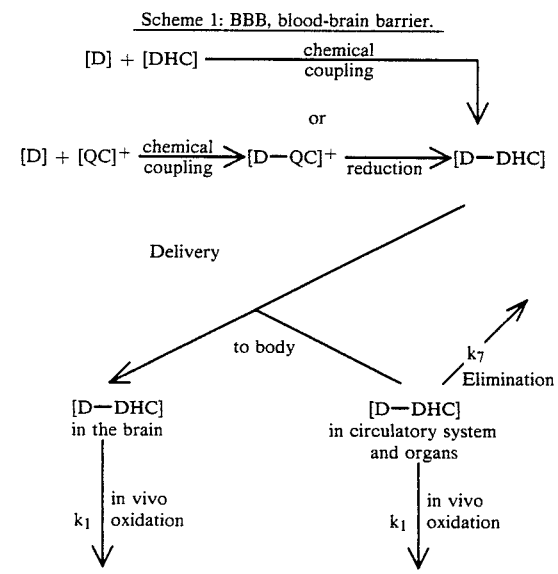

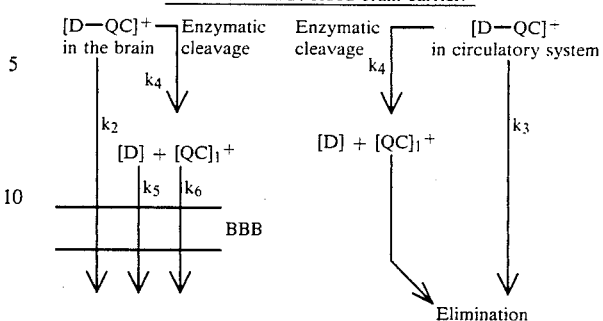

Consistent with the foregoing Scheme 1, any drug species [D] is coupled to a quaternary pyridinium salt carrier [QC]+ and the prodrug [D-QC]+ which results is then reduced chemically to the lipoidal dihydro pro-prodrug form [D-DHC]. Alternativey, the drug species [D] can be directly coupled to the dihydro carrier [DHC] in certain instances to yield said pro-prodrug form [D-DHC]. After administration of the [D-DHC] in vivo, it is rapidly distributed throughout the body, including the brain. The dihydro form [D-DHC] is then in situ oxidized (rate constant, $k_1$) (by the NAD⇌NADH system) to the ideally inactive original [D-QC]+ quaternary salt prodrug, which, because of its ionic, hydrophilic character, is rapidly eliminated from the general circulation of the body, while the blood-brain barrier prevents its elimination from the brain $k_3 >> k_2$; $k_3 >> k_7$). Enzymatic cleavage of the [D-QC]+ that is "locked" in the brain effects a sustained delivery of the drug species [D], followed by its normal elimination ($k_5$), metabolism. A properly selected carrier [QC]+ will also be rapidly eliminated from the brain ($k_6 >> k_2$). Because of the facile eliminaton of [D-QC]+ from the general circulation, only minor amounts of drug are released in the body ($k_3 >> k_4$); [D] is released primarily in the brain ($k_4 > k_2$). The overall result is a brain-specific, sustained release of the target drug species. Cf. Bodor et al, *Science*, 214, 1370 (1981); *C&EN*, 24 (Dec. 21, 1981).

In accord with the foregoing, the present invention provides compounds adapted for the site-specific/sustained delivery of a centrally acting drug species to the brain, said compounds being:

(a) compounds of the formula

[D-DHC]          (I)

wherein [D] is a centrally acting drug species, and [DHC] is the reduced, biooxidizable, blood-brain barrier penetrating lipoidal form of a dihydropyridine⇌pyridinium salt redox carrier, with the proviso that when [DHC] is

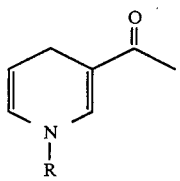

wherein R is lower alkyl or benzyl and [D] is a drug species containing a single $NH_2$ or OH functional group, the single OH group when present being a primary or secondary OH group, said drug species being linked directly through said NH$_2$ or OH functional group to the carbonyl function of [DHC], then [D] must be other than a sympathetic stimulant, steroid sex hormone or long chain alkanol; or (b) non-toxic pharmaceutically acceptable salts of compounds of formula (I) wherein (D) is a centrally acting drug species and [DHC] is the reduced, biooxidizable, blood-brain barrier penetrating lipoidal form of a dihydropyridine⇌pyridinium salt redox carrier. In another aspect, the present invention provides compounds having the formula

[D-QC]$^+$Y$^-$                    (II)

wherein Y$^-$ is the anion of a non-toxic pharmaceutically acceptable acid, [D] is a centrally acting drug species and [QC]$^+$ is the hydrophilic, ionic pyridinium salt form of a dihydropyridine⇌pyridinium salt redox carrier, with the proviso that when [QC]$^+$ is

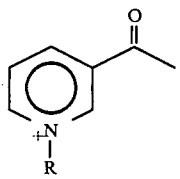

wherein R is lower alkyl or benzyl and [D] is a drug species containing a single NH$_2$ or OH functional group, the single OH group when present being a primary or secondary OH group, said drug species being linked directly through said NH$_2$ or OH functional group to the carbonyl function of [QC]$^+$, then [D] must be other than a sympathetic stimulant, steroid sex hormone or long chain alkanol. The present invention further provides a generic method for specific and/or target enhanced delivery to the brain of a wide variety of centrally acting drug species, such brain-specific drug delivery being effected via the bidirectional transport of the drug species into and out of the brain by means of dihydropyridine⇌pyridinium salt carrier type redox systems.

In yet another aspect, the present invention provides, as an effective dopaminergic chemical delivery system, compounds having the formula

[D-DHC]                         (I)

and non-toxic pharmaceutically acceptable salts thereof, wherein [D] is a dopamine having the structural formula

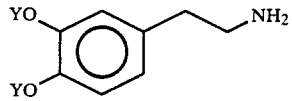

in which each Y is independently hydrogen or a hydrolytically or metabolically cleavable hydroxyl protective group, and [DHC] is the reduced, biooxidizable, blood-brain barrier penetrating, lipoidal form of a dihydropyridine⇌pyridinium salt redox carrier. In still another aspect, the present invention provides compounds having the formula

[D-QC]$^+$Y$^-$                    (II)

wherein Y$^-$ is defined above and [D] is a dopamine having the structural formula

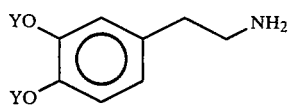

in which each Y is independently hydrogen or a hydrolytically or metabolically cleavable hydroxyl protective group, and [QC]$^+$ is the hydrophilic, ionic pyridinium salt form of a dihydropyridine⇌pyridinium salt redox carrier.

Briefly, one presently preferred chemical delivery system for dopamine according to this invention has the structure (2) in the following Scheme 2, and wherein the amino function of dopamine is appropriately linked to the dihydropyridine-type carrier system, while the catechol function is advantageously protected, for example, as a corresponding ester function, e.g., the dipivalyl ester illustrated. The brain-specific delivery of dopamine, or the otherwise eliciting of a dopaminergic response, requires a succession of processes, including oxidation of the dihydropyridine ring to the corresponding pyridinium salt (for example, structure 3), which provides the basis for "locking-in" the brain the molecule, hydrolysis of the, e.g., pivalyl esters (see structure 4) likely via the 3- and/or 4-monopivalyl esters and, finally, the release of dopamine (1) from 4, which can be either a hydrolysis or a reductive process [a possible reductive release of dopamine was very recently suggested by a model for a presynaptic terminal, L. L. Miller, A. N. K. Lau and E. K. Miller, *J. Am. Chem. Soc.*, 104, 5242 (1982)].

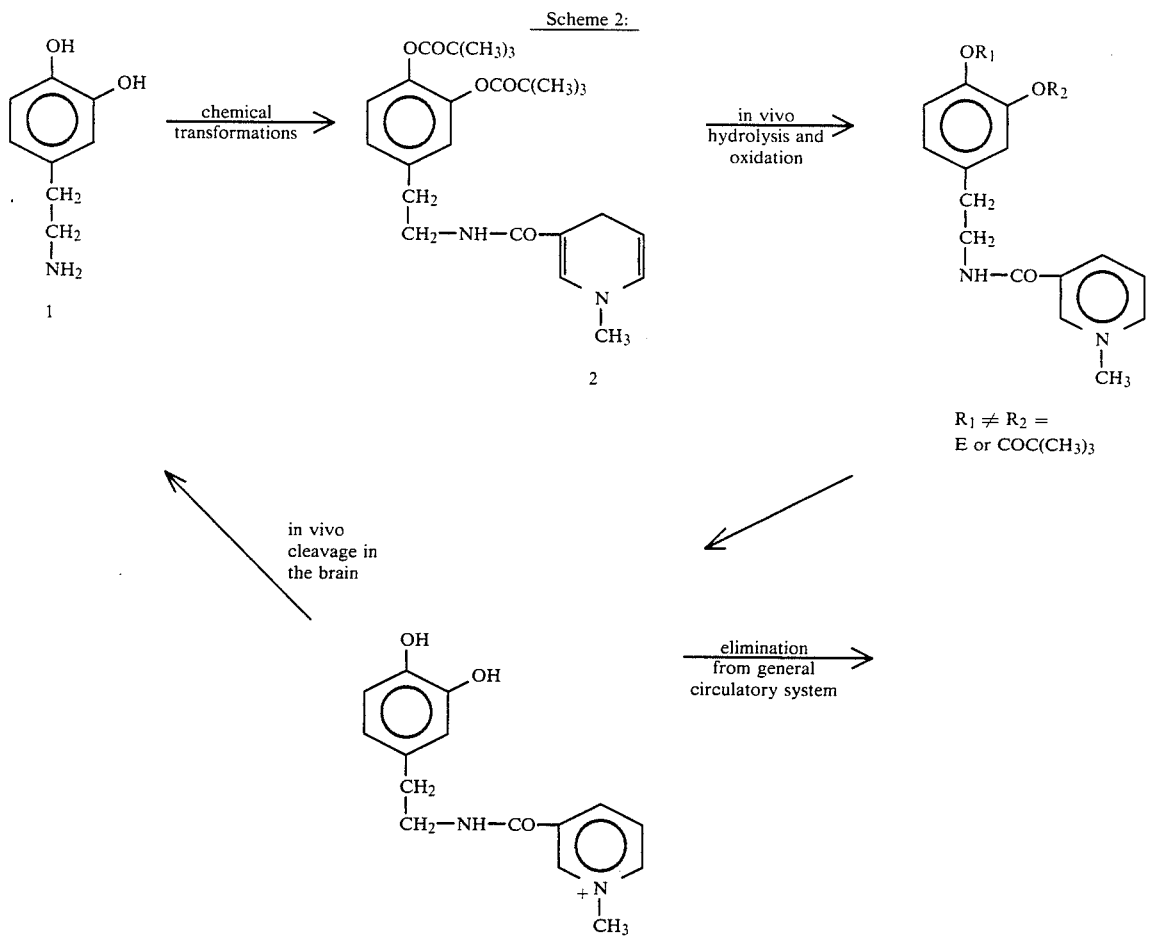

As per the above Scheme 2, for the brain specific delivery of dopamine (1), structure 2 is one chemical delivery system consistent herewith, and 4 is one precursor locked in the brain and eliminated rapidly from the rest of the body. Structures 3 depicts intermediates formed during the stepwise hydrolysis and oxidation processes.

DETAILED DESCRIPTION OF THE INVENTION

Figure 1:
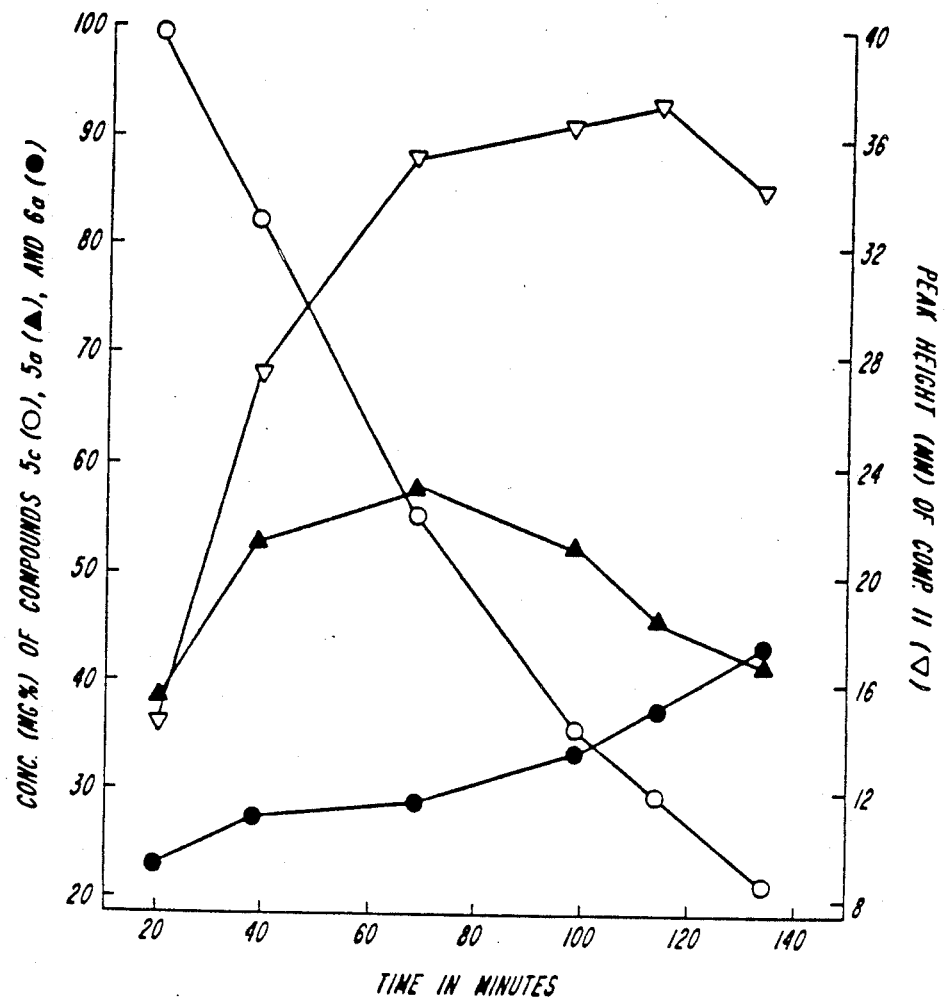
FIG. 1 is a graph plotting the time course of 1-methyl-3-{N-[β-(3,4-dipivalyloxyphenyl)ethyl]}-carbamoyl-1,4-dihydropyridine 5c (O) and its products, monopivalyl-dihydro derivative 11 (▼), the dihydrodopamine derivative 5a (▲) and the quaternary dopamine precursor 6a (●) in plasma.
Figure 2:
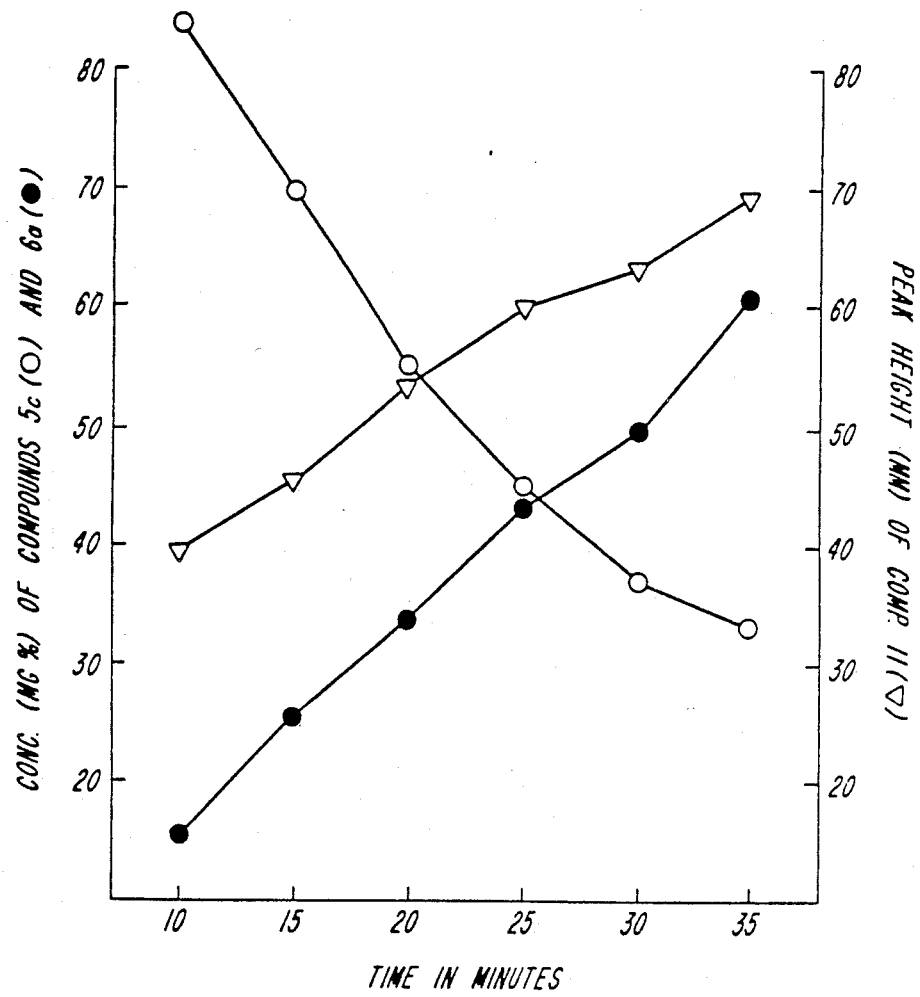
FIG. 2 is a graph plotting the time course of 1-methyl-3-{N-[β-(b 3,4-dipivalyloxyphenyl)ethyl]}-carbamoyl-1,4-dihydropyridine 5c (O) and its products, monopivalyl-dihydro drivative 11 (▼) and the quaternary dopamine precursor 6a (●) in whole blood.
Figure 3:
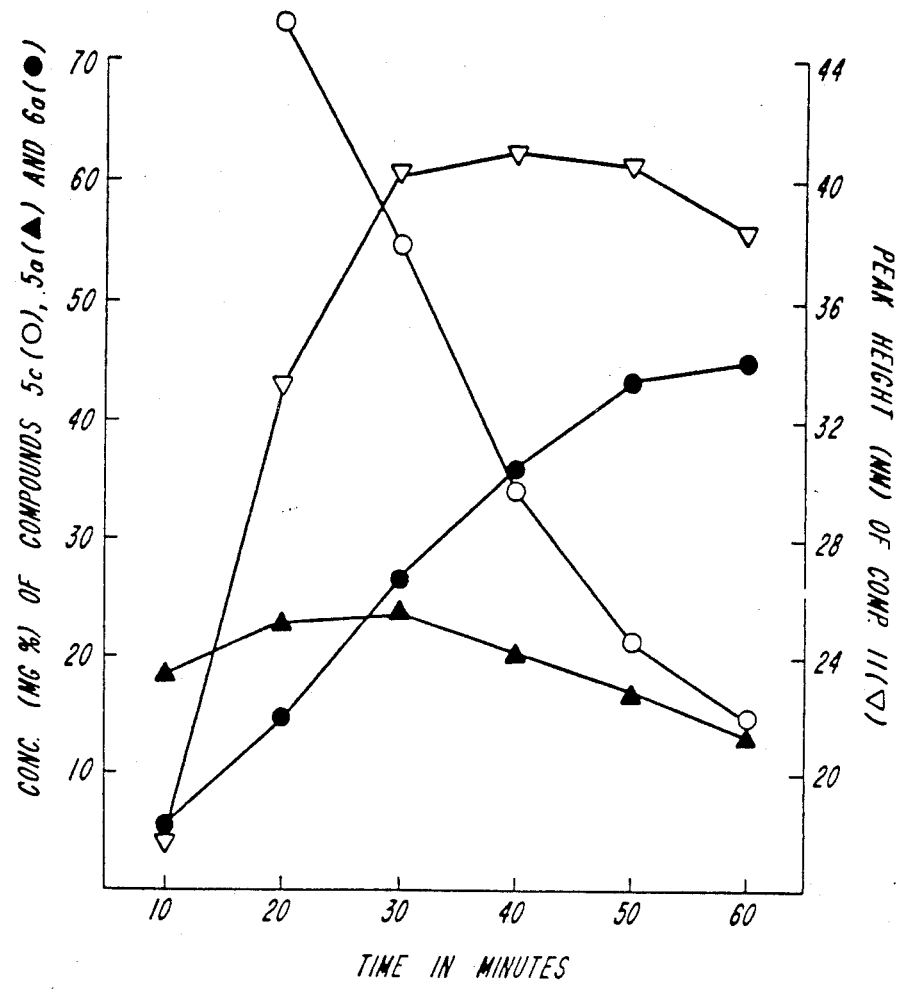
FIG. 3 is a graph plotting the time course of 1-methyl-3-{N-[β-(3,4-dipivalyloxyphenyl)ethyl]}-carbamoyl-1,4-dihydropyridine 5c (O) and its products, monopivalyl-dihydro derivative 11 (▼), the dihydrodopamine derivative 5a (▲) and the quaternary dopamine precursor 6a (●) in 20% brain homogenate.
Figure 4:
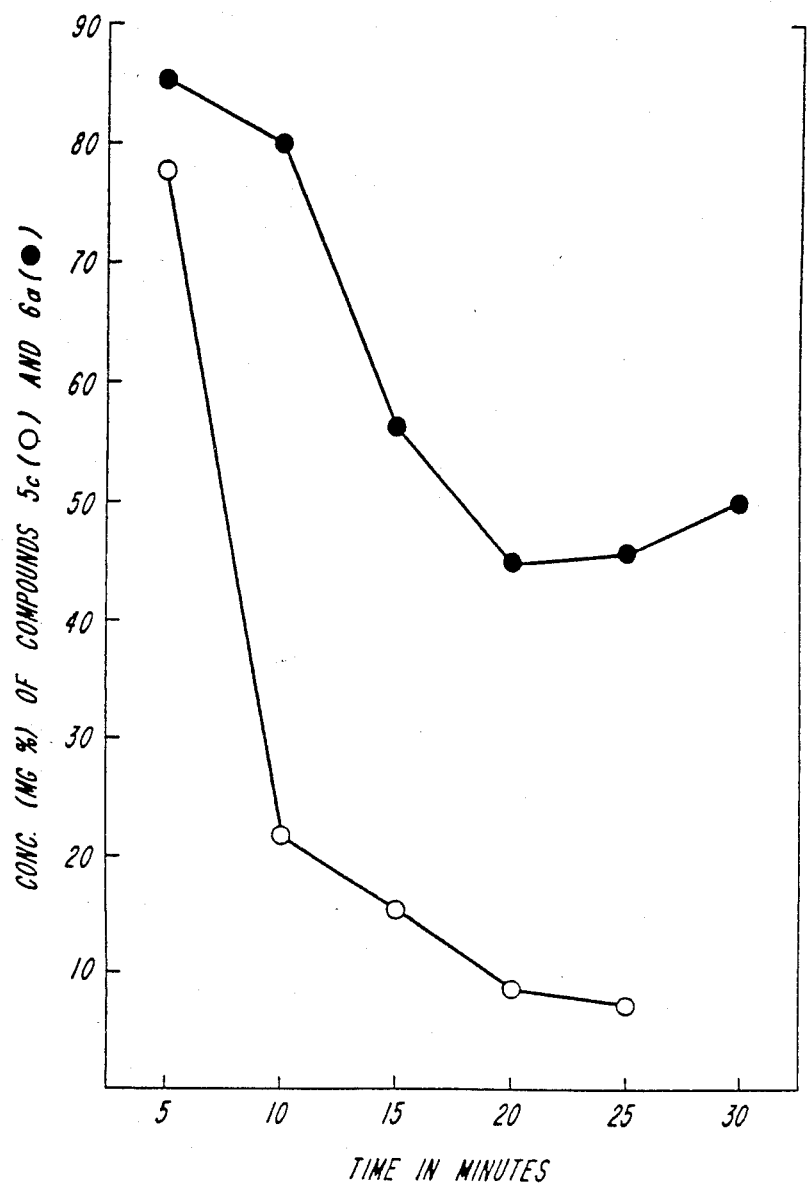
FIG. 4 is a graph plotting the time course of 1-methyl-3-{N-[β-(3,4-dipivalyloxyphenyl)ethyl]}-carbamoyl-1,4-dihydroxypyridine 5c (O) and its product, the quaternary dopamine precursor 6a (●) in 20% liver homogenate.

More particularly in accord with the present invention, the following definitions are applicable:

The term "lipoidal" as used herein is intended to designate a carrier moiety which is lipid-soluble or lipophilic.

The expression "hydroxyl protective group" is intended to designate a group which prevents premature metabolism of an OH group or groups prior to the compound's reaching the desired site in the body. Typical hydroxyl protective groups contemplated by the present invention (e.g., for Y in the case of the dopamine derivatives) are acyl groups and carbonates.

When the hydroxyl protective group is acyl (i.e., when it is an organic radical derived from a carboxylic acid by removal of the hydroxyl group), it preferably represents an acyl radical selected from the group consisting of alkanoyl having 2 to 8 carbon atoms; alkenoyl having one or two double bonds and 3 to 8 carbon atoms;

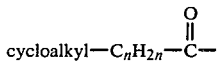

wherein the cycloalkyl portion contains 3 to 7 ring atoms and n is zero, one, two or three; phenoxyacetyl; pyridinecarbonyl; and

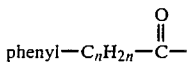

wherein n is zero, one, two or three and phenyl is unsubstituted or is substituted by 1 to 3 alkyl each having 1 to 4 carbon atoms, alkoxy having 1 to 4 carbon atoms, halo, trifluoromethyl, dialkylamino having 2 to 8 carbon atoms or alkanoylamino having 2 to 6 carbon atoms.

When the acyl group is alkanoyl, there are included both unbranched and branched alkanoyl, for example, acetyl, propionyl, butyryl, isobutyryl, valeryl, isovaleryl, 2-methylbutanoyl, pivalyl (pivaloyl), 3-methylpentanoyl, 3,3-dimethylbutanoyl, 2,2-dimethylpentanoyl and the like. Pivalyl and isobutyryl are especially preferred.

When the acyl group is alkenoyl, there are included, for example, crotonyl, 2,5-hexadienoyl and 3,6-octadienoyl.

When the acyl group is

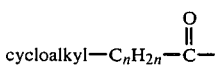

there are included cycloalkanecarbonyl and cycloalkanealkanoyl groups wherein the cycloalkane portion can optionally bear 1 or 2 alkyl groups as substituents, e.g. cyclopropanecarbonyl, 1-methylcyclopropanecarbonyl, cyclopropaneacetyl, α-methylcyclopropaneacetyl, 1-methylcyclopropaneacetyl, cyclopropanepropionyl, α-methylcyclopropanepropionyl, 2-isobutylcyclopropanepropionyl, cyclobutanecarbonyl, 3,3-dimethylcyclobutanecarbonyl, cyclobutaneacetyl, 2,2-dimethyl-3-ethylcyclobutaneacetyl, cyclopentanecarbonyl, cyclohexaneacetyl, cycloheptanecarbonyl and cycloheptanepropionyl.

When the acyl group is pyridinecarbonyl, there are included picolinoyl (2-pyridinecarbonyl), nicotinoyl (3-pyridinecarbonyl) and isonicotinoyl (4-pyridinecarbonyl).

When the acyl group is

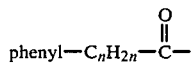

there are included, for example, benzoyl, phenylacetyl, α-phenylpropionyl, β-phenylpropionyl, p-toluyl, m-toluyl, o-toluyl, o-ethylbenzoyl, p-tert-butylbenzoyl, 3,4-dimethylbenzoyl, 2-methyl-4-ethylbenzoyl, 2,4,6-trimethylbenzoyl, m-methylphenylacetyl, p-isobutylphenylacetyl, β-(p-ethylphenyl)-propionyl, p-anisoyl, m-anisoyl, o-anisoyl, m-isopropoxybenzoyl, p-methoxyphenylacetyl, m-isobutoxyphenylacetyl, m-diethylaminobenzoyl, 3-methoxy-4-ethoxybenzoyl, 3,4,5-trimethoxybenzoyl, p-dibutylaminobenzoyl, p-n-butoxybenzoyl, 2,4,6-triethoxybenzoyl, 3,4-diethoxyphenylacetyl, β-(3,4,5-trimethoxyphenyl)propionyl, o-iodobenzoyl, m-bromobenzoyl, p-chlorobenzoyl, p-fluorobenzoyl, 2-bromo-4-chlorobenzoyl, 2,4,6-trichlorobenzoyl, p-chlorophenylacetyl, α-(m-bromophenyl)propionyl, p-trifluoromethylbenzoyl, 2,4-di(trifluoromethyl)benzoyl, m-trifluoromethylphenylacetyl, β-(p-trifluoromethylphenyl)propionyl, 2-methyl-4-methoxybenzoyl, 3-chloro-4-ethoxybenzoyl, β-(3-methyl-4-chlorophenyl)propionyl, p-dimethylaminobenzoyl, p-(N-methyl-N-ethylamino)benzoyl, o-acetamidobenzoyl, m-propionamidobenzoyl, 3-chloro-4-acetamidophenylacetyl and p-acetamidophenylpropionyl.

When the hydroxyl protective group is a carbonate grouping, it has the structural formula

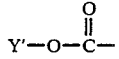

i.e., it is an organic radical which can be considered to be derived from a carbonic acid by removal of the hydroxyl group from the COOH portion. Y' preferably represents alkyl having 1 to 7 carbon atoms; alkenyl having one or two double bonds and 2 to 7 carbon atoms;

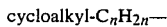

wherein the cycloalkyl portion contains 3 to 7 ring atoms and n is zero, one, two or three; phenoxy; 2-, 3- or 4-pyridyl; or

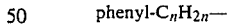

wherein n is zero, one, two or three and phenyl is unsubstituted or is substituted by 1 to 3 alkyl each having 1 to 4 carbon atoms, alkoxy having 1 to 4 carbon atoms, halo, trifluoromethyl, dialkylamino having 2 to 8 carbon atoms or alkanoylamino having 2 to 6 carbon atoms. Most preferably, Y' is $C_1$–$C_7$ alkyl, particularly ethyl or isopropyl.

Similarly, the expression "carboxyl protective group" is intended to designate a group which prevents premature metabolism of a COOH group or groups prior to the compound's reaching the desired site in the body. Typical carboxyl protecting groups are the groups encompassed by Y' above, especially $C_1$–$C_7$ alkyl, particularly ethyl or isopropyl.

By "centrally acting" drug species, active agent or compound as utilized herein, there is of course intended any drug species or the like, the principal pharmacological activity of which is CNS and a result of direct action in the brain.

Exemplary such centrally acting drug species are the CNS-amines and other nervous system agents, whether sympathetic or parasympathetic, e.g., phenylethylamine, dopamine, tyramine, L-DOPA, muscle relaxants, tranquilizers and antidepressants, e.g., benzodiazepine tranquilizers such as diazepam and oxazepam, phenothiazine tranquilizers such as carphenazine, fluphenazine and the like, mild and strong analgesics and narcotics, sedatives and hypnotics, narcotic antagonists, vascular agents, stimulants, anesthetics, small peptides, such as the di, tri-, tetra- and pentapeptides, and other small 6-20 aminoacid unit containing peptides, e.g., the enkephalins (for example, Tyr-Gly-Gly-Phe-Leu), which, besides being analgesics, initiate epileptic activity in the brain at doses that are about tenfold lower than for effecting analgesic activity, larger peptides, such as pituitary hormones and related agents, antiepileptic and anticonvulsant drugs generally, including hydantoins such as phenytoin and ethotoin, barbituates such as phenobarbital, hormones, such as the steroid hormones, e.g., estradiol, testosterone, 17 α-ethynyl testosterone, and the like (recent studies on histological mapping of hormone-sensitive and specific steroid binding cells in the brain have underscored the importance of the steroid action in the brain on sexual behavior), amphetamine-like drugs, anticancer and anti-Parkinsonism agents, antihypertensives, agents to enhance learning capacity and the memory processes, including treatment of dementias, such as Alzheimer's disease, antibacterials, centrally active hypotensive agents, diagnostic agents, such as radiopharmaceuticals, monoamine oxidase (MAO) inhibitor drugs, CNS or brain important/essential amino acids, such as tryptophan, and any like centrally acting compounds.

Other illustrative ultimate species of centrally active drug entities are: amphetamine, dextroamphetamine, levamphetamine, methamphetamine, phenmetrazine and phentermine, which are stimulants and appetite suppressants; codeine, oxycodone, pentazocine, anileridine, hydromorphone, morphine and oxymorphone, which are narcotic analgesics; desipramine, nortriptyline, opipramol and protriptyline, which are stimulants used, e.g., in endogenous depressions; clonidine and methyldopa, which are sympatholytic agents used, e.g., in hypertension; biperiden, cycrimine and procyclidine, which are centrally acting anticholinergics; tranylcypromine, a sympathomimetic stimulant and MAO inhibitor; acetophenazine, carphenazine, fluphenazine, perphenazine and piperacetazine, which are phenothiazine-type tranquilizers; chlordiazepoxide, clorazepate, nitrazepam and temazepam, which are benzodiazepine-type tranquilizers; haloperidol and clopenthixol, which are tranquilizers; norepinephrine, a sympathetic stimulant/adrenergic agent; nalorphine and naloxone, narcotic antagonists; hydralazine, a hypotensive; ethotoin, phenobarbital and aminoglutethimide, anticonvulsants; ethamivan, a medullary stimulant; bemegride, a barbiturate antagonist; amiphenazole, a stimulant; iopydol, iodopyracet, iodouppurate, iodamide and iopanoic acid, which are radiodiagnostics; ephedrine, pseudoephedrine, oxymetazoline and phenylephrine, which are sympathomimetic amines and decongestants; estradiol, estrone and estriol, the natural estrogens; amoxicillin, oxacillin, carbenicillin, benzylpenicillin, phenoxymethylpenicillin, methicillin, nafcillin, ticarcillin and ampicillin, which are penicillin-type antibiotics; amobarbital, a sedative, trihexyphenidyl, a centrally acting anticholinergic; hydroxyzine, a tranquilizer; chlortetracycline, demeclocycline, minocycline, doxycycline, oxytetracycline, tetracycline and methacycline, which are tetracycline-type antibiotics; clindamycin, lincomycin, nalidixic acid, oxolinic acid and phenazopyridine, antibacterials/antibiotics; flurazepam, bromazepam and lorazepam, tranquilizers; phenytoin, an anticonvulsant; glutethimide, a mild hypnotic/sedative; bethanidine and guanethidine, hypotensives/sympatholytics; captopril; methyprylon; propranolol, a β-blocker antihypertensive; dicloxacillin, an antibacterial; butalbital, a barbiturate sedative; GABA, γ-vinyl GABA, γ-acetylenic GABA, neurotransmitters for possible use in epilepsy; valproic acid and its metabolites such as 5-hydroxy-2-n-propylpentanoic acid, 4-hydroxy-2-n-propylpentanoic acid, 3-hydroxy-2-n-propylpentanoic acid, for use as anticonvulsants; apomorphine, a narcotic depressant/emetic; pholcodine, a narcotic antitussive; methotrexate, podophyllotoxin derivatives (etoposide, teniposide), doxorubicin, daunamycin and cyclophosphamide, anticancer/antitumor agents; methylphenidate, a stimulant; thiopental, an anesthetic; ethinyl estradiol and mestranol, estrogens; meptazinol, cyclazocine, phenazocine, profadol, metopon, drocone and myfadol, which are narcotic analgesics; buprenorphine, nalbuphine, butrophanol, levallorphan, naltrexone, alazocine, oxilorphan and nalmexone, which are narcotic antagonists or agonist-antagonists; norgestrel and norethindrone, progestins; cephalothin, cephalexin, cefazolin and cefoxitin, cephalosporin antibiotics; atenolol and metoprolol, β-blockers/hypotensives; ACTH (corticotropin); LH-RH, a neurotransmitter; sulfadiazine and other sulfonamide antibiotics; ribavirin and acyclovir, antiviral agents; chlorambucil and melphalan, nitrogen mustard-type anticancer/antitumor agents; methotrexate and aminopterin, which are folic acid antagonist-type anticancer/antitumor agents; platinum coordination complexes, i.e. cisplatin analogue-type anticancer/antitumor agents; dactinomycin and mitomycin C, used in cancer chemotherapy; thioguanine, a purine/pyrimidine antagonist used in cancer treatment; vincristine and vinblastine, anticancer alkaloids; hydroxyurea and DON, anticancer urea derivatives; FSH and HCS, pituitary and nonpituitary gonadotropins; N,N'-bis(dichloracetyl)-1,8-octamethylene diamine, an agent for male fertility inhibition; levorphanol, a narcotic analgesic; benzestrol and diethylstilbestrol, synthetic estrogens; ethyl β-carboline-3-carboxylate, a benzodiazepine antagonist; furosemide, a diuretic/antihypertensive; and dipyridamole and nifedipine, coronary vasodilators. Yet other ultimate species include non-steroidal anti-inflammatory agents/non-narcotic analgesics, e.g. propionic acid derivatives such as ibuprofen, naproxen, flurbiprofen, fenbufen, fenoprofen, indoprofen, ketoprofen, fluprofen and bucloxic acid; acetic acid derivatives such as indomethacin, zomepirac, tolmetin, sulindac, diclofenac, alclofenac, fenclozic acid and ibufenac; fenamic acid derivatives such as mefenamic acid, meclofenamic acid and flufenamic acid; and biphenylcarboxylic acid derivatives such as diflunisal and flufenisal.

Preferred classes of centrally acting drugs for use herein are the central neurotransmitters, steroids, anticancer and antitumor agents, antiviral agents, tranquilizers, memory enhancers and hypotensives. Among the neurotransmitters, there can be mentioned amino acids, such as GABA, GABA derivatives and other omega-amino acids, as well as glycine, glutamic acid, aspartic acid and other natural amino acids; catecholamines, such as dopamine, norepinephrine and epinephrine; serotonin and tryptamine; and peptides such as neurotensin, luteinizing hormone-releasing hormone (LHRH), somatostatin, enkephalins such as met$^5$-enkephalin and leu$^5$-enkephalin, endorphins such as γ-, α- and β-endorphins, oxytocin M and vasopressin. Synthetic and semi-synthetic analogues, e.g. analogues of LHRH in which one or more amino acid(s) has/have been replaced with one or more different amino acid(s), and which may be agonists or antagonists, are also contemplated. Among the steriods, there can be mentioned antiinflammatory adrenal cortical steroids such as hydrocortisone, betamethasone, cortisone, dexamethasone, flumethasone, fluprednisolone, meprednisone, methyl prednisolone, prednisolone, prednisone, triamcinolone, cortodoxone, fludrocortisone, flurandrenolone acetonide, paramethasone and the like; male sex hormones (androgens), such as testosterone and its close analogues, e.g. methyl testosterone; and female sex hormones, both estrogens and progestins, e.g., ethinyl estradiol, norgestrel, mestranol, norethindrone, norethynodrel, ethisterone, estradiol, estriol, estrone, dimethisterone, allylestrenol, cingestol, ethynerone, lynestrenol, norgesterone, norvinisterone, ethynodiol, oxogestone, tigestol, quinestrol and the like. Among the anticancer and antitumor agents, there can be mentioned Ara-AC, pentostatin(2'-deoxycoformycin), Ara-C, 3-deazaguanine, dihydro-5-azacytidine, tiazofurin, sangivamycin, Ara-A, 6-MMPR, PCNU, spiromustine, bisbenzimidazole, L-alanosine, DON, L-ICRF, trimethyl TMM, 5-methyl tetrahydrohomofolic acid, glyoxylic acid sulfonylhydrazone, DACH, SR-2555, SR-2508, desmethylmisonidazole, mitoxantrone, menogarol, aclacinomycin A, phyllanthoside, bactobolin, aphidocolin, homoharringtonine, levonantradol, acivicin, streptozotocin, hydroxyurea, chlorambucil, cyclophosphamide, uracil mustard, melphalan, 5-FUDR, vincristine, vinblastine, cytosine arabinoside, 6-mercaptopurine, thioguanine, 5-azacytidine, methotrexate, adriamycin (doxorubicin), daunomycin, largomycine polypeptide, aminopterin, dactinomycin, mitomycin C, and podophyllotoxin derivatives, such as etoposide (VP-16) and teniposide. Among the antiviral agents, there can be mentioned ribavirin; acyclovir (ACV); amantadine (also of possible value as an anti-Parkinsonism agent); diarylamidines such as 5-amidino-2-(5-amidino-2-benzofuranyl)indole and 4',6-diimidazolino-2-phenylbenzo(b)thiophene; 2-aminoxazoles such as 2-guanidino-4,5-di-n-propyloxazole and 2-guanidino-4,5-diphenyloxazole; benzimidazole analogues such as the syn and anti isomers of 6[[(hydroxyimino)phenyl]-methyl]-1-[(1-methylethyl)sulfonyl]-1H-benzimidazole-2-amine; bridgehead C-nucleosides such as 5,7-dimethyl-2-β-D-ribofuranosyl-s-triazole(1,5-a)pyrimidine; glycosides such as 2-deoxy-D-glucose, glucosamine, 2-deoxy-2-fluoro-D-mannose and 6-amino-6-deoxy-D-glucose; phenyl glucoside derivatives such as phenyl-6-chloro-6-deoxy-β-D-glucopyranoside; (S)-9-(2,3-dihydroxypropyl)adenine; 6-azauridine; indoxuridine; BDVU (bisdihydroxyvinyluridine); and 5,6-dichloro-1-β-D-ribofuranosylbenzimidazole. Among the tranquilizers, there can be mentioned benzodiazepine tranquilizers such as diazepam, oxazepam, lorazepam, chlordiazepoxide, flurazepam, bromazepam, chlorazepate, nitrazepam and temazepam; hydantoin-type tranquilizers such as phenytoin, ethotoin, mephenytoin; phenothiazine-type tranquilizers such as acetophenazine, carphenazine, fluphenazine, perphenazine and piperacetazine; and others. Among the hypotensives, there can be mentioned clonidine, methyldopa, bethanidine, debrisoquin, hydralazine, and guanethidine and its analogues.

It too will be appreciated that by "dihydropyridine carrier" or "[DHC]", there is intended any nontoxic carrier moiety comprising, containing or including the dihydropyridine nucleus, whether or not a part of any larger basic nucleus, and whether substituted or unsubstituted, the only criterion therefor being capacity for BBB penetration and in vivo oxidation thereof to the corresponding quaternary pyridinium salt carrier [QC]$^+$. As aforesaid, the ionic pyridinium salt drug/-carrier prodrug entity [D-QC]$^+$ which results from such in vivo oxidation is prevented from efflux from the brain, while elimination from the general circulation is accelerated. Subsequently, the covalent or equivalent bond coupling the drup species [D] to the quaternary carrier [QC]$^+$ is metabolically cleaved which results in sustained delivery of the drug [D] in the brain and facile elimination of the carrier moiety [QC]$^+$. Such "covalent or equivalent bond" between the drug and the quaternary carrier can be a simple direct chemical bond, e.g., an amide, an ester, or any other like bond, or same can even be comprised of a linking group or function, e.g., a thiazolidine bridge or a peptide linkage, typically necessitated when the drug species is not susceptible to direct chemical coupling to either the dihydropyridine carrier or the quaternary carrier. Nonetheless, the bond in the formulae [D-QC]$^+$ and [D-DHC] is intended to be, and is hereby defined as inclusive of all such alternatives. And the cleavage of the [D-QC]$^+$ prodrug to sustainedly delivery the drug species [D] in the brain with concomitant facile elimination of the carrier moiety [QC]$^+$ is characteristically enzymatic cleave, e.g., by esterase, amidase, cholinesterase, hydrolytic enzyme, or peptidase, albeit any type of in brain cleavage which might result, whether enzymatic, metabolic or otherwise, of course remains within the ambit of this invention. Thus, the drug release rate controlling parameter of the subject pro-prodrugs is imparted simply via the cleavable bonding between drug and carrier, and not by any release rate controlling substituent(s).

The expression "non-toxic pharmaceutically acceptable salts" as used herein generally includes the non-toxic salts of compounds of formula (I), wherein [D] is a centrally acting drug species and [DHC] is the reduced, biooxidizable, blood-brain barrier penetrating form of a dihydropyridine⇌pyridinium salt redox carrier, formed with nontoxic, pharmaceutically acceptable inorganic or organic acids HX. For example, the salts include those derived from inorganic acids such as hydrochloric, hydrobromic, sulfuric, sulfamic, phosphoric, nitric and the like; and the salts prepared from organic acids such as acetic, propionic, succinic, glycollic, stearic, lactic, malic, tartaric, citric, ascorbic, pamoic, maleic, hydroxymaleic, phenylacetic, glutamic, benzoic, salicylic, sulfanilic, fumaric, methanesulfonic, toluenesulfonic and the like.

In one ambodiment according to this invention, simple nontoxic carrier systems [D-QC]$^+$⇌[D-DHC] are envisaged, utilizing a wide variety of models for D, such as those above outlined. Representative such carrier systems and models are:

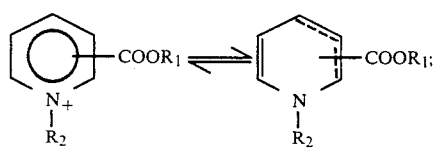

$R_3O-$ or $R_3NH- = D$

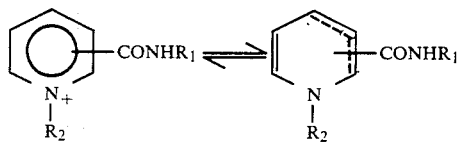

wherein $R_2$ is simply alkyl, e.g., $CH_3$, or benzyl, albeit virtually any other effective substituent is intended. (As depicted above, the isomeric dihydropyridine structure depends on the position of the substituent relative to the pyridine nitrogen.) Exemplary of such simple carrier systems are N-alkyl nicotinamide and nicotinate ester derivatives, tethered to such drug species as dopamine, melphalan and testosterone. The trigonelline (N-methylnicotinic acid) system is quite effective as a carrier; it also is readily eliminated from the circulation and is virtually non-toxic.

Indeed, the present invention provides a flexible arsenal of dihydropyridine⇌pyridinium salt redox carriers for the site-specific/sustained delivery of virtually any centrally acting drug species to the brain. Moreover, any dihydropyridine/pyridinium salt redox carrier entity is contemplated and intended hereby generically, and any such carrier moiety need not be, and is not derivatized with a drug release rate controlling substituent critically tailored to meet, or be coordinated with, the chemical nature and delivery requirements of the particular drug species sought to be preferentially administered to the brain. As utilized herein, the term "carrier" is to be understood as connoting just such a non-derivatized, non-drug/carrier coordinated entity, for consistent herewith it is the "carrier" entity itself and not the nature of any activity or release rate controlling/modifying substituent which is responsible for providing the desired brain-specific result.

Additional examples of such redox carriers include the quaternary pyridinium alcohols (1), the analog isoquinoline acid and alcohol systems (2), and multi-charged delivery forms, exemplified by structure 3 (D represents drug, Z a covalent link) and obviously the corresponding dihydro forms.

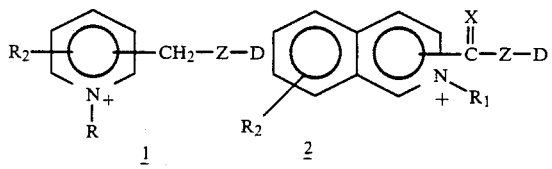

X = $H_2$ or O

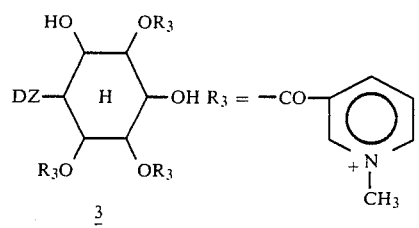

Yet other redox carriers include those comprising an acidic chain directly linked to the heterocyclic nitrogen, in quaternary or tertiary amine form. Also the hydroxide type carriers, e.g., the glucosamine analog indicated below. Representative are:

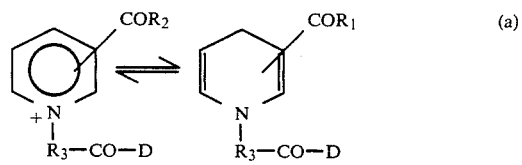

$R_1 = NH_2$; $OR_2$; and the like $R_2 =$ alcohol residue $R_3 = (CH_2)_n$ $n = 1-10$ or $C_1-C_{12}$ branched alkyl, arylalkyl, and the like D = drug—$NH_2$ or —OH;

Preparation:

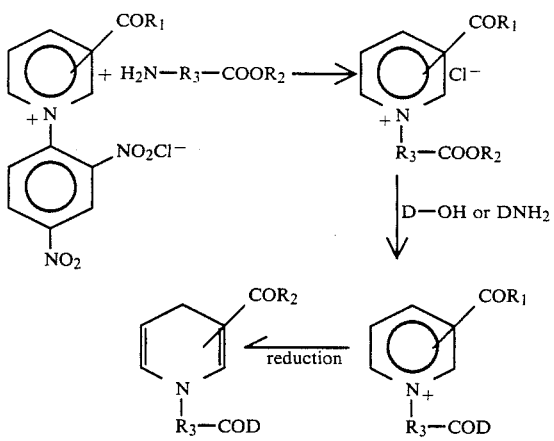

Method of: H. Lattre et al., *Annalen*, 579, 123 (1953).

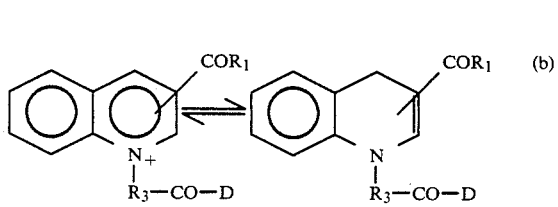

-continued

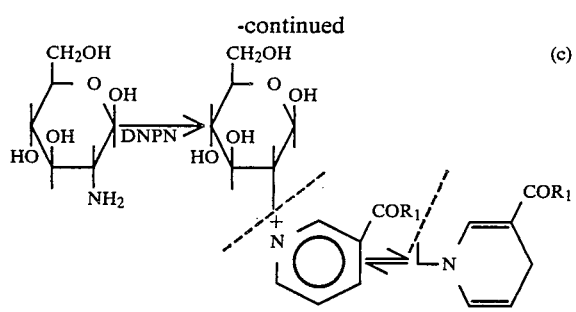

Generally preferred dihydropyridine⇌pyridinium salt redox carriers for use in the present invention include the following (where D represents the drug), and obviously the corresponding dihydro forms:

(a) the pyridinium systems

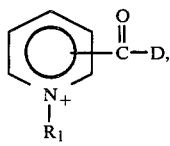 (i)

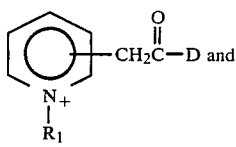 (ii)

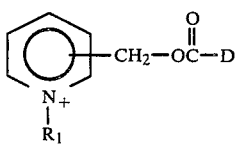 (iii)

in which the depicted substituent is in the 2-, 3- or 4-position, and $R_1$ is $C_1-C_7$ alkyl or $C_7-C_{10}$ aralkyl, preferably methyl or benzyl;

(b) the pyridinium system

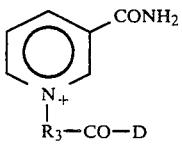 (iv)

in which $R_3$ is $C_1$ to $C_3$ alkylene, i.e., $(CH_2)_n$ where n=1-3;

(c) the isoquinolinium and quinolinium systems

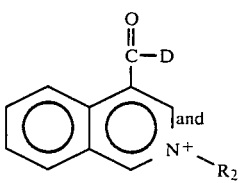 (v)

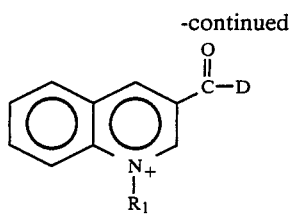 (vi)

in which $R_1$ is defined as above; and (d) the quinolinium and isoquinolinium systems

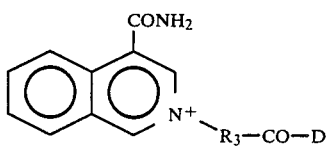 (vii)

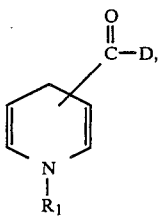 (viii)

in which $R_3$ is defined as above. The corresponding dihydro forms of the foregoing preferred pyridinium salts are depicted below, wherein the position and identity of the structural variables are as indicated above:

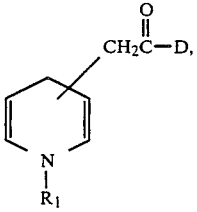 (i)

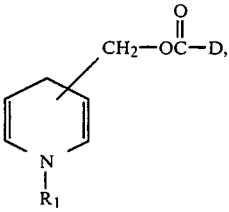 (ii)

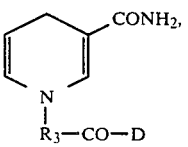 (iii)

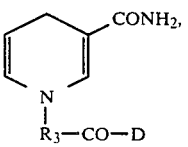 (iv)

-continued

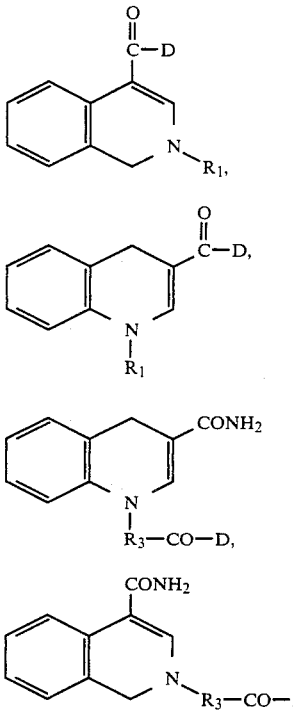

In a preferred embodiment of the present invention, sustained delivery of drug to the brain in pharmacologically effective concentrations has now been demonstrated, paralleled with much lower concentrations in the peripheral circulation and other tissues, utilizing dopamine as the target drug species and a trigonelline-type carrier system, with the catechol moiety thereof in certain instances being acylated, e.g., acetylated or pivalylated. According to Scheme 3 which follows, one specific delivery system for dopamine, compound 5, on administration (e.g., by injection) is distributed throughout the body and by reason of its lipophilic character facilely penetrates the blood-brain barrier and enters the CNS. Following oxidation both in the brain and in the other tissues, the corresponding hydrophilic quaternary salt (6) is formed. The quaternary salt 6 is essentially "locked in" the brain and its concentration is considered to increase with time until reaching a maximum, which depends primarily on the relative rates of entrance of the dihydro compound (5) to the brain ($K_1$) as compared to $K_2$ to the other tissues, the rate of oxidation of the dihydro form to the quaternary ($K_3$ and $K_7$) and the rates of its disappearance from the brain ($K_4 + K_5$). At the same time, the very water soluble quaternary form(s) 6 is/are excreted readily via the kidney and the liver ($K_8 >> K_4$). Derivatives 6 are considered to be essentially inactive forms ($K_8 >> K_9$), and thus systemic activity/toxicity is minimized. Hence, the concentration of 5 and 6 in the blood rapidly increases. The ratio of the quaternary salt 6 in the brain relative to the blood increases to the point where 6, or metabolites thereof, can only be found in the brain. The quaternary 6, whether in the brain, blood or other tissues, is deemed to release dopamine and the non-toxic compound, trigonelline, depending upon the rates of site-specific conversion of the precursor 6 to the drug at each of these sites. The concentration of any released dopamine at any time is much higher in the brain than in the blood or other tissues. Also, as the enzymatic transformation of the quaternary precursor 6 to the drug (dopamine) is relatively slow, same permits a sustained release of dopamine. Too, the simultaneous protection/lipophilic derivatization of the catechol system in dopamine has also now been demonstrated.

It will be appreciated that a compound of formula (I), such as compound 5, may be administered as depicted in Scheme 3, or in the form of a non-toxic pharmaceutically acceptable salt thereof, i.e., a salt which can be represented by the formula

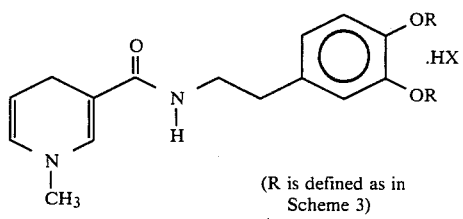

(R is defined as in Scheme 3)

wherein HX is as defined before; and that, regardless of the actual form in which the compound is administered, it will be converted in vivo to a quaternary salt of the compound 6 type, the anion $X^-$ being an anion present in vivo. It is not necessary that the compound 6 anion be introduced as part of the compound 5. And even when the compound 5 is used in its salt form, the anion of 6 is not necessarily the same as that present in compound 5. In any event, the exact identity of the anionic portion of the compound 6 is immaterial to the depicted enzymatic transformation.

Scheme 3:

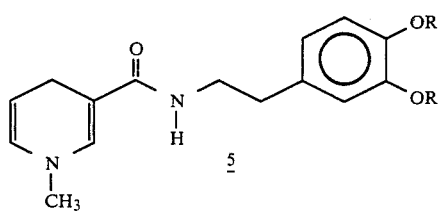

5

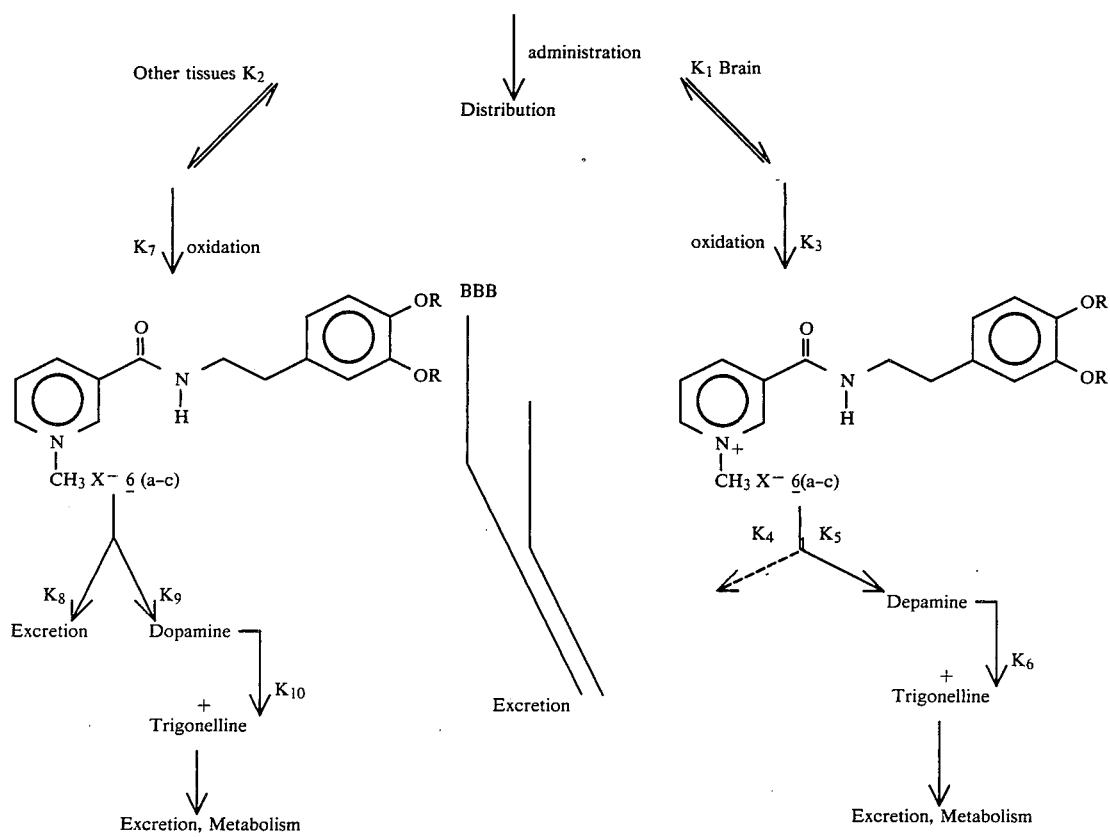
With specific reference to the immediately above, the 1,4-dihydropyridine derivatives (5) were prepared as in the following Scheme 4:
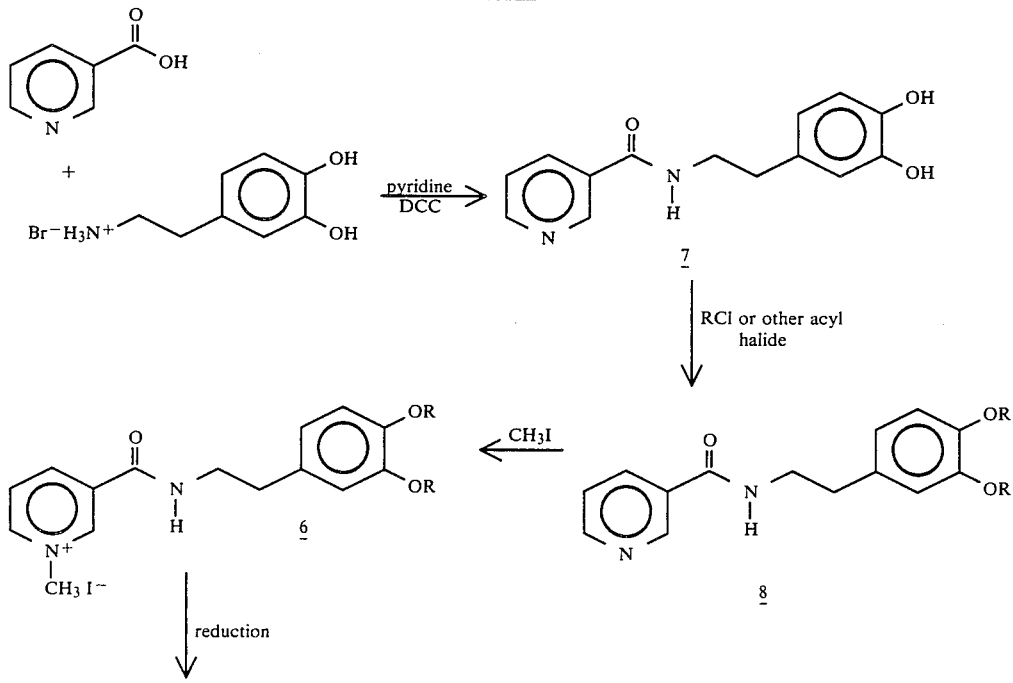

-continued
Scheme 4:

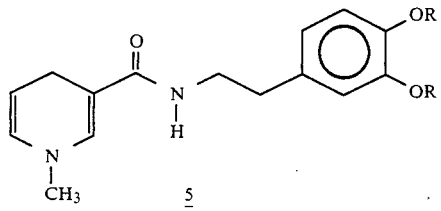

R=H (a), COCH₃ (b), COC(CH₃)₃ (c)
DCC=dicyclohexylcarbodiimide

Similar schemes can be shown for the preparation of the other dopamine derivatives of the invention. The step which introduces the protecting groups is of course only required when it is desired to protect the catechol hydroxyl groups. Moreover, when carbonate rather than acyl protecting groups are desired, the step of introducing the protecting groups will involve reacting the catechol with a halocarbonate of the type Y'OCOCl or Y'OCOBr (formed by reaction of Y'OH with COCl₂ or COBr₂), rather than with an acyl halide YCl or YBr, Y and Y' being as generically defined hereinabove. Also, the order of steps shown in Scheme 4 may be altered; quaternization, followed by reduction, need not be in the final two steps but may be carried out earlier in the reaction sequence. Yet other reaction schemes and reactants (e.g., using an anhydride rather than an acyl halide to convert 7 to 8) will be readily apparent to those skilled in the art, Scheme 4 being simply a preferred approach for the specific compounds there depicted. Variations of this approach are likewise applicable to preparing derivatives of other hydroxy-containing amines.

In an attempt to ascertain whether any biotransformation of the free catechol is taking place by COMT (catechol-O-methyltransferase) either before or after oxidation, the possible O-methyl metabolites (9 and 10) were synthesized separately following Scheme 4 with 3-methoxytyramine hydrochloride as the starting material.

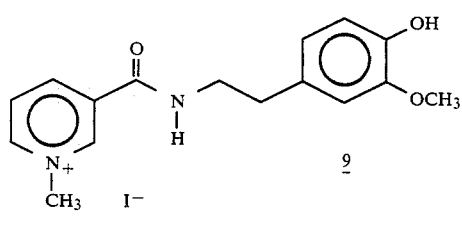

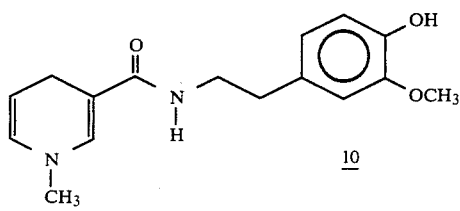

The stability of the 1,4-dihydropyridine derivatives (5) was determined in the presence of the oxidizing agents, alcoholic AgNO₃ and hydrogen peroxide. The in vitro rates of oxidation of the 1,4-dihydropyridine derivative (5c) in 80% plasma, 20% brain homogenate, 20% liver homogenate and in whole blood were determined.

The dihydropyridine derivative (5c) was then selected for the in vivo study. A solution in DMSO (dimethylsulfoxide) was injected through the jugular vein to a group of male Sprague-Dawley rats which were then sacrificed at various time intervals; their blood and brains were analyzed for the quaternary precursor of dopamine (6a). The in vivo dopaminergic activities of the selected compounds 5c vs. 6a were then determined.

Consistent with the above, it was found that N-nicotinoyldopamine (7) could be obtained in good yields by coupling dopamine hydrobromide with nicotinic acid in pyridine as a solvent and with dicyclohexylcarbodiimide as the coupling agent. Attempts to prepare 7 by using dopamine free base were largely unsuccessful. As for the catechol protecting groups, the acetyl and pivalyl moieties were selected due to their rather different steric and partitioning parameters. Acylation could be accomplished with the acyl chlorides by using conventional methods. Reduction of the quaternaries (6a–c and 9) was accomplished by using sodium dithionite in mildly basic aqueous solution, (NaHCO₃). It was observed that the dihydro compound obtained in the case of the quaternary 6b gave a faint green color with ferric ions, indicating partial hydrolysis of at least one of the acetyl moieties during reduction, even in the cold, weakly basic solution used as a medium. The dihydropyridine derivatives isolated (5a–c and 10) were determined to have the expected 1,4-dihydropyridine structure, based on their NMR and UV spectra. Attempts to prepare the β-protonated enamine salts of the isolated dihydro derivatives were also largely unsuccessful, due to acid catalyzed addition reactions. The 1,4-dihydropyridine derivatives (5a–c) were found to be relatively stable towards oxidation. Compound 5c was quantitatively oxidized to the corresponding quaternary salt 6c by H₂O₂ or alcoholic AgNO₃ solution.

The diacetyl derivatives (5b and 6b) appeared to be labile to hydrolysis and therefore were not pursued in vitro. The dipivalyldihydro derivative (5c) was thoroughly investigated for its in vitro rates of disappearance and metabolic degradation in various biological fluids. It is evident that 5c represents a rather complex case, as besides oxidation, a two-step hydrolysis will also take place. Scheme 5 illustrates the interconversion of the possible components.

Scheme 5:

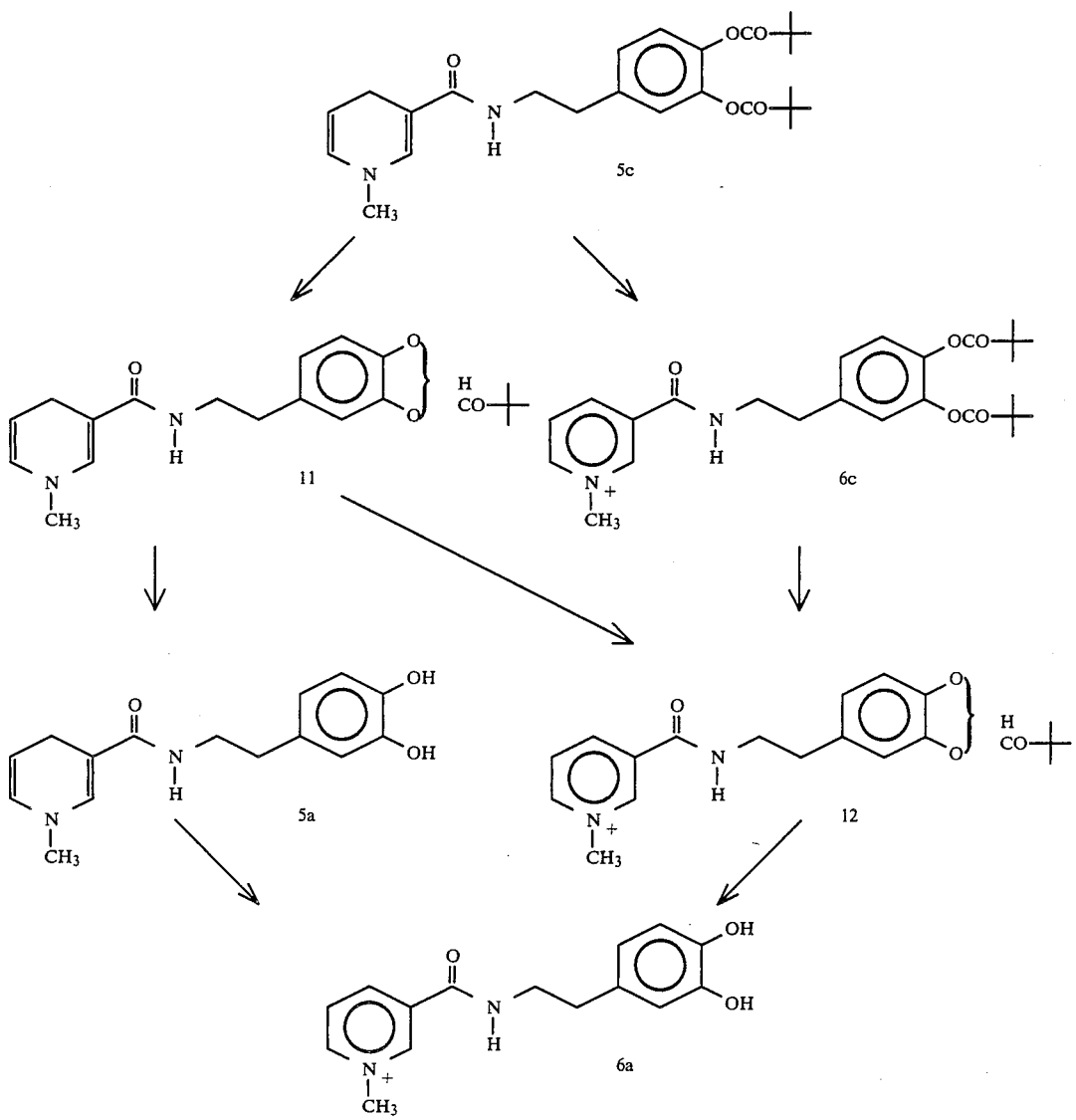

Figure 5:
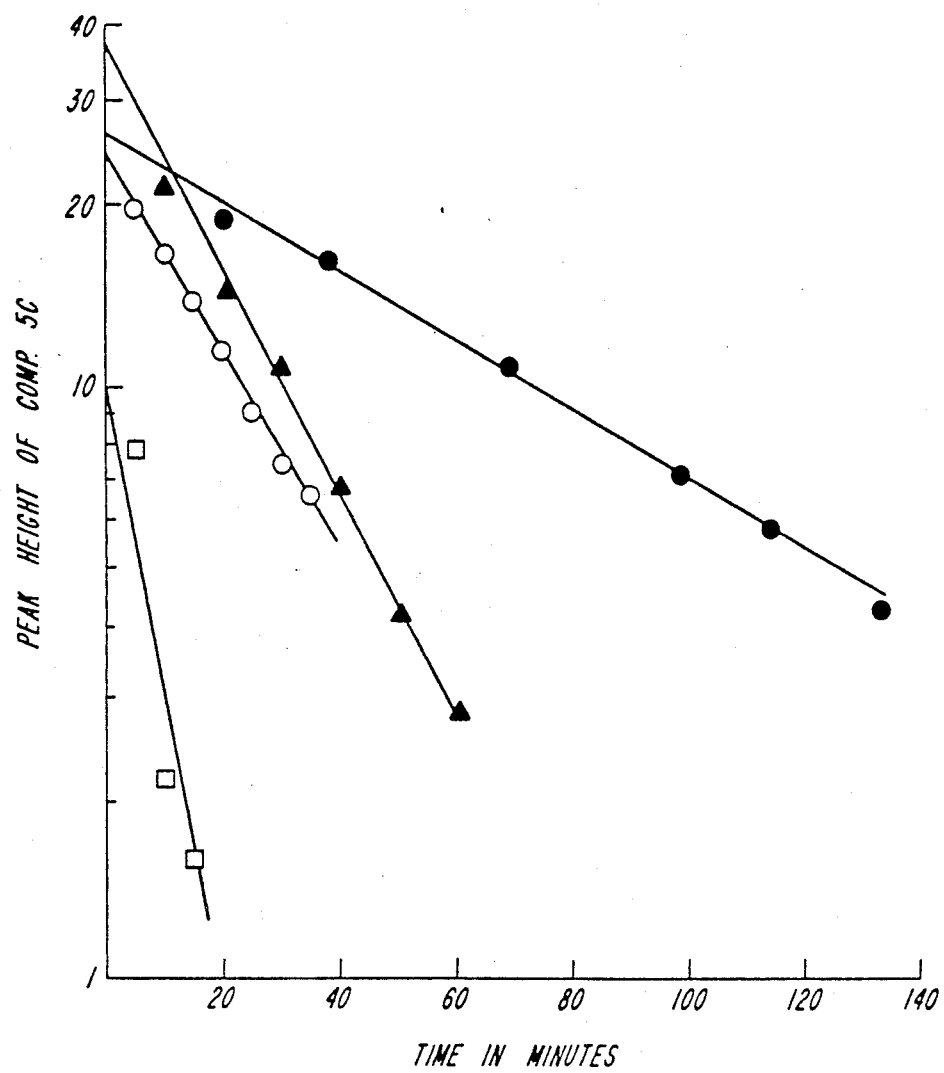
FIG. 5 is a semilog plot of peak heights of 1-methyl-3-{N-[β-(3,4-dipivalyloxyphenyl)ethyl]}-carbamoyl-1,4-dihydropyridine 5c against time in plasma (●), brain homogenate (▲), whole blood (O) and liver homogenate (□)

FIGS. 1-4 illustrate the results of such an investigation. The apparent half-lives for the disappearance of 5c in biological fluids at 37° C. were calculated. Although the process does not truly follow first order kinetics, the data fit very closely a pseudo first order process (FIG. 5). The obtained values, 51 min (80% plasma), 17 min (20% brain homogenate), 18 min (whole citrated blood) and 6 min (20% liver homogenate), reflect an acceptable stability of the dihydro derivative 5c. The disappearance of 5c is accompanied by formation of some monoester (11) and dihydroxy dihydro form (5a) in all the media except the liver homogenate. The rate of hydrolysis of the first ester moiety is faster than the second and a reasonable amount of monoester 11 builds up with time. The monohydroxy quaternary 12 could not be detected except in the blood as a very small peak which does not change significantly with time. A steady increase in the concentration of the dihydroxy quaternary 6a was observed in all media except liver homogenate. Thus, it is established that this derivative, 6a, is forming as the main product of the various interconversion routes and it is the direct precursor thus concluded to be locked in the brain in the in vivo experiment. No formation of the methoxy derivatives 9 and 10 could be detected in any of the biological fluids studied; 5a and 6a does not appear to be good substrates for COMT.

Figure 6:
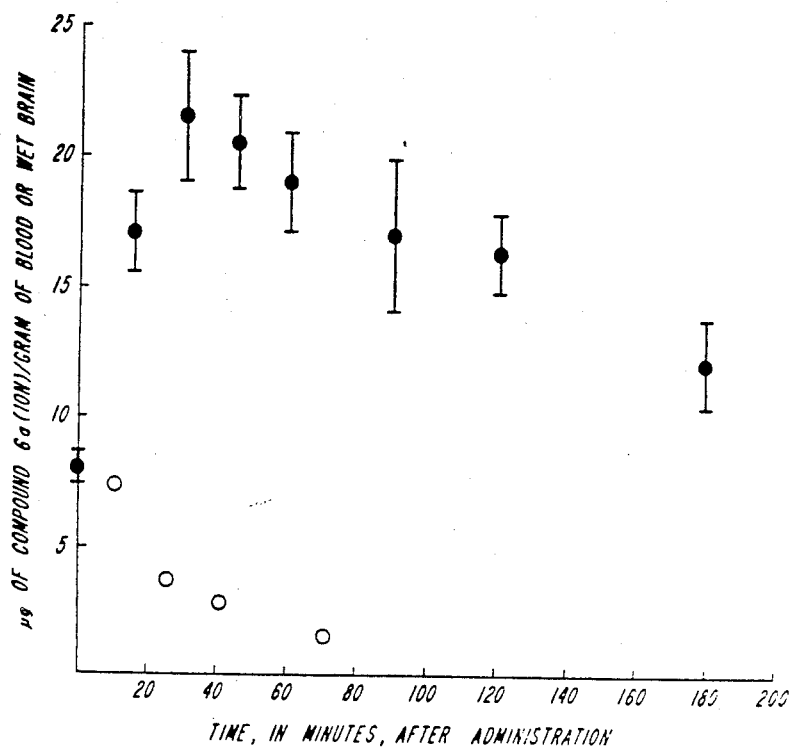
FIG. 6 is a graph plotting concentrations against time of 1-methyl-3-{N-[β-(3,4-dihydroxyphenyl)ethyl]}carbamoyl pyridinium cation (6a) in brain (●) and in blood (O) following administration of 1-methyl-3-{N-[β-(3,4-dipivalyloxyphenyl)-ethyl]}carbamoyl-1, 4-dihydropyridine (5c), with the error bars indicating SEM.

The first objective of the in vivo studies was to trace the appearance and disappearance of 6a in blood and brain following administration of 5c. FIG. 6 summarizes such results, and is consistent with the mechanism shown in Scheme 3. After one single injection of the 1,4-dihydropyridine derivative 5c to the rat, the dihydroxy quaternary 6a (ion), which is the only detectable derivative, could be seen to appear and then to disappear quickly from the blood, with a half-life of 27 min. On the contrary, the concentration of 6a (ion) is increasing in the brain steadily, reaching a maximum at about 30 min following administration. The descending portion indicates a half-life of disappearance from the brain of about 3.2 h. No formation of O-methyl metabolites (9, 10) could be detected in the brain. This confirms the in vitro results that 6a (or 5a) is not a good substrate for COMT.

To determine whether dopamine itself was finally released in the brain upon completion of the aforesaid complex delivery process, 5c was administered intrajugularly and changes in brain-dopamine concentrations following that administration were studied. Some of the rats showed up to threefold increase in the dopamine concentrations, others practically none. Since it is possible (and even desired) that the intrinsic brain metabolism of the dopamine does not permit significant build-up of its concentration, specific pharmacologic activity was investigated, using changes in the in vivo significantly lower effect of 6a when administered I.V. does not unequivocally clarify which alternative is the more responsible. This was resolved by in vitro comparison of the relative activities of dopamine versus 6a.

Fresh anterior pituitaries obtained from female rats were incubated with various concentrations of dopamine (DA) and 6a, respectively, and their effects on the rate of release of prolactin were measured. It was found that at $2 \times 10^{-8}$M concentrations, neither DA nor 6a had any effect, but at $2 \times 10^{-7}$M, DA caused a 57% reduction of the prolactin rate secretion, while 6a had no effect. These results are summarized in the following Table I.

TABLE I

Comparative in vitro activity of 6a vs. dopamine[a]

Prolactin ng/mg./h[b]

| Dopamine (DA)[c] | | | | 6a[d] | | | |
|---|---|---|---|---|---|---|---|
| control | DA $2 \times 10^{-8}$ M | control | DA $2 \times 10^{-7}$ M | control | 6a $2 \times 10^{-8}$ M | control | 6a $2 \times 10^{\times 7}$ M |
| 344 ± 50 | 355 ± 67 | 282 ± 34 | 121 ± 38 | 342 ± 38 | 386 ± 29 | 250 ± 30 | 277 ± 32 |

[a]On freshly obtained anterior pituitary (AP) at 37° C. All values are average of 9 separate AP-S.
[b]Prolactin release rate of the incubated AP-S.
[c]Weight of the AP-S:
control 4.6 ± 0.2 mg.
DA treated 4.5 ± 0.3 mg.
[d]Weight of the AP-S:
control 4.6 ± 0.3
6a treated 4.7 ± 0.4
*P < 0.05 prolactin secretion. It is known that dopamine and its agonists decrease prolactin secretion following their binding to stereospecific receptors located on lactophors in the anterior pituitary (AP) gland [G. P. Mueller, J. W. Simpkins, J. Meites and K. E. Moore, *Neuroendocrinology*, 20, 121 (1976); W. Wuttke, E. Cassell and J. Meites, *Endocrinology*, 88, 737 (1971); J. A. Clemens, E. B. Smalstig and C. J. Shaar, *Acta Endocrinol.*, 79, 230 (1975)]. This effect is dose-dependent and it can also be observed in vitro, incubating anterior pituitaries with dopamine or its agonists [R. M. MacLeod in "Frontiers in Neuroendocrinology", Ed. L. Martini and W. F. Ganong, Raven Press].

Figure 7:
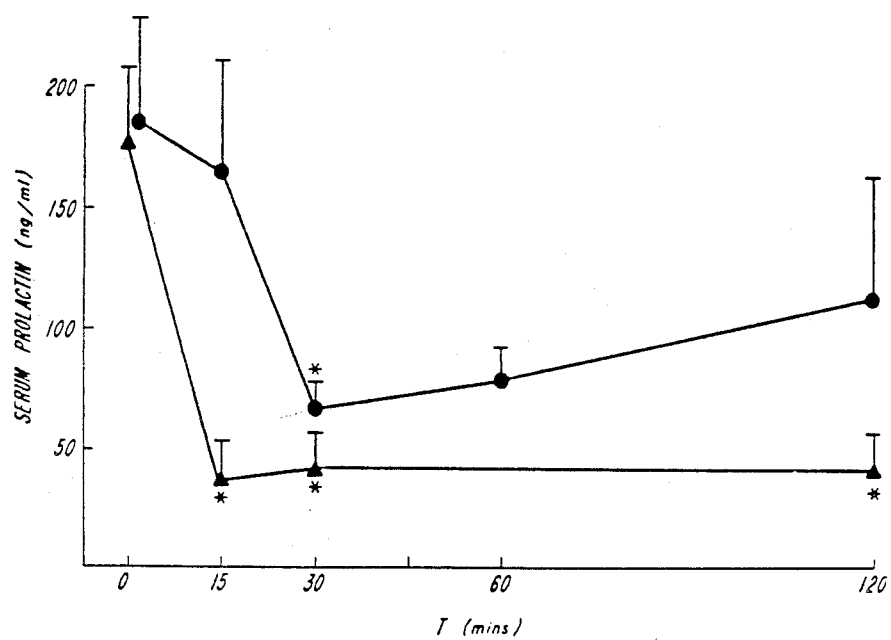
FIG. 7 is a graph plotting the effects of compounds 5c (▲) and 6a (●) administered I.V. at 1 mg/kg dose level, on the serum prolactin levels in rats.

It was then determined that exposure of male rats to 17-β-estradiol for two days elevated serum prolactin levels to greater than 150 ng/ml. Intravenous administration of 5c caused a 79% decrease in serum prolactin concentrations and this dramatic reduction was maintained through 120 min after treatment. In contrast, 6a had no significant effect on the serum prolactin concentrations by 15 min, and caused a 67% reduction by 30 min. Thereafter, serum prolactin levels increased progressively to levels which are not significantly different from vehicle injected controls, by 60 and 120 min. These results are summarized in FIG. 7. The rapid onset and prolonged inhibitory effects of 5c on prolactin secretion is consistent with the time course of the appearance of 6a in the brain following administration of 5c. The "trapping" of 6a in the brain subsequent to I.V. injection of 5c provides a constant source of a potent dopaminergic agent, either dopamine or 6a itself. The These results indicate that if 6a has any activity, it must be significantly less than that of DA. Based on the delayed onset of the activity when 6a was administered I.V. and considering the in vitro results, it logically follows that the high and prolonged activity of the 6a locked in the brain following administration of 5c is due to the fact that 6a is slowly releasing the active DA in the brain.

Accordingly, provided hereby is a potent, brain-specific dopaminergic agent comprising a lipophilic dihydropyridine carrier-type chemical delivery system of dopamine ["pro-prodrug" or "pro-pro-prodrug" in the case of the catechol protective group(s)], which penetrates the BBB by passive transport. The rapid oxidation in the brain of the carrier moiety to the corresponding quaternary pyridinium salt results in an activated amide of dopamine. The oxidation process is much faster than amide cleavage of the beginning compound 5 or of 6. Moreover, the ionic nature of the activated quaternary salt results in a significant slowdown of the efflux of this specific form through the BBB, resulting in a selective concentration enhancement of the precursor 6a in the brain. Too, brain-specific dopaminergic activity is assured, logically as dopamine is released from this activated form upon hydrolytic, enzymatic or metabolic cleavage, as is facile excretion of the carrier moiety from the brain.

In yet another embodiment of the invention, like synthesis of the analogous tyramine system has been carried out, and the corresponding determinations made. Such tyramine system is represented as follows:

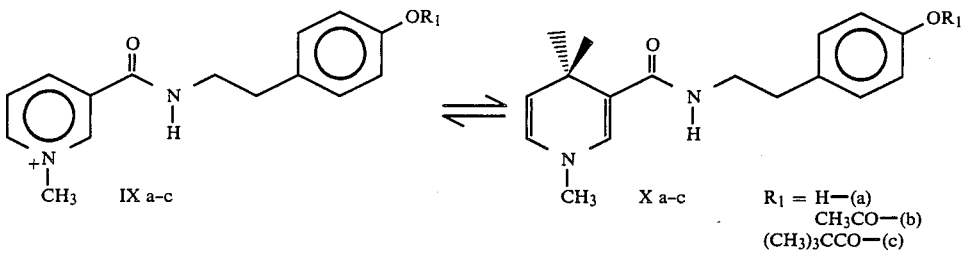

$R_1 = H$—(a)
$CH_3CO$—(b)
$(CH_3)_3CCO$—(c)

Naturally, selection of the particular dihydropyridine⇌pyridinium salt redox carrier to be used will depend on the chemical structure of the specific drug involved. And not only should the nature of the functional group which is to be linked to the carrier system be considered in selecting the carrier, but the manner in which the ultimate compound is prepared should be tailored to the presence of any other reactive groups in the molecule. The following examples of specific drug/carrier combinations and their manner of synthesis are set forth for the purpose of illustration only and are not to be considered limitative in any way whatsoever.

Thus, in one specific illustration, the selected drug is testosterone and the selected carrier system is trigonelline⇌dihydrotrigonelline; according to this embodiment, testosterone is reacted with nicotinoyl chloride, the resultant ester is then quaternized with methyl iodide, and the quaternary iodide is then reduced with $Na_2S_2O_4$ to afford the testosterone-CDS (chemical delivery system)

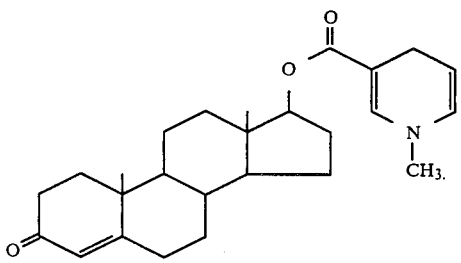

Other steroids can be similarly derivatized, e.g., 17α-ethynyltestosterone, estradiol and the like.

Another specific illustration involves selecting melphalan and the same type of carrier system as above, but forming an amide rather than an ester linkage. Thus, melphalan is converted to its hydrobromide, which is reacted with nicotinic acid to afford the amide having the formula

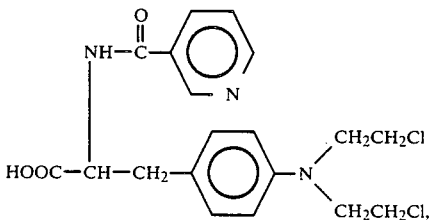

which can be esterified, if desired (to increase lipoidal characteristics), followed by, when the ethyl ester is prepared, quaternizing same with methyl iodide to form

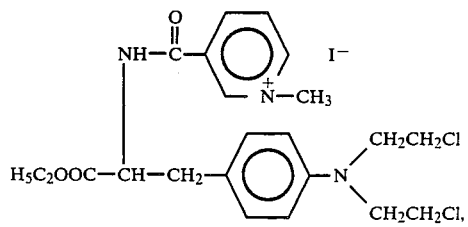

which can then be reduced to afford the melphalan-CDS

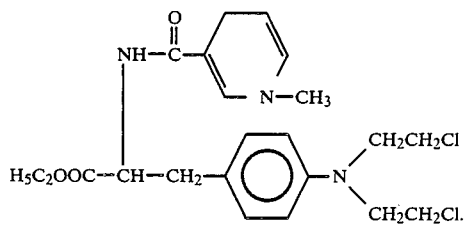

As one of several alternative schemes, melphalan can be derivatized by first esterifying it, e.g., to convert the carboxy function to the ethyl ester, then reacting the resultant melphalan ethyl ester with nicotinoyl chloride to form the amide of the formula

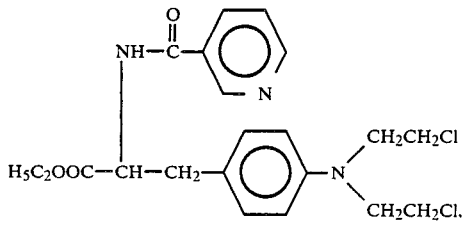

which can then be quaternized and the quaternary salt subsequently reduced as indicated above to afford to same melphalan-CDS as depicted above.

Yet another specific illustration utilizes chlorambucil as the target drug, in which case the desired nicotinic acid carrier system is linked to the drug via a bridging group. Thus, nicotinic acid can be reacted with an appropriate di- or polyhydroxy compound such as ethylene glycol, propylene glycol or inositol and the resultant intermediate is linked via its free hydroxy group(s) to the carboxylic acid function of chlorambucil. That intermediate is then quaternized and the quaternary salt is reduced to afford the chlorambucil-CDS. In the case of nicotinic acid and ethylene glycol starting materials, the chlorambucil-CDS has the formula

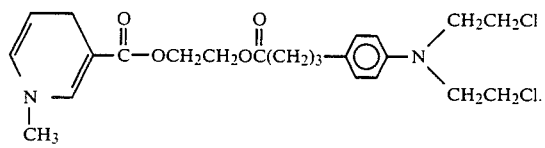

On the other hand, when a polyhydroxy compound is reacted with nicotinic acid in the first step, a variety of products are possible. Thus, for example, when inositol is used, the final product may contain anywhere from 1 carrier/5 drug residues to 5 carrier/1 drug residue. In the case of the inositol trinicotinate intermediate

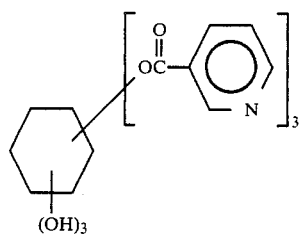

conditions for reacting same with chlorambucil can be selected so that one, two or three of the hydroxy functions react with the acid. When all three hydroxys react, the ultimate chlorambucil-CDS has the formula

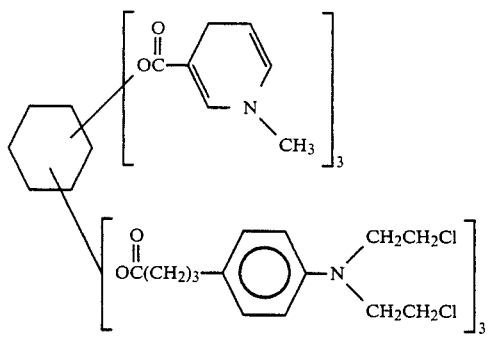

and contains 3 drug residues and 3 carrier groupings.

As another example, methotrexate, which has the structural formula

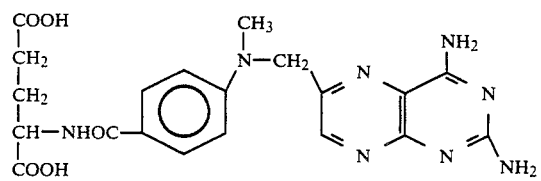

can be derivatized similarly to chlorambucil via its carboxy function(s), e.g., utilizing the inositol trigonellinates or a glucosamine analogue.

As a further example, podophyllotoxin and its derivatives can be linked to a carrier system of this invention. These drugs can be represented by the structual formula

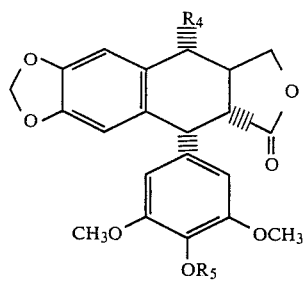

$R_5$ = H or $CH_3$
$R_4$ = OH—podophyllotoxin

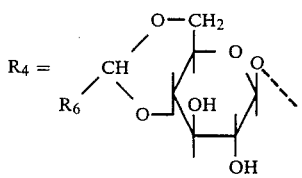

$R_4(R_6 = CH_3$—etoposide

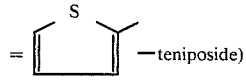 —teniposide)

and can be derivatized by reacting the hydroxy group in podophyllotoxin ($R_4$=OH) or the hydroxy groups in the glycosidic portions in $R_4$ with acidic type redox carriers, e.g., in a manner analogous to the testosterone-CDS depicted above. Known cisplatin analogues, in which typically the amino groups have been replaced with organic radicals, can be similarly derivatized according to the invention, the method of choice depending on the nature of the functional groups in the organic radicals.

Similarly, syntheses and like determinations as regards the redox carrier-linked enkephalins can be carried out. First synthesized is the known leucine enkephalin XI. The quaternary pyridinium analog XII, the corresponding O-benzyl ether XIII and the amide XIV are next synthesized.

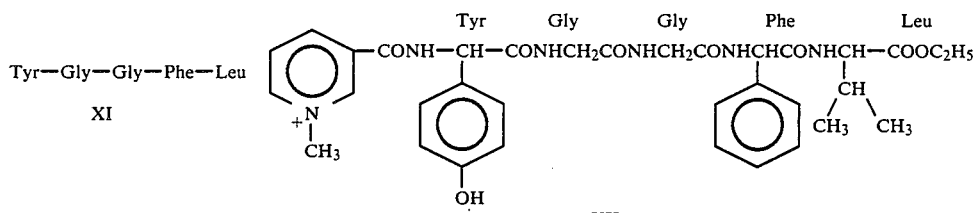

Tyr—Gly—Gly—Phe—Leu

XI

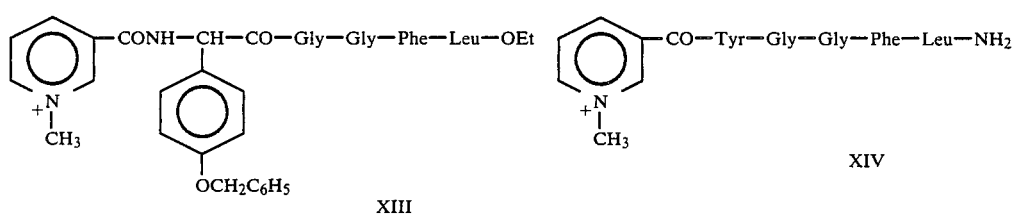

XIII   XIV

The O-benzyl pentapeptide ethyl ester derivative of XI is synthesized sequentially and then coupled with nicotinic acid, followed by methylation. Alternate methods involve introduction of carrier at an earlier stage in the synthesis. The reduction of XII and XIII results in a mixture of products due to the base sensitivity of the ester. Likewise prepared are the corresponding leucinol trigonelline ester XV and its dihydro derivative XVI.

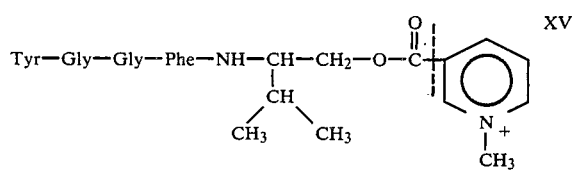

-continued

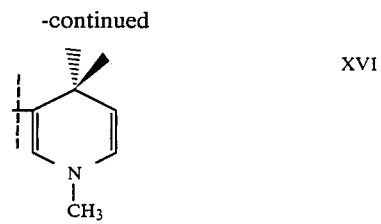

Thus, the site-specific brain delivery of the enkephalins for the treatment of epilepsy is established consistent with the Scheme 1, as is their analgesic activity.

Similarly, as regards the benzodiazepine tranquilizers, e.g.:

1. Oxazepam:

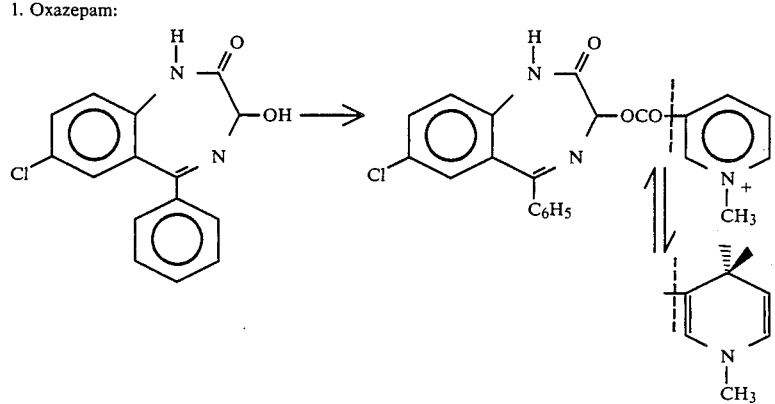

2. Diazepam:

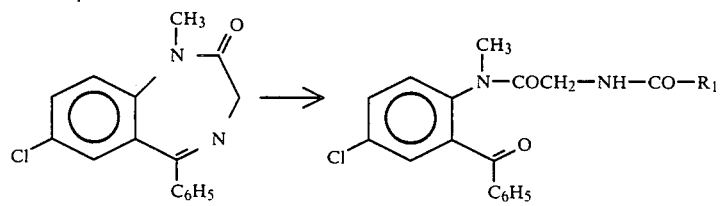

-continued

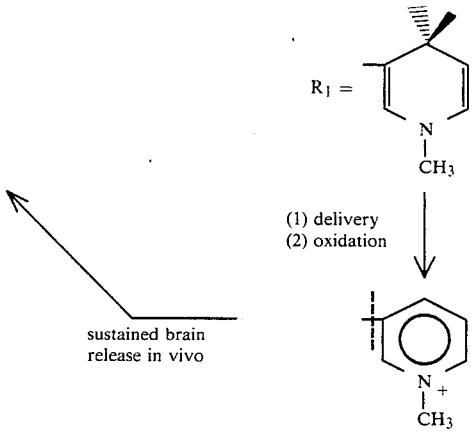

(1) delivery
(2) oxidation sustained brain release in vivo

This reaction scheme utilizes conventional opening of the 7-member ring, accompanied by coupling of the drug to the carrier. The following drugs can be similarly derivatized to the corresponding dihydro derivatives:

with. Model compounds include carboxylic acids, most specifically valproic acid, as well as some of the GABA analogs which inhibit irreversibly the GABA-T, such as γ-vinyl and/or γ-acetylenic GABA. Using the aforesaid trigonelline (N-methylnicotinic acid)⇌dihydrotrigonelline system, for example, the selected compounds can be effectively delivered per Scheme 1. Thus, representative target compounds are the dihydropyridine carrier-drug combinations 1 and the corresponding pyridinium carrier-drug species, for example, GABA and its esters:

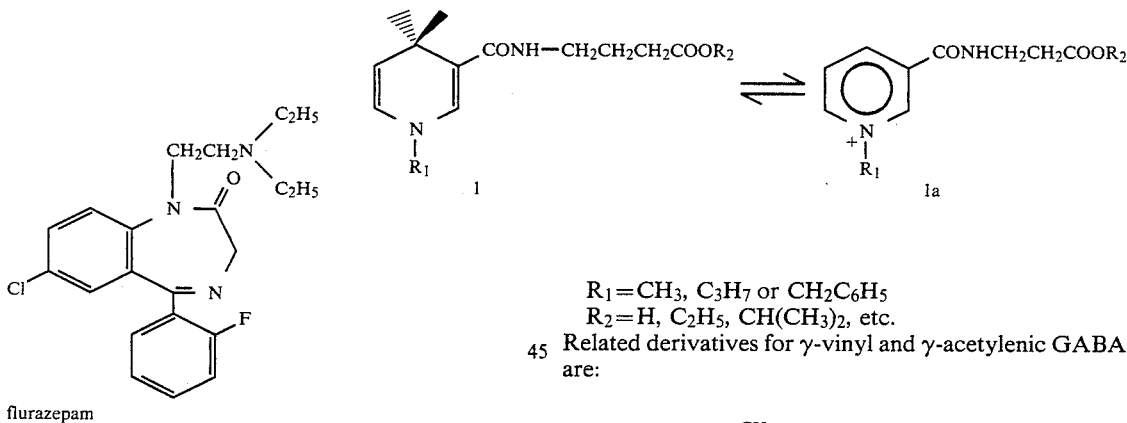

flurazepam bromazepam $R_1 = CH_3$, $C_3H_7$ or $CH_2C_6H_5$
$R_2 = H$, $C_2H_5$, $CH(CH_3)_2$, etc.

Related derivatives for γ-vinyl and γ-acetylenic GABA are:

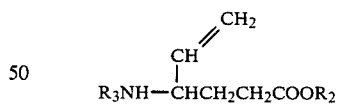

2 and 2a

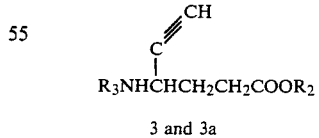

3 and 3a

And in another preferred embodiment of the invention, there is provided the effective, selective and nontoxic treatment of epilepsy, based upon the mechanism illustrated in Scheme 1. Indeed, commencing from the "GABA-hypothesis" of epilepsy, the brain-specific, enhanced and sustained release of GABA (γ-aminobutyric acid) itself, and various other compounds either directly or indirectly affecting the concentrations of GABA in the brain, is circumscribed consistent here-

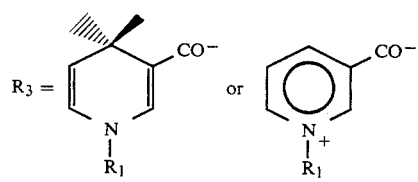

In the case of valproic acid, other alternatives are:

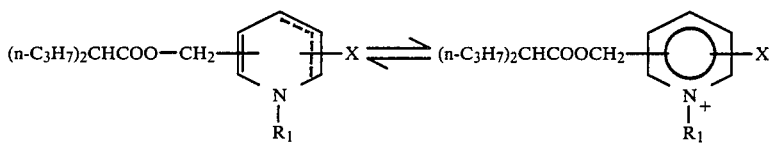

X=H, CONH₂, CHNOR₂, etc.

In another embodiment of like delivery system, applicable for both the GABA and related compounds and for the carboxylic acids, or for any other drug species to be linked to such a carrier, either directly or indirectly, i.e., mediated by a carboxylic acid, e.g., succinic acid, or other linkage, provided is a mono- or poly-substituted nontoxic polyol (such as inositol or sugars) having the trigonelline⇌dihydrotrigonelline system and the compounds to be delivered linked to the same molecule as exemplified by the GABA case (5⇌5a) and valproic acid (6⇌6a):

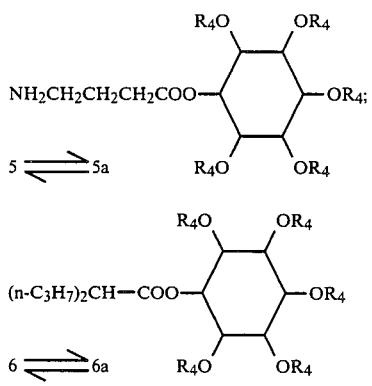

$R_4$=H, GABA or valproic acid, but at least one of $R_4$ is:

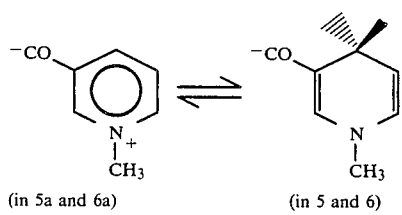

$R_4$ can be partially replaced by additional GABA or valproic acid, changing the carrier/drug ratio as necessary. Some of the valproic acid metabolites can be coupled with carriers of the redox type, via the various hydroxy groups formed during the oxidative degradation:

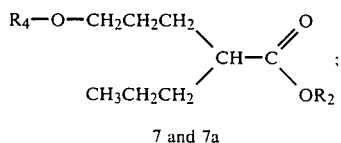

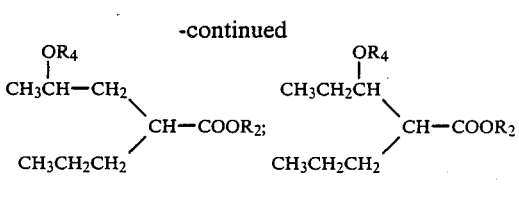

Illustrative examples are the corresponding derivatives of the 5-, 4-, and 3-hydroxy-2-n-propyl pentanoic acid derivatives. Additional carrier systems, such as the isoquinoline⇌dihydroisoquinoline system, can also be developed consistent herewith.

Moreover, based upon the observation that NADH content is significantly reduced in epileptic and like seizures, the use of the subject redox system (in reduced form) will bias the NAD⇌NADH balance towards NADH during the dihydro carrier→quaternary transformation. Also, the brain-specific delivery of small peptides consistent herewith, e.g., the enkephalins, which have been found to initiate epileptic seizures, has led to the design of a variety of long lasting potent antagonists.

And the subject chemical delivery system is also useful for the delivery of other anticonvulsants in a sustained, brain-specific fashion, e.g., the benzodiazepines and hydantoins, and those compounds, like apomorphine, which are useful in the treatment of photosensitive epilepsy.

It will of course be appreciated in the immediately above regard that the drug treatment of epilepsy has always posed formidable problems. There are many different anticonvulsants available, some more specific for different types of seizures. Indeed, there exist a wide variety of opinions as to which is the most suitable drug for any particular type of seizure, and drug mixtures are typically employed. An inevitable result of the traditional therapy is the development of chronic toxicity, but such result is conspicuously avoided according to the present invention.

It too will be appreciated that the desired therapeutic effects of all antiepileptic agents investigated, as well as their undesired toxic effects, reflect a statistically significant correlation with the drug levels in plasma. This correlation is based upon a close relationship between the drug concentrations in plasma and brain tissue. Hence, a primary attribute of this invention is to enable attainment of high and sustained brain levels of the selected active agents, essentially against the plasma-brain concentration gradient and independent of the drug concentration in the blood.

GABA and related compounds are logical candidates. It has been shown that GABA neuron function is impaired in at least certain types of human epilepsy. Animal studies also showed that seizures are induced by reduction of GABA neuron function to a critical degree by (1) inhibition of GABA synthesis, (2) blockade of GABA receptors or (3) inhibition of GABA-receptor mediated ionic events. In addition, enhancement of GABA synaptic activity (by direct receptor stimulation or by increasing GABA levels in the synapse) has a potent and wide spectrum anticonvulsant effect. These findings foreshadowed that an enhanced and sustained GABA brain delivery or a brain-specific delivery in a sustained manner of a good GABA-agonist would be efficacious in different forms of epilepsy. It is well known that GABA itself, when administered systematically, does not penetrate the normal blood-brain barrier to any significant extent. Among the potential sites at which drugs may act to influence GABA-mediated synaptic function, the first target is to effect the BBB transfer of GABA via a redox delivery system. The second main target is to effect the catabolism of GABA. This invention, accordingly, specifically provides for the efficacious delivery of the GABA-T inhibitors, γ-vinyl and γ-acetylene-GABA, but the delivery of valproic acid, specifically to the brain and without requiring high circulating blood levels, is also envisaged. In order to achieve the required activity, sodium valproate must have a relatively high, 50–100 μg/ml, level in the blood. The value of valproic acid is well established in most types of epilepsy. It is evident that valproic acid produces significant increases in both brain and synaptosomal GABA concentrations Valproic acid itself undergoes extensive metabolism.

In capsule summary, the present invention provides for the significantly improved treatment of epilepsy, and concomitant reduction in toxicity of a number of antiepileptic drug species currently in use. And made available to the brain is a variety of important compounds, such as GABA and a wealth of GABA-ergic agents.

It will be apparent from the foregoing discussion of specific drug-carrier combinations that a wide variety of synthetic approaches can be utilized, depending on the chemical nature of the selected drug. Various illustrative synthetic schemes as applied to specific centrally acting drugs in accord with this invention are set forth below in the section entitled "Illustrative Synthetic Methods". While the sequence of reaction steps can be varied in many cases, in general, the final step (except in the case of optional salt formation) will be reduction of a pyridinium compound of formula (II) to the corresponding dihydropyridine compound of formula (I). The reduction is usually conducted at a temperature from about −10° C. to room temperature, for a period of time from about 10 mins to 2 hrs, conveniently at atmospheric pressure. Typically, a large excess of reducing agent is employed, e.g., a 1:5 molar ratio of reducing agent to starting [D-QC]+ compound. The process is conducted in the presence of a suitable reducing agent, preferably an alkali metal dithionite such as sodium dithionite or an alkali metal borohydride such as sodium borohydride or lithium aluminum borohydride, in a suitable solvent. Sodium dithionite reduction is conveniently carried out in an aqueous solution; the dihydro product [D-DHC] is usually insoluble in water and thus can be readily separated from the reaction medium. In the case of sodium borohydride reduction, an organic reaction medium is employed, e.g., a lower alkanol such as methanol, an aqueous alkanol or other protic solvent.

Suitable nontoxic pharmaceutically acceptable carriers for use with the topic compounds [D-DHC], e.g., those less toxic than the target drug species themselves, will be apparent to those skilled in this art. Compare, for example, *Remington's Pharmaceutical Sciences,* 4th Edition (1970). Obviously, the choice of suitable carriers will depend upon the exact nature of the particular dosage form selected, as well as upon the identity of the active drug species [D]. The therapeutic dosage ranges for administration of the compounds according to this invention will generally be the same as, or less than, those characteristically used in this art for administration of the known drug species [D], per se. Naturally, such therapeutic dosage ranges will vary with the size of the patient, the condition for which the [D-DHC] compound is administered, the particular dosage form employed, and the like. The quantity of given dosage form needed to deliver the desired dose of [D] will of course depend upon the concentration of [D-DHC] in any given pharmaceutical composition/dosage form thereof.

The ability of the topic compounds to cross the BBB and to be "locked into" the brain allows administration of the drug in a site-specific manner. A combination of the present dihydropyridine⇌pyridinium salt redox system with a sustained release system will further enhance this site-specificity. Thus, a preferred embodiment of the invention comprises formulating the [D-DHC] compound or the salt of a [D-DHC] compound utilizing a sustained release carrier system and/or route of administration capable of slowly releasing the chemical, e.g., sustained release tablets and capsules for oral administration; subcutaneous injection, or implantation of drugs in solid pellet form (for example, distributed in a biodegradable polymer); intramuscular injection of the compound in solution in oil or suspended in a repository vehicle; a transdermal delivery device or form such as an ointment to be applied locally to the desired site (when the drug is susceptible of delivery through the skin), slow intravenous infusion and the like. The rate of release of compound from the sustained release system should be comparable to the rate of in vivo oxidation of the dihydro form of the redox system in order to achieve the greatest degree of enhancement of specificity.

Illustrative Synthetic Methods

I. Methods for Derivatizing —NH$_2$ or —NH— Functions in Drugs

Method A

The drug is reacted with nicotinoyl chloride, with nicotinic anhydride, or with nicotinic acid in the presence of a suitable dehydrating agent such as dicyclohexylcarbodiimide, in an appropriate organic solvent, to afford the corresponding nicotinamide. The nicotinamide is then quaternized, typically by treatment with methyl iodide in a suitable organic solvent, to afford the quaternary derivative [D-QC]+, which is then reduced by treatment with sodium dithionite or sodium borohydride as generally described hereinabove to afford the desired compound [D-DHC].

The representative drugs listed below may be derivatized in this manner to the corresponding [D-QC]+ and [D-DHC] compounds. Tryptamine, desipramine and nortriptyline may be similarly derivatized.

The foregoing procedure may be repeated using picolinic acid or its acid chloride or anhydride, or isonicotinic acid or its acid chloride or anhydride, in place of nicotinic acid or its acid chloride or anhydride, respectively, to convert drugs such as those specifically mentioned for derivatizing by this Method to the corresponding picolinamides and isonicotinamides and then to the corresponding [D-QC]+ and [D-DHC] compounds.

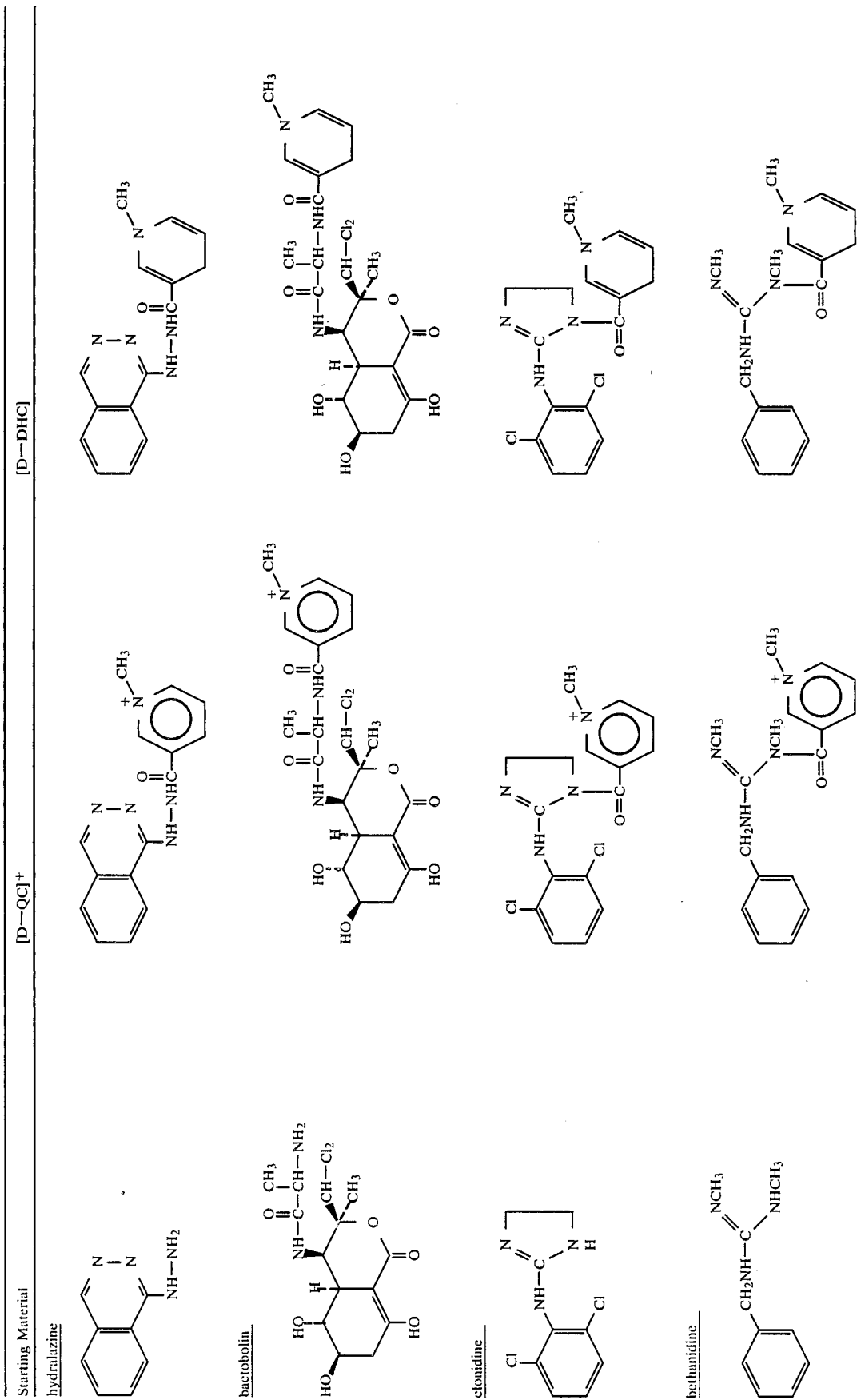

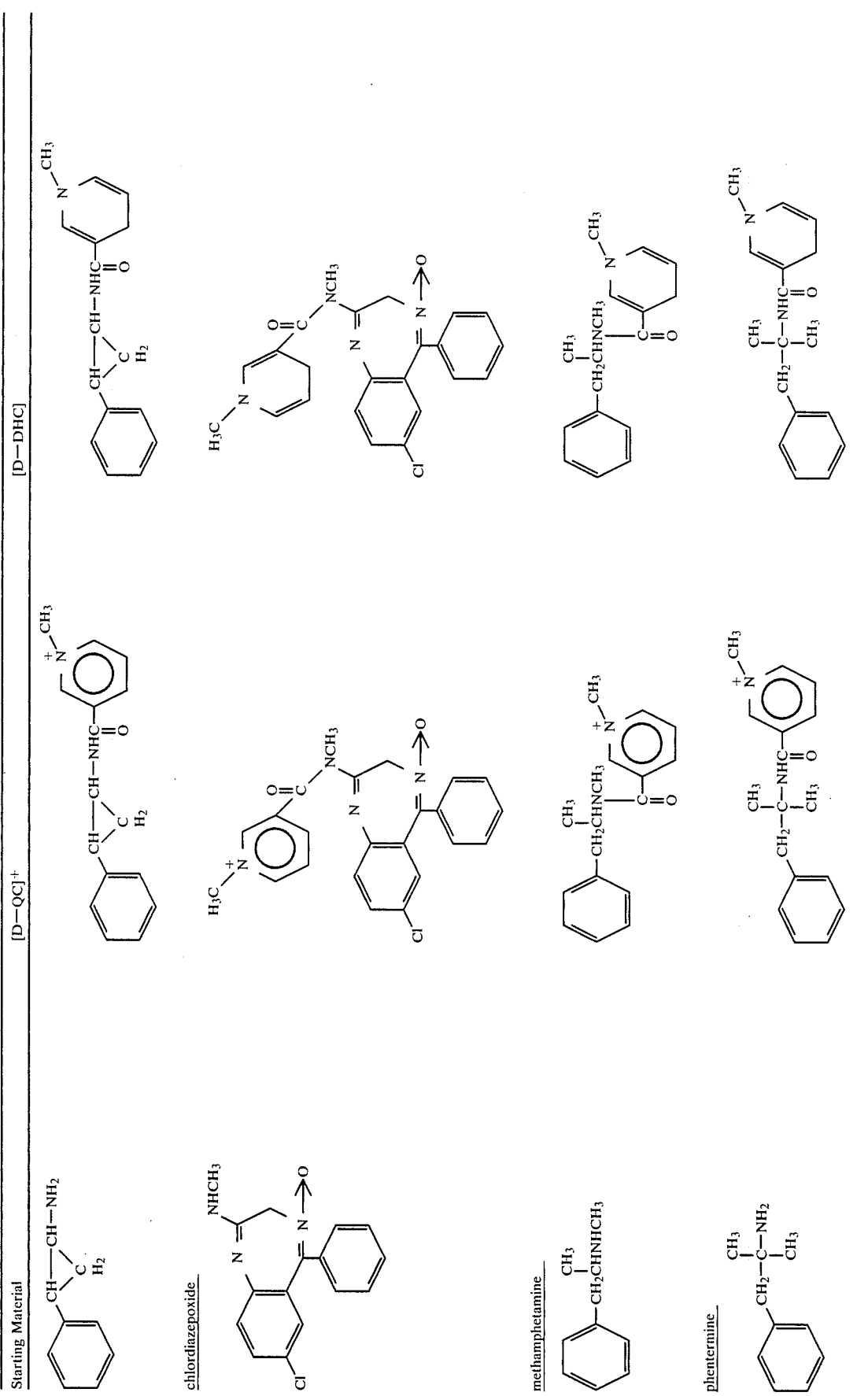

-continued
| Starting Material | [D—QC]+ | [D—DHC] |
|---|---|---|
| 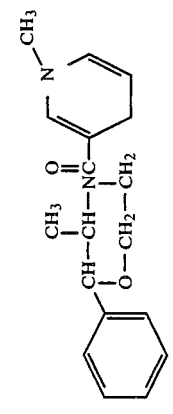 | 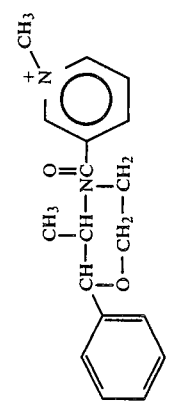 | 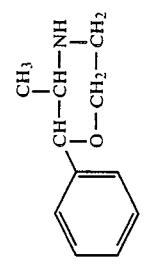 |
| anileridine | | |
| 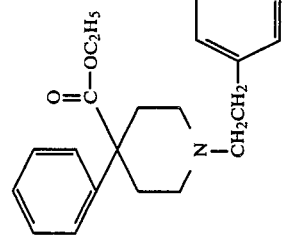 | 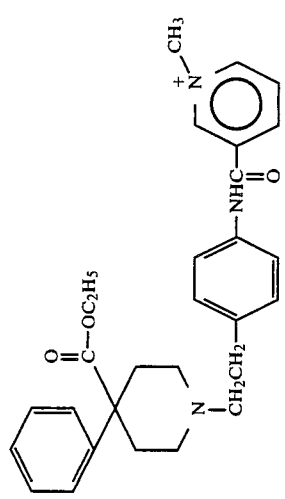 | 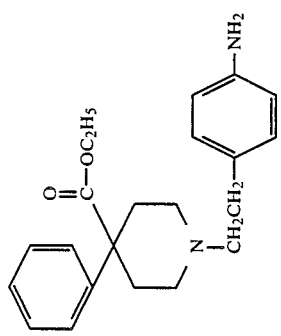 |
| protriptyline | | |
| 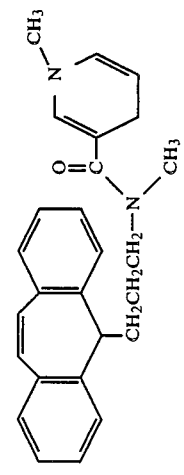 | 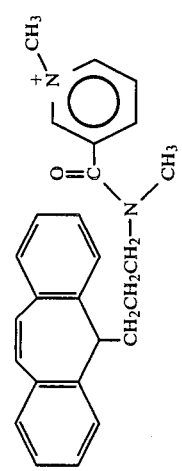 | 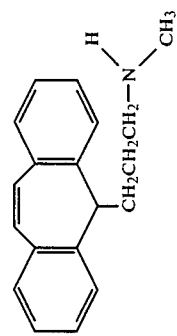 |
| daunomycin | | |

-continued

| Starting Material | [D—QC]+ | [D—DHC] |
|---|---|---|
| d-isomer | d-isomer | d-isomer |
| dextroamphetamine | | |
| l-isomer | l-isomer | l-isomer |
| levamphetamine | | |
| amphetamine | | |
| phenylethylamine | | |

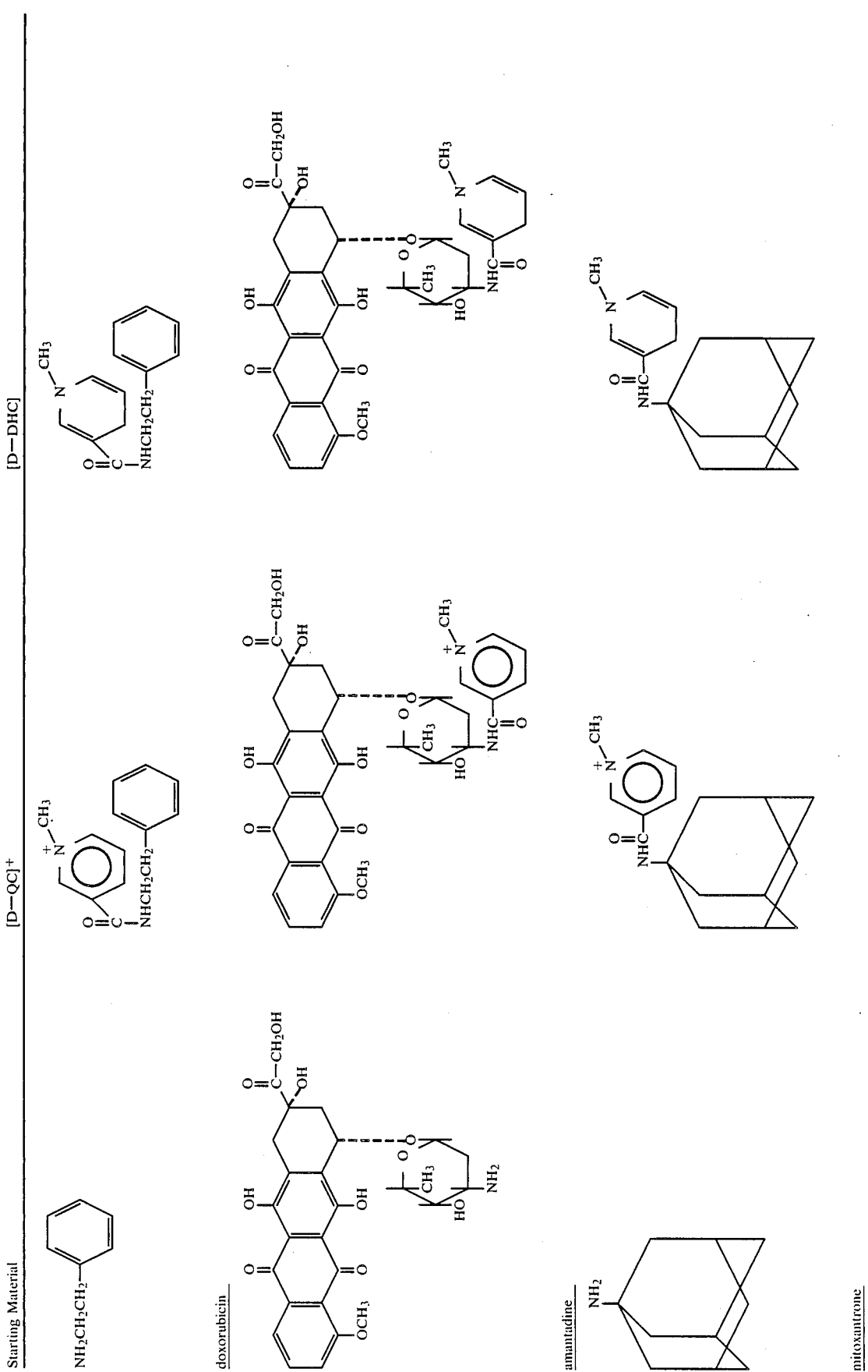

| Starting Material | [D—QC]⁺ | [D—DHC] |
|---|---|---|
| Anthraquinone with 1,4-bis(NH-CH₂CH₂-NH-CH₂CH₂-OH) and 5,8-dihydroxy substituents | Anthraquinone with 1,4-bis[NH-CH₂CH₂-N(CO-pyridinium-N⁺-CH₃)-CH₂CH₂-OH] and 5,8-dihydroxy substituents | Anthraquinone with 1,4-bis[NH-CH₂CH₂-N(CO-1-methyl-1,4-dihydropyridin-3-yl)-CH₂CH₂-OH] and 5,8-dihydroxy substituents |

Method B

This is a variation of Method A used when the drug contains a —COOH function which is to be protected.

The drug is first converted to the corresponding ethyl ester by conventional esterification techniques. That ester is then used as the starting material and Method A is repeated.

Obviously, other esters may be similarly prepared in the first step by use of other esterifying agents.

The representative drugs listed below may be derivatized in this manner to the corresponding [D-QC]+ and [D-DHC] compounds. Omega amino acids other than GABA, other natural amino acids such as glycine, aspartic acid and glutamic acid, and small peptides (2–20 amino acids) may be similarly derivatized.

The picolinamide and isonicotinamide quaternary and dihydro derivatives of the drugs specifically mentioned for derivatizing according to this Method may be similarly prepared. See Method A.

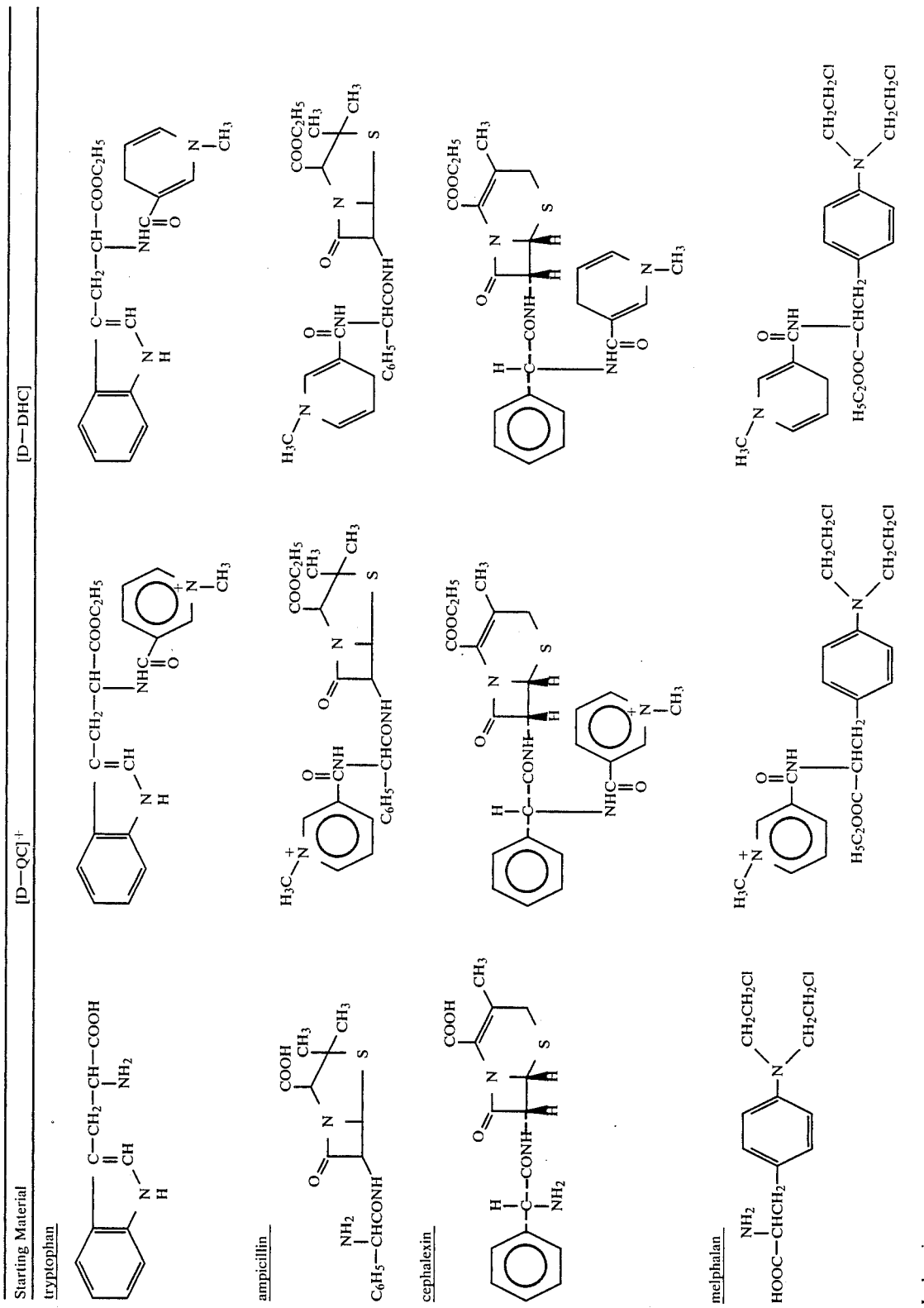

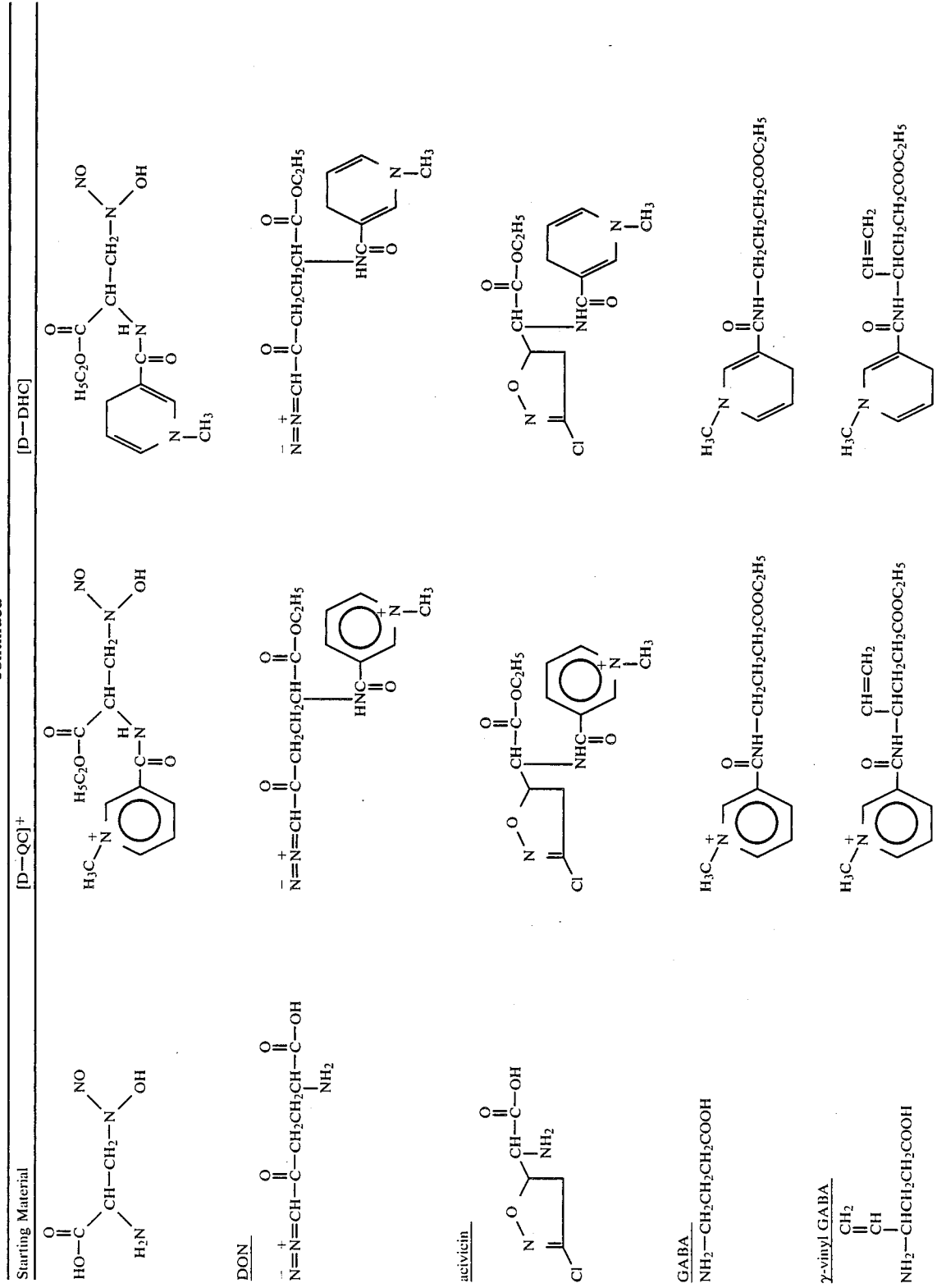

-continued
| Starting Material | [D—QC]+ | [D—DHC] |
|---|---|---|
| γ-acetylenic GABA<br>C≡CH<br>|<br>NH$_2$CHCH$_2$CH$_2$COOH | 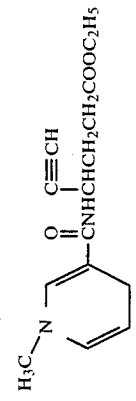 | 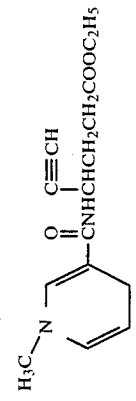 |

Method C

This is a variation of Method A used when the drug contains one or more OH functions which are to be protected.

The drug is first reacted with excess trimethylacetyl chloride to convert the hydroxy group(s) to pivalyloxy group(s). (This process is generally conducted in the presence of a base; however, strongly acid conditions are used if an amine function is present.) That protected derivative is then used as the starting material and subjected to Method A. Alternatively, the first two steps may be reversed, i.e. the drug may be first converted to the nicotinamide, which may then be reacted with trimethylacetyl chloride to form the protected nicotinamide.

Various other hydroxy protecting groups may be introduced in similar fashion.

The representative drugs listed below may be derivatized in this manner to the corresponding [D-QC]+ and [D-DHC] compounds. The corresponding picolinamide and isonicotinamide quaternary and dihydro derivatives may be similarly prepared. See Method A.

| Starting Material | [D—QC]⁺ | [D—DHC] |
|---|---|---|
| serotonin 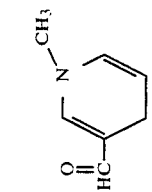 | 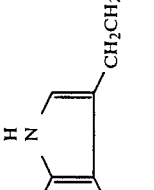 | 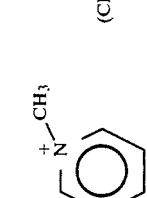 |
| norepinephrine 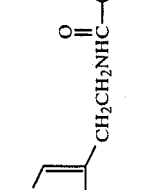 | | |
| epinephrine  | | |
| dopamine 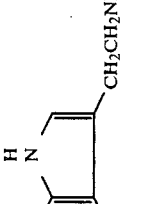 |  | 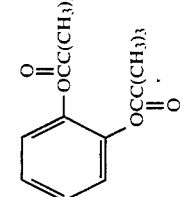 |
| tyramine | | |

| Starting Material | [D—QC]+ | [D—DHC] |
|---|---|---|
| (4-hydroxybenzyl)amine (NH₂CH₂–C₆H₄–OH) | H₃C–N⁺(pyridinium)–C(=O)NHCH₂–C₆H₄–OC(=O)C(CH₃)₃ | H₃C–N(dihydropyridine)–C(=O)NHCH₂–C₆H₄–OC(=O)C(CH₃)₃ |
| phenylephrine: HO–C₆H₄–CH(OH)CH₂NHCH₃ | (CH₃)₃CCO–O–C₆H₄–CH(OH)–CH₂N(CH₃)–C(=O)–(N-methylpyridinium) | (CH₃)₃CCO–O–C₆H₄–CH(OH)–CH₂N(CH₃)–C(=O)–(N-methyl-dihydropyridine) |

Method D

This variation of Method A can be used when the drug contains one or more OH and COOH functions which are to be protected. The protecting groups, typically the ethyl ester and pivalyloxy groups, are introduced as described in Methods B and C, in the sequence considered most convenient. The amine function is derivatized according to Method A.

The representative drugs listed below may be derivatized in this manner to the corresponding [D-QC]+ and [D-DHC] compounds. The corresponding picolinamide and isonicotinamide quaternary and dihydro derivatives may be similarly prepared. See Method A.

in the presence of a suitable dehydrating agent, or with nicotinoyl chloride or nicotinic anhydride, to form the corresponding nicotinic acid ester of the partial formula

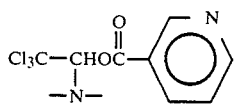

The resultant intermediate is then quaternized and reduced as in Method A.

The representative starting drugs listed below may be derivatized in this manner to the corresponding

| Starting Material | [D—QC]+ | [D—DHC] |
|---|---|---|
| methyldopa | | |

[Structures for methyldopa and levodopa and their [D-QC]+ and [D-DHC] derivatives shown in table]

Method E

This method is of particular use when the —NH— function is a part of an amide or imide or a very low pKa primary or secondary amine.

The drug is first reacted with an aldehyde [e.g. formaldehyde, benzaldehyde, acetaldehyde or chloral (Cl₃CCHO)]; for example, in the case of chloral, one converts the —NH— function to a

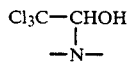

function and thus forms a suitable bridging group. The resultant compound is then reacted with nicotinic acid

[D-QC]+ and [D-DHC] compounds. Aminoglutethimide, phenytoin, butalbital, methylphenidate, 3-deazaguanine, PCNU, spiromustine, L-ICRF, demeclocycline, minocycline, doxycycline, oxytetracycline, ethyl β-carboline 3-carboxylate and nifedipine may be similarly derivatized.

The foregoing procedure may be repeated using picolinic acid or its acid chloride or anhydride, or isonicotinic acid or its acid chloride or anhydride, in place of nicotinic acid or its acid chloride or anhydride, respectively, to convert drugs such as those specifically mentioned for derivatizing according to this Method to the corresponding picolinic acid esters and isonicotinic acid esters and then to the corresponding [D-QC]+ and [D-DHC] compounds.

| Starting Material | [D-QC]+ | [D-DHC] |
|---|---|---|
| cyclophosphamide | | |
| ethotoin | | |
| phenobarbital | | |
| chlortetracycline | | |
| glutethimide | | |

-continued

| Starting Material | [D-QC]⁺ | [D-DHC] |
|---|---|---|

(chemical structures for three starting materials and their [D-QC]⁺ and [D-DHC] derivatives)

uracil mustard bemegride

Method F

Method A is followed, except that in the first step, the drug is reacted with 3-quinolinecarboxylic acid or its acid chloride or anhydride instead of nicotinic acid or its acid chloride.

The representative drugs listed below may be derivatized in this manner to the corresponding [D-QC]+ and [D-DHC] compounds, as may the remaining drugs listed with Method A.

Similarly, Method F may be combined with Methods B, C or D to afford the corresponding N-methyl-3-quinolinecarboxamide derivatives, e.g. of the drugs listed with those methods.

The foregoing procedure can be repeated using 4-isoquinolinecarboxylic acid or its acid chloride or anhydride in place of 3-quinolinecarboxylic acid or its acid chloride or anhydride to convert drugs such as those mentioned with Methods A, B, C or D to the corresponding N-methyl-4-isoquinolinecarboxamide derivatives.

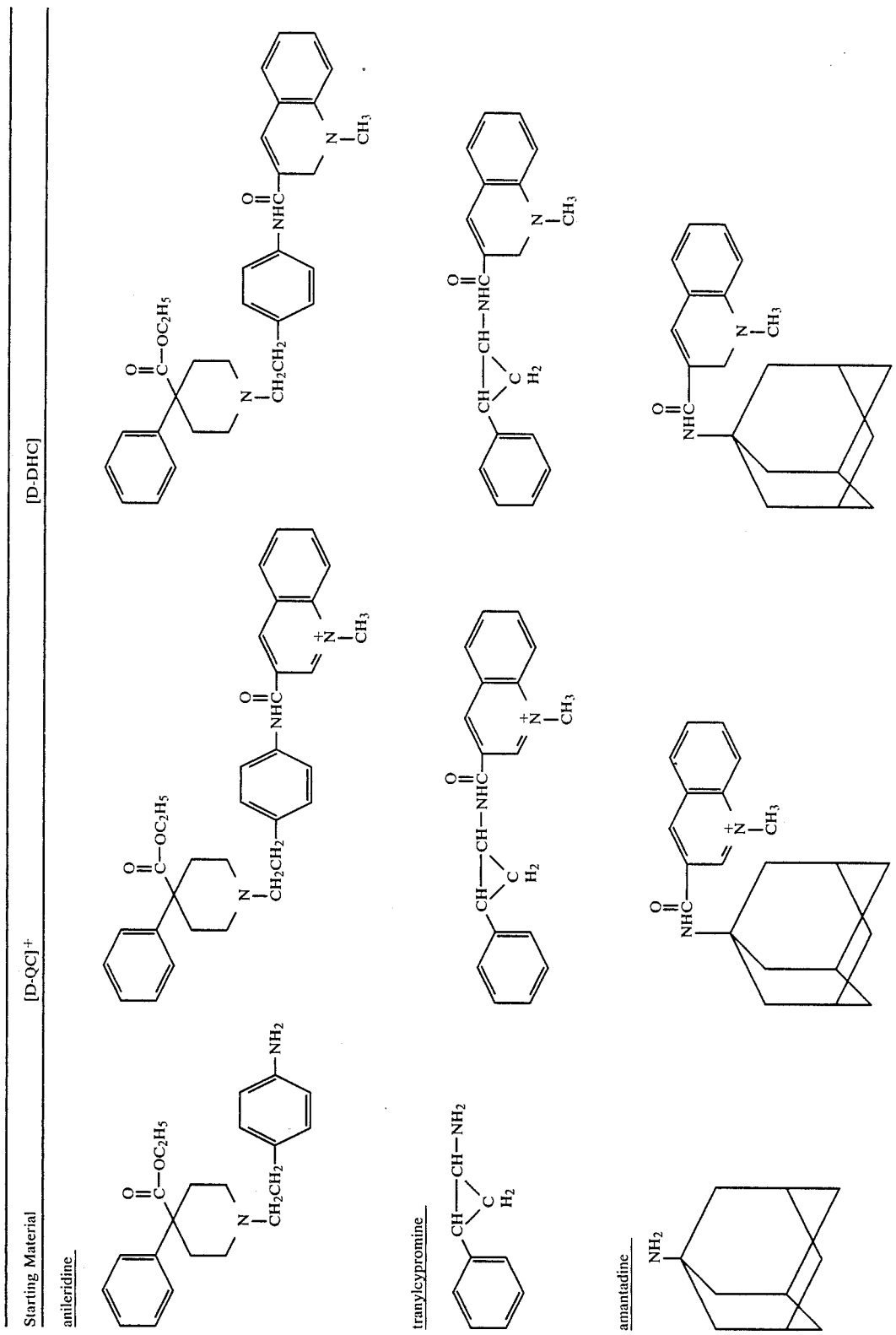

| Starting Material | [D-QC]⁺ | [D-DHC] |
|---|---|---|
| phenylethylamine | | |
| hydralazine | | |
| dextroamphetamine d-isomer | | d-isomer |
| levamphetamine | | |

-continued
| Starting Material | [D-QC]+ | [D-DHC] |
|---|---|---|
| 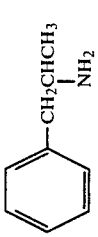 l-isomer | 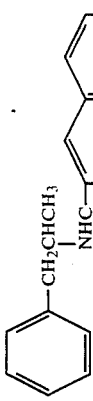 l-isomer | 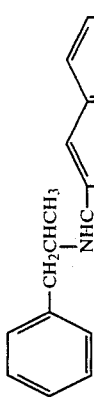 l-isomer |
| phentermine 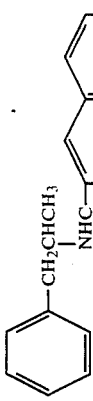 | 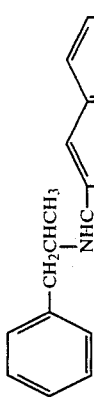 |  |

Method G

Method A is followed, except that in the first step, a starting material of the formula

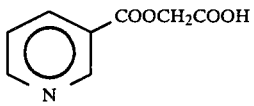

is used in place of nicotinic acid. (That starting material may be prepared by reacting nicotinic anhydride, nicotinoyl chloride or nicotinic acid with glycolic acid.)

The representative drugs listed below may be derivatized in this manner to the corresponding [D-QC]+ and [D-DHC] compounds, as may the remaining drugs listed with Method A.

Similarly, Method G may be combined with Methods B, C or D to afford the corresponding derivatives, e.g. of the drugs listed with those methods.

The foregoing procedure can be repeated using picolinic acid or its acid chloride or anhydride, or isonicotinic acid or its acid chloride or anhydride, in place of nicotinic acid or its acid chloride or anhydride, respectively, in the preparation of the starting material. This variation affords a starting material of the formula

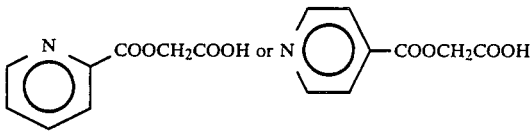

which can then be used in place of nicotinic acid to prepare derivatives of drugs such as those listed with Methods A, B, C or D.

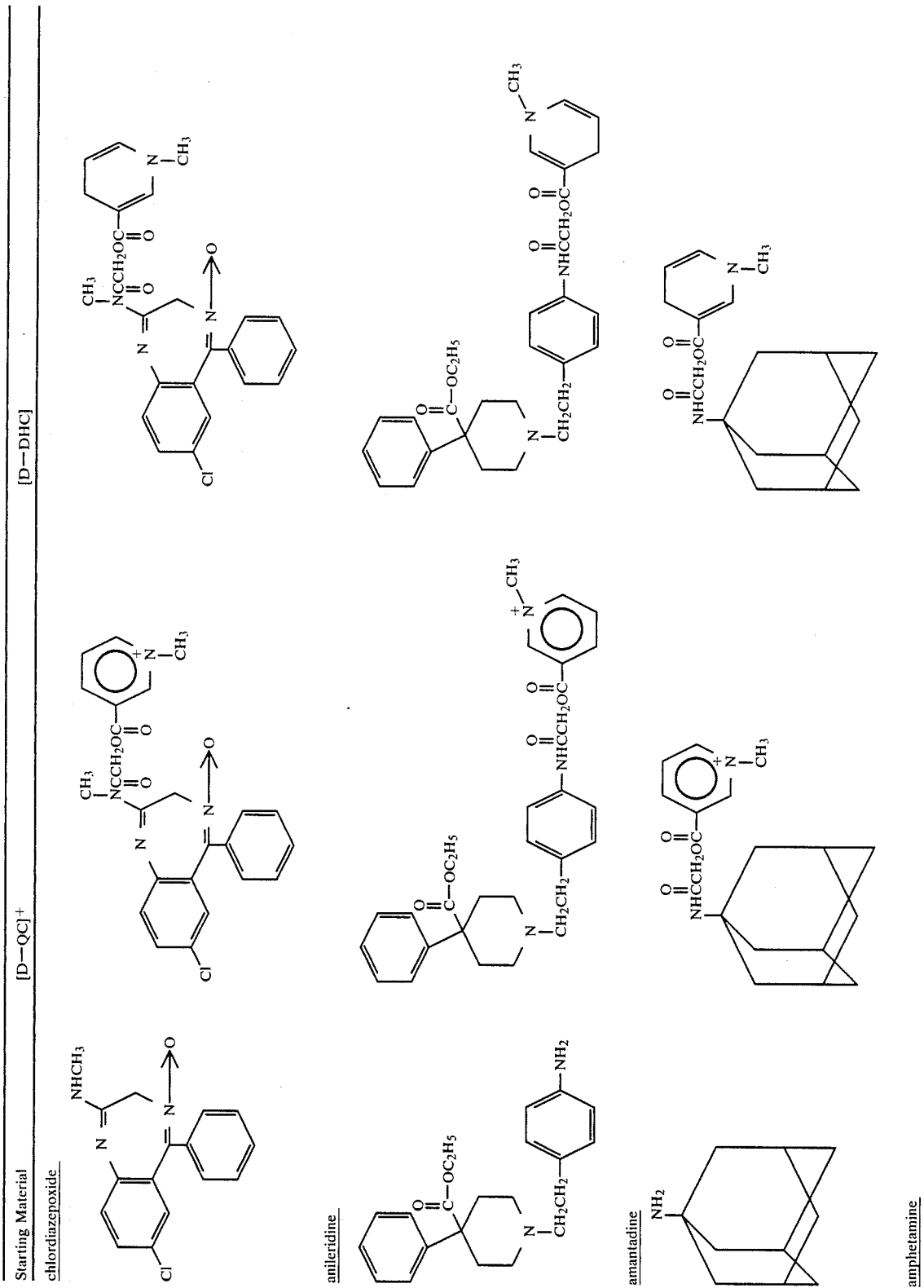

| Starting Material | [D—QC]+ | [D—DHC] |
|---|---|---|
| Ph-CH₂CH(NH₂)CH₃ | Ph-CH₂CH(CH₃)NHC(O)OCH₂-[N-methylpyridinium-3-carbonyl] | Ph-CH₂CH(CH₃)NHC(O)OCH₂-[1-methyl-1,4-dihydropyridine-3-carbonyl] |

Method H

Method A is followed, except that in the first step, a starting material of the formula

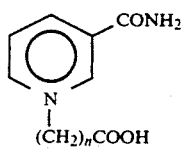

wherein n=1–3, preferably 2, is used in place of nicotinic acid. (That starting material may be prepared from nicotinamide, e.g. when n=2, by reacting 3-iodopropionic acid with nicotinamide.)

The drugs listed below may be derivatized in this manner to the corresponding [D-QC]+ and [D-DHC] compounds, as may the remaining drugs listed with Method A.

Similarly, Method H may be combined with Methods B, C or D to afford the corresponding derivatives, e.g. of the drugs listed with those methods.

The foregoing procedure can be repeated using picolinamide or isonicotinamide in place of nicotinamide in the preparation of the starting material. This variation affords a starting material of the formula

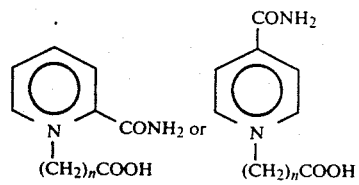

which can then be used in place of nicotinic acid in Methods A, B, C or D to form the corresponding derivatives of drugs such as those listed with those methods.

| Starting Material | [D—QC]+ | [D—DHC] |
|---|---|---|
| amphetamine | | |
| phentermine | | |
| hydralazine | | |

| Starting Material | [D—QC]+ | [D—DHC] |
|---|---|---|
| | | 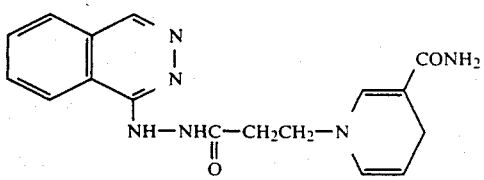 |

II. Methods for Derivatizing —OH and —SH Functions in Drugs

Method I

The drug is reacted with nicotinoyl chloride, with nicotinic anhydride, or with nicotinic acid in the presence of a suitable dehydrating agent such as dicyclohexylcarbodiimide, in an appropriate organic solvent, to afford the corresponding nicotinate. The nicotinate is then quaternized and subsequently reduced as described above in Method A. When the drug contains more than one reactive hydroxyl or thiol function, reaction conditions may be varied so that more than one hydroxyl or thiol function will be converted to nicotinate groupings.

The representative drugs listed below may be derivatized in this manner to the corresponding [D-QC]+ and [D-DHC] compounds. Ara-C, 2-deoxy-D-glucose, 2-deoxy-2-fluoro-D-mannose, 5,6-dichloro-1-β-D-ribofuranosyl benzimidizole, 5,7-dimethyl-2-β-D-ribofuranosyl-s-triazole(1,5-a)pyrimidine, bisdihydroxyvinyluridine (BDVU), pholcodeine, meptazinol, cyclazocine, phenazocine, profadol, metopon, drocode, myfadol, buprenorphine, nalbuphine, butorphanol, levallorphan, naltrexone, alazocine, oxilorphan, nalmexone, idoxuridine, dipyridamole, estriol, cortoxdoxone, fludrocortisone, paramethasone, oxogestone and tigestol may be similarly derivatized.

The foregoing procedure may be repeated using picolinic acid or its acid chloride or anhydride, or isonicotinic acid or its acid chloride or anhydride, in place of nicotinic acid or its acid chloride or anhydride, respectively, to convert drugs such as those specifically mentioned for derivatizing by this Method to the corresponding picolinic acid esters or isonicotinic acid esters and then to the corresponding [D-QC]+ and [D-DHC] compounds.

| Starting Material | [D—QC]+ | [D—DHC] |
|---|---|---|
| thiopental | | |
| testosterone | | |
| pentazocine | | |
| codeine | | |

-continued
| Starting Material | [D—QC]+ | [D—DHC] |
|---|---|---|
| naloxone 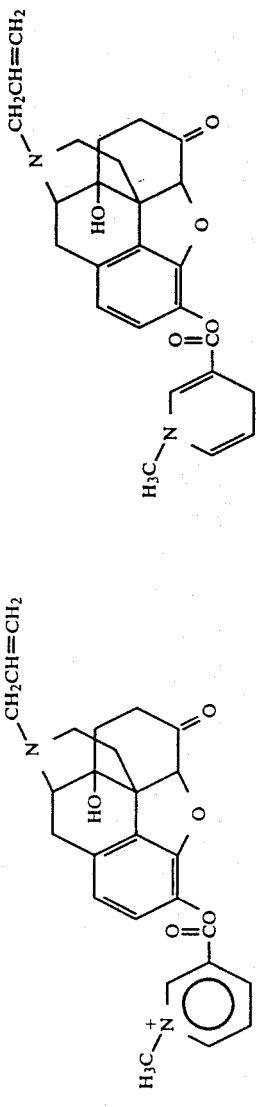 | 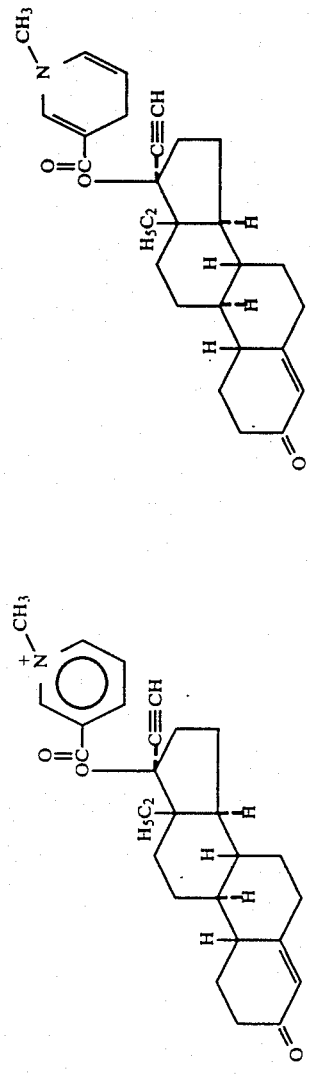 | 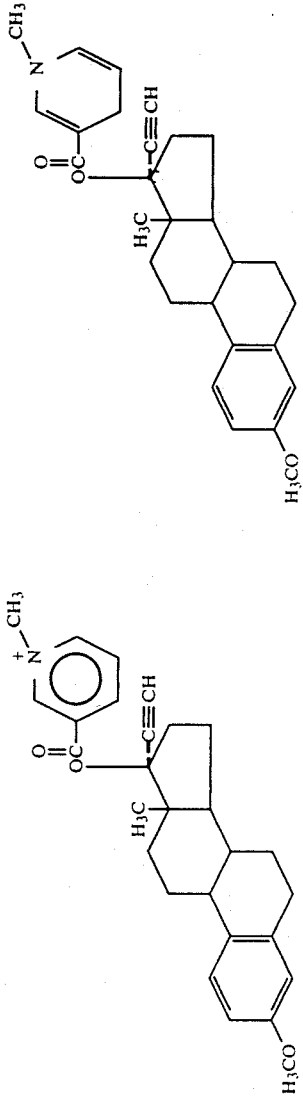 |
| norgestrel 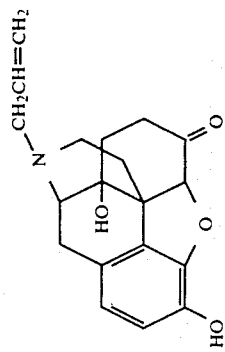 | 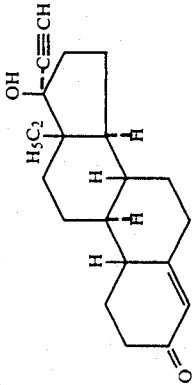 | 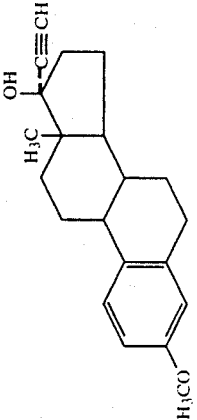 |
| mestranol | | |
| norethindrone | | |
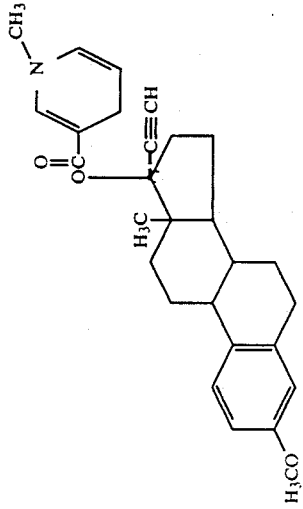

| Starting Material | [D—QC]+ | [D—DHC] |
|---|---|---|
| 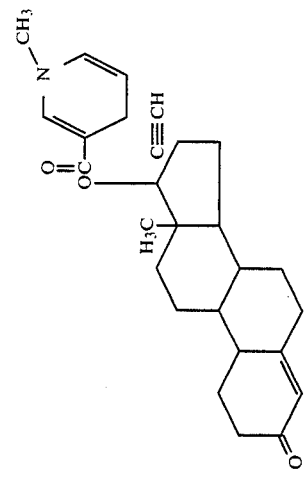 | 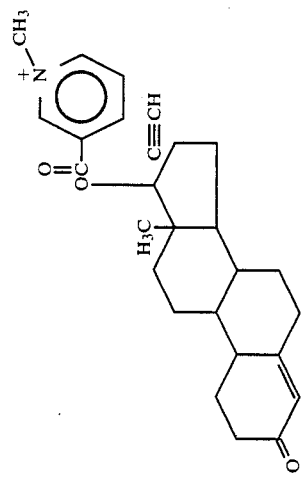 | |
| 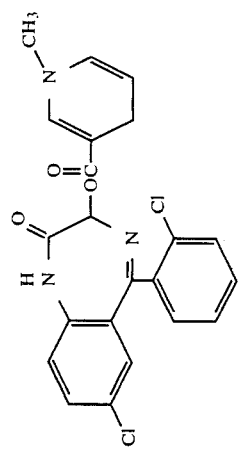 oxazepam | 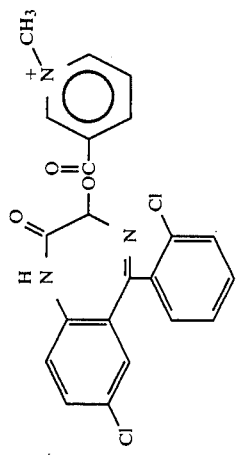 | |
| 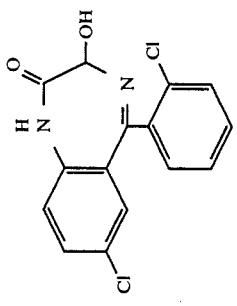 lorazepam | 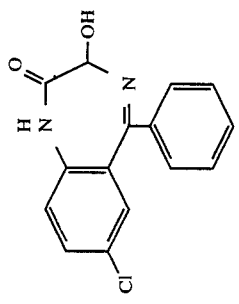 | |
| 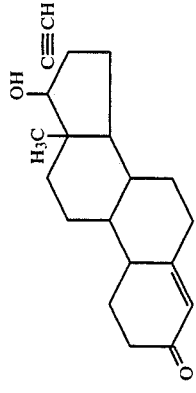 haloperidol | | |

-continued

| Starting Material | [D—QC]+ | [D—DHC] |
|---|---|---| phenytoin ethisterone oxycodone

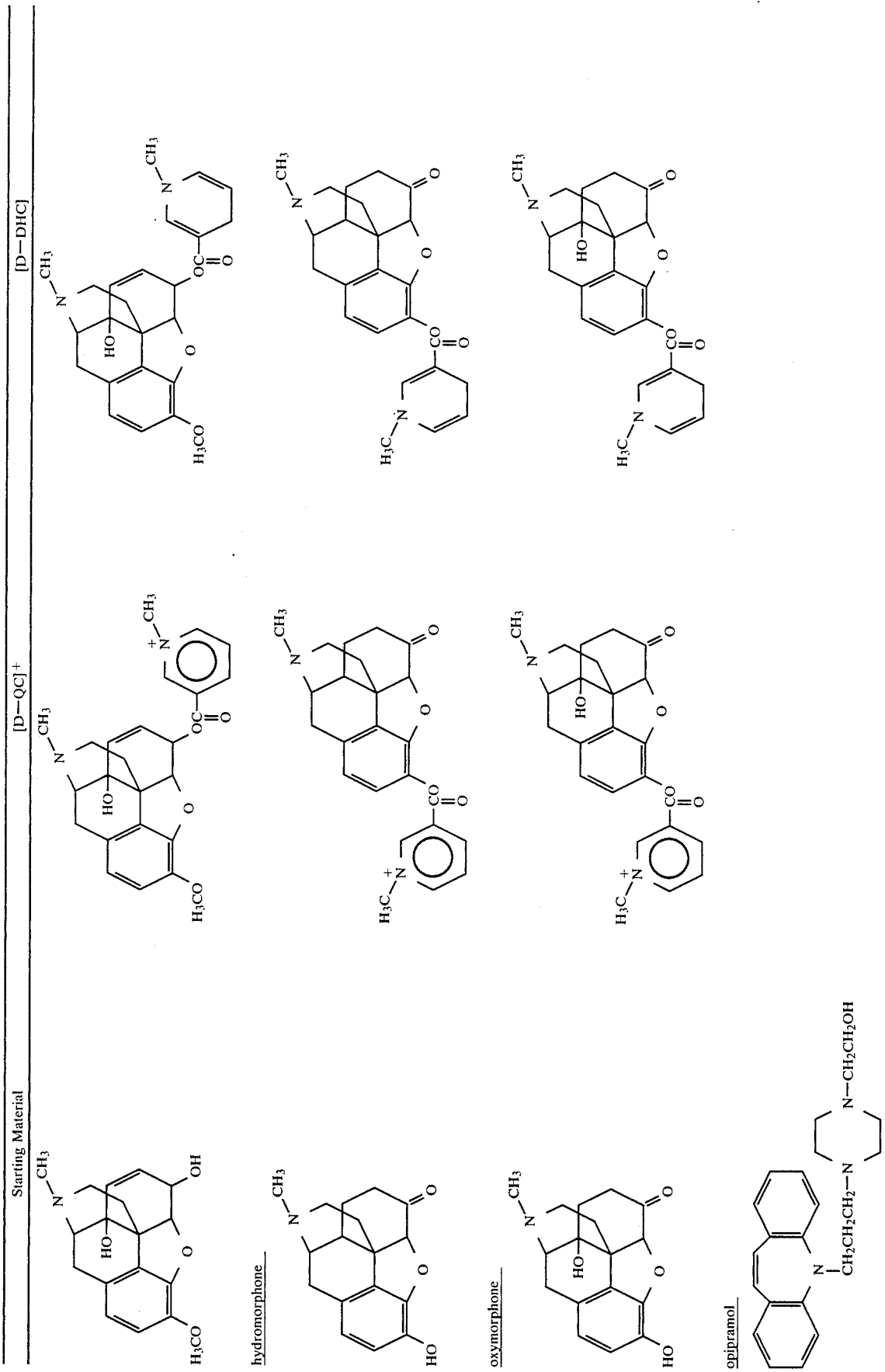

-continued
| Starting Material | [D—QC]+ | [D—DHC] |
|---|---|---|
| 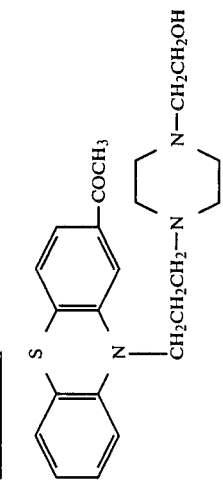 acetophenazine | 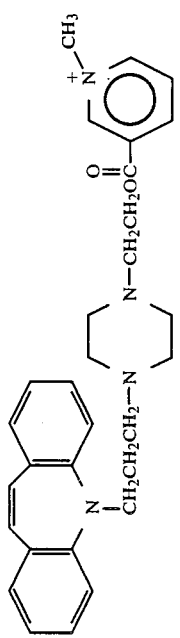 | 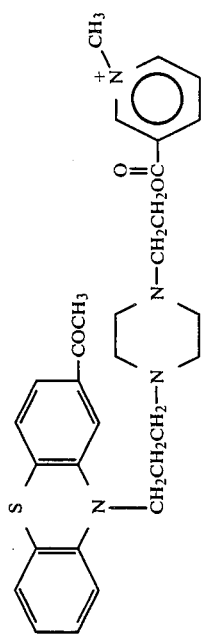 |
| | 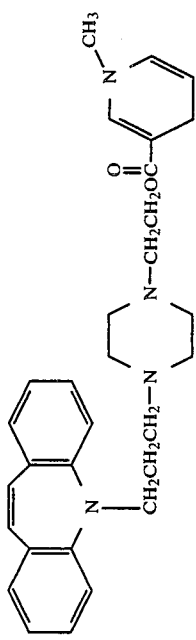 | |

| Starting Material | [D—QC]+ | [D—DHC] |
|---|---|---|

-continued
| Starting Material | [D—QC]+ | [D—DHC] |
|---|---|---|
|  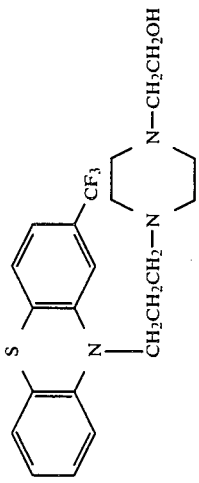 | 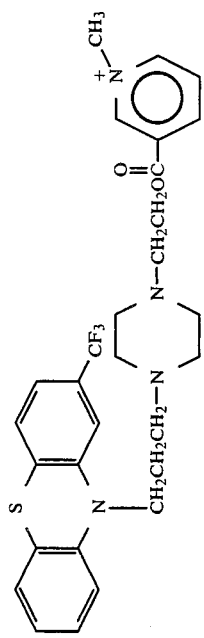 | 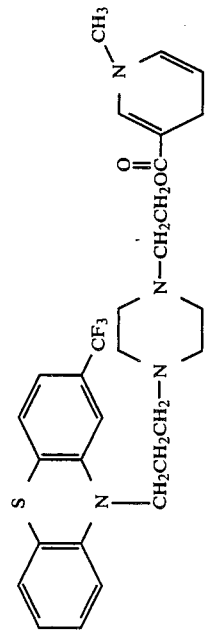 |
| | | |
| perphenazine | | |

-continued
| Starting Material | [D—QC]+ | [D—DHC] |
|---|---|---|
| 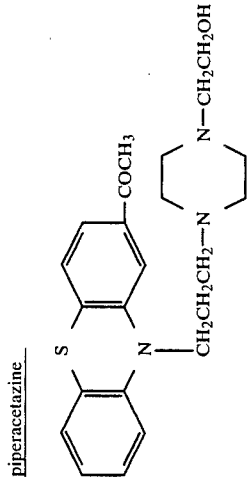 piperacetazine | 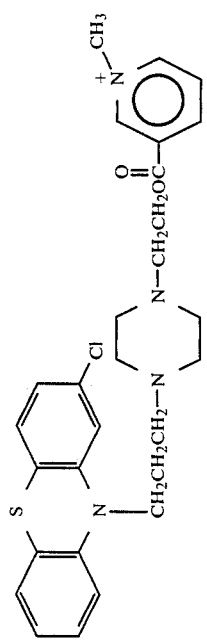 | 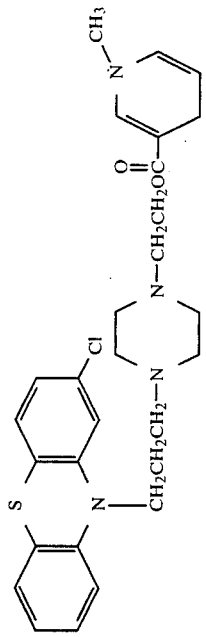 |
| | 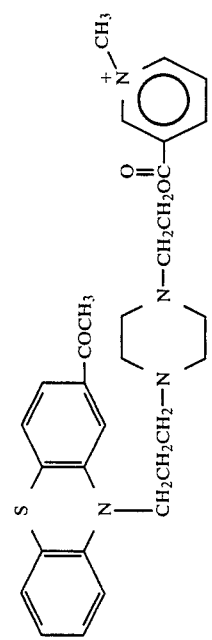 | |

-continued
| Starting Material | [D—QC]+ | [D—DHC] |
|---|---|---|
| 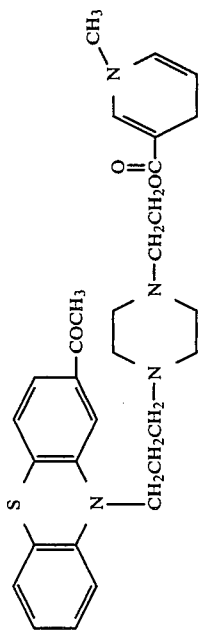 nitrazepam | 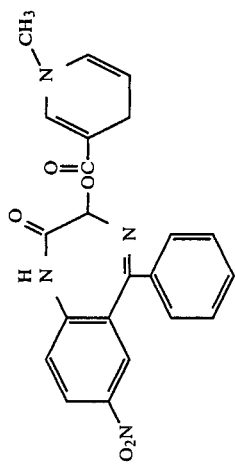 | 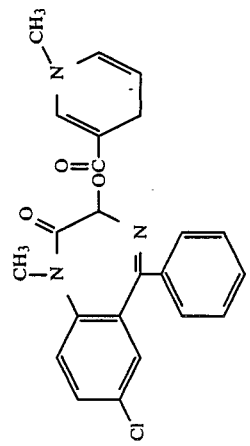 |
| 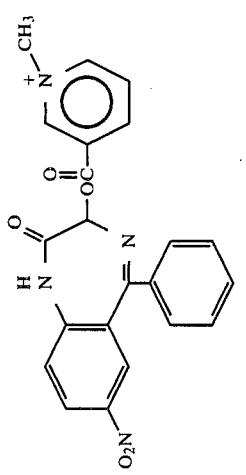 temazepam | 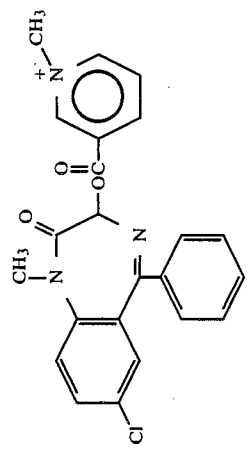 | 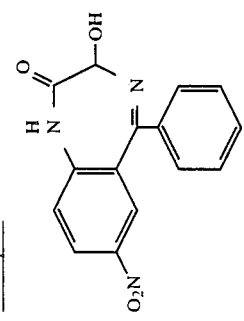 |
| 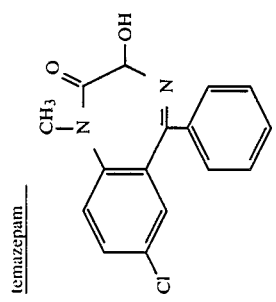 clopenthixol | | 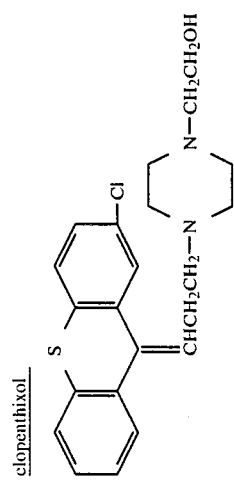 |

-continued
| Starting Material | [D—QC]+ | [D—DHC] |
|---|---|---|
| 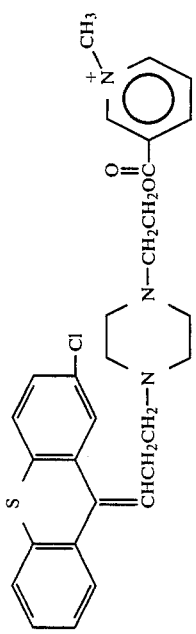 | 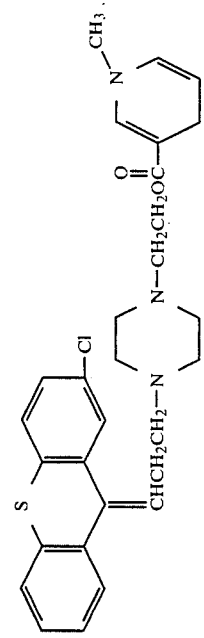 | |
| | 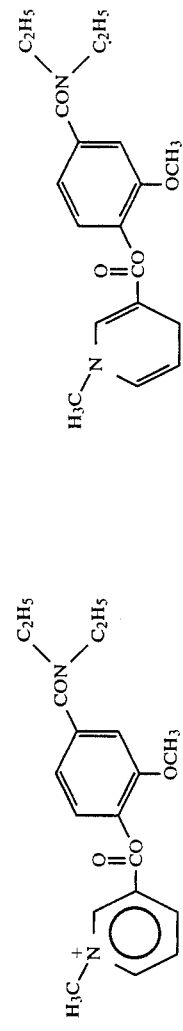 | 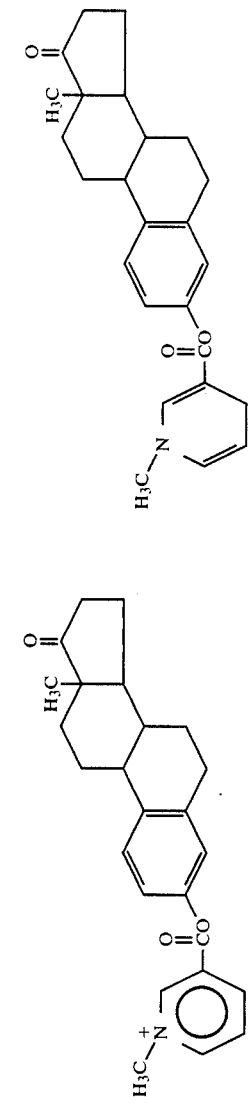 |
| ethamivan | | |
| 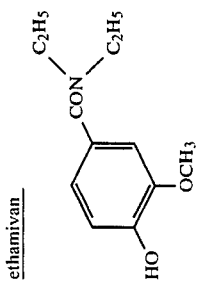 | | |
| estrone | | |
| 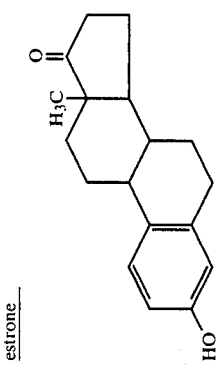 | | |

| Starting Material | [D—QC]+ | [D—DHC] |
|---|---|---|
| hydroxyzine | 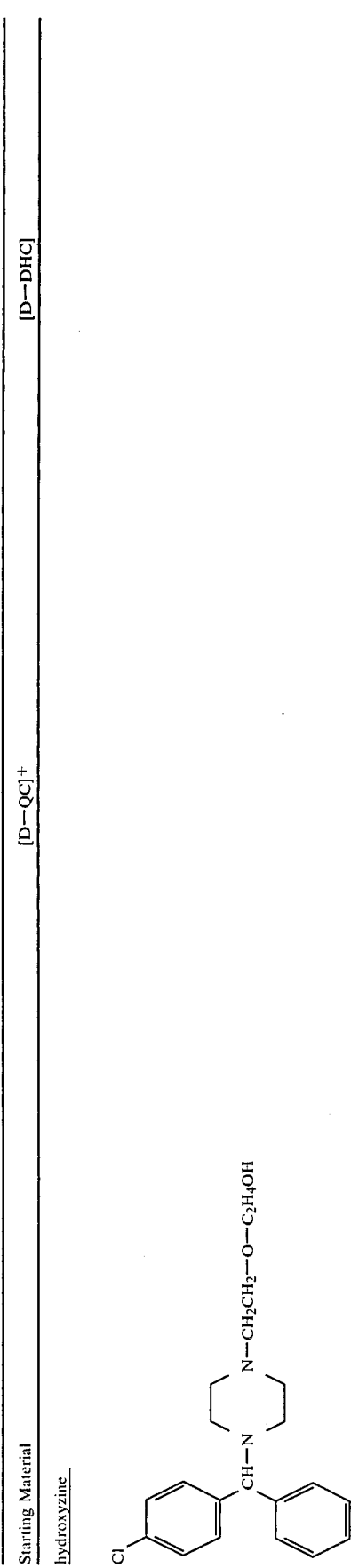 | 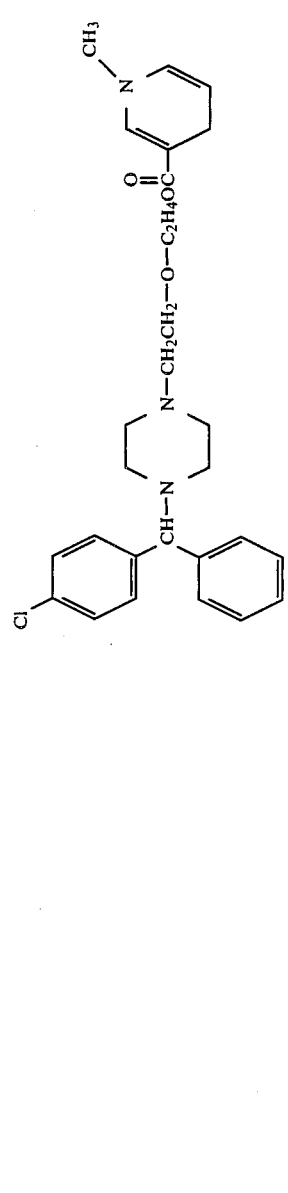 |
| apomorphine | | |

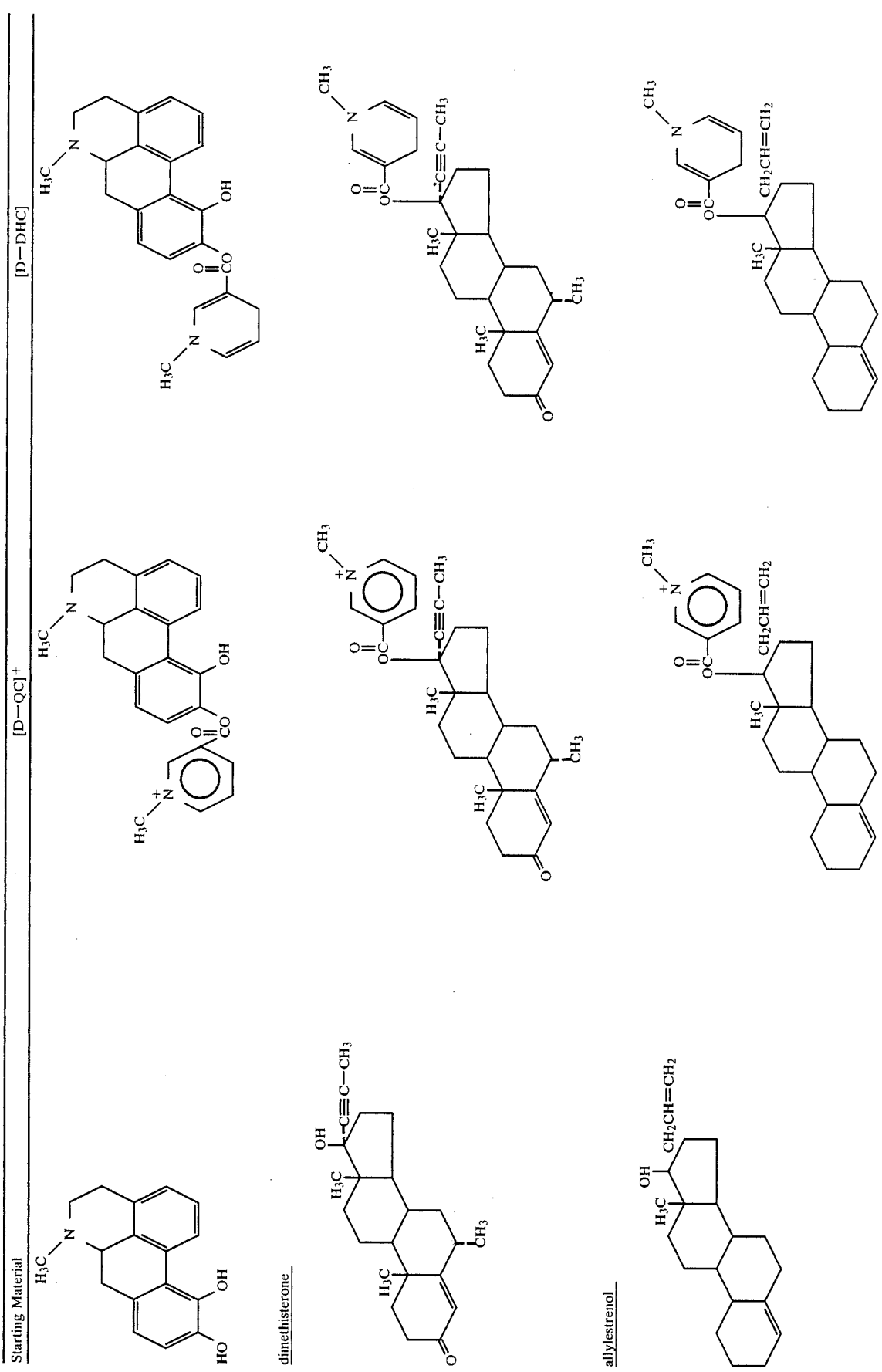

-continued
| Starting Material | [D—QC]+ | [D—DHC] |
|---|---|---|
| cingestol 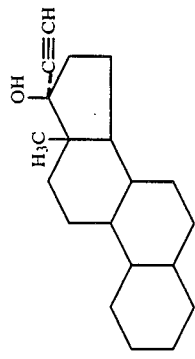 | 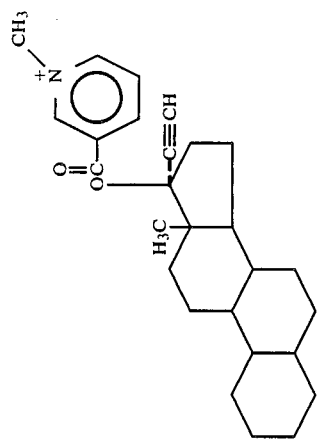 | 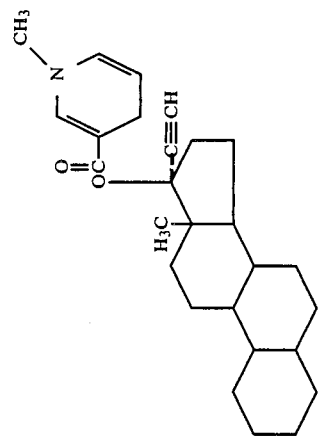 |
| ethynerone 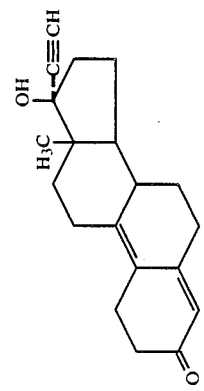 | 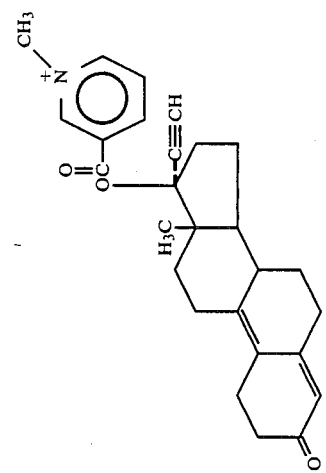 | 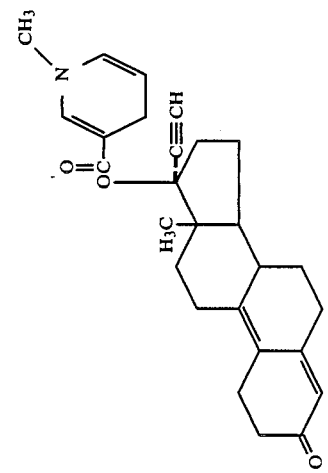 |
| lynestrenol | | |

-continued
| Starting Material | [D—QC]+ | [D—DHC] |
|---|---|---|
| 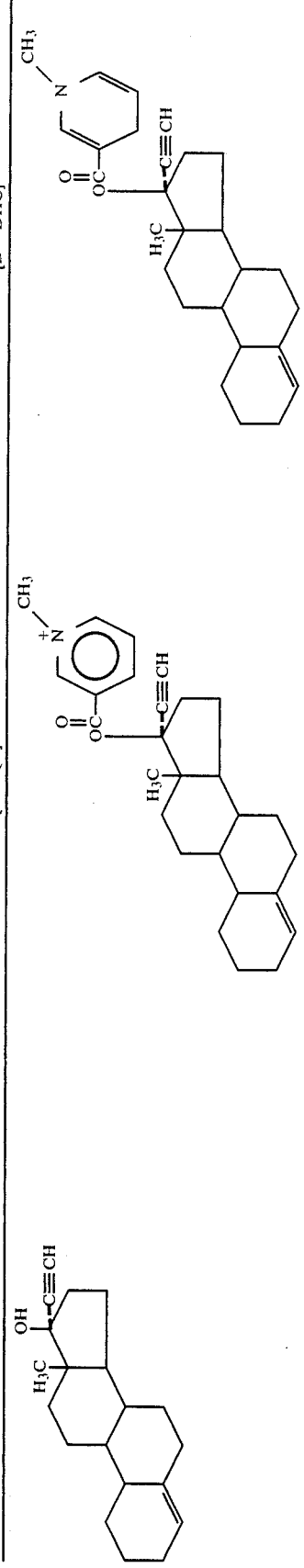 | | |
| norgesterone | 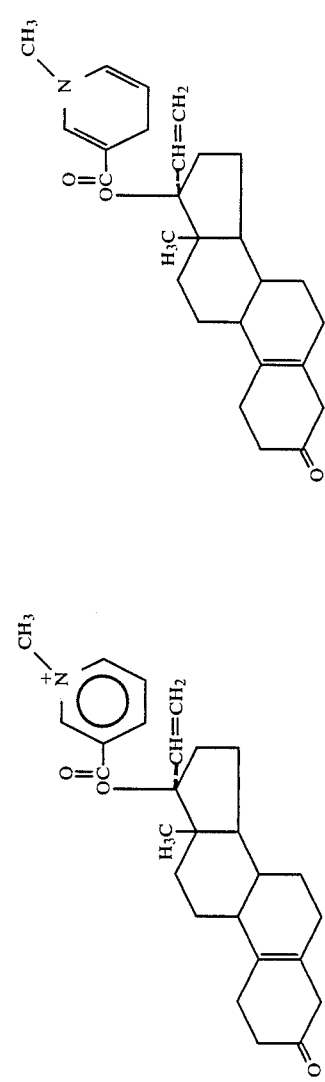 | |
| norvinisterone | 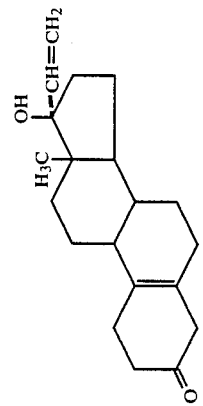 | 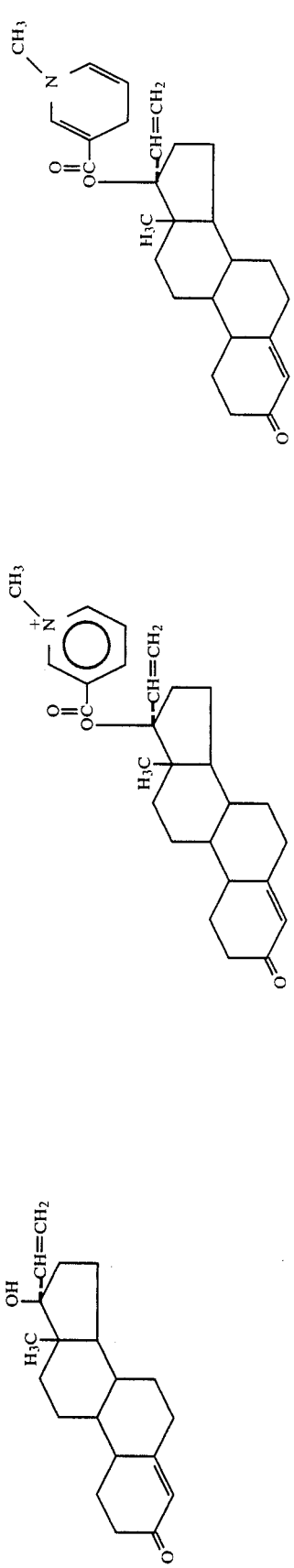 |

-continued
| Starting Material | [D—QC]⁺ | [D—DHC] |
|---|---|---|
| quinestrol 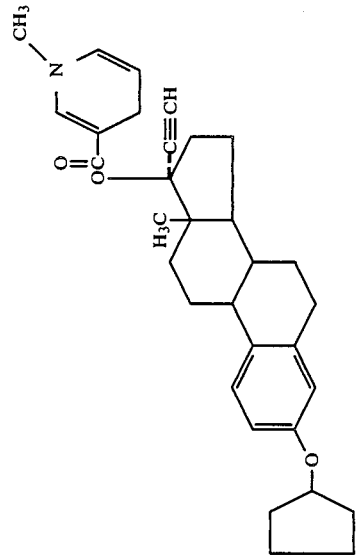 | 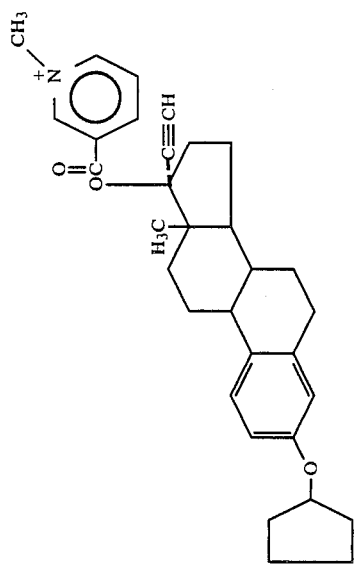 | 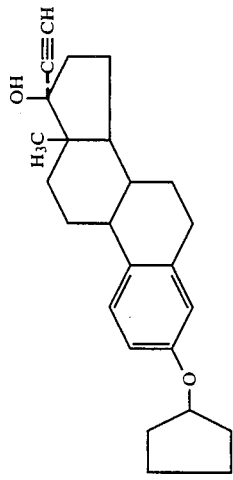 |
| thioguanine 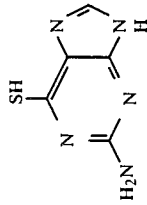 | 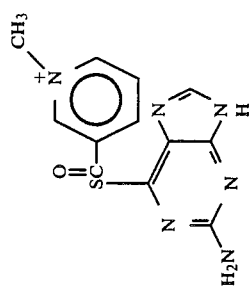 | 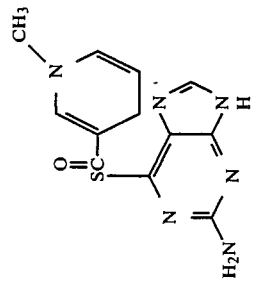 |
| hydroxyurea NH₂—CO—NHOH | 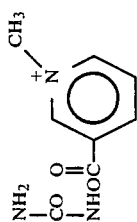 | 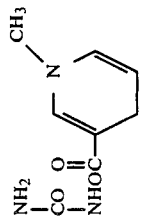 |
| cortisone | | |

| Starting Material | [D—QC]+ | [D—DHC] |
|---|---|---|
| 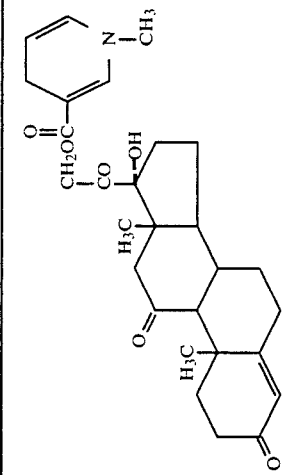 hydrocortisone | 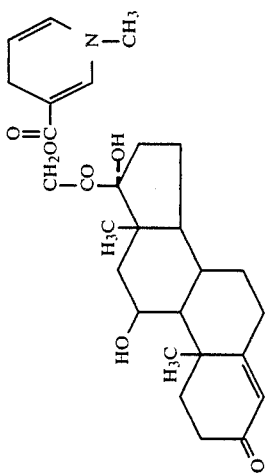 | 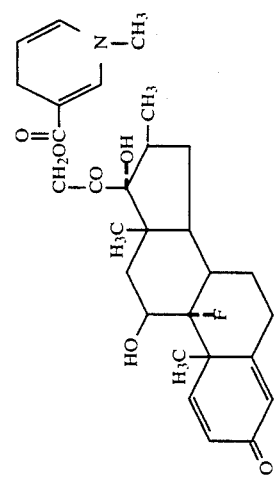 |
| 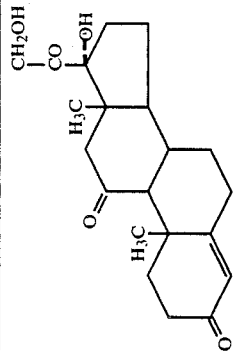 betamethasone | | 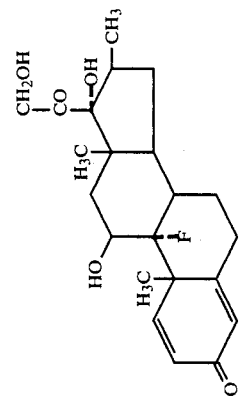 |
| dexamethasone | | |

-continued
| Starting Material | [D—QC]+ | [D—DHC] |
|---|---|---|
| 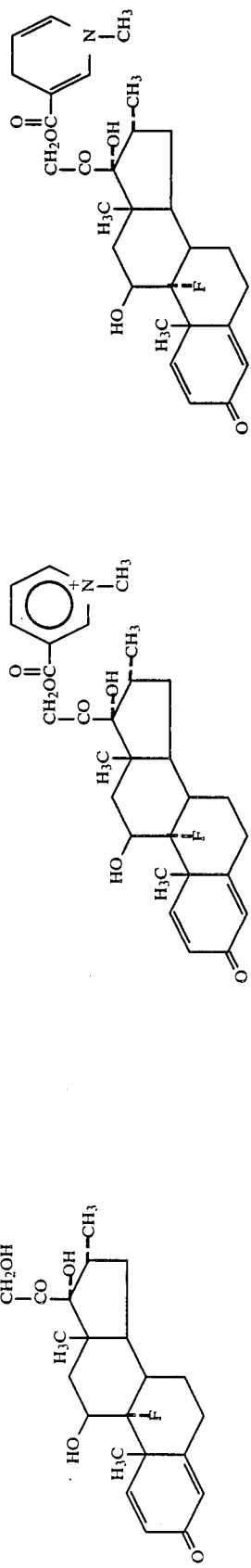 flumethasone fluprednisolone methyl prednisolone | 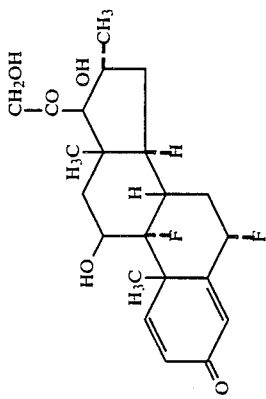 | 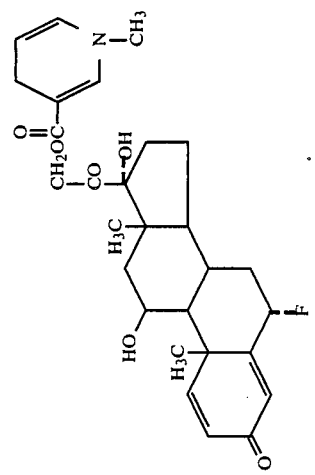 |

| Starting Material | [D—QC]+ | [D—DHC] |
|---|---|---|
| 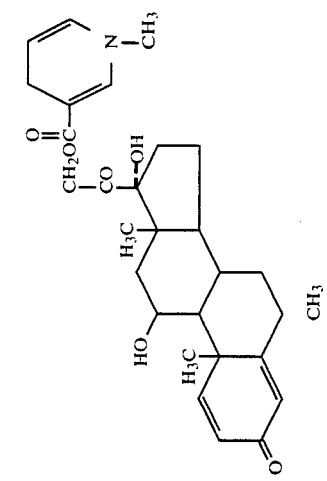 meprednisone | 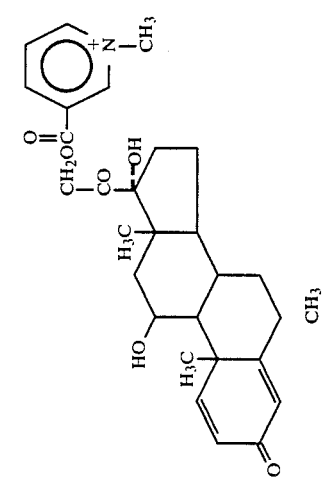 | 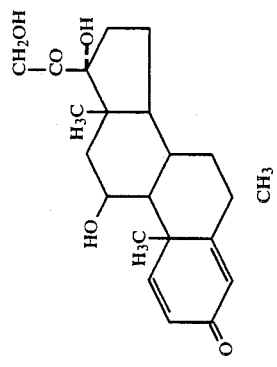 |
| 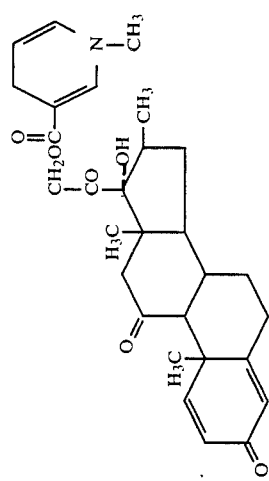 prednisolone | 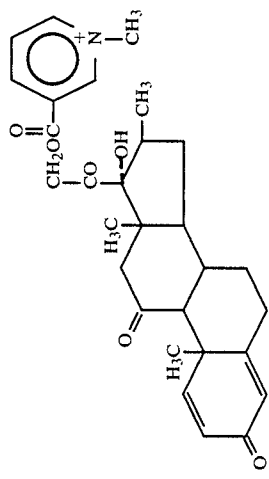 | 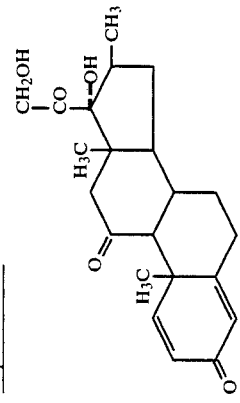 |
| 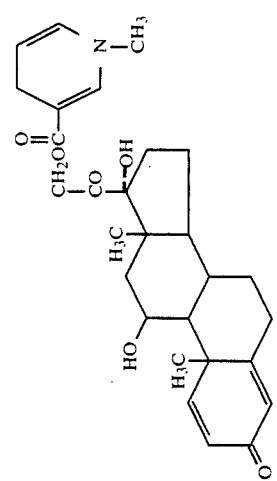 prednisone | 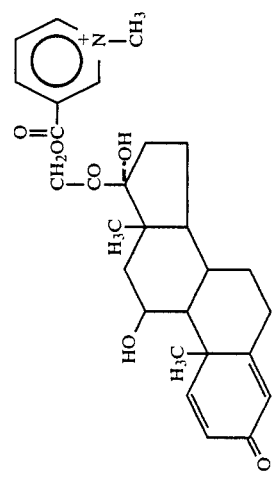 | 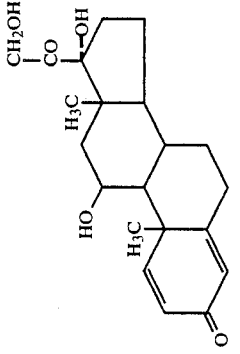 |

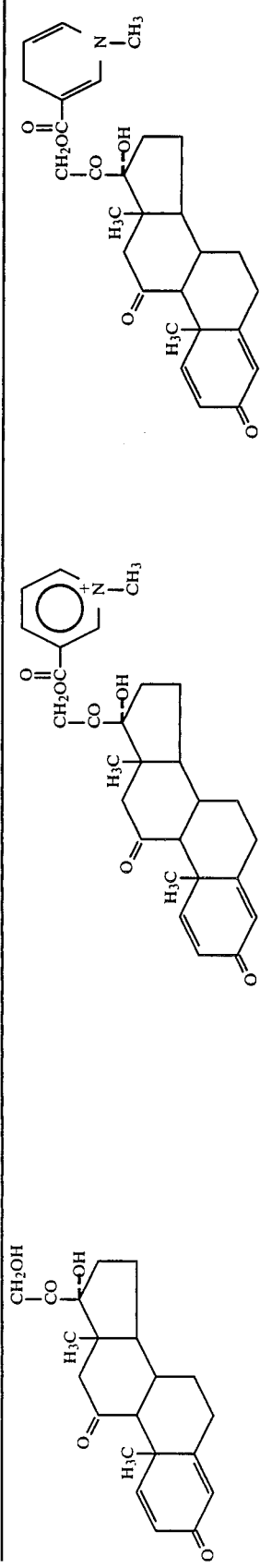

| Starting Material | [D—QC]+ | [D—DHC] |
|---|---|---|
| methyl testosterone 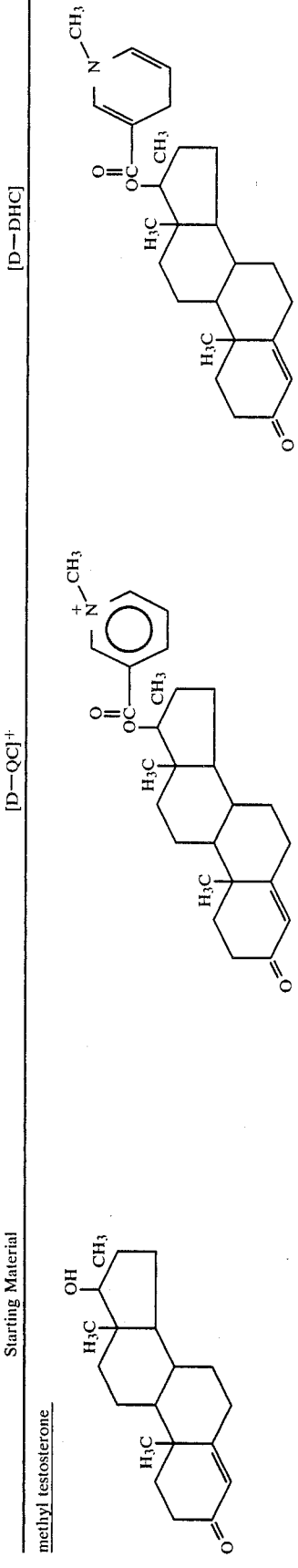 | | |
| levorphanol 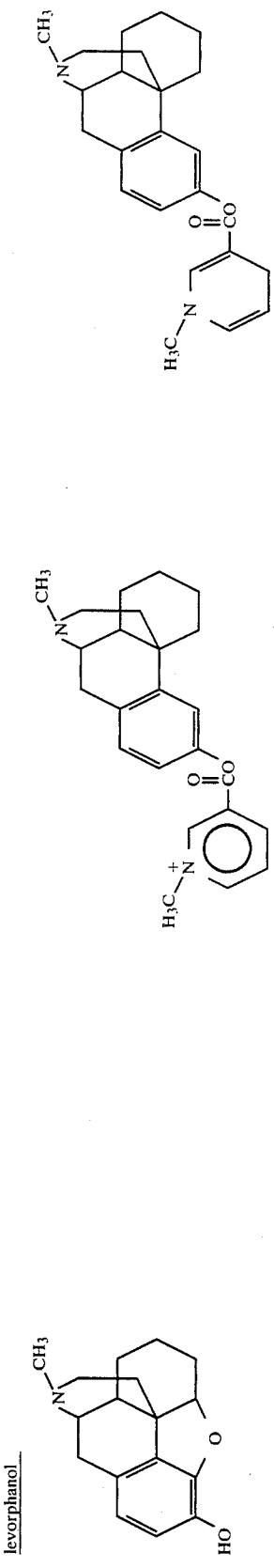 | | |
| bisbenzimidazole 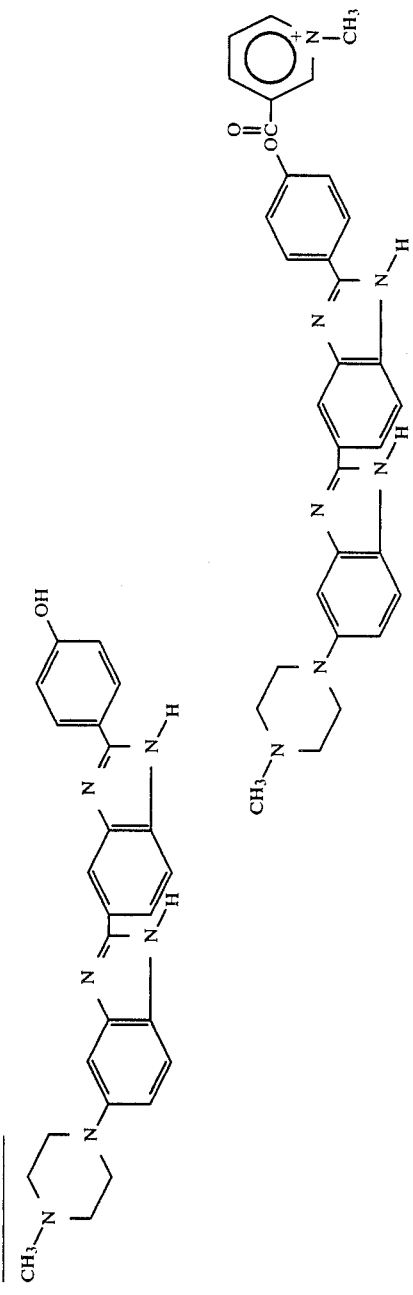 | | |

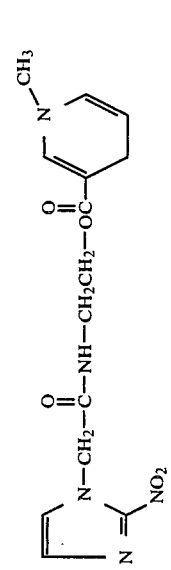

-continued

| Starting Material | [D—QC]+ | [D—DHC] |
|---|---|---|

6-mercaptopurine anti-6-[[(hydroxyimino)-
phenyl]methyl]-1-
[(1-methylethyl)sulfonyl]-
1H—benzimidazol-2-amino morphine

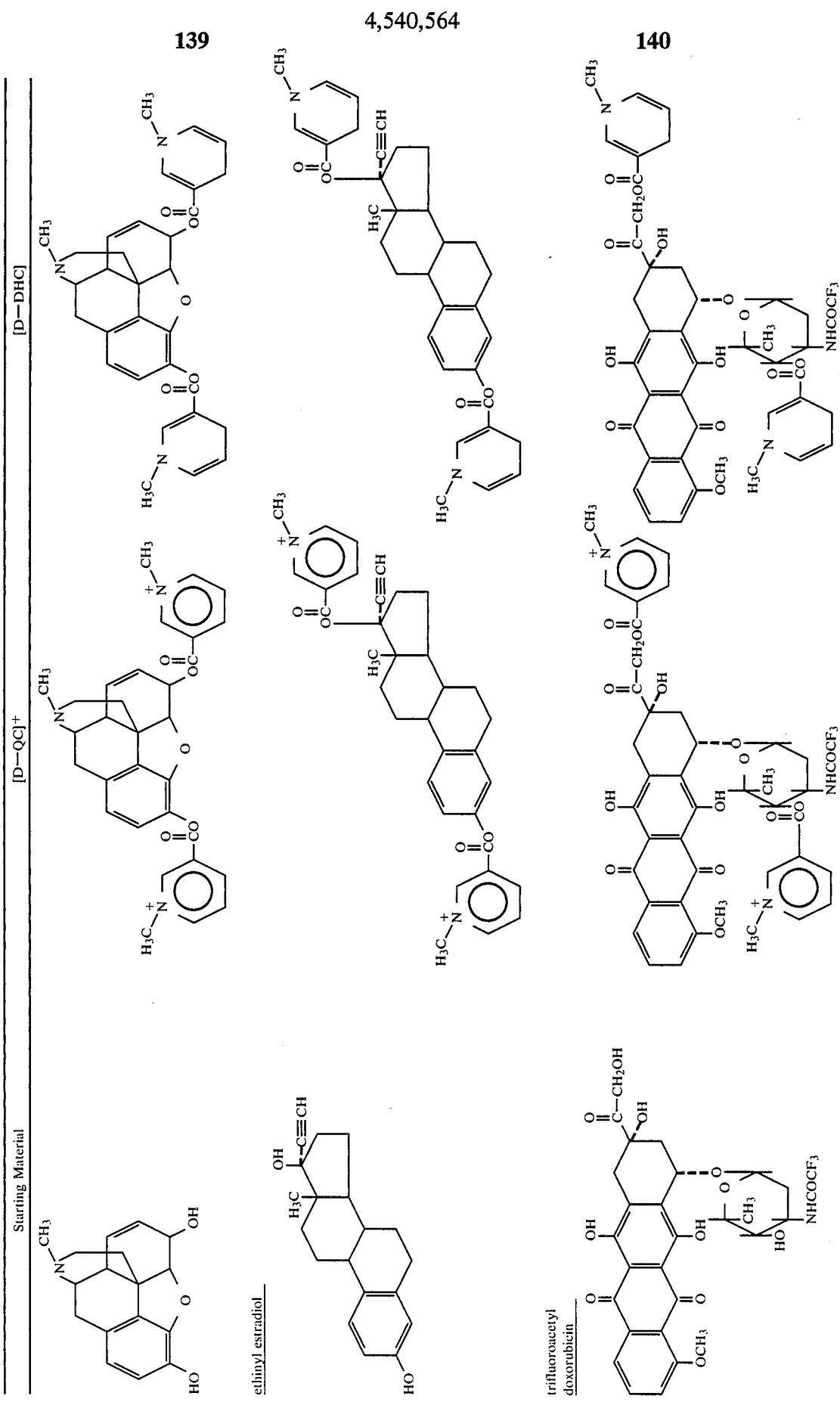

-continued
| Starting Material | [D—QC]+ | [D—DHC] |
|---|---|---|
| estradiol 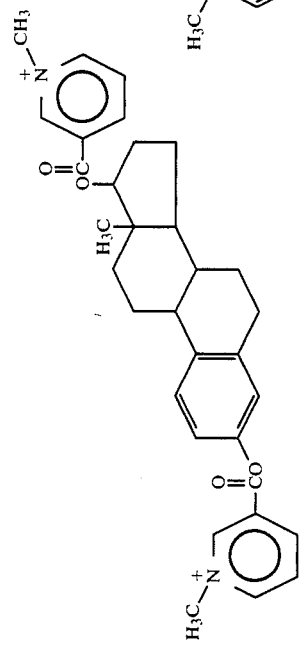 | 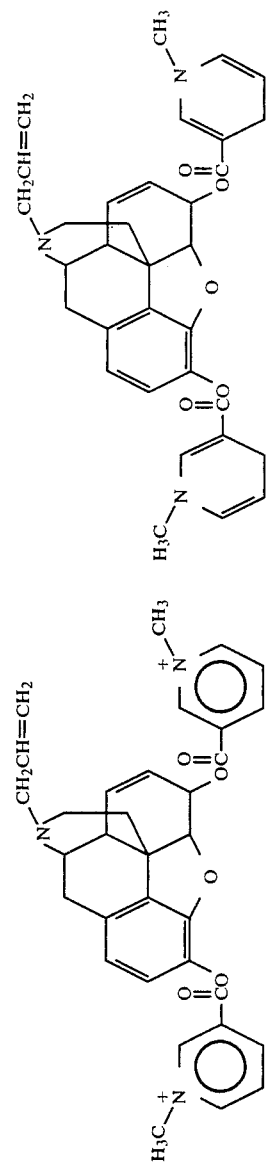 | |
| nalorphine 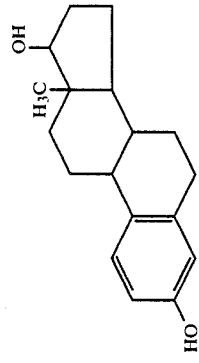 | 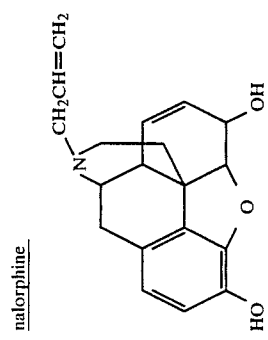 | |
| iopydol 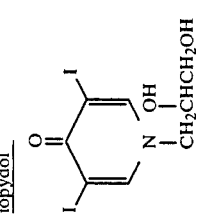 | 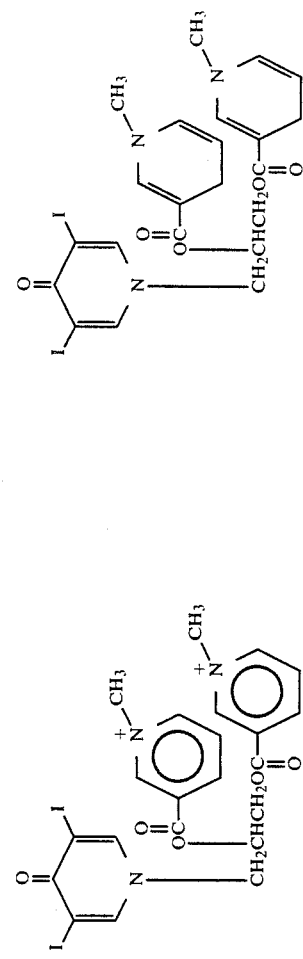 | |
| clindamycin | | |

-continued

| Starting Material | [D—QC]+ | [D—DHC] |
|---|---|---|
| lincomycin | | |
| triamcinolone | | |
| etoposide | | |

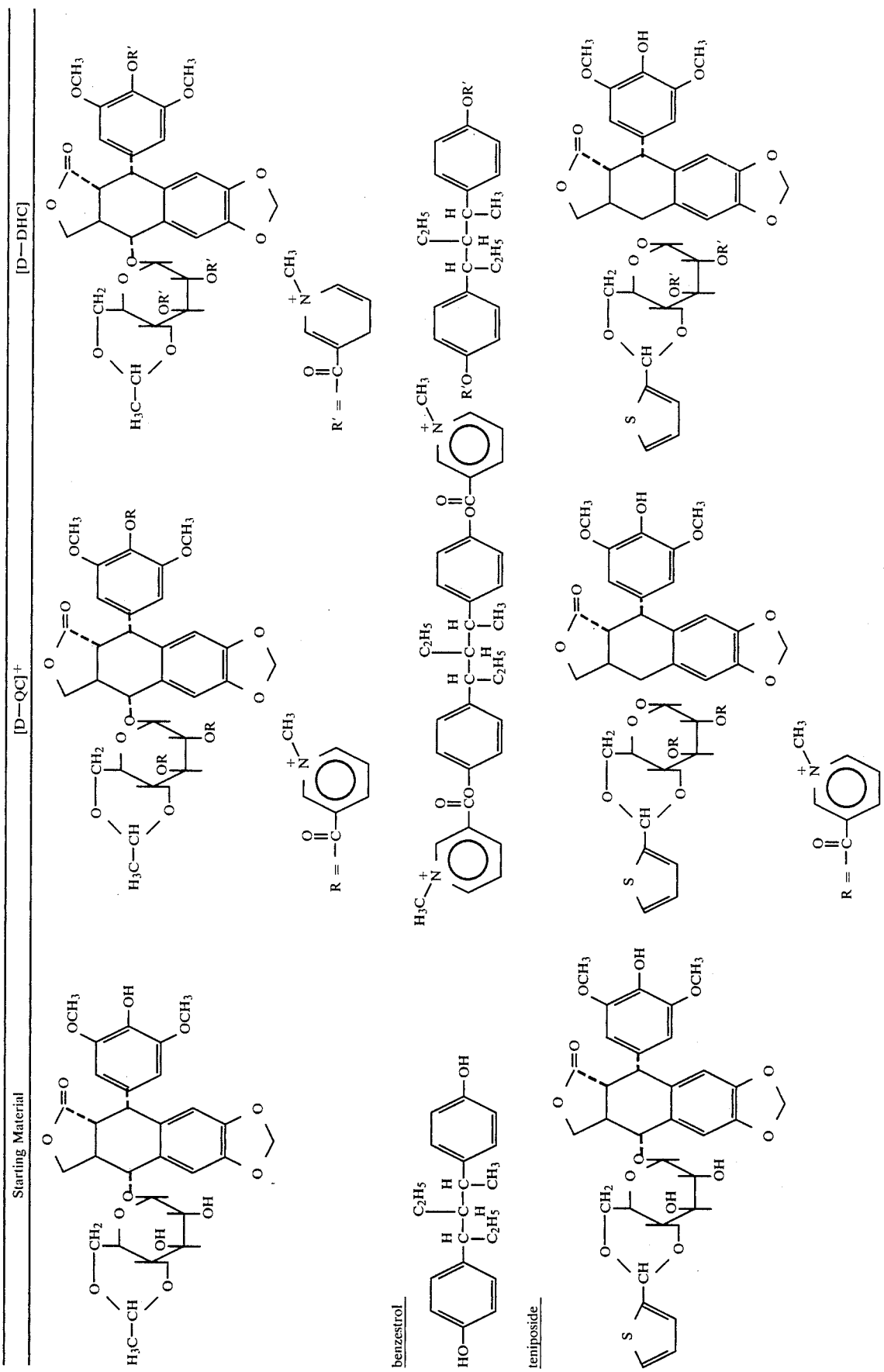

-continued

| Starting Material | [D—QC]⁺ | [D—DHC] |
|---|---|---| ethynodiol diethylstilbestrol

Ara-AC pentostatin
(2'-deoxycoformycin)

-continued
| Starting Material | [D—QC]+ | [D—DHC] |
|---|---|---|
| 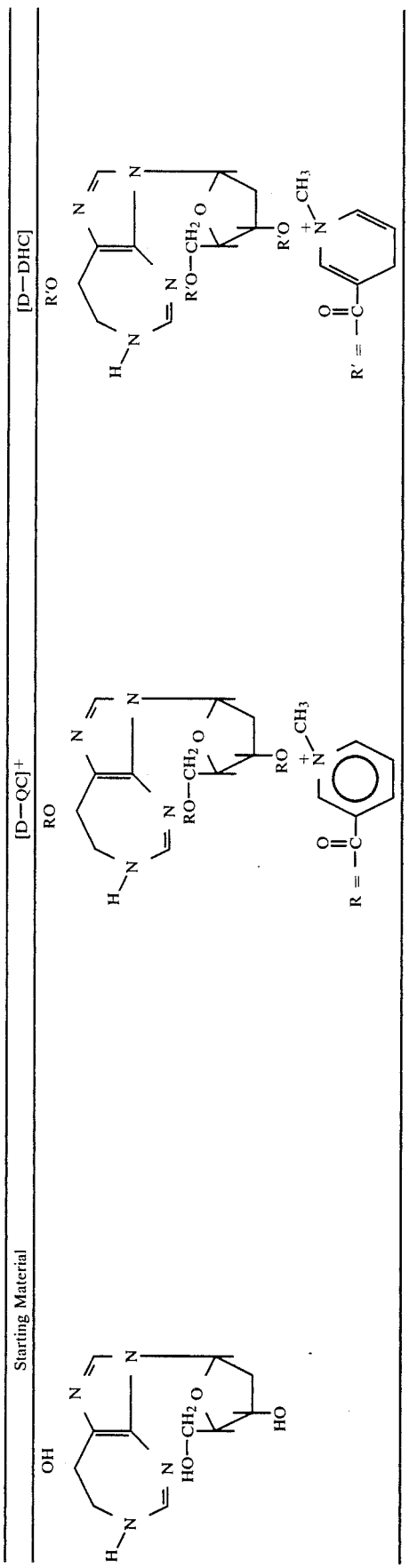 | 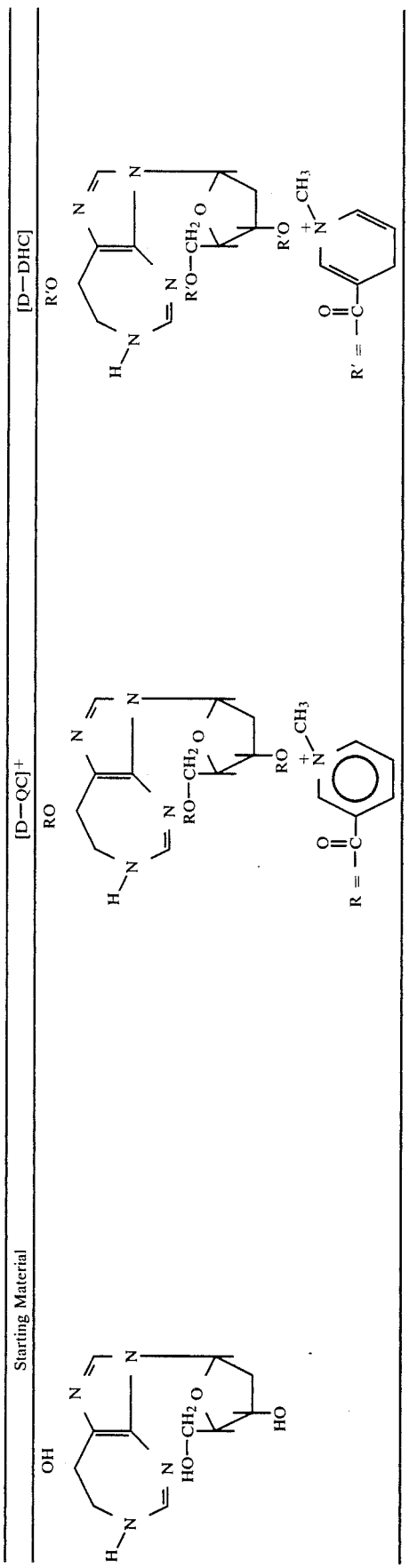 | |

| Starting Material | [D—QC]+ | [D—DHC] |
|---|---|---|
| dihydro-5-azacytidine 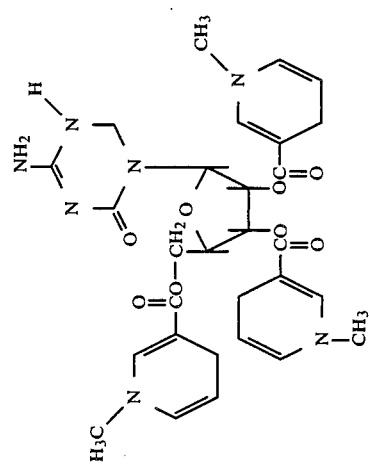 | 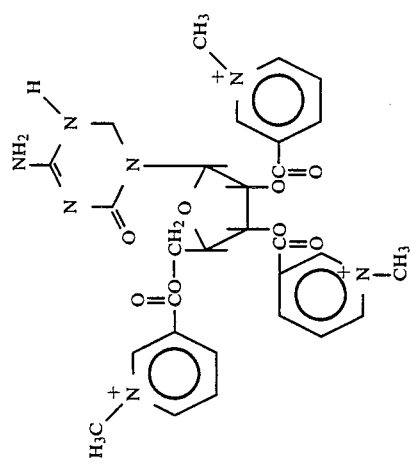 | 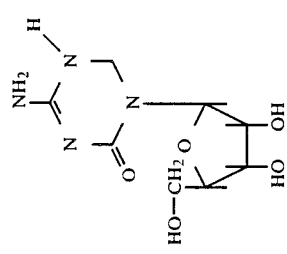 |
| tiazofurin 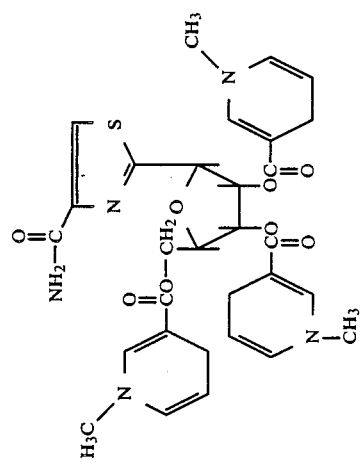 | 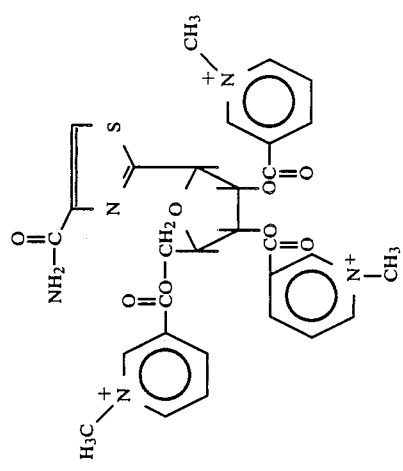 | 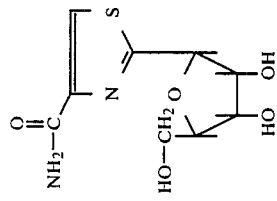 |
| sangivamycin | | |

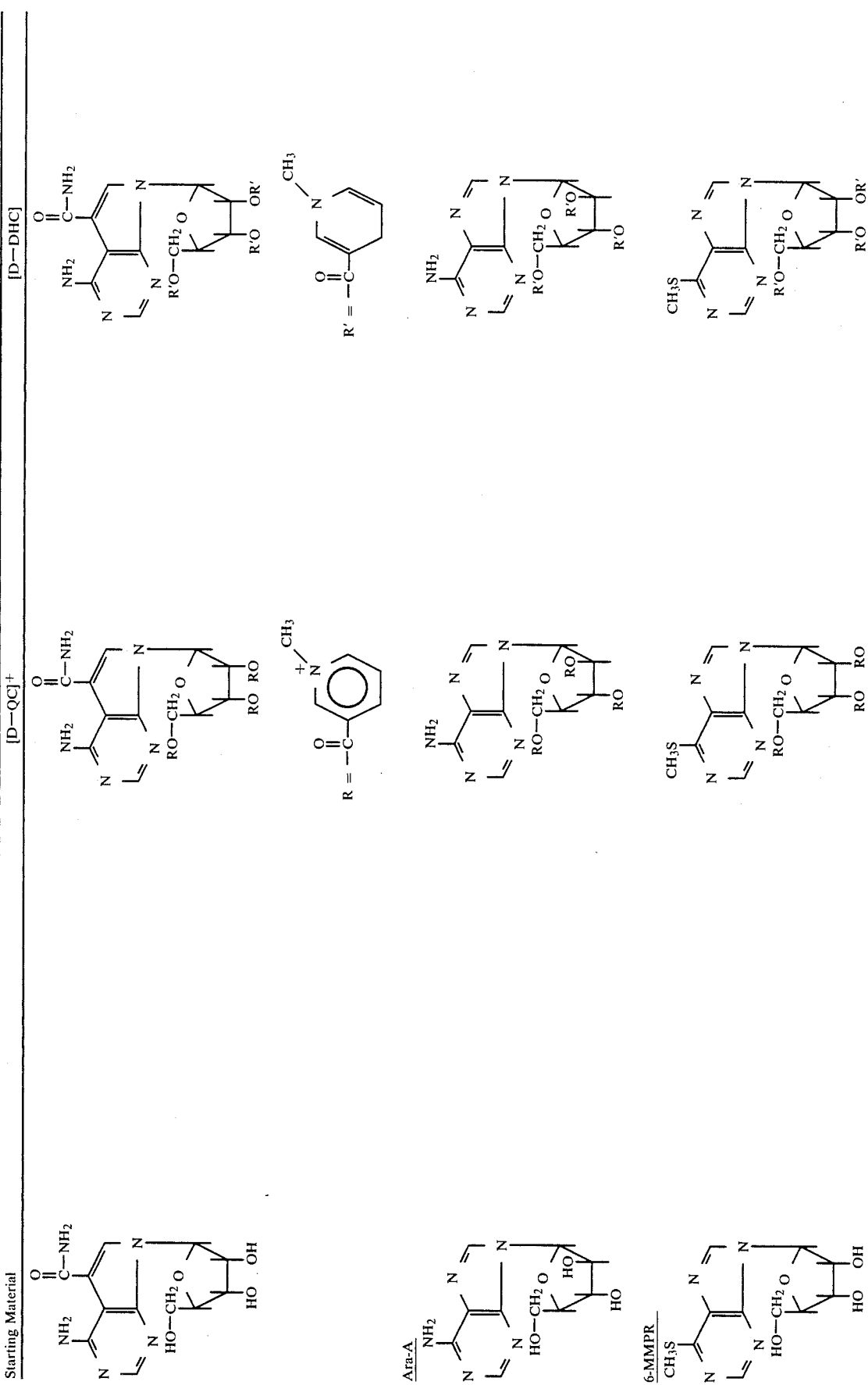

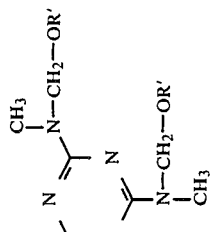

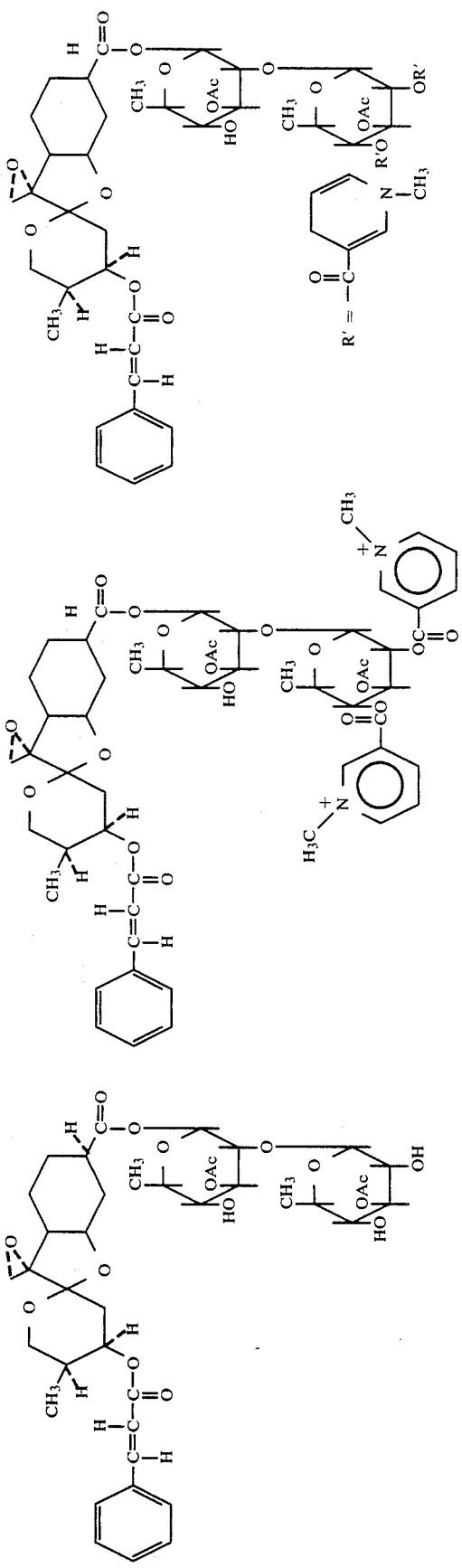
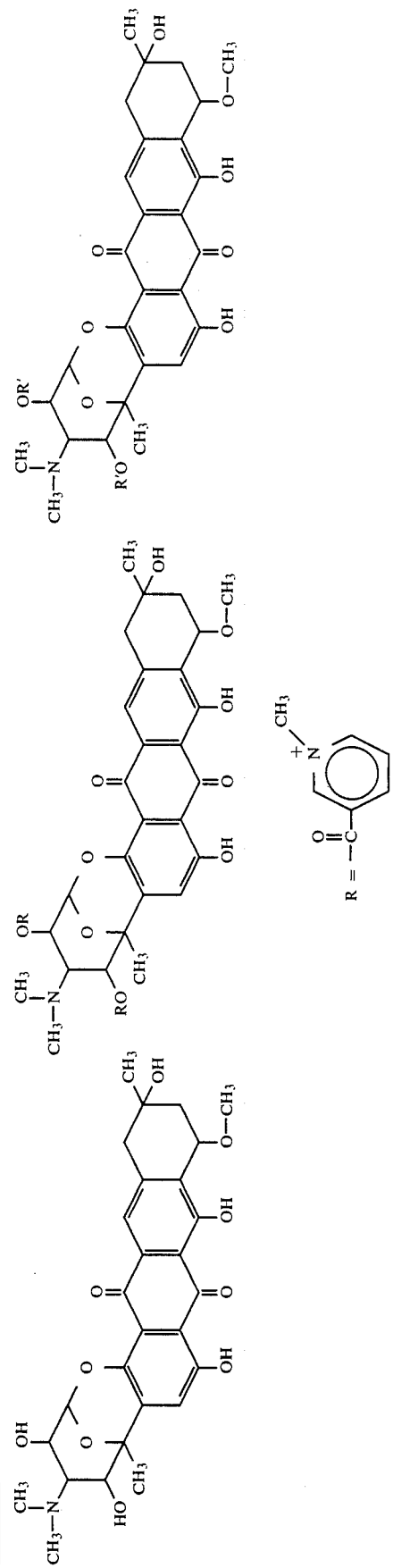

-continued
| Starting Material | [D—QC]+ | [D—DHC] |
|---|---|---|
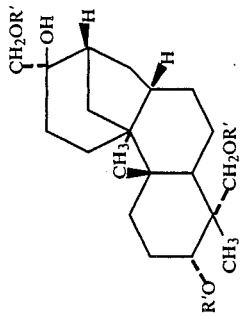
5-FUDR
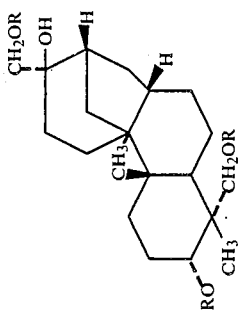
cytosine arabinoside
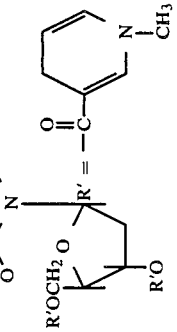
VP-16 (etoposide)

| Starting Material | [D—QC]+ | [D—DHC] |
|---|---|---|

5-azacylidine phenyl-6-chloro-6-deoxy-β-D-glucopyranoside

| Starting Material | [D—QC]+ | [D—DHC] |
|---|---|---|
| |  |  |
| ribavirin | | |
| (S)-9-(2,3-dihydroxypropyl)-adenine | | |
| 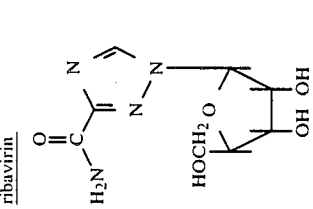 | | |
| norethynodrel | 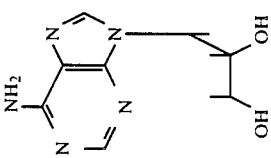 | |

| Starting Material | [D—QC]+ | [D—DHC] |
|---|---|---|
| 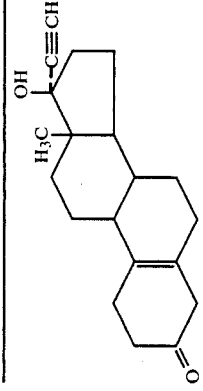 | 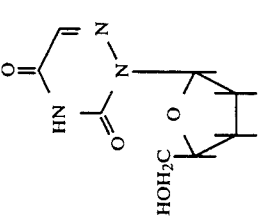 | 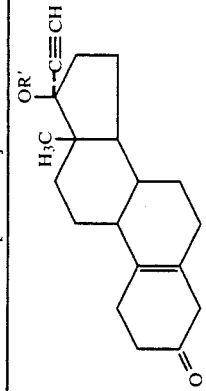 |
| 6-azauridine | | |
| 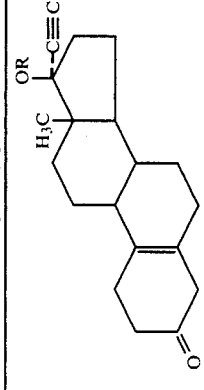 | 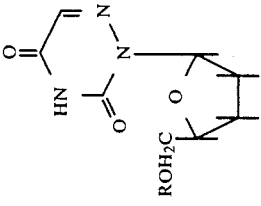 | 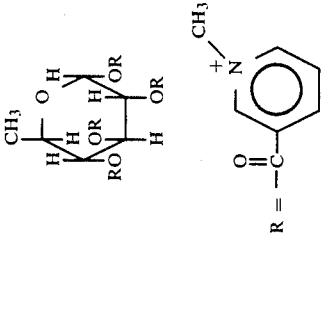 |
| 6-deoxy-D-glucose | | |
| 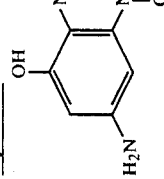 | 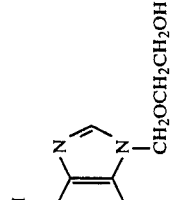 | 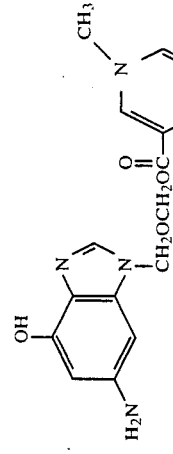 |
| acyclovir | | |

Method J

This is a variation of Method I used when the drug contains a —COOH function which is to be protected.

The drug is first converted to the corresponding ethyl ester by conventional esterification techniques. That ester is then used as the starting material and Method I is repeated. The —COOH group may be similarly converted to other ester groups.

The representative drugs listed below may be derivatized in this manner to the corresponding [D-QC]+ and [D-DHC] compounds. Diflunisal and clorazepate may be similarly derivatized.

The picolinic acid ester and isonicotinic acid ester quaternary and dihydro derivatives of the drugs specifically mentioned for derivatizing according to this method may be similarly prepared. See Method I.

[D-DHC] compounds, as may the remaining drugs listed with Method I.

Similarly, Method K may be combined with Method J to afford the corresponding derivatives, e.g. of the drugs listed with that method.

A starting material of the formula set forth immediately above can also be substituted for nicotinic acid in Method E to afford the corresponding derivatives, e.g. of the drugs listed with that method.

Method K may also be useful in preparing derivatives of drugs in which the hydroxy function is hindered, e.g., biperiden, cycrimine, procyclidine and trihexyphenidyl. Alternatively, Method K may follow Method I except that, in the first step, it employs a starting material of the formula

| Starting Material | [D—QC]+ | [D—DHC] |
|---|---|---|
| 5-hydroxy-2-n-propylpentanoic acid | | |
| 4-hydroxy-2-n-propylpentanoic acid | | |
| 3-hydroxy-2-n-propylpentanoic acid | | |

Method K

Method I is followed, except that in the first step, a starting material of the formula

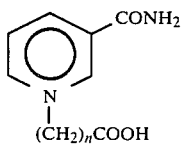

wherein n=1–3, preferably 2, is used in place of nicotinic acid.

The representative drugs listed below may be derivatized in this manner to the corresponding [D-QC]+ and

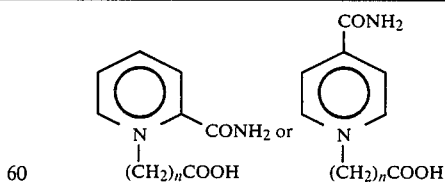

(prepared as described in Method H), to afford derivatives of the drugs indicated with Method I. This alternative form of Method K may also be combined with Method J, to afford the corresponding derivatives of the drugs listed with Method J. Also, these alternative Method K starting materials may be substituted for nicotinic acid in Method E to give the corresponding derivatives of the drugs listed with that method.

| Starting Material | [D—QC]+ | [D—DHC] |
|---|---|---|
| codeine | | |
| norgestrel | | |
| piperacetazine | | |

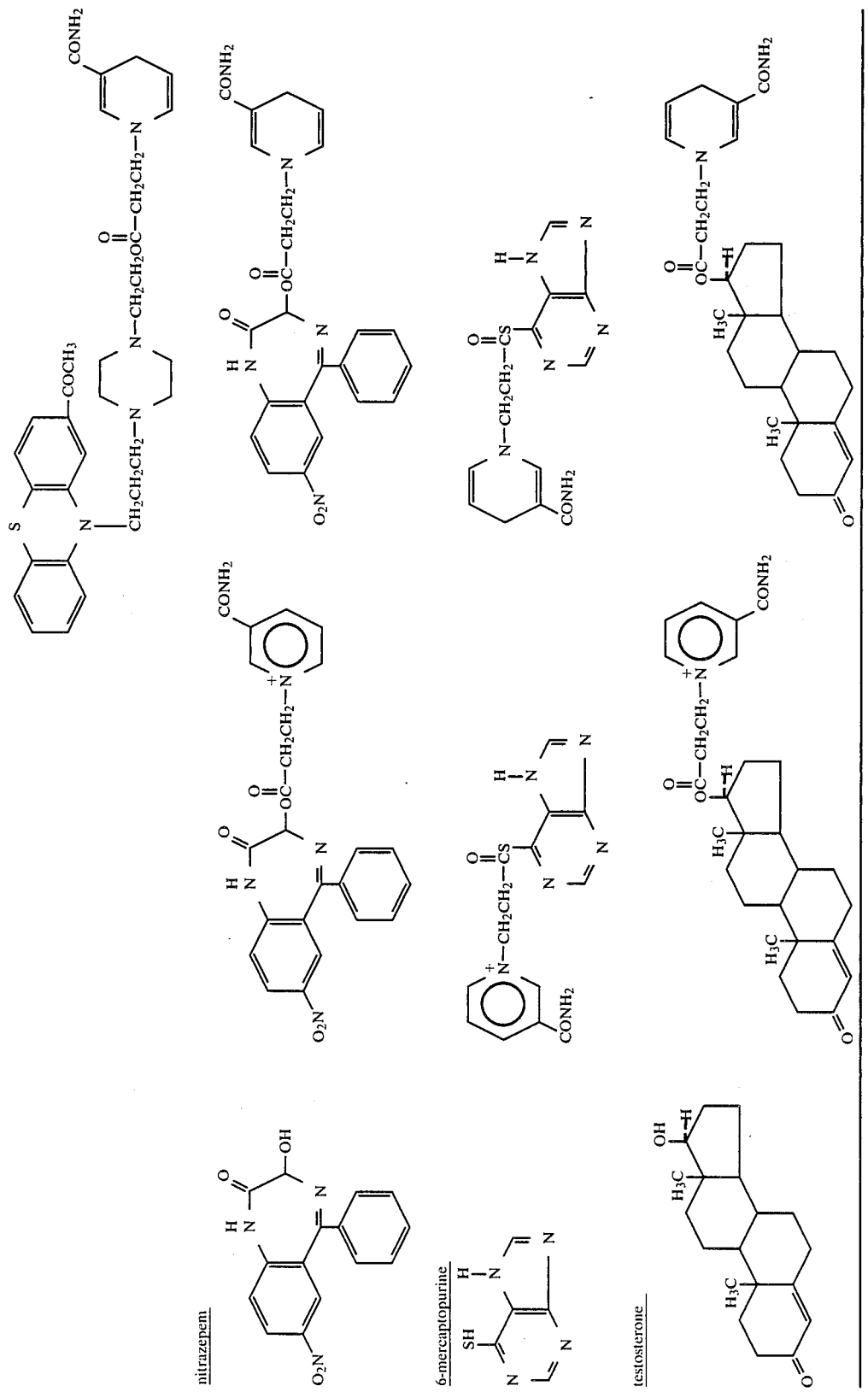

Method L

Method I is followed, except that in the first step, the drug is reacted with 3-quinolinecarboxylic acid or its acid chloride or anhydride instead of nicotinic acid or its acid chloride.

The representative drugs listed below may be derivatized in this manner to the corresponding [D-QC]+ and [D-DHC] compounds, as may the remaining drugs listed with Method I.

Similarly, Method L may be combined with Method J to afford the corresponding derivatives, e.g. of the drugs listed with that method.

The procedure of Method L may be repeated using 4-isoquinolinecarboxylic acid or its acid chloride or anhydride in place of 3-quinolinecarboxylic acid or its acid chloride or anhydride, to afford the corresponding derivatives of drugs such as those indicated with Methods I and J.

3-Quinolinecarboxylic acid or its acid chloride or anhydride or 4-isoquinolinecarboxylic acid or its acid chloride or anhydride can also be substituted for nicotinic acid or its acid chloride in Method E to afford the corresponding derivatives, e.g., of the drugs listed with that method.

| Starting Material | [D—QC]+ | [D—DHC] |
|---|---|---|
| hydroxyurea $NH_2-CO-NHOH$ | 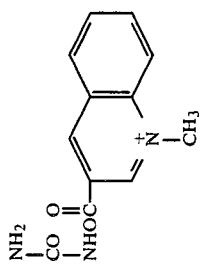 | 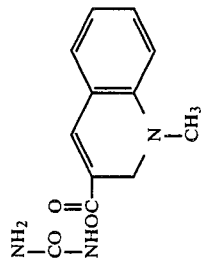 |
| bisbenzimidazole 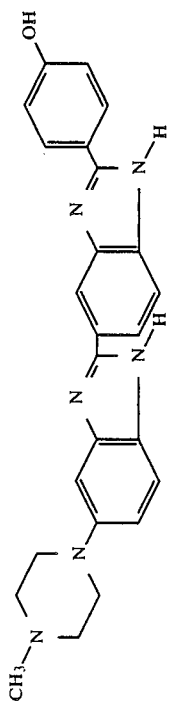 | 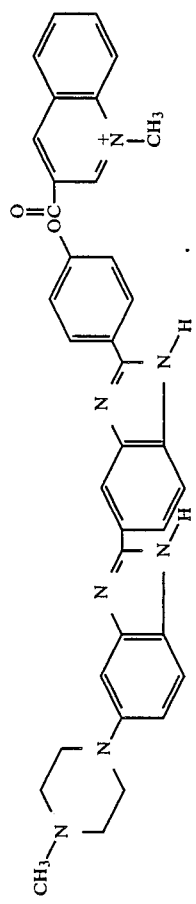 | 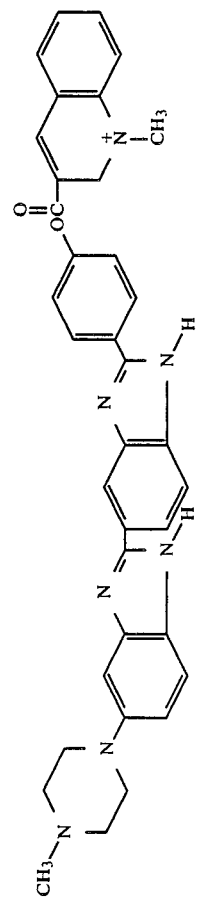 |
| mestranol | | |

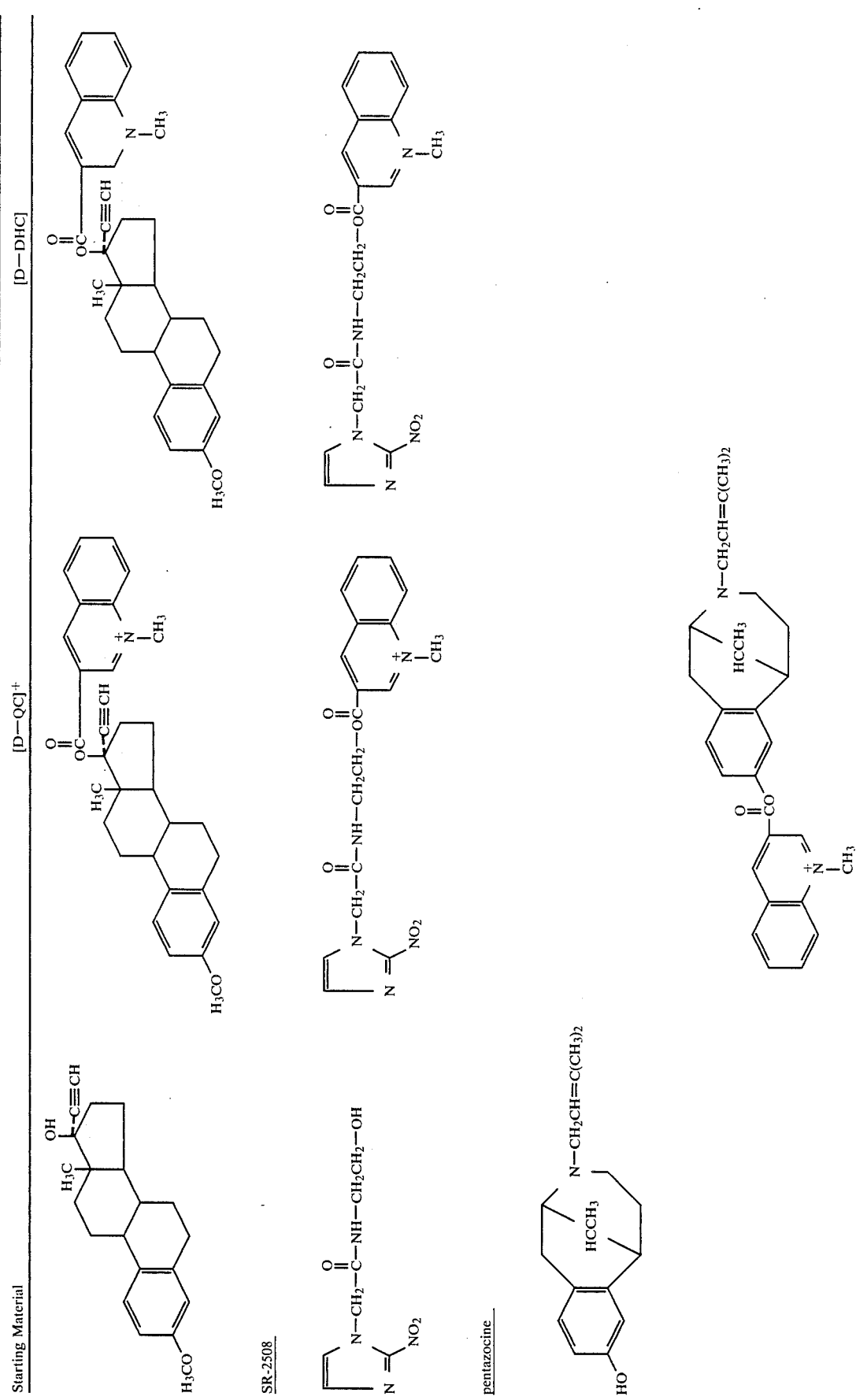

| Starting Material | [D—QC]+ | [D—DHC] |
|---|---|---|
-continued
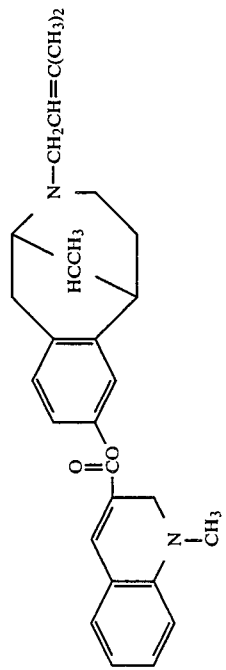
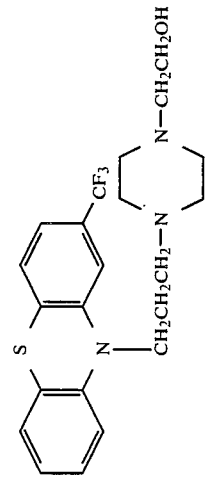
fluphenazine
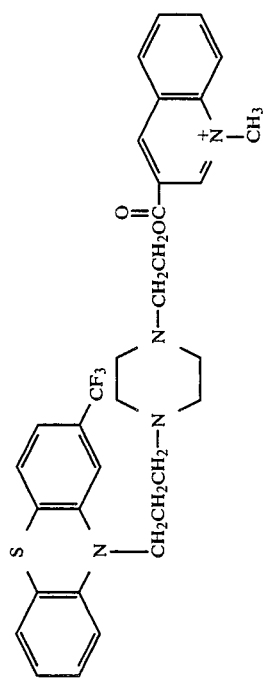
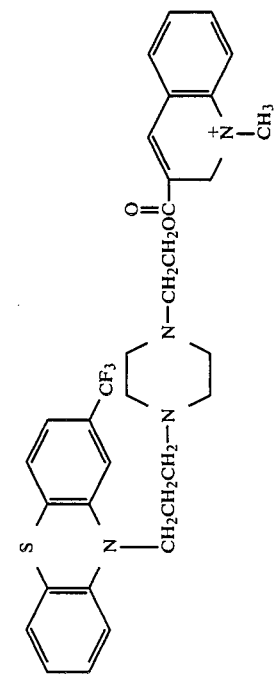

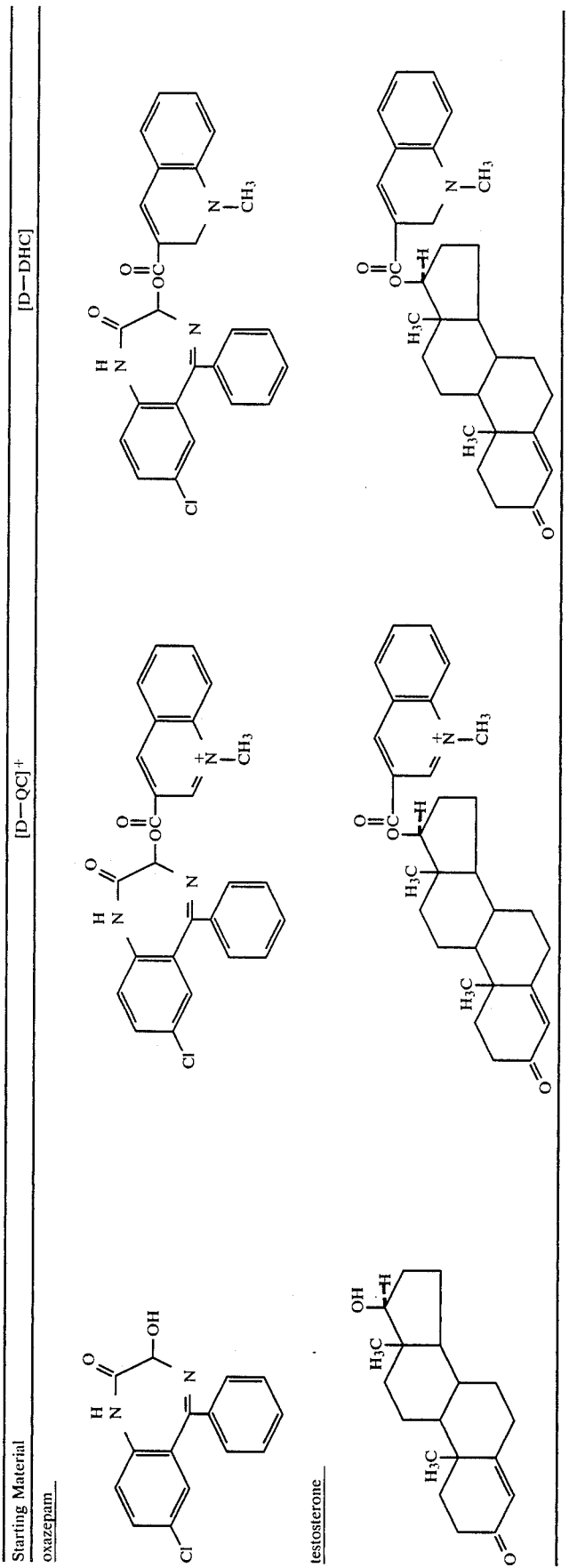

Method M

Method I is followed, except that in the first step, a starting material of the formula

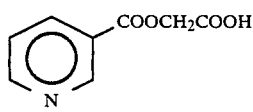

is used in place of nicotinic acid.

The representative drugs listed below may be derivatized in this manner to the corresponding [D-QC]+ and [D-DHC] compounds, as may the remaining drugs listed with Method I.

Similarly, Method M may be combined with Method J to afford the corresponding derivatives, e.g. of the drugs listed with that method.

A starting material of the formula set forth immediately above can also be substituted for nicotinic acid in Method E to afford the corresponding derivatives, e.g. of the drugs listed with that method.

Alternatively, Method M may follow Method I except that, in the first step, it employs a starting material of the formula

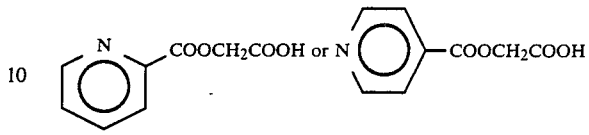

(prepared as described in Method G), to afford derivatives of the drugs indicated with Method I. This alternative form of Method M may also be combined with Method J, to afford the corresponding derivatives of the drugs listed with Method J. Also, these alternative Method M starting materials may be substituted for nicotinic acid in Method E to give the corresponding derivatives of the drugs listed with that method.

| Starting Material | [D—QC]⁺ | [D—DHC] |
|---|---|---|
| testosterone | | |
| naloxone | | |
| norethindrone | | |
| thioguanine | | |

-continued
| Starting Material | [D—QC]+ | [D—DHC] |
|---|---|---|
| 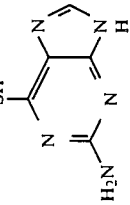 | 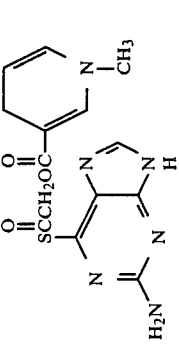 | 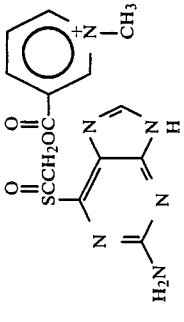 |
| lorazepam 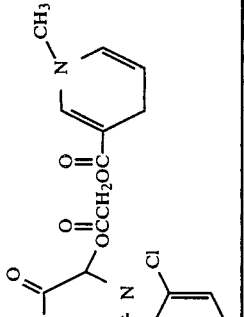 | 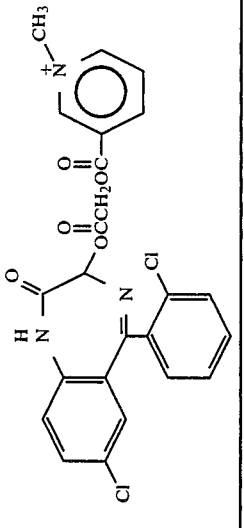 | |

III. Methods for Derivatizing —COOH Functions in Drugs

Method N

The drug is reacted with excess alcohol of the formula

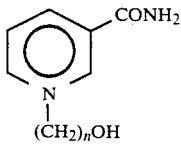

wherein n=1-3, preferably 2, to convert the —COOH function to the corresponding

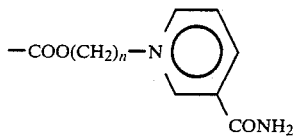

ester grouping. That ester is then quaternized and subsequently reduced as described above in Method A. When the drug contains more than one reactive carboxyl function, reaction conditions may be varied so that more than one carboxyl function will be converted to ester groupings. (The starting alcohol may be prepared from nicotinamide, e.g. when n=2, by reacting 2-iodoethanol with nicotinamide.)

The representative drugs listed below may be derivatized in this manner to the corresponding [D-QC]+ and [D-DHC] compounds. Benzylpenicillin, phenoxymethylpenicillin, methicillin, nafcillin, ticarcillin, furosemide, oxacillin, carbenicillin, dicloxacillin, fenbufen, fenoprofen, indoprofen, ketoprofen, fluprofen, bucloxic acid, tolmetin, alclofenac, fenclozic acid, ibufenac, meclofenamic acid, flufenamic acid and flufenisal may be similarly derivatized.

The procedure of Method N may utilize a starting alcohol of the formula

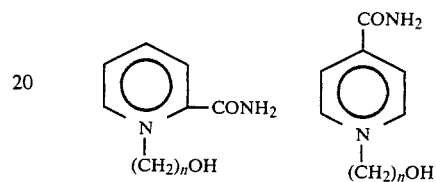

(prepared from picolinamide or isonicotinamide, respectively) in place of the starting alcohol depicted above, to afford the corresponding derivatives of the drugs indicated with this method.

| Starting Material | [D-QC]+ | [D-DHC] |
|---|---|---|
| cephalothin | | |
| valproic acid | | |
| cefoxitin | | |
| chlorazepate | | |
| iopyracet | | |

-continued
| Starting Material | [D-QC]+ | [D-DHC] |
|---|---|---|
| 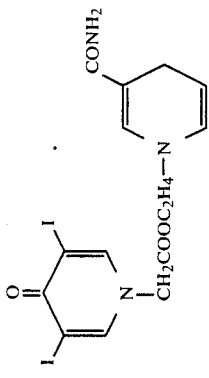 | 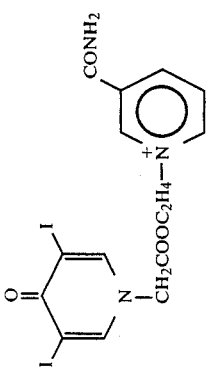 | 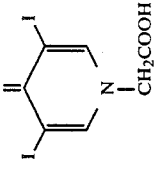 |
| iodouppurate | | |
| 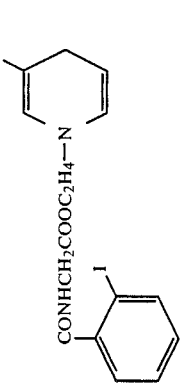 | 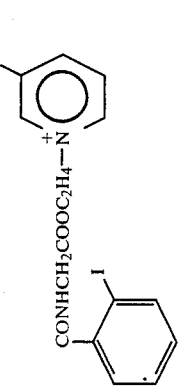 | 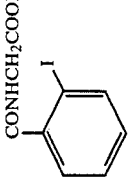 |
| iodamide | | |
| | | 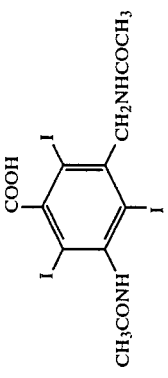 |
| iopanoic acid | | |
| | 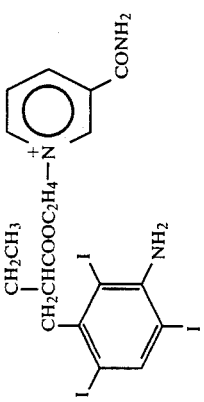 | 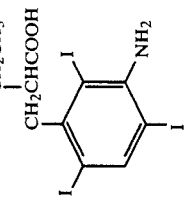 |
| nalidixic acid | | |

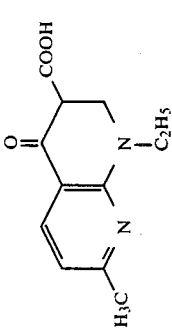

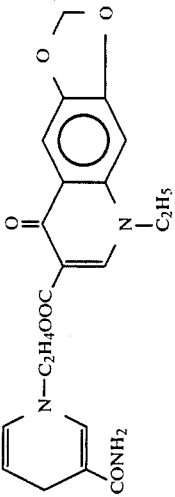

| Starting Material | [D-QC]+ | [D-DHC] |
|---|---|---|
| 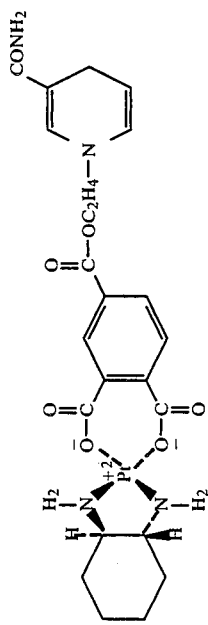 methotrexate | 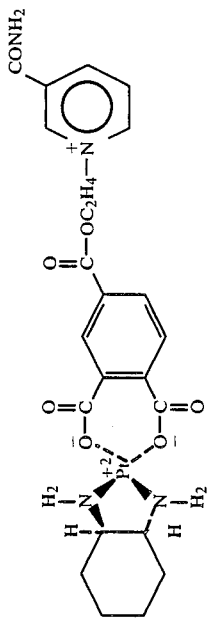 | 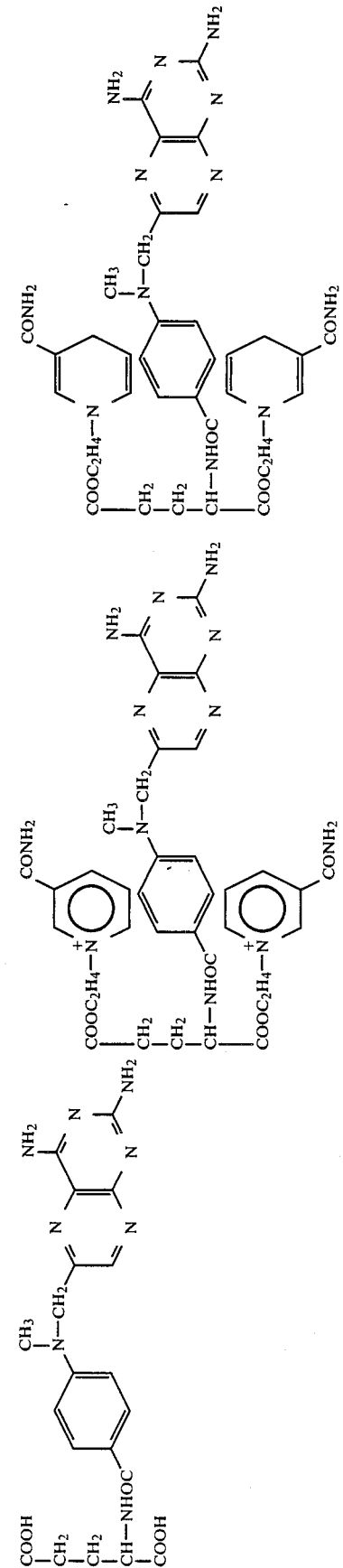 aminopterin |

-continued

| Starting Material | [D-QC]+ | [D-DHC] |
|---|---|---|

5-methyl tetrahydrohomofolic acid

| Starting Material | [D-QC]+ | [D-DHC] |
|---|---|---|
| cefazolin | | |
| ibuprofen | | |
| naproxen | | |
| flurbiprofen | | |

| Starting Material | [D-QC]+ | [D-DHC] |
|---|---|---|
| zomepirac | | |
| mefenamic acid | | |
| sulindac | | |
| diclofenac | | |
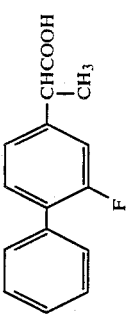

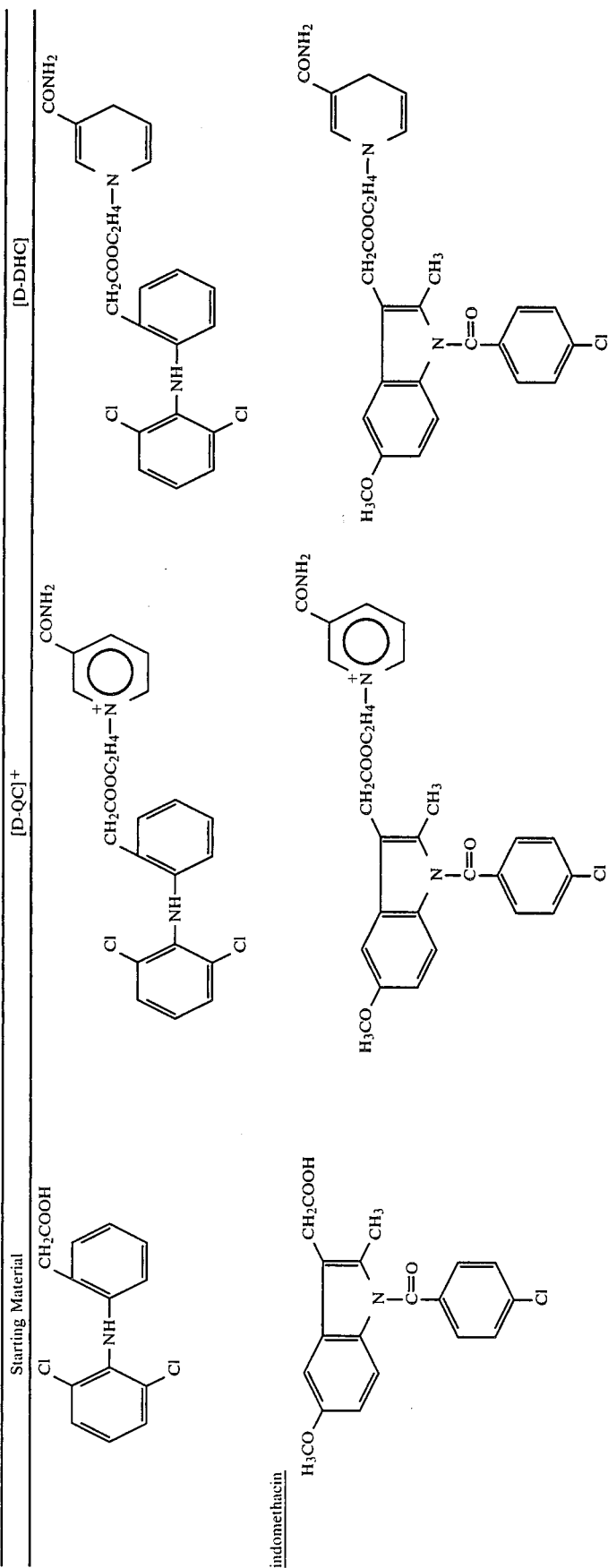

Method O

Method N is repeated, except that the starting alcohol employed has the formula

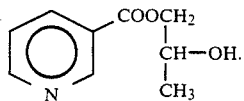

(That starting material may be prepared by reacting nicotinic acid with 1,2-propylene glycol in the presence of dicyclohexylcarbodiimide.)

The representative drugs listed below may be derivatized in this manner to the corresponding [D-QC]+ and [D-DHC] compounds, as may the remaining drugs listed with Method N.

The procedure of Method O may be repeated using a starting alcohol of the formula

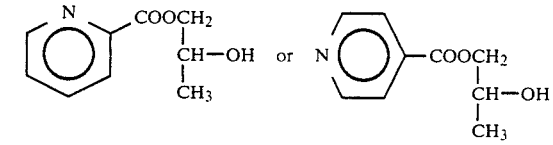

in place of the starting alcohol depicted above (prepared is an analogous manner using picolinic acid or isonicotinic acid in place of nicotinic acid in the reaction with 1,2-propylene glycol), to afford the corresponding derivatives of the drugs indicated in Method N.

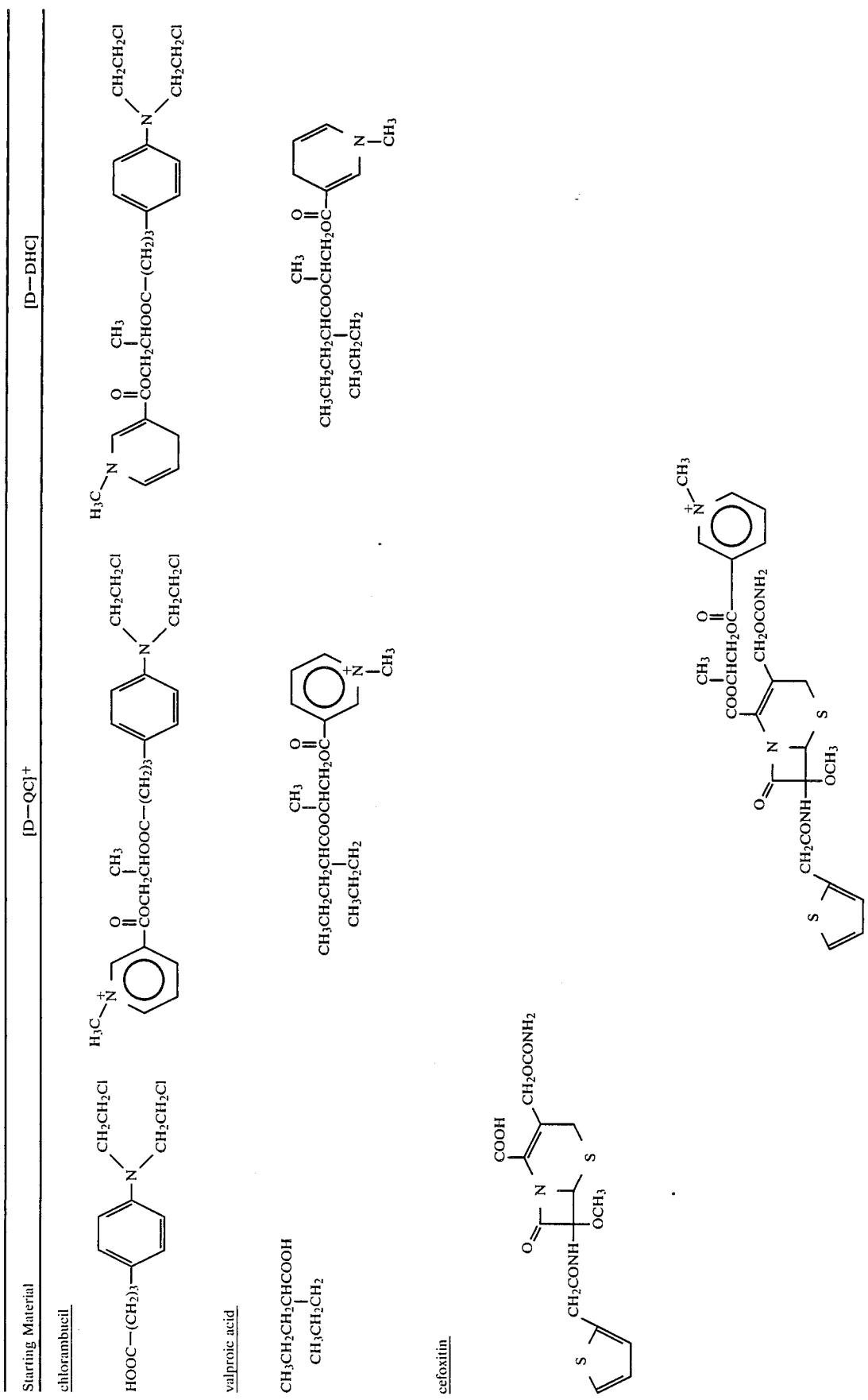

| Starting Material | [D—QC]+ | [D—DHC] |
|---|---|---|
| ibuprofen | | |
| naproxen | | |
| flurbiprofen | | |

Method P

Method N is repeated, except that the starting alcohol employed has the formula

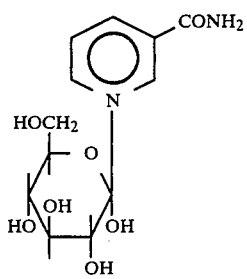

(That starting material may be prepared by reacting bromoglucose with nicotinamide.)

The drugs listed below may be derivatized in this manner to the corresponding [D-QC]+ and [D-DHC] compounds, as may the remaining drugs listed with Method N.

Alternatively, Method P may utilize a starting alcohol of the formula

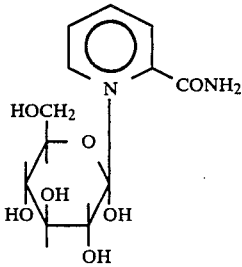 or 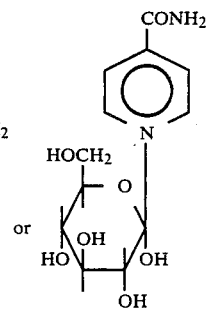

(prepared by reacting bromoglucose with picolinamide or isonicotinamide), to afford the corresponding derivatives of the compounds listed with Method N.

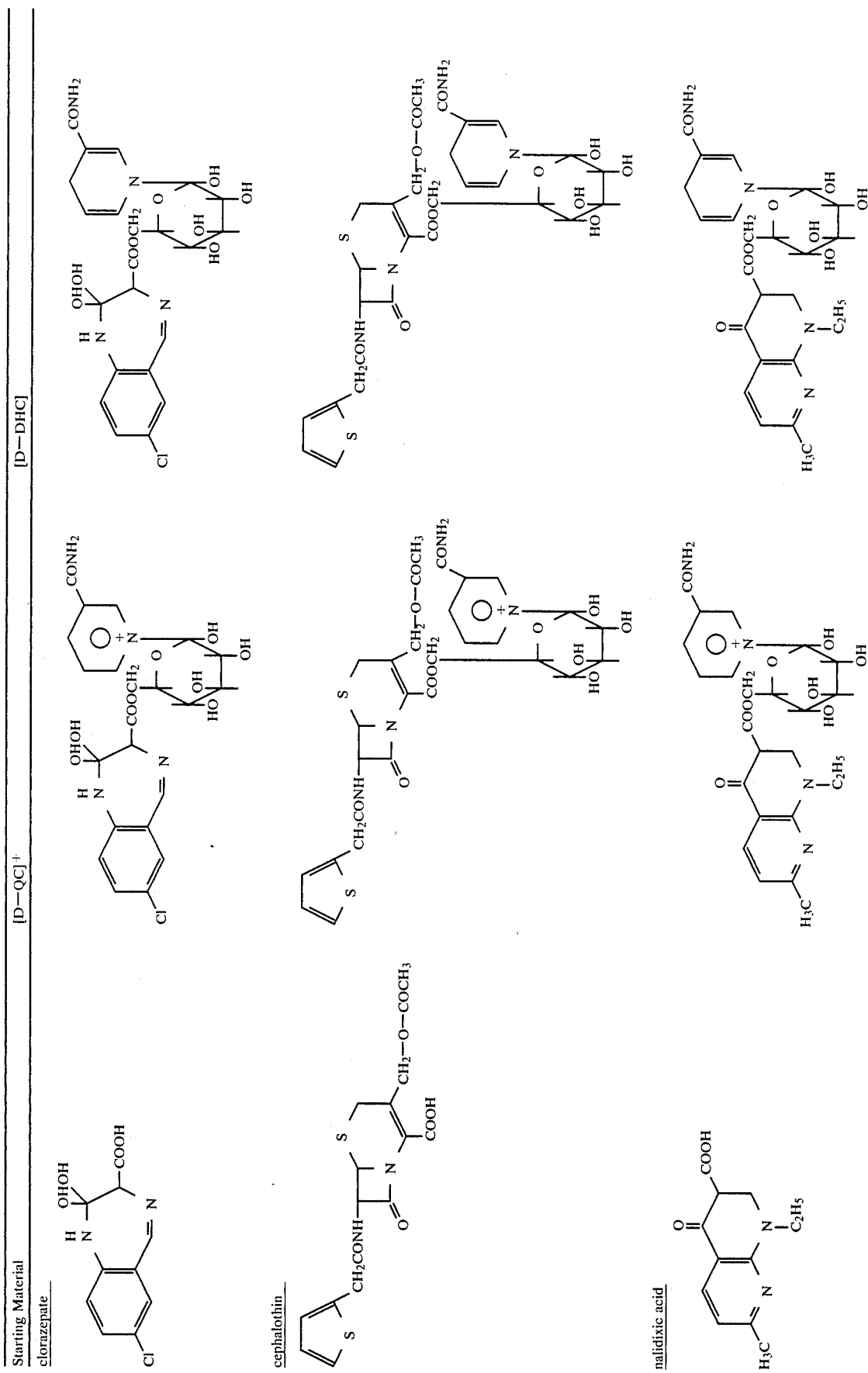

-continued
| Starting Material | [D—QC]+ | [D—DHC] |
|---|---|---|
| chlorambucil 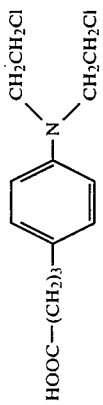 | 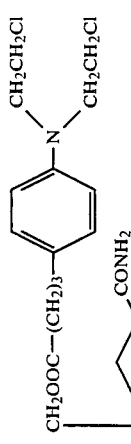 | 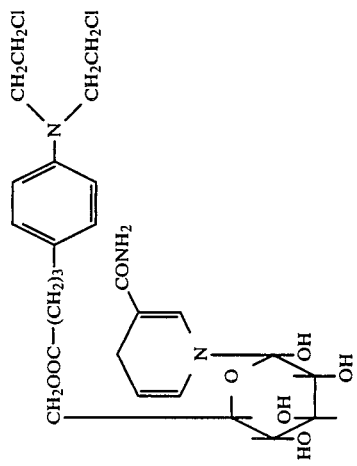 |
| valproic acid $CH_3CH_2CH_2CHCOOH$ $\quad\quad\quad\; |$ $\quad\quad\; CH_3CH_2CH_2$ | 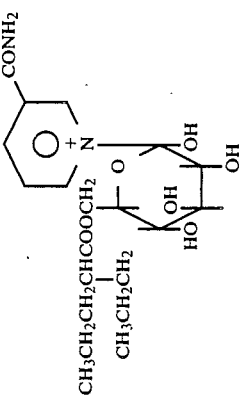 | 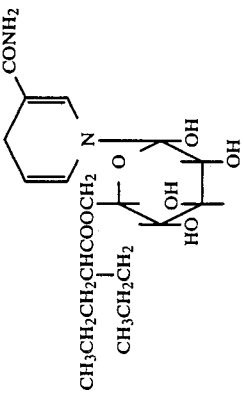 |
| cefazolin | | |

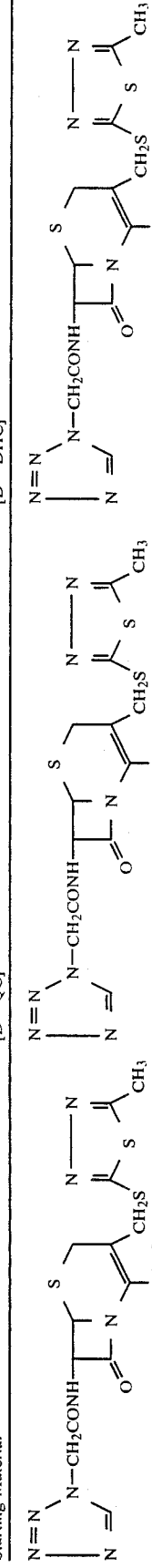

| Starting Material | [D—QC]+ | [D—DHC] |
|---|---|---|
| 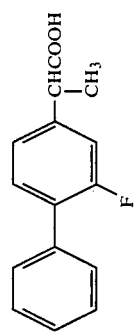 | 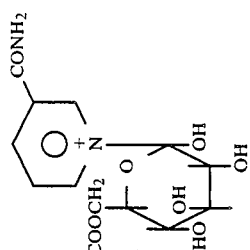 | 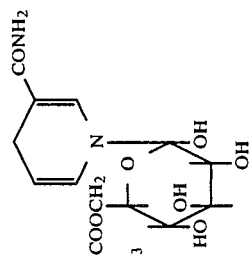 |

IV. Methods for Salt Formation

Method Q

An ether solution of [D-DHC] is treated with an equivalent amount of anhydrous p-toluenesulfonic acid dissolved in dry ether. Mixing at room temperature is continued until the imminium salt precipitates out of solution. The salt is then removed by filtration.

Imminium salts which may be prepared in this manner are those derived from the following [D-DHC]:

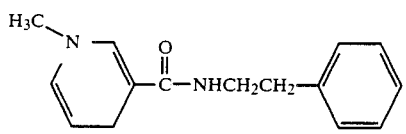
(from phenylethylamine)

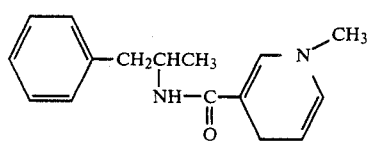
(from amphetamine)

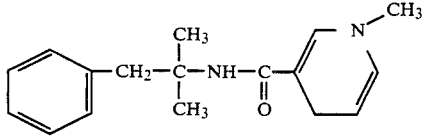
(from phentermine)

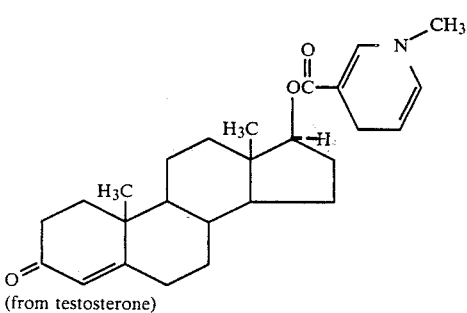
(from testosterone)

In order to further illustrate the present invention and the advantages thereof, the following specific examples are given, it being understood that same are intended only as illustrative and in nowise limitative.

In the examples immediately to follow, all melting points were taken on a Mel-Temp apparatus and are not corrected. Elemental analyses were performed at Atlantic Microlab, Inc., Altanta, Ga. Infrared spectra were determined using a Beckman Acculab 1 double-beam recording spectrophotometer. NMR spectra were determined by means of a Varian T60A or FX100 spectrometer. All chemical shifts reported are in $\delta$ units (parts per million) relative to tetramethylsilane. Ultraviolet absorbance spectra were determined using a Cary Model 219 spectrophotometer. HPLC analysis were performed on Waters Associates Liquid chromatograph with Model 6000A solvent delivery system, Model U6K injector and Model 440 absorbance detector. And in all cases where Anal. C, H, N is indicated, the elementary analysis of the compound was found within ±0.4 of the calculated value.

EXAMPLE 1

Preparation of N-($\beta$-Phenethyl)nicotinamide:

To 10.25 g (0.083 mol) of nicotinic acid, 27.5 ml of thionyl chloride were gradually added. The mixture was stirred at room temperature for 10 min and then refluxed while stirring for 2 hrs. Excess thionyl chloride was then distilled off under reduced pressure. Dry benzene (over sodium, 50 ml) was added and then distilled off under reduced pressure (to remove traces of $SOCl_2$). A white crystalline acid chloride hydrochloride was left, which was used as such for the preparation of amides.

To the solid acid chloride hydrochloride, 150 ml of dry and freshly distilled pyridine were added. To the stirred mixture, 10.45 ml (0.083 mol) of phenethylamine were dropped over 15 min. The mixture was then heated on a water bath while stirring for 2 hrs. Pyridine was distilled off on rotavap. The brown oily residue was poured onto crushed ice. The cream-white solid which separated was filtered by suction, washed with cold water and dried in vacuum; yield 13.3 g (70%), m.p. 79°–80° C.; ir (KBR) 3320 (NH) and 1630 cm$^{-1}$ (C=O), NMR (CDCl$_3$) $\delta$ 8.66 (bs, 1H, C$_4$ pyridine proton), 8.46 (bd, 1H, C$_6$ pyridine proton), 8.0–7.6 (m, 1H, C$_4$ pyridine proton), 7.33–6.90 (bs, 6H, C$_6$H$_5$+C$_5$ pyridine proton), 7.0–6.57 (hump, 1H, CONH), 3.73

(q, 2H, —N—CH$_2$), 2.97 (t, 2H, CH$_2$—$\phi$). Anal. (C$_{14}$H$_{14}$N$_2$O) C, H, N.

EXAMPLE 2

Preparation of 1-Benzyl-3-(N-$\beta$-phenethyl)carbamoylpyridinium bromide

To a solution of 2.26 g (0.01 mol) of N-($\beta$-phenethyl)-nicotinamide in 5 ml of methanol, 1.4 ml (0.0114 mol) of benzyl bromide were added. The mixture was refluxed for 3 hrs. Methanol was distilled off on rotavap. The yellow, oily residue left was scratched when it suddenly solidified into buff, gritty solid. Crystallized from acetone/ether, yield 3.7 g (95%), m.p. 142°–144° C., U.V. max (buffer pH 7.4) 210 and 260 nm; ir (KBr) 3180 (NH) and 1670 cm$^{-1}$ (C=O). NMR (CDCl$_3$/DMSO-d$_6$) $\delta$10.26 (bs, 1H, C$_2$ pyridine proton), 9.53–8.90 (m, 2H, C$_6$ and C$_4$ pyridine protons), 8.16–7.13 (m, 12H, 2C$_6$H$_5$+CONH+C$_5$ pyridine protons), 6.13

(s, 2H, —$\overset{+}{N}$—CH$_2$), 3.96–3.50 (m, 2H, —N—CH$_2$), 3.26–2.83 (m, 2H, CH$_2$—$\phi$). Anal. (C$_{21}$H$_{21}$BrN$_2$O) C, H, N.

EXAMPLE 3

Preparation of 1-Methyl-3-(N-$\beta$-phenethyl)carbamoyl iodide

To a solution of 2.26 g (0.01 mol) of N-($\beta$-phenethyl)-nicotinamide in 5 ml of methanol, 1.3 ml (0.02 mol) of methyl iodide were added. The mixture was refluxed for 3 hours. Methanol was distilled off on rotavap and the yellow, oily residue was cooled and scratched when a yellow gritty solid was obtained. Crystallized from acetone, yield 3.5 g (95%), m.p. 134°–136° C., U.V. max (buffer pH 7.4) 210, 225 and 226 nm. Ir (KBr) 3240 (NH) and 1665 cm$^{-1}$ (C=O). NMR (CDCl$_3$/DMSO-d$_6$) δ 9.63 (s, 1H, C$_2$ pyridine proton), 9.4–8.9 (m, 2H, C$_4$ and C$_6$ pyridine protons), 8.32–8.06 (m, 1H, C$_5$ pyridine proton), 4.6

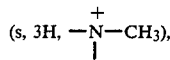

(s, 3H, $-\overset{+}{\underset{|}{N}}-CH_3$), 3.9–3.46 (m, 2H, —N—CH$_2$), 3.2–2.8 (m, 2H, CH$_2$—φ). Anal. (C$_{15}$H$_{17}$IN$_2$O) C, H, N.

EXAMPLE 4

Preparation of 1-Benzyl-3-(N-β-phenethyl)carbamoyl-1,4-dihydropyridine

To a solution of 3.97 g (0.01 mol) of 1-benzyl-3-(N-β-phenethyl)carbamoylpyridinium bromide in 200 ml of deaerated water, 5.0 g (0.06 mol) of sodium bicarbonate and 200 ml of ether was added. The mixture was stirred in an ice bath and 7.1 g (0.04 mole) of sodium dithionite were added gradually over a period of 5 min. The mixture was stirred for 3 hrs under nitrogen. The ether layer was then separated, washed with water, dried with Na$_2$SO$_4$ and distilled under vacuo. Yield 2.3 g (72%) of bright yellow, viscous oil was obtained which gave positive test for dihydropyridine with alcoholic silver nitrate solution. U.V. max (buffer pH 7.4) 210 and 355 nm. NMR (CDCl$_3$) δ two overlapping singlets at 7.2 (10H, 2C$_6$H$_5$), 7.1 (bs, 1H, C$_2$ pyridine proton), 5.68 (doublet of doublets, 1H, J=8 and 2 cps, C$_6$ pyridine proton), 6.4–5.0 (hump, 1H, CONH), 4.84–4.60 (m, 1H, C$_5$ pyridine proton), 4.35 (s, 2H, N—CH$_2$), 3.5

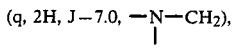

(q, 2H, J—7.0, $-\underset{|}{N}-CH_2$), 3.0 (bs, 2H, C$_4$ pyridine proton) and 2.8 (t, 2H, J=7.0, CH$_2$—φ).

EXAMPLE 5

Preparation of 1-Methyl-3-(N-β-phenethyl)carbamoyl-1,4-dihydropyridine

By the similar method described above, 1-methyl-3-(N-β-phenethyl)carbamoyl iodide (3.68 g, 0.01 mol) was reduced using sodium dithionite (7.1 g, 0.04 mol) and sodium bicarbonate (5.0 g, 0.06 mol). Yield 1.8 g (76%) of bright yellow, viscous oil which reduced alcoholic silver nitrate solution. U.V. max (buffer ph 7.4) 210, 290 and 360 nm; NMR (CDCl$_3$) δ 7.2 (s, 5H, C$_6$H$_5$), 6.9 (bs, 1H, C$_2$ pyridine proton), 5.6 (doublet of doublets, 1H, J=8, 2 cps. C$_6$ pyridine proton), 5.3–5.1 (hump, 1H, CONH), 4.5–4.7 (m, 1H, C$_5$ pyridine protons+N—CH$_3$+CH$_2$—φ). Anal. (C$_{15}$H$_{18}$N$_2$O) C, H, N.

EXAMPLE 6

Preparation of Diethyl 3,5-pyridinedicarboxylate

To suspension of 8.35 g (0.05 mol) of 3,5-pyridinedicarboxylic acid in 30 ml of absolute ethanol, 10 ml of concentrated sulfuric acid were dropped while stirring. The mixture was then refluxed on a water bath for 5 hrs and poured onto crushed ice. The solution was then made alkaline by the addition of solid KHCO$_3$ in small amounts. A white solid which separated was filtered, washed with water and dried. M.p. 42°–44° C. The mother liquid was extracted with CH$_2$Cl$_2$ when another crop of the diester was obtained. The overall yield of the crude ester was 9.1 g (82%) of sufficient purity for the examples to follow. NMR (CDCl$_3$) δ 9.62 (d, 2H, J-2 Hz, C$_2$ and C$_6$ pyridine protons), 8.76 (t, 1H, J=2Hz, C$_4$ pyridine proton), 4.43 (q, 4H, J=7 Hz, 2 OCH$_2$), 1.41 (t, 6H, J=7 Hz, 2CH$_3$).

EXAMPLE 7

Preparation of 5-Carboethoxy-3-pyridinecarboxylic acid

To a solution of 10 g (0.045 mol) of diethyl 3,5-pyridinedicarboxylate in 75 ml of ethyl alcohol, 25 ml of 2N alcoholic KOH were added while stirring. Stirring was continued for ½ hour at room temperature. To the mixture, 12.5 ml of 4N HCl were added while stirring. The solid which separated was filtered and washed with alcohol. The combined filtrate and washings were distilled on rotovap and the residue was washed with water, filtered and crystallized from ethanol. Yield 7.5 g (86%), m.p. 180°–182° C., NMR (CDCl$_3$/DMSO-d$_6$) δ 10.56 (bs, 1H, COOH), 9.26 (d, 2H, J=2 Hz, C$_2$ and C$_6$ pyridine protons), 8.75 (t, 1H, J=2 Hz, C$_4$ pyridine protons), 4.4 (q, 2H, J=7 Hz, O—CH$_2$), 1.42 (t, 3H, J=7 Hz, CH$_3$).

EXAMPLE 8

Preparation of 5-Carboethoxy-3-(N-β-phenethyl)carbamoylpyridine

To 10 g (0.05 mol) of 5-carboethoxy-3-pyridinecarboxylic acid, 30 ml of thionyl chloride were added and the mixture was warmed on a water bath while stirring until clear (≅3 hrs). Excess thionyl chloride was distilled under vacuum. The residue was cooled to room temperature and 50 ml of sodium-dry benzene was added. The solution was cooled in an ice bath and a solution of 6.2 g (0.051 mol) of phenethylamine and 4 ml of pyridine in 50 ml of dry benzene was dropped while stirring over 1 hr and the mixture was left overnight at room temperature. The mixture was then washed with water until free from Cl$^-$ (tested by AgNO$_3$TS). The organic layer was dried with Na$_2$SO$_4$ and distilled. The residue was crystallized from ether/pet. ether mixture. Yield 9.0 g (67%), m.p. 159°–161° C.; ir (KBr) 3300 (NH), 1725 (ester CO) and 1650 cm$^{-1}$ (amide CO), NMR (CDCl$_3$) δ 9.13–9.96 (two doublets, 2H, J=2 Hz, C$_2$ and C$_6$ pyridine protons), 8.53 (t, 1H, J=2 Hz, C$_4$ pyridine proton), 7.16 (s, 6H, C$_6$H$_5$+CONH), 4.36 (q, 2H, J=7 Hz, OCH$_2$), 3.4 (q, 2H, J=7 Hz, N—CH$_2$), 2.9 (5, 2H, J=7 Hz, CH$_2$—φ), 1.33 (t, 3H, J=7 Hz, CH$_3$). Anal. (C$_{17}$H$_{18}$N$_2$O$_3$) C, H, N.

EXAMPLE 9

Preparation of 5-Carboethoxy-1-methyl-3-(N-β-phenethyl)carbomoylpyridinium iodide To a solution of 2.9 g (0.01 mol) of 5-carboethoxy-3-(N-β-phenethyl)carbamoylpyridine in 5 ml of acetone, 3 ml of methyl iodide were added. The mixture was refluxed while stirring for 8 hrs and then left overnight. The yellow crystalline solid which precipitated was filtered, washed with acetone, dried and crystallized from acetone. Weight 3.5 g (82%), m.p. 168°–170° C., ir (KBr) 3250 (NH), 1725 (ester CO) and 1670 cm$^{-1}$ (amide CO), U.V. max (buffer pH 7.4) 2.68 (weak plateau) and 268 nm ($\epsilon$=53, 667), NMR (DMSO-d$_6$) δ 9.53 (bs, 2H, C$_2$ and C$_6$ pyridine protons), 9.33–9.10 (m, 1H, C$_4$ pyridine proton), 7.16 (s, 5H, C$_6$H$_5$), 4.63–4.26

(complex multiplet, 5H, $-\overset{+}{\underset{|}{N}}-CH_3 + OCH_2$), 3.56 (q, 2H, J=6 Hz,

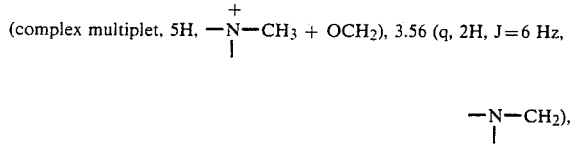

2.90 (t, 2H, J=6, CH$_2$—φ), 1.4 (t, 3H, J=7 Hz, CH$_3$). Anal. (C$_{18}$H$_{21}$IN$_2$O$_3$) C, H, N.

EXAMPLE 10

Preparation of 5-Carboethoxy-1-methyl-3-(N-β-phenethyl)carbamoyl-1,4-dihydropyridine This compound was prepared following the same procedure as in Example 4 using 1.0 g (0.002 mol) of 5-carboethoxy-1-methyl-3-(N-β-phenethyl)carbamoyl-pyridinium iodide, 1.0 g (0.012 mol) sodium bicarbonate and 1.42 g (0.008 mol) sodium dithionite. Yield, 0.60 g (84%) of orange-yellow viscous oil which reduced alcoholic silver nitrate, but very slowly. U.V. max (buffer pH 7.4) 205 and 390 nm. NMR (CDCl$_3$) 7.33 (s, 5H, C$_6$H$_5$), 7.0 (s, 2H, C$_2$ and C$_6$ pyridine protons), 5.8–5.3 (hump, 1H, CONH), 4.2 (q, 2H, J=7, O—CH$_2$), 3.66

(q, 2H, J=7 Hz, $-\overset{+}{\underset{|}{N}}-CH_2$), 3.16 (bs, 2H, C$_4$ pyridine proton), 3.0 (q, 2H, J=7, CH$_2$—φ), 1.4 (t, 3H, J=7, CH$_3$).

EXAMPLE 11

Preparation of 3,5-Di(N-β-phenethyl)carbamoylpyridine

To a solution of 2.53 g (0.01 mole) of diethyl 3,5-pyridinedicarboxylate in 10 ml of methanol, 3.0 g (0.025 mol) of phenethylamine were added. The mixture was refluxed overnight and then distilled. The residue was washed with very dilute HCl solution and water, dried and crystallized form ethanol. Yield 2.9 g (80%), m.p. 189°–190° C. NMR (CDCl$_3$) δ 9.00 (d, J=2 Hz, 2H, 2,6-dipyridyl), 8.33 (5, J=2, 1H, 4-pyridyl), 7.30 (s, 10H, 2C$_6$H$_5$), 6.93–6.40 (hump, 2H, 2 COHN), 3.83 (q, J=7, 4H, 2—N—CH$_2$), 3.00 (t, J=7, 4H, 2—CH$_2$—φ). Anal. (C$_{23}$H$_{23}$N$_3$O$_2$) C, H, N.

EXAMPLE 12

Preparation of 1-Methyl-3,5-di(N-β-phenethyl)carbamoyl pyridinium iodide

To a solution of 2.0 g (5.3 mmol) of 3,5-di(N-β-phenethyl)carbamoylpyridine in 10 ml of acetone, 2 ml of methyl iodide were added and the mixture was refluxed for 24 hrs. The yellow crystalline solid which separated was filtered, washed with acetone and dried. Weight 1.4 g (51%), m.p. 186°–188° C. U.V. spectrum of a solution in phosphate buffer 7.4 showed a plateau at 275 nm, a shoulder at 225 nm and a sharp peak at 203 nm ($\epsilon$=67,356). Ir (KBr) 3240 (NH), 1665 and 1650 cm$^{-1}$ (twin band, C=O). NMR (CDCl$_3$/D$_2$O) δ 9.35 (d, 2H, J=2, C$_2$ and C$_6$ pyridine protons), 8.56 (d, 1H, J=2 Hz, C$_4$ pyridine proton), 7.20 (s, 10H, 2C$_6$H$_5$), 4.56

(s, 3H, $-\overset{+}{\underset{|}{N}}-CH_3$), 3.66 (t, 4H, J=7 Hz, 2—N—CH$_2$), 2.96 (t, 4H, J=7 Hz, 2CH$_2$—φ). Anal. (C$_{24}$H$_{26}$IN$_3$O$_2$).

EXAMPLE 13

Preparation of 1-Methyl-3,5-di(N-β-phenethyl)carbamoyl-1,4-dihydropyridine

This compound was prepared following the same procedure as in Example 4, using 1 g (0.002 mol) of 1-methyl-3,5-di(N-β-phenethyl)carbamoyl pyridinium iodide, 1.0 g (0.012 mol) sodium bicarbonate and 1.4 g (0.008 mol) sodium dithionite. Yield 0.65 g (86%) of orange-yellow semisolid which could not be crystallized. Its alcoholic solution shows a slow reduction with alcoholic silver nitrate solution. U.V. max (buffer pH 7.4) 388 and 210 nm. NMR (CDCl$_3$) 7.13 (s, 5H, C$_6$H$_5$), 6.76 (s, 1H, C$_2$ pyridine protons), 3.51

(q, 4H, J = 7 Hz, 2 $-\underset{|}{N}-CH_2$), 3.06–2.60 (m, 9H, O—CH$_2$+C$_4$ pyridine proton+—N—CH$_3$).

EXAMPLE 14

Preparation of N-Nicotinoyldopamine (compound 7)

To a pyridine solution containing 11.7 g (0.05 mol) dopamine hydrobromide and 6.15 g (0.05 mol) nicotinic acid at 0° C. were added 10.3 g (0.05 mol) dicyclohexylcarbodiimide (DCC). The reaction mixture was stirred at room temperature for 24 hours and the formed dicyclohexylurea was removed by filtration. The pyridine was removed in vacuo and the residue was crystallized from water at 0° C. The product was isolated by filtration and dried over phosphorous pentoxide. Recrystallization from isopropanol gave 9.0 g (0.035 mol), 70% N-nicotinoyldopamine, m.p. 159°–162° C.; aqueous solution of the compound gave a green color with Fe$^{+3}$ and reduced AgNO$_3$; ir (KBr) 3300, 2960, 1725, 1630, 1590, 1520, 1430, 1290, 1190, 1115, 720 and 710 cm$^{-1}$; NMR (d$_6$-DMSO) δ 9.25–6.25 (m, 7H), 3.3 (m, 2H) and 2.65 (m, 2H) ppm. Anal. (C$_{14}$H$_{14}$N$_2$O$_3$) C, H, N.

EXAMPLE 15

Preparation of 3-{N-[β-(3,4-Diacetoxyphenyl)ethyl]}carbamoylpyridine

To an ice cold suspension of 2.06 g (8 mmol) finely powdered nicotinoyldopamine in 50 ml of chloroform, 1.56 g (10 mmol) of acetyl chloride were dropped while stirring. The mixture was refluxed for 3 hrs, then filtered. The filtrate was washed with water until the washing did not give test for chloride ions with AgNO$_3$ T.S. Chloroform was distilled on rotavap and the residue was crystallized from ether/pet. ether. Yield 2.2 g (81%) NMR (CDCl$_3$) 8.90 (bs, 1H, C$_2$ pyridine proton), 8.56 (bd, 1H, C$_6$ pyridine proton), 8.16–7.83 (m, 1H, C$_4$ pyridine proton), 7.36–7.03 (m, 5H, C$_6$H$_3$+C$_5$ pyridine proton+NH), 3.60

(q, 2H, J = 7 Hz, —N—CH$_2$),
|

2.90 (t, 2H, J=7 Hz, —CH$_2$).

EXAMPLE 16

Preparation of
3-{N-[β-(3,4-Dipivalyloxyphenyl)ethyl]}carbamoylpyridine (compound 8c)

To a suspension of 5.16 g (0.02 mol) finely powdered nicotinoyldopamine in 100 ml chloroform, 7.23 g (0.06 mol) trimethylacetyl chloride were added under stirring. The mixture was refluxed for 6 hrs and then filtered. The filtrate was washed with water free of chloride ions, then washed once with a 5% solution of NaHCO$_3$, then with water. The chloroform was evaporated and the residue was chromatographed by using a silica gel G column and 2% methanol in chloroform as the eluent. The first fraction was collected and evaporated and the residue was crystallized from ether/petroluem ether. Yield, 6.2 g (73%) of a white crystalline solid, m.p. 112°–114° C., NMR (CDCl$_3$) δ 9.06 (bs, 1H, C$_2$ pyridine proton), 8.73 (bd, 1H, C$_6$ pyridine proton), 8.30–8.13 (m, 1H, C$_4$ pyridine proton), 7.46–7.10 (m, 5H, C$_6$H$_3$+C$_5$ pyridine proton+CONH), 3.66 (q, 2H, J=6.25 Hz, —N—CH$_2$), 3.0 (t, 2H, J=6 Hz, —CH$_2$), 1.41 (s, 18H, 2-C(CH$_3$)$_3$). Anal. Calcd for C$_{24}$H$_{30}$N$_2$O$_5$: C, 67.58; H, 7.09; N, 6.56. Found: C, 67.61; H, 7.10; N, 6.54.

EXAMPLE 17

Preparation of
1-Methyl-3-{N-[β-(3,4-dihydroxyphenyl)ethyl)]}caramoylpyridinium iodide (compound 6a)

To a solution of 1.26 g (5 mmol) of nicotinoyldopamine (7) in 10 ml of acetone, 1.41 g (10 mmol) of methyl iodide were added and the mixture was refluxed under stirring for 6 hrs. The acetone was removed and the residue was crystallized from methanol/ether. Yield, 1.7 g (87%), m.p. 155°–157° C.(dec). Aqueous solution gave a green color with Fe$^{+3}$, NMR (D$_2$O) δ 9.30–8.28 (ms, 4H, C$_5$H$_4$N$^+$), 7.00 (bs, 3H, C$_6$H$_3$), 4.60 (s, 3H, —N$^+$—CH$_3$), 3.80 (t, 2H, J=7 Hz, —N—CH$_2$), 2.93 (t, 2H, J=7 Hz, CH$_2$). Anal. Calcd for C$_{15}$H$_{17}$IN$_2$O$_3$.H$_2$O: C, 43.11; H, 4.55; N, 6.70. Found: C, 43.83; H, 4.23; N, 6.81.

EXAMPLE 18

Preparation of
1-Methyl-3-{N-[β-(3,4-diacetoxyphenyl)ethyl]}carbamoylpyridinium iodide (compound 6b)

To a solution of 1.71 g (5 mmol) of 3-{N-[β-(3,4-diacetoxyphenyl)ethyl]}carbamoylpyridine (prepared like compound 8c), 1.41 g (10 mmol) of methyl iodide were added and the mixture was refluxed overnight under stirring. The acetone solution was then decanted from the insoluble oily residue. Ether was added to the acetone solution and the solid which separated was crystallized from acetone/ether. Yield, 1.9 g (78%) of yellow crystalline needles, m.p. 171°–173° C. U.V. (methanol) 215, 265 nm; NMR (D$_2$O) δ 8.86–7.63 (ms, 4H, C$_5$H$_4$N$^+$), 6.66 (bs, 3H, C$_6$H$_3$), 4.4 (s, 3H, —N$^+$—CH$_3$), 3.50 (t, 2H, —N—CH$_2$), 3.03 (t, 2H, CH$_2$), 2.21 (bs, 6H, 2COCH$_3$). Anal. Calcd for C$_{19}$H$_{21}$IN$_2$O$_5$: C, 47.12; H, 4.37; N, 5.78. Found: C, 47.23; H, 4.38; N, 5.78.

EXAMPLE 19

Preparation of
1-Methyl-3-{N-[β-(3,4-dipivalyloxyphenyl)ethyl]}carbamoylpyridinium iodide (compound 6c)

To a solution of 5.0 g (11.7 mmol) of compound 8c in 20 ml of acetone, 3.3 g (23.4 mmol) of methyl iodide were added and the mixture was refluxed under stirring for 6 hrs, then cooled. The orange crystalline solid which separated was filtered, washed with ether and crystallized for acetone/ether. Yield, 5.6 g (85%), m.p. 163°–165° C. U.V. (buffer pH 7.4) 270, 215 nm. NMR (DMSO-d$_6$) δ 7.68–7.06 (ms, 7H, C$_5$N$_4$N$^+$+C$_6$H$_3$+NH), 4.56 (s, 3H, —N$^+$—CH$_3$), 3.42 (q, 2H, J=7 Hz, —N—CH$_2$), 3.19 (t, 2H, J=7 Hz, CH$_2$), 1.32 (s, 18H, 2—C(CH$_3$)$_3$). Anal. Calcd for C$_{25}$H$_{33}$IN$_2$O$_5$: C, 52.82; H, 5.85; N, 4.92. Found: C, 52.76; H, 5.87; N, 4.90

EXAMPLE 20

Preparation of
1-Methyl-3-{N-[β-(4-hydroxy-3-methoxyphenyl)ethyl]}carbamoylpyridinium iodide (compound 9)

N-nicotinoyl-3-methoxytyramine was prepared by following the procedure used for the preparation of compound 7. The isolated crude amide was quaternized directly with methyl iodide following the method used for the preparation of compound 6a. Crystallization from methanol gave a yellow crystalline compound, m.p. 192°–194° C. with overall yield of 84%, calculated on the basis of 3-methoxytyramine starting material. NMR (D$_2$O) closely similar to that of 6a except for the singlet at δ 3.66 for OCH$_3$.

EXAMPLE 21

Preparation of
1-Methyl-3-{N-[β-(3,4-dihydroxyphenyl)ethyl]}carbamoyl-1,4-dihydropyridine (compound 5a)

To an ice cold solution of 1.0 g (2.5 mmol) of compound 6a in 200 ml of deaerated water, 1.26 g (15 mmol) sodium bicarbonate were added. Nitrogen was bubbled into the mixture and 1.74 g (10 mmol) of sodium dithionite were added gradually to the mixture under stirring. Stirring was continued for 1 hr and the mixture was then extracted twice with 50 ml of ether. The ether extract was washed with water, dried with anhydrous Na$_2$SO$_4$ and evaporated to dryness.

Yield, 0.36 g (54%) of a yellow solid, m.p. 90°–93° C. (dec.) which gave a green color with ferric chloride test and reduced alcoholic AgNO$_3$ instantly. UV (CH$_3$OH) 220, 350 nm. NMR (CDCl$_3$/D$_2$O) δ 7.2–6.9 (ms, 4H, C$_6$H$_3$+C$_2$ dihydropyridine proton), 5.6 (m, 1H, C$_6$ dihydropyridine proton), 4.6–4.4 (m, 1H, C$_5$ dihydropyridine proton), 3.4 (m, 2H, —N—CH$_2$), 3.1–2.7 (m, 7H, N—CH$_3$+C$_4$ dihydropyridine protons+CH$_2$). Anal. Calcd for C$_{15}$H$_{18}$N$_2$O$_3$.½H$_2$O: C, 63.59; H, 6.76; N, 9.88. Found: C, 63.56; H, 6.85; N, 9.72.

EXAMPLE 22

Preparation of 1-Methyl-3-{N-[β-(3,4-diacetoxyphenyl)ethyl}carbamoyl-1,4-dihydropyridine (compound 5b)

To an ice cold solution of 1.4 g (3 mmol) of compound 6b in 200 ml of deaerated water, 1.5 g (18 mmol) of sodium bicarbonate was added. A stream of $N_2$ was bubbled into the mixture and 2.1 g (12 mmol) of sodium dithionite were gradually added under stirring. Stirring was continued for 30 min and then the mixture was extracted with ethyl acetate. The extract was washed with water, dried with anhydrous $Na_2SO_4$ and evaporated to dryness. The yellowish semisolid mass remaining gave a faint green color with ferric chloride test indicating partial hydrolysis of the ester functions. It reduced alcoholic silver nitrate instantly. U.V. ($CH_3OH$) 220, 273 and 355 nm; NMR ($CDCl_3/D_2O$) δ 7.13-6.80 (ms, 4H, $C_6H_3+C_2$ dihydropyridine proton), 5.53 (doublet of doublets, 1H, $C_6$ dihydropyridine proton), 4.63-4.46 (m, 1H, $C_5$ dihydropyridine proton), 3.33 (t, 2H, J=6.5 Hz, —N—$CH_2$), 3.06-2.66 (m, 7H, —N—$CH_3$+$C_4$ dihydropyridine proton+$CH_2$), 1.8 (s, ≅6H, 2$COCH_3$).

EXAMPLE 23

Preparation of 1-Methyl-3-{N-[β-(3,4-dipivalyloxyphenyl)ethyl]}carbamoyl-1,4-dihydropyridine (compound 5c)

To a cold mixture of 2.0 g (3.5 mmol) of compound 6c, 200 ml of deaerated water and 100 ml of ethyl acetate, 1.14 g (14 mmol) of sodium bicarbonate and 2.43 g (14 mmol) of sodium dithionite were added. The mixture was stirred under $N_2$ for 20 mins. The ethyl acetate layer was separated and the aqueous layer was re-extracted with 100 ml of ethyl acetate. The combined ethyl acetate was washed with cold deaerated water, dried over anhydrous $Na_2SO_4$ and distilled on rotovapor. The viscous yellow oily residue was dissolved in 5 ml of acetone, filtered under $N_2$ atmosphere and then evaporated under reduced pressure. The solid residue was dried under vacuum over $P_2O_5$ in $N_2$ atmosphere. It reduced alcoholic $AgNO_3$ instantaneously and gave no color with $FeCl_3$ test. Yield, 1.3 g (83%) m.p. 45°-48° C.; UV ($CH_3OH$) 210 and 355 nm; NMR ($CDCl_3$) δ 7.04-6.92 (m, 4H, $C_6H_3+C_2$ dihydropyridine proton), 5.71-5.61 (doublet of doublets, 1H, $C_6$ dihydropyridine proton), 4.81 (bs, 1H, CONH), 4.60-4.51 (m, 1H, $C_5$ dihydropyridine proton), 3.53 (q, 2H, J=6.3 Hz, —N—$CH_2$), 2.36 (bs, 2H, $C_4$ dihydropyridine proton), 2.91 (s, 3H, N—$CH_3$), 2.79 (t, 2H, J=6.3 Hz, $CH_2$), 1.33 (s, 18H, CO—C($CH_3$)$_3$). Anal. Calcd for $C_{25}H_{34}N_2O_5 \cdot 1\frac{1}{2}H_2O$: C, 63.9; H, 7.93; N, 5.96. Found: C, 63.4; H, 7.81; N, 5.94.

EXAMPLE 24

Preparation of 1-Methyl-3-{N-[β-(4-hydroxy-3-methoxyphenyl)ethyl]}carbamoyl-1,4-dihydropyridine (compound 10)

This compound was prepared following the same method as for the preparation of compound 5c. The crude solid obtained showed the same NMR ($CDCl_3/D_2O$) pattern as compound 5a, except for a peak at δ 3.5 for the $OCH_3$ protons. It was sufficiently pure for the determination of its retention time following the HPLC method of analysis detailed in Example 37 below. No trials were made for its further crystallization or elemental analysis.

EXAMPLE 25

Preparation of N-Nicotinoyltyramine

To an ice cold suspension of 3.69 g (0.03 mol) nicotinic acid in a solution of 5.2 g (0.03 mol) tyramine hydrochloride in 100 ml of pyridine, 6.18 g (0.03 mol) of dicyclohexylcarbodiimide (DCC) were gradually added while stirring. Stirring was continued at room temperature for 24 hrs and the formed dicyclohexylurea was removed by filtration. The pyridine was removed by distillation in vacuo and the residue was triturated with cold water, filtered and crystallized from 50% aqueous methanol. Yield, 6.25 g (86%), m.p. 179°-181° C. PMR (DMSO-$d_6$/$D_2O$) δ 9.0-8.66 (m, 2H, $C_2$ and $C_6$ pyridine protons), 8.33-8.10 (m, 1H, $C_4$ pyridine proton), 7.66-7.46 (m, 1H, $C_5$ pyridine proton), 7.23-6.70 (m, rH, $C_6H_4$), 3.56

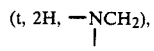
(t, 2H, —N$CH_2$), 2.90 (t, 2H, $CH_2$). Anal. ($C_{14}H_{14}N_2O_2$) C, H, N.

EXAMPLE 26

Preparation of 3-{N-[β-(4-pivalyloxyphenyl)ethyl]}carbamoylpyridine

To an ice cold suspension of 4.84 g (0.02 mol) N-nicotinoyltyramine in 100 ml chloroform, 3.6 g (0.03 mol) of trimethylacetyl chloride were dropped while stirring. The mixture was refluxed overnight and the non-reacted nicotinoyltyramine was filtered off. The filtrate was washed with water until free from chloride ions, washed once with 5% solution of $NaHCO_3$ and then with water. Chloroform was evaporated on rotavap and the residue was crystallized from ether/pet. ether. Yield 3.9 g (60%), m.p. 80°-82° C. PMR ($CDCl_3$) δ 8.66-6.93 (m, 8H, $C_5H_4N+C_6H_4$), 3.56

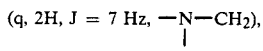
(q, 2H, J = 7 Hz, —N—$CH_2$), 2.86 (5, 2H, J=7 Hz, $CH_2$), 1.33 (s, 9H, C—($CH_3$)$_3$).

EXAMPLE 27

Preparation of 1-Methyl-3-{N-[β-(4-hydroxyphenyl)ethyl]}carbamoylpyridinium iodide To a solution of 1.21 g (5 mmol) of nicotinoyltyramine in 10 ml of acetone, 1.41 g (10 mmol) of methyl iodide were added and the mixture was refluxed while stirring for 6 hrs. The fine, yellow solid which separated was filtered and crystallized from methanol ether. Yield 1.78 g (93%), m.p. 208°-210° C. PMR (DMSO-$d_6$/$D_2O$) δ 9.23-8.26 (m, 4H, $C_5H_4N^+$), 7.33-6.83 (m, 4H, $C_6H_4$), 4.50

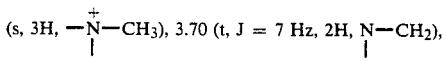
(s, 3H, —$\overset{+}{N}$—$CH_3$), 3.70 (t, J = 7 Hz, 2H, N—$CH_2$), 2.93 (t, J=7 Hz, 2H, $CH_2$).

EXAMPLE 28

Preparation of
1-Methyl-3-{N-[β-(4-pivalyloxyphenyl)ethyl]}carbamoylpyridinium iodide To a solution of 1.63 g (5 mmol) of the product of Example 26 in 10 ml of acetone, 1.41 g (10 mmol) methyl iodide were added and the mixture was refluxed overnight while stirring. The acetone layer was separated by decantation and the yellowish, oily residue was crystallized from methanol/ether.

Yield, 1.94 g (83%), m.p. 155°–157° C. PMR ($D_2O$) δ 9.16–8.00 (m, 4H, $C_5H_4N^+$), 7.33–6.83 (m, 4H, $C_6H_4$), 4.40 (s, 3H, $N^+$—$CH_3$), 3.5

(t, 2H, J = 7 Hz, —N—$CH_2$),
|

2.90 (t, 2H, J=7 Hz, $CH_2$), 1.30 (s, 9H, C—$(CH_3)_3$). Anal. ($C_{20}H_{25}N_2O_3I$) C, H, N.

EXAMPLE 29

Preparation of
1-Methyl-3-{N-[β-(4-hydroxyphenyl)ethyl]}carbamoyl-1,4-dihydropyridine To an ice cold solution of 1.15 g (3 mmol) of the product of Example 27 in 200 ml of deaerated water, 1.5 g (18 mmol) sodium bicarbonate were added. While the mixture was bubbled with $N_2$ gas, 2.09 g (12 mmol) of sodium dithionite were gradually added to the mixture. The mixture was stirred under $N_2$ for 1 hr and then extracted twice, each with 100 ml of ethyl acetate. The combined extract was washed with water, dried over anhydrous $Na_2SO_4$ and distilled on rotovap. Yield, 0.38 g (50%) of yellowish semisolid which reduced alcoholic $AgNO_3TS$ instantaneously. (PMR as expected.)

EXAMPLE 30

Preparation of
1-Methyl-3-{N-[β-4-pivalyloxyphenyl)}carbamoyl-1,4-dihydropyridine To an ice cold mixture of 2.34 g (5 mmol) of the product of Example 28, 200 ml of deaerated water and 100 ml of ethyl acetate, 1.63 g (20 mmol) sodium bicarbonate and 3.47 g (20 mmol) sodium dithionite were added while stirring the mixture. Stirring was continued under $N_2$ gas for 30 min. The ethyl acetate layer was separated and the aqueous layer was extracted with 100 ml of ethyl acetate. The combined ethyl acetate extract was washed with 100 ml cold deaerated water, dried over anhydrous $Na_2SO_4$ and evaporated on rotavap. The viscous, yellow residue was dissolved in 5 ml of acetone, filtered under $N_2$ gas through folded filter paper and distilled on rotavap. The solid residue was dried under vacuo over $P_2O_5$ in $N_2$ atmosphere. It reduced alcoholic $AgNO_3$ instantaneously. Yield, 1.06 g (62%). (PMR as expected.)

EXAMPLE 31

Preparation of 3,5-Pyridinedicarboxylic acid didecyl ester hydrochloride 3,5-Pyridinedicarboxylic acid (9.6 g, 0.06 mole) was converted to the diacid chloride by treatment with excess $SOCl_2$. The mixture was refluxed at 100° C. for 6 hrs. Excess $SOCl_2$ was distilled under reduced pressure and 25 ml of decyl alcohol dissolved in benzene were added. The solution was refluxed for 5 hrs after which benzene was distilled and the residue dissolved in ethyl ether. The organic phase was extracted with bicarbonate solution and later dried over $Na_2SO_4$. The ethyl ether solution was acidified with HCl (gas) and 24.2 g of compound (95% yield, m.p. 80°–90° C.) were obtained. 1H (NMR) $CDCl_3/d_6DMSO$ δ9.3 (3H, bs), 8.7 (1H, bs), 4.3 (4H, bT) and 1.4 (38H, bm) ppm.

EXAMPLE 32

Preparation of Didecyl
3,5-dicarboxylate-1-methylpyridinium iodide

The product of Example 31 (10 g, 0.025 mole) was dissolved in an ethyl ether/bicarbonate solution. The organic phase was rinsed with water and dried over $Na_2SO_4$. The solvent was evaporated and the residue was dissolved in acetone and an excess of methyl iodide was added. The solution was refluxed for 8 hrs, after which the solvent was evaporated and ethyl ether was added to the residue. A yellow solid was obtained which was filtered and rinsed with more ethyl ether. The solid was recrystallized from a minimum amount of ethyl acetate to yield 12.5 g (85%) m.p. 104°–105° C. Analytical data: Theory: C, 57.04; H, 8.21. Found: C, 57.18; H, 8.09. Spectrophotometric data in methanol: λ219 $\epsilon=2.7\times10^4$ l/mol cm; λ277 $\epsilon=3.6\times10^3$ l/mol cm.

EXAMPLE 33

(i) Oxidation by Hydrogen Peroxide

To 10 ml of 30% $H_2O_2$ was added 0.2 g of the dihydropyridine derivative (products of Examples 4, 5, 10 or 13). The mixture was stirred and samples were taken to check the UV spectrum. Complete oxidation to the corresponding quaternary salts was observed.

(ii) Oxidation by Silver Nitrate

To 5 ml of saturated methanolic $AgNO_3$ solution was added 1 ml of 5% methanolic solution of the dihydropyridine derivative. The mixture was shaken and left for 5 min for complete precipitation of silver, centrifuged and an aliquot was taken to check the UV spectrum. Complete oxidation to the quaternary salts was observed.

(iii) Calibration Curves

UV study of the compounds prepared in Examples 2–5, 9, 10, 12 and 13 revealed that they obey Beer's Law with good coefficients and at a wide range of dilution levels. The study was done at 350 nm for the dihydro derivatives and at 262 and 220 nm for all the quaternary and dihydro.

EXAMPLE 34

Kinetics of Oxidation of the Dihydro Derivatives

In Plasma: 0.2 ml ($6.25\times10^{-4}$M) freshly prepared solution of the dihydro derivative in methyl alcohol was diluted to 10 ml with 20% plasma (diluted with phosphate buffer pH 7.4). The solution was kept at 37° C. and UV spectrum was scanned from 400 nm to 300 nm every 10 min for 2 hrs against reference made by dilution of 0.2 ml methyl alcohol with 20% plasma to 10 ml.

In Whole Blood: In each of 5 tubes, 0.1 ml of $10\times10^{-4}$M methanolic solution of the freshly prepared dihydro derivative, was added to 2 ml of fresh heparinized whole human blood and the tubes were kept at 37° C. in a water bath. At the end of the time period to be investigated, 8 ml of acetonitrile was added, and the tubes were shaken vigorously and centrifuged. The extension of the supernatant solution at 350 nm was measured. A reference sample was made by addition of 0.1 ml of methyl alcohol instead of the sample solution following the same procedure.

In Brain Homogenate: 2.0 g of rat brain tissue were homogenized in 10 ml of phosphate buffer, pH 7.4. The homogenate was centrifuged for 15 min at 3000 rpm, decanted, heated in a water bath at 50° C. for 5 min and then centrifuged again. The supernatant solution was diluted to 100 ml with phosphate buffer, pH 7.4.

Reference Sample: 0.2 ml of methyl alcohol was diluted to 10 ml with the brain homogenate solution, and the solution was used to record the base line on a Cary 219 spectrophotometer and as a reference for the dihydro derivative sample solution.

Dihydro Derivative Sample Solutions: 0.2 ml of $6.25 \times 10^{-4}$ methanolic solution of the freshly prepared dihydro derivative was diluted to 10 ml with the brain homogenate solution. The mixture was scanned at 37° C. from 400 nm to 300 nm every 10 min for 2 hrs on a Cary 219 spectrophotometer.

In Liver Homogenate

Liver Homogenate Solution: 5.0 g of rat liver tissue were homogenized in 50 ml of phosphate buffer, pH 7.4. The homogenate was centrifuged, decanted, heated in a water bath at 50° C. for 5 min and then centrifuged again. The supernatant homogenate was diluted to 250 ml with phosphate buffer, pH 7.4.

Reference Sample: 0.2 ml of methyl alcohol was diluted to 10 ml with the liver homogenate solution and the solution was used to record the base line on a Cary 219 spectrophotometer and as a reference for the dihydro derivative sample solution.

Dihydro Derivative Sample Solution: 0.2 ml of $6.25 \times 10^{-4}$M solution of the freshly prepared dihydro derivative in methyl alcohol was diluted to 10 ml with liver homogenate solution. The mixture was scanned at 37° C. from 400 nm to 300 nm every 5 min for 1 hr.

TABLE II

| | Kinetics of Oxidation | | | |
|---|---|---|---|---|
| | Comp. | | | |
| | 1-Methyl-3-(N—β-phenethyl)-carbamoyl-1,4-dihydropyridine | | 1-Benzyl-3-(N—β-phenethyl)-carbomyl-1,4-dihydropyridine | |
| Medium | K sec$^{-1}$ | t½ m | K sec$^{-1}$ | t½ m |
| Plasma | $1.8 \times 10^{-4}$ | 64.2 | $7.4 \times 10^{-5}$ | 156.1 |
| | n = 13 r = .998 | | n = 12 r = .998 | |
| Whole Blood | $8.4 \times 10^{-4}$ | 13.7 | $4.7 \times 10^{-4}$ | 24.4 |
| | n = 5 r = .952 | | n = 5 r = .974 | |
| Brain Homogenate | $4.1 \times 10^{-4}$ | 28.2 | $2.1 \times 10^{-4}$ | 55 |
| | n = 8 r = .996 | | n = 13 r = .999 | |
| Liver Homogenate | $8.0 \times 10^{-4}$ | 14.4 | $7.5 \times 10^{-4}$ | 15.3 |
| | n = 7 r = .999 | | n = 5 r = .998 | |
| | Comp. | | | |
| | 1-Methyl-3,5-di(N—β-phenethyl)-carbamoyl-1,4-dihydropyridene | | 5-Carboethoxy-1-methyl-3-(N—β-phenethyl)carbomyl-1,4-dihydropyridine | |
| Medium | | | | |
| Brain Homogenate | $8.4 \times 10^{-6}$ | 22.9 | $1.74 \times 10^{-5}$ | 11.1 h |
| | n = 6 r = .997 | | n = 6 r = .993 | |
| Whole Blood | $4.9 \times 10^{-5}$ | 3.9 | $1.13 \times 10^{-4}$ | 1.7 h |
| | n = 5 r = .949 | | n = 5 r = .972 | |

EXAMPLE 35

In Vivo Study on 1-Methyl-3-(N-β-phenethyl)carbamoyl-1,4-dihydropyridine

A group of rats of average weight (about 350 g) was injected through the jugular with a solution of the freshly prepared dihydro derivative in DMSO (0.05 g/ml solution) in a dose level of 125 mg/kg animal body weight. After the appropriate time period, 1 ml of blood was withdrawn from the heart and the animal was perfused with 20 ml of saline solution. The animal was decapitated. The brains were weighed, kept in the refrigerator overnight and homogenized in 2 ml of water. Acetonitrile, 8 ml, was added and the mixture was homogenized again and then centrifuged. The amount of the quaternary was determined from the HPLC spectrum in relation to a recovery experiment made by adding a specific amount of the quaternary to a blank brain and hybrid in the same manner of homogenization and extraction.

| Brain Results: | | | |
|---|---|---|---|
| t | Normalized value amt in mg/weight lb in grams | t | Normalized value |
| 5 | .055 | 40 | .1132 |
| 5 | .0423 | 47 | .125 |
| 10 | .099 | 66 | .148 |
| 15 | .0553 | 90 | .1626 |
| 15 | .100 | 90 | .1294 |
| 20 | .0935 | 145 | .0949 |
| 21 | .0743 | 180 | .0838 |
| 25 | .101 | 185 | .1001 |
| 30 | .1242 | 210 | .0707 |
| 32 | .095 | 220 | .0753 |
| 33 | .0778 | | |

Blood Concentration: The blood withdrawn was left in the refrigerator overnight and 3 ml of saline was added and the mixture shaken, then 17 ml of acetonitrile was added and the mixture was shaken vigorously for 1 min and then centrifuged. The supernatant solution was injected directly into the HPLC.

| Results: | |
|---|---|
| t (m) | mg/ml |
| 25 | .0235 |
| 40 | .0117 |
| 21 | .0205 |
| 33 | .0058 |
| 5 | .0294 |
| 75 | .0058 |
| 40 | .0088 |
| 15 | .0235 |

EXAMPLE 36

Kinetics of Disappearance of the Quaternary from Brain Homogenate

A fresh perfused rat brain was homogenized in 20 ml of phosphate buffer, pH 7.4. A solution of 10.0 mg of 1-methyl-3-(N-β-phenethyl)carbamoylpyridinium iodide in 2 ml aqueous methanol (1:1) was added and the thoroughly mixed mixture was kept at 37° C. in a waterbath. At each time period, 1 ml of the mixture was taken and shaken thoroughly with 8 ml of acetonitrile, centrifuged and injected to HPLC. The amount of the quaternary in the sample was determined in comparison with a sample taken at time 0. Linear regression of t against log C shows that $K=4.8\times10^{-5}$ sec$^{-1}$, $t\frac{1}{2}=3.50$ h (in vivo exp.) which was found to be $K=8.45\times10^{-5}$ sec$^{-1}$, $t\frac{1}{2}=2.1$ h, $r=0.957$.

Studies of the Dopamine Derivatives

EXAMPLE 37

Analytical Methods

A high pressure liquid chromatography (HPLC) method was developed for the studies of the degradation of the dihydropyridine dopamine derivative. The chromatographic analysis was performed on a component system consisting of a Waters Associate Model 6000A solvent delivery system, Model U6K injector and Model 440 dual channel absorbance detector operated at 254 and 280 nm. A 30 cm×3.9 mm (internal diameter) reverse phase $\mu$Bondapak $C_{18}$ column (Waters Associates), operated at ambient temperature, was used for all separations. The mobile phase used for the separation of the dihydropyridine derivative, its degradation products and oxidation products consisted of 0.005M solution of 1-heptanesulfonic acid sodium salt (PIC B-7 Eastman Kodak) in $CH_3CN$; 0.01M aqueous dibasic ammonium phosphate (2.5:1). At a flow rate of 2.0 ml/min, 6a had a retention time of 5.1 min; 6c, 11.8 min; 5a, 1.7 min; 5c, 3:1 min. A peak was always shown at a retention time of 2.2 min which is believed to be a monodeacylated dihydropyridine derivative, since it eventually did result in 6a.

EXAMPLE 38

Determination of the Enzymatic Hydrolytic Cleavage and Rate of Oxidation of Compound 5c In Human Plasma The freshly collected plasma used was obtained at the Civitan Regional Blood Center, Inc. (Gainesville, Fla.) and contained about 80% plasma diluted with anticoagulant citrate phosphate dextrose solution U.S.P. The plasma was stored in a refrigerator and used the next day. One hundred $\mu$l of a freshly prepared 0.61M solution of compound 5c in methanol was added to 20 ml of plasma, previously equilibrated to 37° C. in a water bath and mixed thoroughly to result in an initial concentration of $3.05\times10^{-3}$ moles/liter. One ml samples of plasma were withdrawn from the test medium, added immediately to 5 ml of ice cold acetonitrile, shaken vigorously and placed in a freezer. When all samples had been collected, they were centrifuged and the supernatants were filtered through Whatman 1 filter papers and analyzed by HPLC.

In Human Blood

The freshly collected heparinized blood was obtained at the Civitan Regional Blood Center, Inc. (Gainesville, Fla.). The blood was stored in a refrigerator and used the next day. One hundred $\mu$l of a freshly prepared 0.19 solution of compound 5c in methanol was added to 20 ml of blood, previously equilibrated to 37° C. in a water bath and mixed thoroughly to result in an initial concentration of $9\times10^{-4}$ moles/liter. One ml samples of blood were withdrawn from the test medium every 5 minutes, added immediately to 5 ml of ice cold acetonitrile, shaken vigorously and placed in a freezer. When all samples had been collected, they were centrifuged and the supernatants were filtered using Whatman 4 filter paper and analyzed by HPLC.

In Rat Brain Homogenate

The brain homogenate was prepared by the following method. Five Sprague-Dawley rats were killed by decapitation and the brains were removed, weighed (total weight 9.85 g) and homogenized in 49.3 ml of aqueous 0.11M phosphate buffer, pH 7.4. The homogenate was centrifuged and the supernatant was used for the test. 100 $\mu$l of 0.18M solution of compound 5c was mixed with 10 ml of homogenate, previously equilibrated to 37° C. in a water bath, to result in an initial concentration of $1.8\times10^{-3}$ moles/liter. Samples of 1.0 ml were withdrawn every 10 minutes from the test medium, added immediately to 5 ml of ice cold acetonitrile and placed in a freezer. When all samples had been collected, they were centrifuged. Each supernatant was filtered through two Whatman 1 filter papers and analyzed by HPLC.

In Rat Liver Homogenate

The liver homogenate was prepared by the following method. Three Sprague-Dawley rats were killed by decapitation and the livers were removed, weighed and homogenized by tissue homogenizer in 0.11M aqueous phosphate buffer, pH 7.4, to make 20% liver homogenate. The homogenate was centrifuged and the supernatant was used for the test. 100 $\mu$l of 0.1M solution of compound 5c in methanol were mixed with 20 ml of the homogenate, previously equilibrated to 37° C. in a water bath, to result in an initial concentration of $9\times10^{-4}$ moles/liter. Samples of 1.0 ml were withdrawn every 5 minutes from the test medium, added immediately to 5 ml of ice cold acetonitrile, shaken vigorously and placed in a freezer. When all samples had been collected, they were centrifuged and each supernatant was filtered through Whatman 1 filter paper and analyzed by HPLC.

Rates of disappearance (overall oxidation and degradation) of compound 5c:
(i) in Plasma:
  $R=2.25\times10^{-4}$ sec$^{-1}$
  $t\frac{1}{2}=51.3$ min
  $r=0.998$
  $n=(3\times6)$
(ii) In 20% Brain Homogenate:
  $R=6.7\times10^{-4}$ sec$^{-1}$
  $t\frac{1}{2}=17.2$ min
  $r=0.996$
  $n=(3\times6)$
(iii) In Blood:
  $R=6.3\times10^{-4}$
  $t\frac{1}{2}=18.2$ min
  $r=0.997$
  $n=(3\times7)$
(iv) In Liver:
  $R=193\times10^{-3}$
  $t\frac{1}{2}=5.9$ min
  $r=0.950$
  $n=(3\times5)$

EXAMPLE 39

Determination of Concentration of Compound 6a in Brain and Blood after Parenteral Administration of 5c Male Sprague-Dawley rats of average weight of $150\pm10$ g were used. The rats were anesthetized with IM injection of Inovar and the jugular was exposed.

Compound 5c was injected intrajugularly in the form of 10% solution in DMSO at a dose of 64.2 mg/kg (equivalent to 50 mg/kg compound 6a). The injection was given at a rate of 24 μl/min using a calibrated infusion pump. After appropriate time periods, 1 ml of blood was withdrawn from the heart and dropped immediately into a tared tube containing 3 ml acetonitrile, which was afterwards weighed to determine the weight of the blood taken. The animal was then perfused with 20 ml of saline solution, decapitated and the brain was removed. The weighed brain was homogenized with 0.5 ml of distilled water, 3 ml of acetonitrile was added and the mixture was rehomogenized thoroughly, centrifuged, filtered and then analyzed for compound 6a using the HPLC method. The tubes containing the blood were shaken vigorously, centrifuged, decanted and also analyzed for compound 6a using the HPLC method. Quantitation was done by using a recovery standard curve obtained by introducing a known amount of 6a in either brain homogenate or blood and then treated in the same manner. See FIG. 6 and the discussion thereof hereinabove.

EXAMPLE 40

Pharmacological studies

In vivo effect on pituitary prolactin secretion

Adult male rats (Charles Rivers, CD-1) weighing 200 to 225 g were provided food and water ad libitum for at least one week period to experimentation. To elevate serum prolactin levels, each rat received a single s.c. implant of a Silastic tube (1.57 mm interior diameter, 5 mm×3.15 mm overall size) packed with crystalline 17-β-estradiol. Two days later the rats were lightly anesthetized with ether and a small incision was made over the right jugular vein for intravenous (I.V.) administration of the test drugs. Compound 6a was injected at a dose of 1 mg/kg body weight/ml saline and groups of six rats were decapitated at 15, 30, 60 and 120 min later to collect blood samples. Control rats (time 0) received an I.V. injection of the saline vehicle and were decapitated 30 min later. Compound 5c was dissolved in 10% ethanol in saline and was injected IV. Rats were decapitated at 15, 30 and 120 min later. Control (time 0) animals received the 10% ethanol vehicle and were sampled 30 min later.

Trunk blood was collected, allowed to clot for 2 h and the serum was separated and stored at −20° C. for subsequent assay for prolactin concentrations. Each serum sample was assayed in duplicate by the double-antibody radioimmunoassay procedure described by the National Pituitary Agency Hormone Distribution Program. Serum prolactin concentrations are expressed in terms of the PRL-RP-2 reference preparation provided. The intraassay coefficient of variation for 10 replicate samples of pooled serum obtained from male rats was 13.8%.

The effects of compounds 5c and 6a on serum prolactin concentrations were evaluated by one-way analysis of variance and Student-Newman Keuls tests. A probability level of less than 0.05 was selected for significance. See FIG. 7 and the discussion thereof hereinabove.

The foregoing procedure was repeated, except for the following changes:

Compound 5c (the dihydropyridine dipivalyl ester derivative of dopamine) was dissolved in 10% dimethylsulfoxide in saline and administered intravenously at a dosage of 1 mg/kg to groups of five or six rats; the rats were decapitated at 1, 2, 4, 8, 12 and 24 hours following administration. Compound 5a (the dihydropyridine dihydroxy derivative) was dissolved in 10% dimethylsulfoxide and administered intravenously at a dosage of 1 mg/kg to groups of six rats; the rats were decapitated at 1, 2 and 4 hours after administration. Control groups of animals received 10% dimethylsulfoxide in saline and were sacrificed 2 hours later. Intravenous administration of 5c was found to maintain a dramatic reduction in serum prolactin concentrations for at least 12 hours following administration. Again, the rapid onset and very prolonged inhibitory effects of 5c on prolactin secretion is consistent with the time course of the appearance of 6a in the brain following administration of 5c and the "trapping" of 6a in the brain. Compound 5a did produce a significant reduction in serum prolactin concentration at 2 hours, but by 4 hours the prolactin levels had increased substantially; thus 5a did not show as prolonged an inhibitory effect as that exhibited by 5c.

In vitro evaluation of the prolactin inhibitory effect of 6a

Adult female rats (Charles Rivers Lab.) weighing 225–250 g were maintained on food and water ad libitum. Animals were sacrificed by decapitation; their pituitary glands were quickly removed from the cranium. The anterior pituitary (AP) of each animal was dissected into two equal halves and placed into incubation media. (Gibco's Minimal Essential Media supplied by Grand Island Biological Co. was used.) The incubation was conducted at 37° C., under continuous aeration (95% $O_2$, 5% $CO_2$); the pH was 7.2. After one hour of preincubation, the media were discarded and replaced with fresh ones containing either DA ($2\times10^{-8}$M), 6a ($2\times10^{-8}$) or ascorbic acid ($10^{-4}$M). In all cases, one-half of AP received the test drug; the other, the ascorbate control. After one hour, samples were taken from the media and the remaining media were discarded. Fresh media containing DA ($2\times10^{-7}$), 6a ($2\times10^{-7}$) and ascorbate, respectively, were then added. One hour later, the second samples were taken. After the 3 h incubation period, each half AP's were weighed.

The samples were diluted 1:50 with phosphate buffered saline and then assayed in triplicate by the radioimmunoassay method described. The data are given as ng prolactin released/mg wet weight/h. Paired Student's T-test was used to evaluate the significance of the inhibitory effects of the test drugs on prolactin secretion. The control AP half and the drug treated half were employed in each paired comparison. See TABLE I and the discussion thereof hereinabove.

Further in vitro evaluation of the prolactin inhibitory effect of 6a vs. dopamine Eighteen female rats (Charles River Lab.) weighing 225–250 g were maintained on food and water ad libitum for one week. Animals were sacrificed by decapitation, the pituitary gland was removed from the cranium and the anterior pituitary (AP) was separated from the posterior and intermediate lobes. The AP was dissected into two equal halves and each half was placed in an incubation media consisting of Gibco's Minimal Essential Media containing 25 mM Hepes Buffer (Grand Island Biological Company, Grand Island, N.Y.). The media was maintained at a pH of 7.2 under continuous aeration (95% $O_2$, 5% $CO_2$) at a temperature of 37° C. Following a one hour preincubation period, the media were discarded and replaced with fresh media containing either DA ($10^{-6}$M) or 6a ($10^{-6}$M). The control AP half received media containing $10^{-4}$M ascorbic acid, the vehicle for the drugs. After one hour, the media were sampled and the remaining media were discarded. Fresh media containing DA ($10^{-5}$M) or 6a ($10^{-5}$M) or ascorbic acid ($10^{-4}$M) were then added to the AP halves. One hour later, second samples were taken and the AP halves were weighed to the nearest tenth of a milligram.

Samples of media were diluted 1:50 with phosphate buffered saline and then assayed in triplicate by radioimmunoassay methods. Data are expressed as ng prolactin released/mg net weight/h. Paired student's "t" tests were used to evaluate the significance of the effects of the drugs on the prolactin release rate. The control AP half and its respective drug-treated AP half were employed in each paired comparison. The results are tabulated below:

| Prolactin ng/mg/h | | | | | | | |
|---|---|---|---|---|---|---|---|
| Dopamine (DA) | | | | 6a | | | |
| control | DA ($10^{-6}$ M) | control | DA ($10^{-5}$ M) | control | 6a ($10^{-6}$ M) | control | 6a ($10^{-5}$ M) |
| 306 ± 50 | 128 ± 22 | 219 ± 26 | 59 ± 20 | 349 ± 49 | 301 ± 51 | 205 ± 25 | 206 ± 28 |

Thus, control AP halves released prolactin at a rate of 300 to 350 ng/mg wet weight/h during the first incubation period and about 200 ng/mg wet weight/h during the second incubation period. Dopamine (DA) concentration of $10^{-6}$ and $10^{-5}$M caused a 58 and 73% decrease in prolactin secretion, respectively. In contrast, N-methylnicotinoyldopamine 6a did not alter the rate of prolactin secretion at concentrations of $10^{-6}$ or $10^{-5}$M. These results confirm the conclusions drawn from the earlier studies which were done at lower concentrations.

In the examples immediately to follow, all melting points were taken on a Mel-Temp apparatus and are not corrected. Elemental analyses were performed at Atlantic Microlab, Inc., Atlanta, Ga. Infrared spectra were determined by using a Beckman Acculab 1 double-beam recording spectrophotometer. NMR spectra were determined by means of Varian T60A or FX100 spectrometers. All chemical shifts reported are in $\delta$ units (parts per million) relative to tetramethylsilane. Ultraviolet absorbance spectra were determined using a Cary Model 210 spectrophotometer. HPLC analyses were performed on a Beckman 345 ternary liquid chromatograph with Model 112 solvent delivery system, Model 210 injector, Model 160 absorbance detector and Model 421 controller.

EXAMPLE 41

Preparation of Testosterone nicotinate (compound 41)

Thionyl chloride (2 ml) was added to 0.7 g (5.7 mmol) of nicotinic acid and the mixture was refluxed for 3 hrs. Excess thionyl chloride was removed under reduced pressure. To the cold residue, 10 ml of dry pyridine was added, followed with 1.44 g (5.0 mmol) of testosterone. The mixture was heated with continuous stirring at 100° C. over a water bath for 4 hrs. Pyridine was removed in vacuo and 5 ml of methanol was added to the oily residue. The mixture was cooled and the solid that crystallized was filtered and recrystallized from methanol/acetone mixture to give 1.4 g of 41 as white crystals (yield 71%), m.p. 187°–188° C. This intermediate was used directly for the synthesis of the chemical delivery system.

EXAMPLE 42

Preparation of 17β-[(1-Methyl-3-pyridiniumcarbonyl)oxy]androst-4-en-3-one iodide (compound 42) (Testosterone-17-nicotinate N-methyl iodide)

To a solution of 1.0 g (2.5 mmol) of testosterone nicotinate 41 in 15 ml of acetone, 1 ml of methyl iodide was added and the mixture was refluxed overnight. The yellow solid that separated was removed by filtration, washed with acetone and crystallized from methanol/ether to yield 1.25 g (92% yield) of pure 42 as yellow crystals, m.p. 215°–220° C. (dec.). U.V. (CH$_3$OH) $\lambda$270 nm (shoulder) $\epsilon$=4579; 240 (shoulder), $\epsilon$=19375. NMR (CDCl$_3$) $\delta$10.0–8.3 (ms, 4H, pyridinium protons), 5.73 (s, 1H, C$_4$ testosterone proton), 4.86 (s, 3H, +N—CH$_3$), 2.40–1.06 (ms, 26H, testosterone skeleton protons). Analysis calculated for C$_{26}$H$_{34}$INO$_3$: C, 58.32; H, 6.40; N. 2.62. Found: C, 58.17; H, 6.48; N, 2.60.

EXAMPLE 43

Preparation of 17β-[(1,4-Dihydro-1-methyl-3-pyridinylcarbonyl)oxy]androst-4-en-3-one (compound 43)

To an ice cold solution of 1.1 g (2 mmol) of testosterone nicotinate N-methyl iodide 42 in 150 ml of deaerated 10% aqueous methanol, 0.67 g (8 mmol) of sodium bicarbonate and 1.37 g (8 mmol) of sodium dithionite were added. The mixture was stirred for 20 minutes and the pale yellow solid which separated was filtered, washed with water and dried over P$_2$O$_5$ under vacuum. Wt. 0.82 g (98% yield), m.p. 172°–175° C. UV (CH$_3$OH) $\lambda$356 nm, $\epsilon$=9511; ir (KBr) 1700, 1660 cm$^{-1}$ (two C=O stretching). NMR (d$_6$-DMSO) $\delta$6.90 (bs, 1H, C$_2$ dihydropyridine proton), 5.83–5.70 (m, 1H, C$_6$ dihydropyridine proton), 5.56 (s, 1H, C$_4$ testosterone proton), 4.7–4.33 (m, 1H, C$_5$ dihydropyridine proton), 3.26 (bs, 2H, C$_4$ dihydropyridine protons), 2.93 (s, 3H, N—CH$_3$), 2.5–0.83 (m, 26H, testosterone skeleton protons with the angular methyl protons at 1.16 and 0.83). Analysis calculated for C$_{26}$H$_{35}$NO$_3$: C, 76.25; H, 8.61; N, 3.42. Found: C, 76.07; H, 8.65; N, 3.38.

EXAMPLE 44

Analytical Methods

A high pressure liquid chromatograph (HPLC) method was developed for the studies of the degradation of the quaternary 42 and dihydropyridine derivative 43. The chromatographic analyses were performed on the Beckman described hereinabove. The absorbance detector was operated at 254 nm. A 15 cm×4.6 mm (internal diameter), 5 μm particle size ultrasphere reverse phase C$_{18}$ column (Altex), operated at ambient temperature, was used for all separations. The mobile phase used for the separation of the dihydropyridine derivative, its degradation products and oxidation products consisted of 0.002M solution of 1-heptanesulfonic acid sodium salt (PIC B-7 Eastman Kodak) in $CH_3CN$, 0.01M aqueous dibasic ammonium phosphate (7:3). At a flow rate of 2.0 ml/min, compound 42 had a retention time of 12 min and compound 43, 5 min. For the analysis of testosterone in the in vivo brain delivery studies, a solvent system consisted of 0.002M solution of PIC B-7 in $CH_3CN$, 0.1M aqueous dibasic ammonium phosphate (1:1). At a flow rate of 2.0 ml/min, testosterone had a retention of 3.3 min and compound 42 had a retention time of 36.5 min (very broad peak).

EXAMPLE 45

Chemical Oxidation Studies (i) By Silver Nitrate 1 ml of 5% methanolic solution of the dihydropyridine compound 43 was added to 5 ml of saturated methanolic $AgNO_3$ solution. The mixture was shaken, left 10 minutes for complete oxidation, centrifuged and the UV spectrum checked.

(ii) By Hydrogen Peroxide

To a standardized solution of $H_2O_2$ (0.18M) contained in a UV cuvette equilibrated at 37° C., a solution of dihydropyridine compound 43 was added to the sample cuvette to make a concentration of approximately $5 \times 10^{-6}M$. The mixture was thoroughly mixed and monitored for the disappearance of the dihydropyridine maximum at 356 nm using a Cary 210 interfaced with an Apple II microprocessor and using an enzyme kinetic software package.

(iii) By Diphenylpicrylhydrazyl Free Radical

To 2 ml of $9.3 \times 10^{-5}M$ solution of 2,2-diphenyl-1-picrylhydrazyl free radical in acetonitrile, equilibrated at 26° C., 20 ml of $1.5 \times 10^{-2}M$ solution of the dihydropydine compound 43 in acetonitrile was added to make a final concentration of $1.48 \times 10^{-4}M$. The mixture was monitored at 515 nm against a reference cuvette containing the same mixture in exactly the same concentrations, but previously prepared and left for at least 10 minutes and used as reference for $A\infty$. The instrument used was a Cary 210 interfaced with an Apple II microprocessor and using an enzyme kinetic software package.

EXAMPLE 46

Determination of In Vitro Rates of Oxidation of Compound 43 in Biological Media:

In Human Plasma

The freshly collected plasma used was obtained at the Civitan Regional Blood Center, Inc. (Gainesville, Fla.) and contained about 80% plasma diluted with anticoagulant citrate phosphate dextrose solution U.S.P. The plasma was stored in a refrigerator and used the next day. 100 μl of a freshly prepared 0.024M solution of compound 43 in DMSO were added to 10 ml plasma, previously equilibrated to 37° C. in a water bath and mixed thoroughly to result in an initial concentration of $2.4 \times 10^{-4}$ moles/liter. One ml samples of plasma were withdrawn every 20 minutes from the test medium, added immediately to 5 ml of ice cold acetonitrile, shaken vigorously and placed in a freezer. When all samples had been collected, they were centrifuged and the supernatants were filtered through nitrocellulose membrane filters (por 0.45) and analyzed by HPLC, following appearance of 42 (Method A).

In Human Blood

The freshly collected heparinized blood was obtained at the Civitan Regional Blood Center, Inc. (Gainesville, Fla.). The blood was stored in a refrigerator and used the next day. 100 μl of a freshly prepared 0.048M solution of compound 43 in DMSO were added to 20 ml blood, previously equilibrated to 37° C. in a water bath and mixed thoroughly, to result in an initial concentration of $2.4 \times 10^{-4}$ moles/liter. One ml samples of blood were withdrawn from the test medium every 10 minutes, added immediately to 5 ml of ice cold acetonitrile, shaken vigorously and placed in a freezer. When all samples had been collected, they were centrifuged and the supernatants were filtered using nitrocellulose membrane filters (por 0.45) and analyzed by HPLC, following appearance of 42 and disappearance of 43.

In Rat Brain Homogenate

The brain homogenate was prepared by the following method. Five female Sprague-Dawley rats were killed by decapitation and the brains were removed, pooled, weighed (total weight 9.2 g) and homogenized in 36.8 ml of aqueous 0.11M phosphate buffer, pH 7.4. 100 μl of 0.024M solution of compound 43 in DMSO were mixed with 20 ml of the homogenate, previously equilibrated to 37° C. in a water bath, to result in an initial concentration of $2.4 \times 10^{-4}$ moles/liter. Samples of 1.0 ml were withdrawn every 10 minutes from the test medium, added immediately to 5 ml of ice cold acetonitrile, shaken vigorously and placed in a freezer. When all samples had been collected, they were centrifuged and the supernatants were filtered through nitrocellulose membrane filter (por 0.45) and analyzed by HPLC (Method A).

EXAMPLE 47

In Vitro Determination of the Site-Specific Conversion of the Prodrug 42 to Testosterone A fresh brain homogenate was prepared as above described. 100 μl of 0.017M solution of the quaternary compound 42 in methanol were mixed with 10 ml of the brain homogenate, previously equilibrated to 37° C. to result in an initial concentration of $1.7 \times 10^{-4}M$. Samples of 1.0 ml were withdrawn every 20 minutes from the test medium, added immediately to 5 ml of ice cold acetonitrile and placed in a freezer. When all the samples had been collected they were centrifuged and the supernatant was filtered through nitrocellulose membrane filter (por 0.45) and analyzed for the quaternary compound 42.

EXAMPLE 48

In Vivo Brain Delivery of Testosterone Following Administration of the Dihydro Compound 43

Female Sprague-Dawley rats of average weight of 225±10 g were used. The rats were anaesthetized with IM injection of Innovar ® (0.13 ml/kg) and the external jugular was exposed. Compound 43 was injected intrajugularly in the form of 2.5% solution in DMSO at a dose of 40 mg/kg (equivalent to 52.3 mg quaternary 42 or 28.2 mg testosterone). The injection was given at a rate of 44.4 μl/minute using a calibrated infusion pump. After appropriate time periods, 1 ml of blood was withdrawn from the heart and dropped immediately into a tared tube containing 5 ml acetonitrile which was later weighed to determine the weight of the blood taken. The animal was then perfused with 20 ml of saline solution, decapitated and the brain was removed. The weighed brain was homogenized with 1 ml of distilled water, 5 ml of acetonitrile was added and the mixture was rehomogenized thoroughly, centrifuged, filtered and then analyzed using the HPLC method. The tubes containing the blood were shaken vigorously, centrifuged, filtered and also analyzed using the HPLC method described at 0.05 sensitivity limit for determination of the quaternary 42 and at 0.001 sensitivity limit for determination of liberated testosterone. Quantitation was done using a recovery standard curve obtained by introducing a known amount of either compound 42 or testosterone in either brain homogenate or blood and then treated in the same manner of extraction and analysis.

EXAMPLE 49

In Vivo Brain Delivery of Testosterone Following its Administration

Female Sprague-Dawley rats with an average weight of 225±10 g were injected with testosterone at a dose level of 28.2 mg/kg following the same procedure previously described. Samples of brain and blood collected were analyzed for testosterone using HPLC.

EXAMPLE 50

In Vivo Brain Delivery of Quaternary 42 Following its Administration

Following the same procedure, female Sprague-Dawley rats were injected I.V. with the quaternary solution (0.18%) in DMSO at a dose level of 13.0 mg/kg (it was found to be toxic at higher doses). The brain samples collected were analyzed for presence of the quaternary 42 using HPLC.

EXAMPLE 51

Results of Experiments of Examples 45–50

The rates of oxidation of the dihydro derivative 43 with silver nitrate, hydrogen peroxide and diphenylpicrylhydrazyl free radical (DPP.) were determined. The reactions were carried out under pseudo first order conditions, either with higher concentrations of the oxidant in the case of hydrogen peroxide or higher concentrations of 43 in the case of the picryl reagent. With DPP., a reference sample was made using the same amounts as the test sample, but prepared 10 minutes before mixing and monitoring the test sample. This reference is used as a measure of $A\infty$ and these were the data used to calculate the kinetic parameters. The in vitro rates of oxidation of the dihydro derivative were also determined in biological fluids, e.g. 80% plasma, whole blood, 20% brain homogenate and 20% liver homogenate. The rate of disappearance of the ester 42 and appearance of testosterone in the medium was also determined. Finally, the in vivo brain delivery and blood concentration profile of the quaternary derivative and testosterone released, against time, was determined following a single injection of the dihydropyridine derivative 43 to female rats. These results were compared to blood and brain kinetics of testosterone following administration of such.

Chemical Oxidation of the Dihydropyridine Derivative 43

(i) By Silver Nitrate

It was observed that this dihydro derivative 43 is more stable towards oxidation than the monophenethylamine type derivatives reported hereinabove; it takes a few minutes standing for the silver to form. The product is exclusively the quaternary salt 42, as verified by the change in the UV and NMR spectra.

(ii) By Hydrogen Peroxide

At low concentrations of the dihydro compound 43 ($5\times 10^{-6}$M), compared to the high concentration of the peroxide (0.18M), the oxidation proceeds according to a first order kinetics. $k=2.7\pm 0.3\times 10^{-3}$ sec$^{-1}$ $t_{\frac{1}{2}}=3.98\pm 0.7$ min, r=0.995 At higher concentrations, the dihydro compound is insoluble in $H_2O_2$.

(iii) By Diphenylpicrylhydrazl (DPP.) Free Radical

The reaction was carried out under pseudo first order conditions using excess of the dihydropyridine derivative. With the concentrations used, all runs gave good first order plots over 3 half lives, with correlation coefficient better than 0.9998. $k=4.87\pm 0.31\times 10^{-2}$ sec$^{-1}$ $t_{\frac{1}{2}}=14.1\pm 0.6$ seconds Trials to determine the second order rate constant using different concentrations of DPP. were unsuccessful.

(iv) In Vitro Oxidation and Hydrolysis in Biological Media

Table III shows the rates, half-lives and correlation coefficient for the process of oxidation of the 1,4-dihydropyridine derivative 43 in different biological media.

The rate of hydrolysis of the quaternary 42 in 20% brain homogenate was also determined and it was found to be $3.6\times 10^{-5}$ sec$^{-1}$, corresponding to a half-life, $t_{\frac{1}{2}}$, of 5:16 h.

TABLE III

Kinetics of in vitro oxidation of the dihydropyridine ester 43 to the quaternary derivative 42 in biological fluids.[a]

| Medium | k (sec$^{-1}$) | $t_{\frac{1}{2}}$ (min.) | r | Method[b] |
|---|---|---|---|---|
| 80% Plasma | 8.12 × 10$^{-5}$ | 142 | .959 | A |
| 20% Brain Homogenate | 1.72 × 10$^{-4}$ | 67 | .997 | A |
| Whole Blood | 1.74 × 10$^{-4}$ | 66 | .997 | A, B |

[a]At 37° C., initial concentration of [43] = 2.4 × 10$^{-4}$ M
[b]Method A: Following appearance of [42]
Method B: Following disappearance of [43]

(v) In Vivo Administration of Compound 43 and Testosterone

Figure 8:
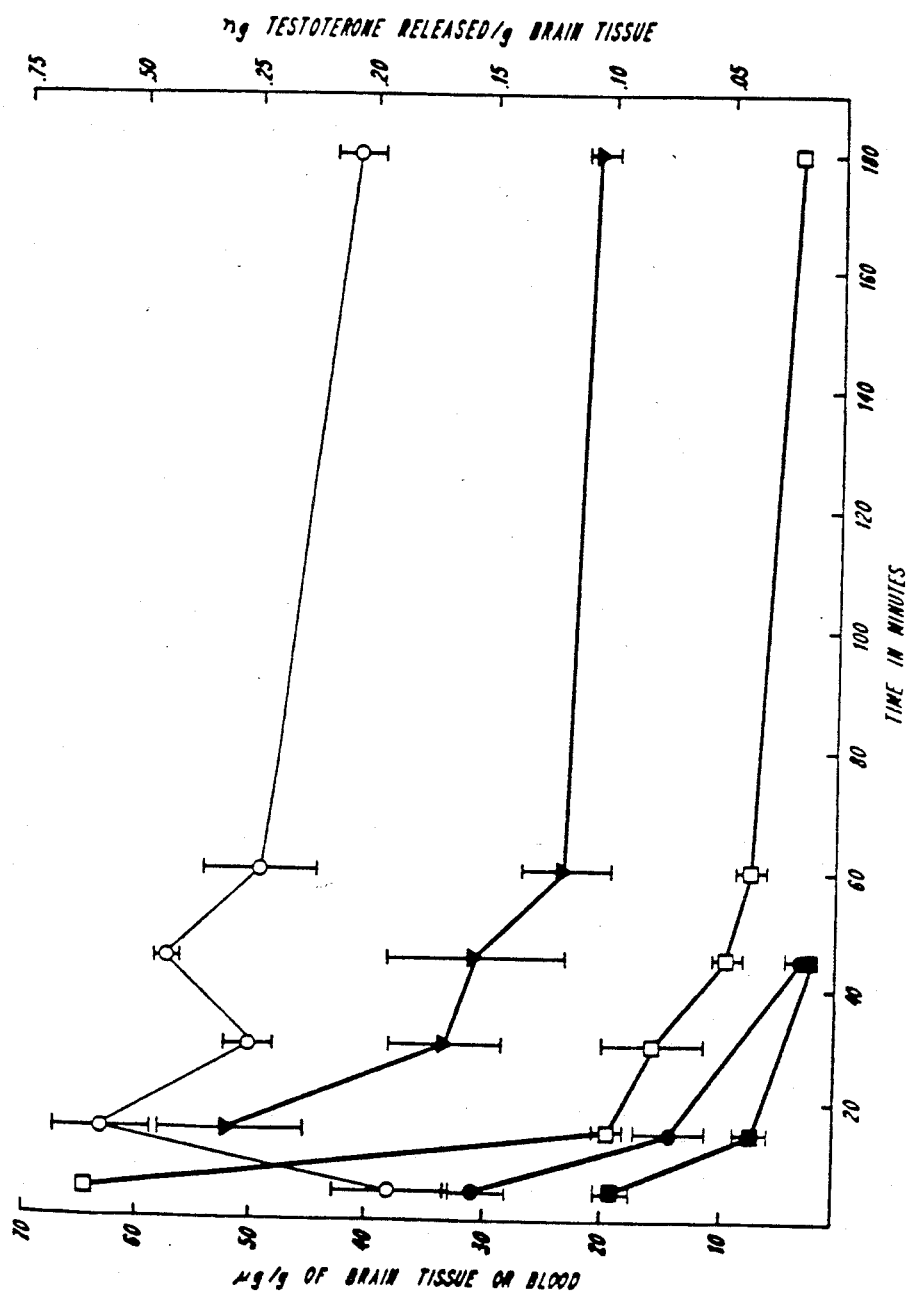
FIG. 8 is a graph plotting concentrations with standard errors against time for testosterone-17-nicotinate-N-methyl cation, calculated as iodide, in brain (O) and in blood (□) and concentration of released testosterone (ng/g) in brain (▼), all following administration of the corresponding dihydropyridine compound. Also plotted are concentrations of testosterone in brain (●) and blood (■) following administration of testosterone, per se.

FIG. 8 illustrates the concentration of the quaternary derivative 42 in brain and blood and concentration of testosterone released in the brain, following intravenous administration of the 1,4-dihydropyridine derivative 43. Also, FIG. 8 shows the concentration of testosterone in brain and blood following administration of testosterone. Statistical analysis of the descending portions of the curves shown in FIG. 8 provides the following results:

(1) Rates of disappearance of the quaternary compound 42:
from brain=$2\times 10^{-3}$ min$^{-1}$, $t_{\frac{1}{2}}$=5.7 h, r=0.833
from blood=$1.27\times 10^{-2}$ min$^{-1}$, $t_{\frac{1}{2}}$=54 min, r=0.833

(2) Rate of disappearance of released testosterone following administration of dihydro compound 43 = $2.65 \times 10^{-3}$ min$^{-1}$, $t_{\frac{1}{2}}$ = 4.4 h, r = 0.768 (Results analyzed for up to 5 hrs, the data shown in FIG. 8 are for 3 hrs).

(3) Rate of disappearance of testosterone following administration of testosterone:

from brain = $5.5 \times 10^{-2}$ min$^{-1}$, $t_{\frac{1}{2}}$ = 12.6 min, r = 0.994
from blood = $4.74 \times 10^{-2}$ min$^{-1}$, $t_{\frac{1}{2}}$ = 14.5 min, r = 0.959

Thus, 17$\beta$-[(1,4-dihydro-1-methyl-3-pyridinylcarbonyl)oxy]androst-4-en-3-one 43 could be obtained in a high yield (more than 90%) from testosterone 17$\beta$-nicotinate by simple chemical procedures. The dihydro product obtained directly from the reduction reaction medium was found by HPLC to be quite pure and a single crystallization from hot methanol afforded an analytically pure product. No signs of oxidation were observed during crystallization, even from hot methanol, filtration or drying. The crystalline solid dihydro compound did not show signs of oxidation, decomposition or polymerization when tested by HPLC, during the 2-month shelf storage at ambient temperature under nitrogen. This compound 43 was found to be quantitatively oxidizable to the corresponding quaternary derivative 42, as identified by UV spectroscopy, whether by silver nitrate or hydrogen peroxide. The process of oxidation with silver nitrate is slower than that with the dihydropyridine derivative of phenethylamine reported hereinabove. Oxidation with hydrogen peroxide or DPP., at pseudo first order conditions, was found to take place at measurable rates ($t_{\frac{1}{2}}$ = 3.98±0.7 min and 14.1±0.6 seconds, respectively) compared to the rates of oxidation of the corresponding phenethylamine and dopamine derivatives which were found to be too fast to be monitored using the same procedure. The in vitro investigation in biological fluids indicated a facile oxidative conversion of the dihydro form 43 to the corresponding quaternary 42, but at a slower rate than that of the analogous amides of phenethylamine or dopamine.

Insofar as concerns the in vivo studies of compound 43, the results shown in FIG. 8 indicate that the dihydro derivative penetrates the BBB and is readily oxidized in the brain to the quaternary precursor 42. The in vivo rate of oxidation of the dihydro seems faster than that obtained from the in vitro experiment. No dihydro derivative could be detected in the brain without the sensitivity limits of the procedure. After 42 reaches its maximum concentration, within about 15 minutes, its concentration starts a decline phase corresponding to overall excretion and/or metabolism-hydrolysis. The overall rate of this phase was calculated to be $2 \times 10^{-3}$ min$^{-1}$ ($t_{178}$ = 5.7 h). In the same time, the concentration of 42 in blood was decreasing progressively from the beginning at a rate $1.27 \times 10^{-2}$ min$^{-1}$ or with a half life of 54 min. Equimolar administration of testosterone using the same solvent (DMSO) and the same route of administration showed a rapid absorption of testosterone into the brain, reaching a maximum concentration within 5 minutes, followed by fast clearance from both brain and blood ($t_{\frac{1}{2}}$ = 12.6 min and 14.5 min respectively). The ratio of brain/blood concentration for testosterone was found to be 1.6 at 5 minutes and 1.8 at 15 minutes from administration. The ratio of brain/blood concentration of the quaternary 42 was found to increase progressively with time (3.23 at 15 min, 6.33 at 45 min and 12 at 3 hrs from administration). This indicates the predicted "lock in" property for the quaternary 42. Testosterone was found to be released from the quaternary ester 42 and could be detected in the brain following administration of the dihydro derivative 43. Analysis of the time concentration curve for release of testosterone indicated two phase kinetics for disappearance from the brain. The first phase is a fast descending one at a rate of $1.2 \times 10^{-2}$ min$^{-1}$ followed by a slow clearance phase with a rate of $5.8 \times 10^{-4}$ min$^{-1}$ and a half life of about 20 hrs which corresponds to about 130 hrs for complete clearance from the brain. This result, if compared to that obtained by H. Frey, A. Aadvaag, D. Saahum and J. Falch, *Eur. J. Clin. Pharmacol.*, 16, 345 (1979), for the clearance of testosterone from plasma after oral administration (about 6 hrs), is very promising. Although the concentrations of testosterone in the brain following administration of compound 43 are low compared to that following administration of testosterone, this is by no means a disadvantage because such high concentration of testosterone may not be needed for receptor saturation. By dose manipulation of the dihydro derivative, a concentration of testosterone just sufficient for receptor saturation for a delayed period could be attained.

In the examples immediately to follow, all melting points were taken on a Mel-Temp apparatus and are not corrected. Elemental analyses were performed at Atlantic Microlabs, Inc., Atlanta, Ga. Infrared spectra were determined by means of a Beckman Acculab 1 double-beam recording spectrophotometer. NMR spectra were determined by means of a Varian T60A spectrometer. All chemical shifts reported are in $\delta$ (parts per million) relative to tetramethylsilane. Ultraviolet absorbance spectra were determined using a Carey Model 219 spectrophotometer. HPLC analyses were performed on a Waters Associates Liquid chromatograph with Model 6000A solvent delivery system, Model U6K injector and Model 440 absorbance detector.

EXAMPLE 52

Preparation of the 1-Methyl-3-carbamoylpyridinium derivative of Tyr-Gly-Gly-Phe-Leu-OC$_2$H$_5$ (1-Methyl-3-carbamoylpyridinium derivative of leu$^5$-enkephalin ethyl ester)

N-$\alpha$-t-Butoxycarbonyl-O-benzyl-L-tyrosine (7 g, 0.019 mol) was dissolved in tetrahydrofuran in a three-neck round bottom flask which was cooled to approximately $-10°$ C. in an ice/acetone bath under a nitrogen atmosphere. N-methylmorpholine (6.3 ml, 0.06 mol) was added to the stirred solution, followed by 2.5 ml (0.019 mol) of isobutyl chloroformate. Immediately after the addition of isobutyl chloroformate, N-methyl morpholine hydrochloride precipitated. After 5 min, 3.7 g (0.019 mol) of L-leucine ethyl ester hydrochloride, dissolved in dimethylformamide, were added. The reaction mixture was stirred at this temperature for an hour, after which the solvent was evaporated. The residue obtained was dissolved in ethyl acetate/water and the organic layer was extracted with sodium bicarbonate solution, water, 0.01N HCl and water. The organic layer was dried over Na$_2$SO$_4$ and after evaporation of the solvent an oil was obtained. Crystallization from CHCl$_3$/petroleum ether yielded 7.4 g (0.014 mol, 76%) m.p. 104°-107° C., of N-$\alpha$-t-butoxycarbonyl-O-benzyl-L-tyrosylglycylglycine ethyl ester. $^1$H NMR (CDCl$_3$) $\delta$ 7.2 (5H, s), 6.9 (4H, doublet of doublets), 5.0 (2H, s), 1.1 (12H, m). The ethyl ester was cleaved by treating 6.2 g (0.012 mol) of it with an equivalent amount of 2N NaOH in methanol. The solution was stirred at room temperature for half an hour after which the solvent was evaporated. An equivalent amount of 2N HCl was added to the cooled residue and the solid obtained was filtered and dried to yield 3.5 g (96%), m.p. 118°–122° C., of the free (t-butoxycarbonyl-O-benzyl)tyrosylglycylglycine. t-Butoxycarbonylphenylalanylleucine ethyl ester was prepared starting with 6 g (0.019 mol) of t-butoxycarbonyl-L-phenylalanine, and 3.7 g (0.019 mol) of leucine ethyl ester hydrochloride. Work up and crystallization from CHCl$_3$/petroleum ether yielded 6.5 g (84%), m.p. 109°–112° C., of the desired compound. $^1$H NMR (CDCl$_3$) δ 7.2 (5H, s), 6.4 (1H, bm), 5.1 (1H, bm), 4.3 (4H, bm), 3.1 (2H, bm), 1.3 (20H, m).

The t-butoxycarbonyl protecting group was cleaved by treatment of 4.9 g (0.012 mol) of t-butoxycarbonylphenylalanylleucine ethyl ester with 60 ml of 33% trifluoroacetic acid/CH$_2$Cl$_2$. The solution was stirred at room temperature for half an hour, after which the solvent was evaporated and the residue was treated with a bicarbonate solution which resulted in the formation of a solid. The solid, phenylalanylleucine ethyl ester, was filtered, rinsed with water and dried to yield 5.6 g (97%), m.p. 150°–154° C.

t-Butoxycarbonyl-O-benzyltyrosylglycylglycylphenylalanylleucine ethyl ester was prepared by the same method using 0.01 mol of starting materials, (t-butoxycarbonyl-O-benzyl)tyrosylglycylglycine and phenylalanylleucine ethyl ester. A white solid was obtained which was recrystallized from methyl alcohol/water to yield 4.9 g (63%), m.p. 149°–152° C.

The t-butoxycarbonyl group of t-butoxycarbonyl-O-benzyltyrosylglycylglycylphenylalanylleucine ethyl ester was cleaved as previously described to give O-benzyl-tyr-gly-gly-phe-leu-OEt.TFA (trifluoroacetic acid) salt. Anal. calc. of C$_{39}$H$_{48}$O$_9$N$_5$F$_3$.H$_2$O: C, 58.13; H, 6.25; N, 8.69. Found: C, 58.06; H, 6.26; N, 8.69).

Nicotinic acid (160 mg, 1.3 mmole) and O-benzyltyr-gly-gly-phe-leu-OEt.TFA salt (1 g, 1.3 mmole) were dissolved in pyridine and 268 mg (1.3 mmole) of dicyclohexylcarbodiimide were added. The mixture was stirred at room temperature for 24 hours, after which the dicyclohexylurea was filtered and the pyridine distilled in vacuo. Water was added to the residue and the solid obtained was filtered and washed with more water. The solid N-nicotinoyl-O-benzylpentapeptide ethyl ester was recrystallized by methanol-water. $^1$H NMR gave the expected pattern.

The N-nicotinoyl pentapeptide derivative (500 mg, 0.64 mmol) obtained above was dissolved in 10% formic acid/methanol, followed by addition of 500 mg of palladium black. The mixture was stirred overnight at room temperature, after which the solvent was evaporated. The residue was neutralized with a saturated NaHCO$_3$ solution and extracted with ethyl acetate. The solvent was evaporated and the residue recrystallized from ethyl acetate/ethyl ether to yield 370 mg (0.54 mmol), 84% of product. $^1$H NMR gave the expected pattern, corresponding to

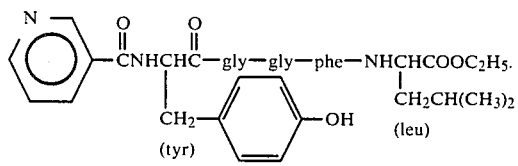

Anal. calc. for C$_{36}$H$_{44}$O$_8$N$_6$.4H$_2$O: C, 56.83; H, 6.89; N, 11.04. Found: C, 56.88; H, 6.56; N, 10.48. That product (30 mg, 0.44 mmol) was dissolved in acetone and an excess of methyl iodide was added. The solution was refluxed for 8 hrs, after which the solvent was evaporated and the residue was filtered from ethyl ether. A yellowish (260 mg, 0.31 mm), 71%, product was obtained, corresponding to the 1-methyl-3-carbamoylpyridinium derivative of leu$^5$-enkephalin ethyl ester. Anal. calc. for C$_{37}$H$_{47}$O$_8$N$_6$I: C, 53.50; H, 5.70; N, 10.12. Found: C, 53.44; H, 4.77; N, 10.07.

EXAMPLE 53

Preparation of N-[2-(3-Indolyl)ethyl]nicotinamide

To a solution of 1.97 g (10 mmol) of tryptamine hydrochloride and 1.23 g (10 mmol) of nicotinic acid in 10 ml of dry pyridine at 0° C. were added 2.20 g (10.7 mmol) of dicyclohexylcarbodiimide. The reaction mixture was stirred at room temperature for 24 hrs, and the formed dicyclohexylurea was removed by filtration (2.34 g). The pyridine was removed in vacuo, and 10 ml of methanol were added to the residue. Insoluble dicyclohexylurea in methanol was removed by filtration (0.05 g). The methanol was removed in vacuo and 10 ml of methylene chloride was added to the residue. Insoluble compound in methylene chloride was removed by filtration (0.04 g). The methylene chloride was removed in vacuo and the residue was crystallized from isopropanol. Recrystallization from methanol/isopropanol gave 1.92 g (72.5%) of N-[2-(3-indolyl)ethyl]nicotinamide as pale brown plates, m.p. 150°–152° C. IR (KBr) 3280, 3050, 2940, 1646, 1526, 1412, 1302, 1102, 740, 697 cm$^{-1}$. Anal. calc. for C$_{16}$H$_{15}$N$_3$O: C, 72.42; H, 5.91; N, 15.84. Found: C, 72.51; H, 5.74; N, 15.77.

EXAMPLE 54

Preparation of 1-Methyl-3-{[N-2-(3-indolyl)ethyl]}carbamoylpyridinium iodide

To a solution of 1.06 g (4 mmol) of N-[2-(3-indolyl)ethyl]nicotinamide in 5 ml of methanol, 1 ml (16 mmol) of methyl iodide was added. The mixture was refluxed for 5 hrs. The methanol and excess methyl iodide were removed in vacuo. The residue was recrystallized from methanol/isopropanol to yield 1.42 g (87.4%) of 1-methyl-3{[N-2-(3-indolyl)ethyl]}carbamoyl pyridinium iodide as yellow needles, m.p. 215°–217° C. IR (KBr): 3280, 3000, 2940, 1660, 1540, 1500, 1316, 1220, 735 cm$^{-1}$. Anal. calc. for C$_{17}$H$_{18}$N$_3$OI: C, 50.13; H, 4.46; N, 10.32; I, 31.16. Found: C, 50.22; H, 4.49; N, 10.27; I, 31.06.

EXAMPLE 55

Preparation of 1-Methyl-3-{N-[2-(3-indolyl)ethyl]}carbamoyl-1,4-dihydropyridine

To a solution of 0.61 g (1.5 mmol) of 1-methyl-3{[N-2-(3-indolyl)ethyl]}carbamoylpyridinium iodide in 50 ml of deaerated water and 50 ml of ethyl acetate, 1.00 g (12 mmol) of sodium bicarbonate was added. The mixture was stirred in an ice bath and 1.65 g (8 mmol) of sodium dithionite was added gradually under nitrogen. The mixture was stirred for 6 hrs, the ethyl acetate layer was decanted and the water layer was extracted with ethyl acetate. The combined solution was washed with water, dried with anhydrous sodium sulfate and the solvent removed in vacuo. A yield of 1-methyl-3{N-[2-(3-indolyl)ethyl]}carbamoyl-1,4-dihydropyridine of 0.29 g (69%) was obtained as yellow semisolid, m.p. 40°–70° C. IR (KBr) 3250, 2900, 1670 cm$^{-1}$. Anal. calc. for $C_{17}H_{19}N_3O.\frac{1}{2}H_2O$: C, 70.32; H, 6.94; N, 14.47. Found: C, 70.47; H, 6.76; N, 14.52.

EXAMPLE 56

Preparation of 5-Benzyloxygramine

A solution of 8.90 g (0.04 mol) of 5-benzyloxyindole in 40 ml of dioxane was added dropwise, over the course of 30 mins, to an ice-cooled, stirred mixture of 40 ml of dioxane, 40 ml of acetic acid, 3.2 ml of 37% aqueous formaldehyde (0.04 mol) and 8.8 ml of 25% aqueous dimethylamine (0.05 mol). The solution was stirred and cooled for two hrs and then allowed to warm to room temperature overnight. The next day, 500 ml of water were added, and the turbid mixture which resulted was filtered after the addition of charcoal. The filtrate was made alkaline (to pH 8–9) with 400 ml of 10% sodium hydroxide solution. The gramine quickly solidified and was filtered off after cooling in the refrigerator overnight. Washing with water, and drying gave 9.20 g (82.0%) of coarse powder, m.p. 125°–128° C. Recrystallization from ethyl acetate gave slightly green glittering cubes, m.p. 136°–137° C., of the desired 5-benzyloxygramine. IR (KBr) 3110, 3020, 2920, 2840, 2800, 2755, 1610, 1575, 1470, 1455, 1480, 1210, 1190, 1000 and 780 cm$^{-1}$.

EXAMPLE 57

Preparation of 5-Benzyloxyindole-3-acetamide

A solution of 8.41 g (0.03 mol) of 5-benzyloxygramine, 7.5 g (0.15 mol) of sodium cyanide, 120 ml of ethanol and 30 ml of water was refluxed for 90 hours. The solution, which contained some precipitate, was diluted with 200 ml of water and cooled in the refrigerator. The crystalline material which separated was washed thoroughly with water and dried, giving 4.40 g (52.3%) of a slightly brown sticky tan powder, m.p. 137°–140° C. Recrystallization from methanol/benzene gave small needles, m.p. 156°–158° C., of 5-benzyloxyindole-3-acetamide. IR (KB) 3400, 3290, 3180, 1645, 1610, 1580, 1485, 1450, 1275, 1210, 1200 and 795 cm$^{-1}$.

EXAMPLE 58

Preparation of 5-Benzyloxytryptamine hydrochloride 4.21 g (0.015 mol) of 5-benzyloxyindole-3-acetamide which were dissolved in 200 ml of tetrahydrofuran were added gradually to a solution of 3.80 g (0.1 mol) of lithium aluminum hydride in 200 ml of ether over a 30 minute period and under a nitrogen atmosphere. The solution was refluxed for 24 hrs. The excess hydride was decomposed with ethanol and then water was added to ensure complete decomposition of the precipitated complex. The ether layer was decanted and the residue was washed with fresh ether. The combined solution was washed with water and dried over solid potassium hydroxide. The solvent was evaporated in vacuo and the oily residue was taken up in ether and precipitated with hydrogen chloride gas. The pale purple 5-benzyloxytryptamine hydrochloride was recrystallized from ethanol/ether, yield 3.00 g (66.0%), m.p. 263°–265° C. IR (KBr) 3290, 3010, 2910, 1600, 1580, 1480, 1200, 1100 and 1000 cm$^{-1}$.

EXAMPLE 59

Preparation of N-{2-[3-(5-benzyloxy)indolyl]ethyl}nicotinamide

To a solution of 303 mg (1 mmol) of 5-benzyloxytryptamine hydrochloride and 123 mg (1 mmol) of nicotinic acid in 5 ml of pyridine at 0° C. was added 220 mg (1.07 mmol) of dicyclohexylcarbodiimide. The reaction mixture was stirred at room temperature for 24 hrs and the formed dicyclohexylurea was removed by filtration. The pyridine was removed in vacuo, and the residue was recrystallized from methanol/isopropanol. Yield 218 mg (58.9%), m.p. 192°–194° C. of N-{2-[3-(5-benzyloxy)indolyl]ethyl}nicotinamide. IR (KBr) 3280, 3050, 2900, 1655, 1590, 1535, 1480, 1310, 1220, 1200, 1185, 1020, and 710 cm$^{-1}$.

EXAMPLE 60

Preparation of 1-Methyl-3-N-{2-[3-(5-benzyloxy)indolyl]ethyl}carbamoylpyridinium iodide To a solution of 185 mg (0.5 mmol) of N-{2-[3-(5-benzyloxy)indolyl]ethyl}nicotinamide in 2 ml of methanol there was added 0.2 ml (3.2 mmol) of methyl iodide. The mixture was refluxed for 3 hrs. The methanol and excess methyl iodide were removed in vacuo. The residue of yellow solid gradually turned purplish. Yield 128 mg (50.0%), m.p. 228°–230° C., IR (KBr) 3210, 3020, 1670, 1495, 1480, 1190, 1025, 1000, 770 cm$^{-1}$. The product has the formula

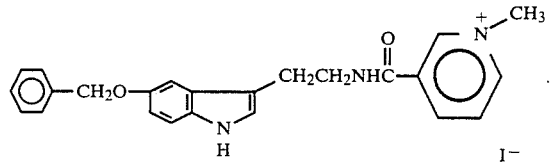

Catalytic hydrogenolysis, using palladium-on-charcoal catalyst, of 1-methyl-3-N-{2-[3-(5-benzyloxy)indolyl]ethyl}carbamoylpyridinium iodide affords 1-methyl-3-N-{2-[3-(5-hydroxy)indolyl]ethyl}carbamoylpyridinium iodide. Subsequent esterification with trimethylacetyl chloride affords the corresponding pivalyl ester of the formula

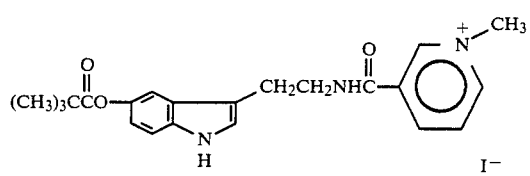

which can then be reduced as described hereinabove to the corresponding dihydro derivative of the formula

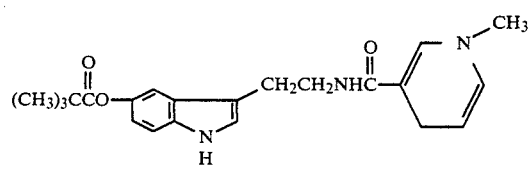

EXAMPLE 61

Preparation of
1-Methyl-3-{{N-{1-ethoxycarbonyl-2-[4-bis(2-chloroethyl)aminophenyl]}ethyl}}carbamoylpyridine Melphalan ethyl ester hydrochloride (153 mg, 0.41 mmol) was dissolved in acetonitrile (5 ml). A mixture of dicyclohexylcarbodiimide (89 mg, 0.43 mmol) and nicotinic acid (50.9 mg, 0.41 mmol) in acetonitrile (1 ml) and pyridine (1 ml) was added to the stirred solution of hydrochloride at 0° C. After approximately 5 minutes, the clear mixture became cloudy. The mixture was allowed to warm to room temperature and stirred for 44 hr, after which time the precipitate was removed by filtration. Solvents were removed at reduced pressure to give an orange oil which was taken into chloroform (15 ml) and washed with cold water (5 ml). Removal of solvent in vacuo gave 90 mg of a soft yellow solid (50% yield) which was used without further purification in the following step. δ (CDCl₃): 9.3 (bs, 1H, pyridine H-2); 8.9–9.2 (m, 1H, pyridine H-4); 7.9–8.2 (m, 1H, pyridine H-6); 7.5 (m, 1H, pyridine H-5); 6.95 (AB$_q$, 4-H); 4.9–5.3 (m, 1H, C-H); 4.3 (q, 2H, OCH₂); 3.5–3.9 [bs, 8H, (CH₂CH₂)₂]; 3.2 (dist. d, 2H, ArCH₂); 1.3 (t, 3H, CH₃). The product has the formula:

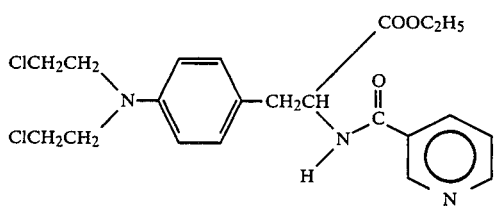

EXAMPLE 62

Preparation of
1-Methyl-3-{{N-{1-ethoxycarbonyl-2-[4-bis(2-chloroethyl)aminophenyl]}ethyl}}carbamoylpyridinium iodide The product of Example 61 (76.5 mg, 0.173 mmol) in acetone (10 ml) was treated with methyl iodide (0.1 ml, 1 mmol) and the mixture was heated at gentle reflux; further methyl iodide (0.1 ml) was added after 4 hours. Thin layer chromatography (CHCl₃: methanol, 10:1) showed several spots, including a quaternary compound at the origin. No further change in TLC was apparent after 6 hours, at which time heat was removed and solvents were evaporated in vacuo to leave a red-orange oil (118 mg). The oil was dissolved in d₆ acetone and insoluble particles were removed by filtration through a cotton plug. δ[(CD₃)₂CO] 9.7 (bs, 1H, pyridine H-2); 8.9–9.5 (m, 2-H, pyridine H-4, H-6); 8.1–8.4 (m, 1H, pyridine H-5); 4.8–5.1 (m, 1H, CH); 4.7 (s, 3H, N⁺CH₃); 4.2 (q, 2H, OCH₂); 3.75 [bs, 8H, (CH₂CH₂)₂]; 3.2 (s, HOD+ArCH₂); 1.25 (5, 3H, CH₃). The product is further characterized by the structural formula:

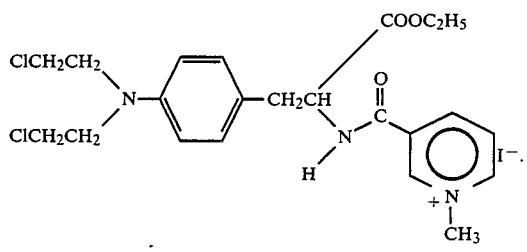

EXAMPLE 63

Preparation of
1-Methyl-3-{{N-{1-ethoxycarbonyl-2-[4-bis(2-chloroethyl)aminophenyl]}ethyl}}carbamoyl-1,4-dihydropyridine The product of Example 62 (101 mg, 0.174 mol) and sodium bicarbonate (5.8 mg, 6.8 mmol), as a suspension in ice cold N₂ deaerated water (15 ml) and methanol (2 ml), were treated with sodium dithionite (91 mg, 5.2 mmol) and ethyl acetate (20 ml). The original pale yellow suspension became yellow instantly, and after 2 hours the mixture was clear. Aqueous and organic layers were separated and the aqueous layer was extracted with ethyl acetate (4×20 ml). The combined organic layers were dried over sodium sulfate at 0° C. in the dark. Removal of solvent in vacuo gave a yellow-orange oil which reduced methanolic AgNO₃: yield 77 mg, 97%, δ(CDCl₃) 6.5–5.9 (bd, 1H, pyridine H-6); 4.5–5.1 (m, 2H, pyridine 4–5+C-H); 4.2 (q, 2H, OCH₂); 3.75 [bs, 8H, (CH₂CH₂)₂]; 3.05–3.3 [m, 4H, CH₂Ar+pyridine H-4 (CH₂)]; 3.0 (s, 3H, NCH₃); 1.3 (t, 3H, CH₃). λmax (methanol) 356.5 nm. The product has the formula:

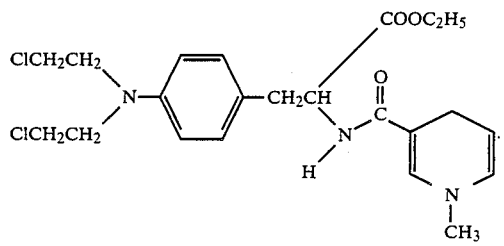

EXAMPLE 64

Preparation of
3-Nicotinoyloxyestra-1,3,5(10)-trien-17-one (Estrone Nicotinate)

To nicotinic acid (41 g, 0.333 mol) at 0° C. was added thionyl chloride (115 ml, 1.58 mol) with stirring. The mixture was refluxed for one hour, and the white crystalline product was filtered and washed sparingly with dry benzene. Excess thionyl chloride was azeotroped off with dry benzene immediately before use. Yield 90% (53.97 g) of nicotinoyl chloride hydrochloride; NMR, IR identical with literature values.

To nicotinoyl chloride hydrochloride (2.65 g, 0.015 mol) in pyridine (20 ml) at 0° C. was added estrone (2 g, 0.0074 mol). The mixture was refluxed for one hour and then poured over 100 ml of ice cold water, filtered, and dried over P₂O₅ under vacuum. Yield 72% (2.0076 g), m.p. 207°–210° C. NMR (CDCl₃) δ 9.3–9.1 (br s, 1H, C₂ pyridinium proton), 8.8–8.6 (br d, 1H, C₆ pyridinium proton, 8.4–8.2 (br d, 1H, $C_4$ pyridinium proton), 7.5–7.1 (m, 2-H,$C_5$ pyridinium proton+$C_1$ estrone proton), 7.0–6.7 (m, 2H, $C_{2,4}$ estrone protons), 3.2–1.3 (estrone skeletal protons, 15), 1.0–0.9 (s, 3H, $C_{18}$ estrone protons). IR (KBr) 1750–1730 cm$^{-1}$ (broad C=O stretching). Anal. calculated for $C_{24}H_{25}NO_3$: C, 76.76; H, 6.72; N, 3.73. Found: C, 76.37; H, 6.96; N, 3.67. The product is further characterized by the structural formula:

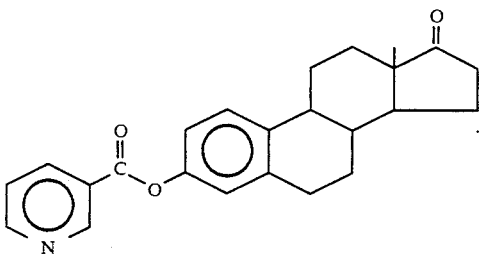

EXAMPLE 65

Preparation of 3-[(1-Methyl-3-pyridiniumcarbonyl)oxy]estra-1,3,5(10)-trien-17-one iodide To estrone nicotinate (0.5 g, 0.0013 mol) in acetone (20 ml) was added methyl iodide (1 ml, 0.016 mol) and the mixture was refluxed overnight. The deep yellow precipitate was filtered, washed with acetone, and dried. Yield 90% (0.6226 g); m.p. 245°–248° C. (dec.). NMR (d$_5$-DMSO) δ 9.8–9.7 (br s, 1H, $C_2$ pyridinium proton), 9.4–9.0 (m, 2H, $C_4$, $C_6$ pyridinium protons), 8.4–8.0 (m, 1H, $C_5$ pyridinium proton), 7.4–7.2 (m, 1H, $C_1$ estrone proton), 7.1–6.9 (m, 2H, $C_{2,4}$ estrone protons), 3.2–1.3 (estrone skeletal protons, 15), 1.0–0.9 (s, 3H, $C_{18}$ estrone protons). IR (KBr) 1755–1740 (broad C=O stretching). Anal. calculated for $C_{25}H_{28}NO_3I$: C, 58.03; H, 5.47; N, 2.71. Found: C, 58.16; H, 5.51; N, 2.67. The product has the formula:

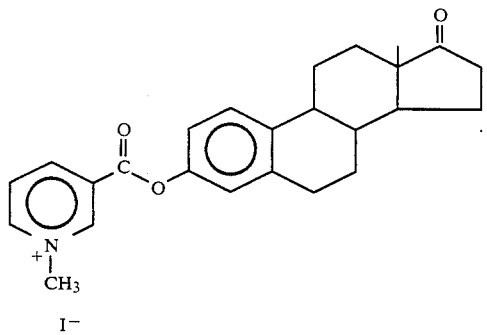

EXAMPLE 66

Preparation of 3-[(1-Methyl-1,4-dihydro-3-pyridinylcarbonyl)oxy]estra-1,3,5(10)-trien-17-one To 3-[(1-methyl-3-pyridiniumcarbonyl)oxy]estra-1,3,5(10)-trien-17-one iodide (0.600 g, 1.16 mmol) in a 50:50 mixture of methanol and deaerated water (80 ml) were added NaHCO$_3$ (0.58 g, 7.0 mmol) and Na$_2$S$_2$O$_4$ (0.81 g, 4.6 mmol). The mixture was stirred under N$_2$ for 2 hours. The precipitate was filtered, dissolved in methanol at room temperature, filtered, and then reprecipitated with deaerated water. This precipitate was then filtered and dried over P$_2$O$_5$ under vacuum. Yield 67% (0.3029 g). The product decomposes over the range 130°–180° C. NMR (CDCl) δ 7.2–7.0 (m, 2H, $C_1$ estrone protons+$C_2$ dihydro proton), 6.8–6.6 (m, 2H, $C_{2,4}$ estrone protons), 5.8–5.3 (m, 1H, $C_6$ dihydro proton), 5.0–4.6 (m, 1H, $C_5$ dihydro proton), 3.2–3.0 (m, 2H, $C_4$ dihydro protons), 3.0–2.8 (s, 3H, N-CH$_3$), 2.5–1.2 (estrone skeletal protons, 15), 1.0–0.9 (s, 3H, $C_{18}$ estrone protons). IR (KBr) 1745–1740 (C=O stretching). Anal. calculated for $C_{25}H_{29}NO_3$ (+½H$_2$O): C, 74.96; H, 7.56; N, 3.50. Found: C, 75.44; H, 7.27; N, 3.38. The product is further characterized by the structural formula:

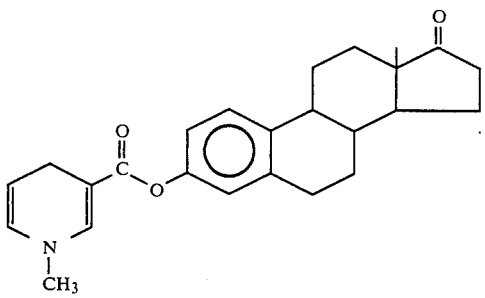

EXAMPLE 67

Preparation of 17β-Nicotinoyloxyestra-1,3,5(10)-trien-3-ol 3-methyl ether

To nicotinoyl chloride hydrochloride (3.15 g, 0.017 mol) in pyridine (20 ml) at 0° C. was added estradiol 3-methyl ether (2 g, 0.0070 mol). After refluxing one hour, the mixture was poured over 100 ml of ice water, filtered and dried over P$_2$O$_5$ under vacuum. Yield 76% (2.0674 g), m.p. 140°–142° C. NMR (CDCl$_3$) δ 9.3–9.0 (br s, 1H, $C_2$ pyridinium proton, 8.8–8.6 (m, 1H, $C_6$ pyridinium proton), 8.4–8.1 (br d, 1H, $C_4$ pyridinium proton), 7.5–7.0 (m, 2H, $C_5$ pyridinium proton+$C_1$ estradiol proton), 6.8–6.5 (m, 2H, $C_{2,4}$ estradiol protons), 5.1–4.7 (m, 1H, $C_{17\alpha}$ estradiol proton), 3.8–3.6 (s, 3H, O-CH$_3$), 3.0–1.2 (15H, estradiol skeletal protons), 1.0–0.9 (s, 3H, $C_{18}$ estradiol protons). IR (KBr) 1725 (C=O stretching). Anal. calculated for $C_{25}H_{29}NO_3$: C, 76.68; H, 7.48; N, 3.58. Found: C, 76.49; H, 7.50; N, 3.55. The product has the formula:

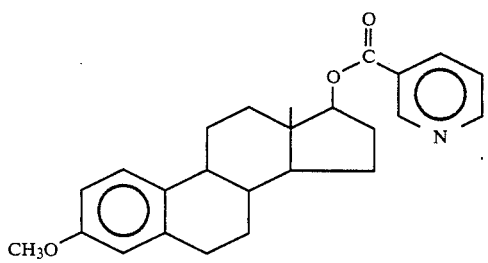

EXAMPLE 68

Preparation of 17β-[(1-Methyl-3-pyridiniumcarbonyl)oxy]estra-1,3,5(10)-trien-3-ol 3-methyl ether iodide To 17β-nicotinoyloxyestra-1,3,5(10)-trien-3-ol 3-methyl ether (1.5 g, 0.0038 mol) in acetone (20 ml) was added methyl iodide (1 ml, 0.016 mol) and the mixture was refluxed overnight. The pale yellow precipitate was filtered, washed with acetone, and dried. Yield 76% (1.5595 g), m.p. 230°–234° C. (dec.). NMR (d$_6$-DMSO) δ 9.5–9.3 (br s, 1H, C$_2$ pyridinium proton), 9.2–8.8 (m, 2H, C$_{4,6}$ pyridinium protons), 8.3–8.0 (m, 1H, C$_5$ pyridinium proton), 7.2–7.0 (m, 1H, C$_1$ estradiol proton), 6.8–6.5 (m, 2H, C$_{2,4}$ estradiol protons); 5.2–4.8 (m, 1H, C$_{17\alpha}$ estradiol proton), 4.6–4.4 (s, 3H, N-CH$_3$), 3.8–3.6 (s, 3H, O-CH$_3$), 3.0–1.2 (15H, estradiol skeletal protons), 1.0–0.9 (s, 3H, C$_{18}$ estradiol protons). IR (KBr) 1745 (C=O stretching). Anal. calculated for C$_{26}$H$_{32}$NO$_3$I: C, 58.53; H, 6.06; N, 2.63. Found: C, 58.25; H, 6.07; N, 2.59. The title compound has the formula:

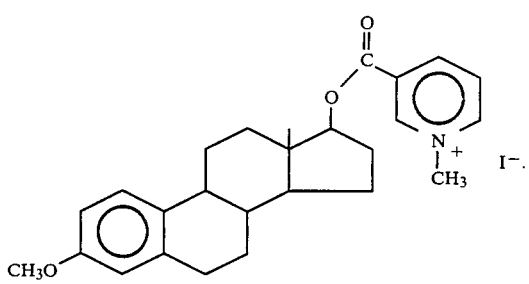

EXAMPLE 69

Preparation of 17β-[(1-Methyl-1,4-dihydro-3-pyridinylcarbonyl)oxy]estra-1,3,5(10)-trien-3-ol 3-methyl ether To 17β-[(1-methyl-3-pyridiniumcarbonyl)oxy]estra-1,3,5(10)-trien-3-ol 3-methyl ether (0.600 g, 1.12 mmol) in a 50:50 mixture of methanol and deaerated water (80 ml) were added NaHCO$_3$ (0.57 g, 6.7 mmol) and Na$_2$S$_2$O$_4$ (0.78 g, 4.5 mmol). The mixture was stirred under N$_2$ for 2 hours. The precipitate was filtered, dissolved in methanol at room temperature, filtered, and then re-precipitated with deaerated water. This precipitate was then filtered and dried over P$_2$O$_5$ under vacuum. Yield 74% (0.3383 g). The product decomposes over the range 120°–170° C. NMR (CDCl$_3$) δ 7.3–7.2 (m, 1H, C$_1$ estradiol proton), 7.0–6.9 (s, 1H, C$_2$ dihydro proton), 6.8–6.6 (m, 2H, C$_{2,4}$ estradiol protons), 5.8–5.6 (m, 1H, C$_6$ dihydro proton), 5.0–4.6 (m, 2H, C$_5$ dihydro proton+C$_{17\alpha}$ estradiol proton), 3.9–3.7 (s, 3H, O-CH$_3$), 3.2–3.0 (m, 2H, C$_4$ dihydro protons), 3.0–2.8 (s, 3H, N-CH$_3$), 2.4–1.2 (15H, estradiol skeletal protons), 1.0–0.9 (s, 3H, C$_{18}$ estradiol protons). IR (KBr) 1705 (C=O stretching). Anal. calculated for C$_{26}$H$_{33}$NO$_3$: C, 76.61; H, 8.18; N, 3.44. Found: C, 76.75; H, 8.43; N, 3.37. The product is further characterized by the structural formula:

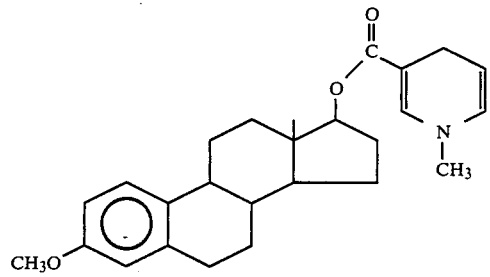

EXAMPLE 70

Preparation of Estra-1,3,5(10)-triene-3,17β-diol 3,17-dinicotinate (Estradiol 3,17β-dinicotinate)

Estradiol (2 g, 0.0073 mol) was added to nicotinoyl chloride hydrochloride (5.3 g, 0.029 mol) in dry pyridine (30 ml) at 0° C. The mixture was refluxed for 1 hour and then poured over 100 ml of ice water, filtered and dried over P$_2$O$_5$ under vacuum. Yield 90% (3.18 g), m.p. 148°–150° C. NMR (CDCl$_3$) δ 9.2–9.0 (br s, 2H, C$_2$ pyridinium protons), 8.7–8.3 (m, 2H, C$_6$ pyridinium protons), 8.4–8.0 (m, 2H, C$_4$ pyridinium protons), 7.5–7.1 (m, 3H, C$_5$ pyridinium protons+C$_1$ estradiol proton), 6.9–6.7 (m, 2H, C$_{2,4}$ estradiol protons), 5.0–4.7 (m, 1H, C$_{17\alpha}$ estradiol proton), 3.2–1.3 (estradiol skeletal protons, 15), 1.0–0.9 (s, 3H, C$_{18}$ estradiol protons). IR (KBr) 1750, 1725 cm$^{-1}$ (2C=O stretching). Anal. calculated for C$_{30}$H$_{31}$N$_2$O$_4$: C, 74.50; H, 6.47; N, 5.79. Found: C, 74.40; H, 6.32; N, 5.75. The product has the formula:

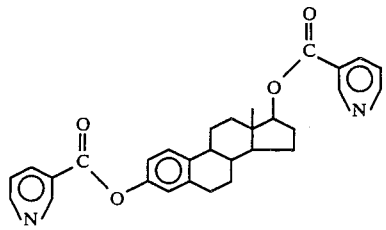

EXAMPLE 71

Preparation of 3,17β-Bis[(1-methyl-3-pyridiniumcarbonyl)oxy]estra-1,3,5(10)-triene diiodide Methyl iodide (1 ml, 0.016 mol) was added to estradiol 3,17β-dinicotinate (1 g, 0.0021 mol) in acetone (20 ml) and the mixture was refluxed overnight. The deep yellow precipitate which formed was filtered, washed with acetone, and dried. Yield 72% (1.262 g), m.p. 256°–258° C. (dec.). NMR (d$_6$-DMSO) δ 9.6–9.2 (br s, 2H, C$_2$ pyridinium protons), 9.2–8.7 (m, 4H, C$_4$+C$_6$ pyridinium protons), 8.4–8.0 (m, 2H, C$_5$ pyridinium protons), 7.3–7.1 (m, 1H, C$_1$ estradiol proton), 7.1–6.9 (m, C$_{2,4}$ estradiol protons), 5.0–4.7 (m, 1H, C$_{17\alpha}$ estradiol proton), 4.5–4.3 (s, 6H, N-CH$_3$), 3.2–1.3 (estradiol skeletal protons, 15), 1.0–0.9 (s, 3H, C$_{18}$ estradiol protons). IR (KBr) 1750–1735 cm$^{-1}$ (broad C=O stretching). Anal. calculated for C$_{32}$H$_{36}$N$_2$O$_4$I$_2$: (+1H$_2$O): C, 48.99; H, 4.89; N, 3.57. Found: C, 48.78; H, 4.66; N, 3.63. The product is further characterized by the structural formula:

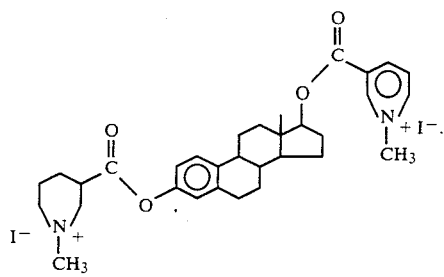

That compound was converted to the corresponding 3-hydroxy steroid of the formula

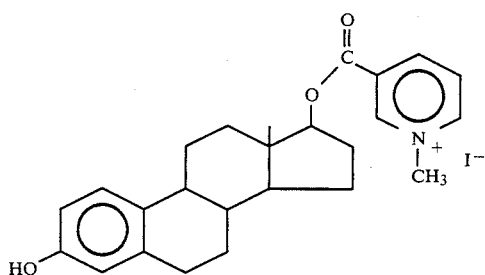

by partial hydrolysis; the resultant 3-hydroxy compound was then reduced, as generally described hereinabove, to afford the corresponding dihydro derivative of the formula

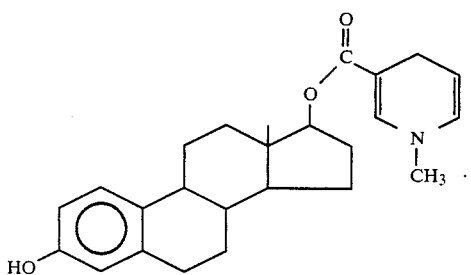

When that dihydro derivative was administered to male rats, the corresponding 3-hydroxy-17-quaternary derivative was found in the brain.

EXAMPLE 72

In Vitro Testing of Estrogenic Steroid Derivatives

The products of Examples 66 and 69 both reduce methanolic silver nitrate. The product of Example 66 requires more time and some warming.

The two above-mentioned dihydro derivatives show disappearance of UV absorption at 359 and 358 nm, respectively, upon addition of $H_2O_2$. Diphenylpicrazyl radical absorption at 516 nm can also be shown to decrease upon addition of either of these compounds.

Disappearance of the product of Example 66 in brain and plasma homogenates was studied using the Cary 210 and Apple II microprocessor.

| Concentration | $t_{\frac{1}{2}}$ (min.) | k (sec$^{-1}$) | r |
|---|---|---|---|
| Brain Homogenate | | | |
| $2.68 \times 10^{-4}$ M | 11.2 | $1.03 \times 10^{-3}$ | 0.9998 |
| $1.18 \times 10^{-4}$ M | 8.7 | $1.33 \times 10^{-3}$ | 0.9998 |
| $4.07 \times 10^{-5}$ M | 7.5 | $1.53 \times 10^{-3}$ | 0.9989 |

| Concentration | $t_{\frac{1}{2}}$ (min.) | k (sec$^{-1}$) | r |
|---|---|---|---|
| Plasma Homogenate | | | |
| $1.43 \times 10^{-4}$ M | 39.7 | $2.97 \times 10^{-4}$ | 0.992 |
| $7.04 \times 10^{-5}$ M | 52.7 | $2.19 \times 10^{-4}$ | 0.969 |
| $2.75 \times 10^{-5}$ M | 66.2 | $1.75 \times 10^{-4}$ | 0.953 |

The present invention can thus be seen to provide a variety of classes of novel chemical compounds adapted for the site-specific and sustained delivery of centrally acting drugs to the brain. Among the classes of compounds provided hereby, the following are particularly noteworthy:

(A) Compounds adapted for the site-specific/sustained delivery of a centrally acting drug species to the brain, said compounds being:

(i) compounds of the formula $$D'(-Q)_n \qquad (I')$$

wherein D' is the residue of a centrally acting drug containing at least one —NH$_2$ or —NH— functional group, said residue being formed by removal of a hydrogen atom from at least one of the —NH$_2$ or —NH— functional groups in said drug; n is a positive integer equal to the number of said —NH$_2$ or —NH— functional groups from which a hydrogen atom has been removed; and —Q is a radical of the formula

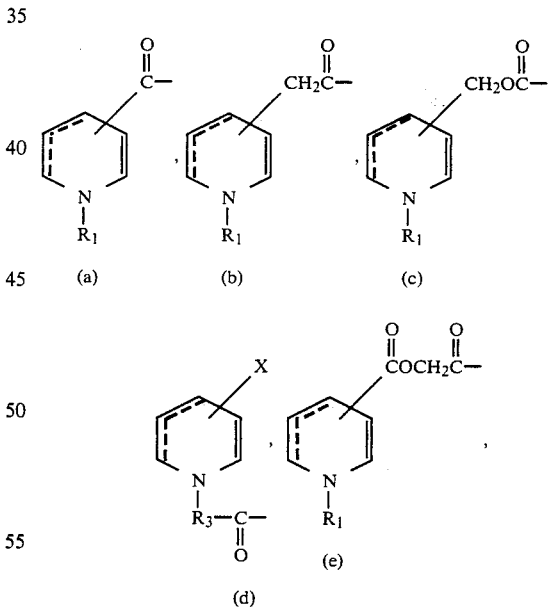

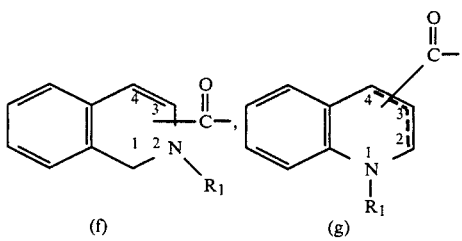

-continued

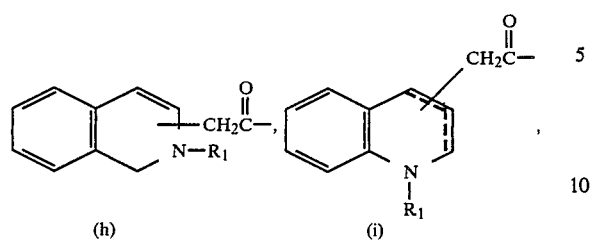

(h)  (i)

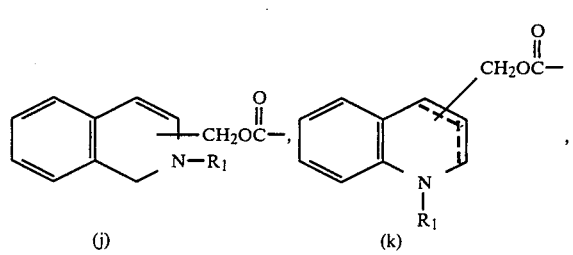

(j)  (k)

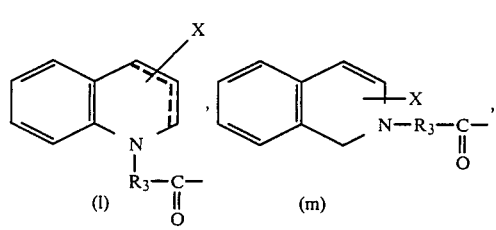

(l)  (m)

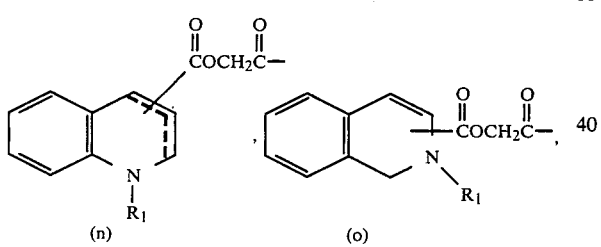

(n)  (o)

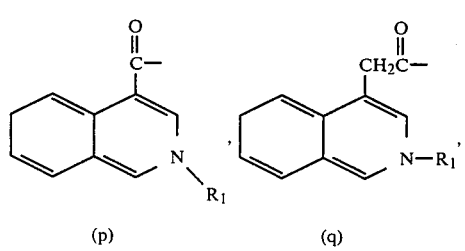

(p)  (q)

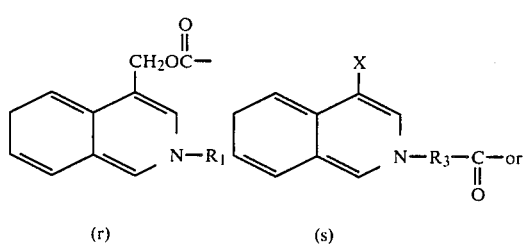

(r)  (s)

-continued

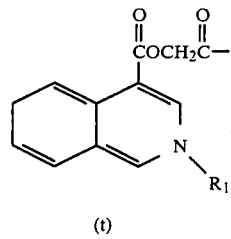

(t)

wherein the dotted line in formulae (a), (b), (c), (d) and (e) indicates the presence of a double bond in either the 4 or 5 position of the dihydropyridine ring; the dotted line in formulae (g), (i), (k), (l) and (n) indicates the presence of a double bond in either the 2 or 3 position of the dihydroquinoline ring; $R_1$ is $C_1$-$C_7$ alkyl or $C_7$-$C_{10}$ aralkyl; $R_3$ is $C_1$ to $C_3$ alkylene; X is —CONR'R'' wherein R' and R'', which can be the same or different, are each H or $C_1$-$C_7$ alkyl, or X is —CH=NOR'''— wherein R''' is H or $C_1$-$C_7$ alkyl; the

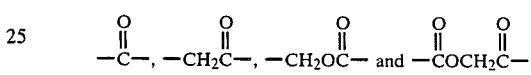

groupings in formulae (a), (b), (c) and (e) and the X substituent in formula (d) can each be attached at the 2, 3 or 4 position of the dihydropyridine ring; the

groupings in formulae (g), (i), (k) and (n) and the X substituent in formula (l) can each be attached at the 2, 3 or 4 position of the dihydroquinoline ring; and the

groupings in formulae (f), (h), (j) and (o) and the X substituent in formula (m) can each be attached at the 1, 3 or 4 position of the dihydroisoquinoline ring; and (ii) non-toxic pharmaceutically acceptable salts of compounds of formula (I');

with the proviso that when the compound is other than a salt as defined in (ii) above, when n is 1, when —Q is

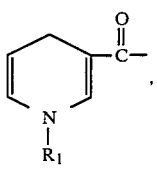

wherein $R_1$ is defined as above, and when the centrally acting drug from which D' is derived contains only one —$NH_2$ functional group and no other functional groups, then D' must be the residue of a centrally acting drug other than a sympathetic stimulant. Within this class of compounds, preferred compounds are those wherein —Q is a radical of the formula:

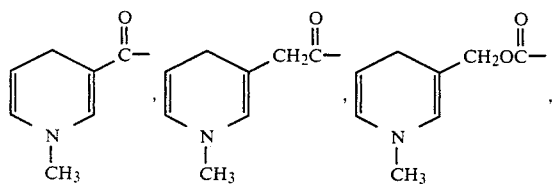

(a')  (b')  (c')

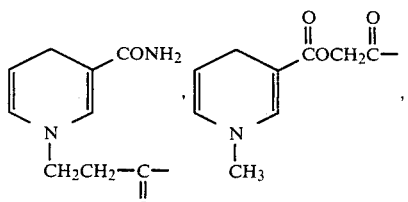

(d')  (e')

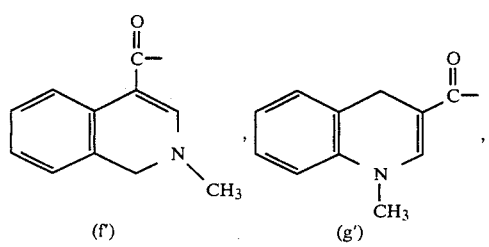

(f')  (g')

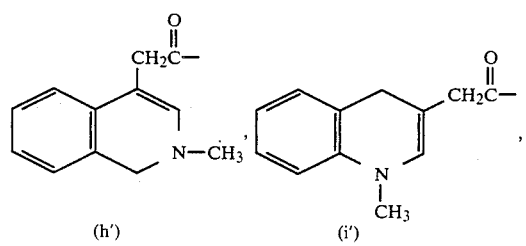

(h')  (i')

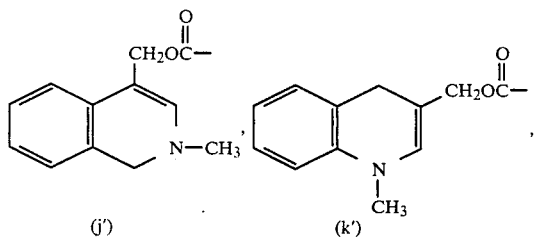

(j')  (k')

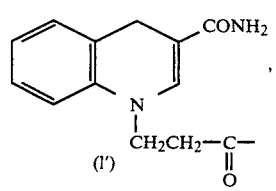

(l')

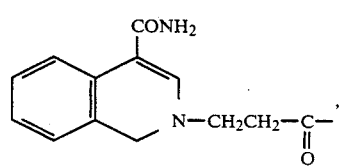

(m')

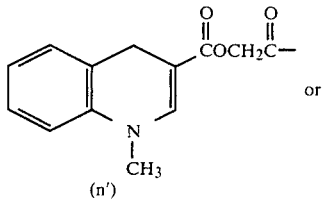

(n')

or

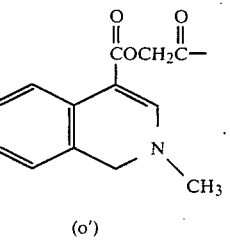

(o')

Also preferred are those compounds of class (A) wherein D' is the residue of hydralazine, bactobolin, clonidine, bethanidine, tranylcypromine, chlordiazepoxide, methamphetamine, phentermine, phenmetrazine, anileridine, protriptyline, daunamycin, dextroamphetamine, levamphetamine, amphetamine, phenylethylamine, doxorubicin, amantadine, mitoxantrone, tryptamine, desipramine or nortriptyline.

(B) Compounds of Class (A) as defined above, wherein the centrally acting drug from which D' is derived also contains at least one —COOH functional group, and D' contains, in place of at least one of the —COOH functional groups in said drug, at least one —COOY' group wherein Y' is a hydrolytically or metabolically cleavable carboxyl protective group. Within Class (B), preferred compounds are those in which Y' is $C_1$-$C_7$ alkyl and/or wherein D' is the residue of an amino acid or of a peptide containing 2 to 20 amino acid segments (especially an enkephalin or an endorphin). Also preferred are the compounds of Class (B) wherein D' is the residue of tryptophan, ampicillin, cephalexin, melphalan, L-alanosine, DON, acivicin, GABA, γ-vinyl GABA, or γ-acetylenic GABA, met$^5$-enkephalin, leu$^5$-enkephalin, γ-endorphin, α-endorphin, β-endorphin, LH-RH, neurotensin, oxytocin M or vasopressin.

(C) Compounds of Class (A) as defined above, wherein the centrally acting drug from which D' is derived also contains at least one —OH functional group, and D' contains, in place of at least one of the —OH functional groups in said drug, at least one —OY group wherein Y is a hydrolytically or metabolically cleavable hydroxyl protective group. Within Class (C), preferred compounds are those wherein Y is an acyl group or a carbonate group and/or wherein D' is the residue of a neurotransmitter, especially a catecholamine. At the present time, preferred compounds in this general class include those in which D' is the residue of serotonin, norepinephrine, epinephrine, dopamine, tyramine or phenylephrine.

(D) Compounds of Class (A) as defined above, wherein the centrally acting drug from which D' is derived also contains at least one —OH functional group and at least one —COOH functional group, and D' contains, in place of at least one of the —OH functional groups and at least one of the —COOH functional groups in said drug, at least one —OY group and at least one —COOY' group, respectively, wherein Y is a hydrolytically or metabolically cleavable hydroxyl protective group and Y' is a hydrolytically or metabolically cleavable carboxyl protective group. Within Class (D), preferred compounds are those wherein Y is an acyl group or a carbonate group and/or Y' is $C_1-C_7$ alkyl. Of particular interest are the compounds in which D' is the residue of methyldopa or levodopa.

(E) Compounds adapted for the site-specific/sustained delivery of a centrally acting drug species to the brain, said compounds being:

(i) compounds of the formula $$(D''(—Q')_{n'} \tag{I''}$$

wherein D'' is the residue of a centrally acting drug containing at least one —NH— functional group which is part of an amide or imide structure or at least one low pKa primary or secondary amine functional group, said residue being formed by removal of a hydrogen atom from at least one of said functional groups in said drug; n' is a positive integer equal to the number of said functional groups from which a hydrogen atom has been removed; and —Q' is a radical of the formula

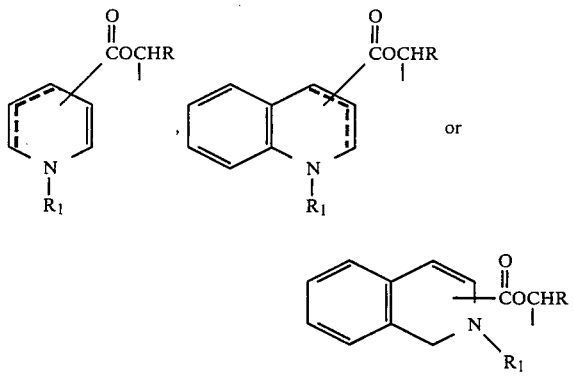

wherein the dotted lines indicate the presence of a double bond in either the 4 or 5 position of the dihydropyridine ring and in either the 2 or 3 position of the dihydroquinoline ring; $R_1$ is $C_1-C_7$ alkyl or $C_7-C_{10}$ aralkyl; R is hydrogen, $C_1-C_7$ alkyl, $C_3-C_8$ cycloalkyl, $C_1-C_7$ alkyl substituted by one or more halogen atoms, pyridyl, furyl, phenyl, or phenyl substituted by one or more halo, lower alkyl, lower alkoxy, carbamoyl, lower alkoxycarbonyl, lower alkanoyloxy, lower haloalkyl, mono(lower alkyl)carbamoyl, di(lower alkyl)carbamoyl, lower alkylthio, lower alkylsulfinyl or lower alkylsulfonyl; and the

grouping can be in the 2, 3 or 4 position of the dihydropyridine ring, in the 2, 3 or 4 position of the dihydroquinoline ring and in the 1, 3 or 4 position of the dihydroisoquinoline ring; and (ii) non-toxic pharmaceutically acceptable salts of compounds of formula (I''). Within Class (E), preferred compounds are those wherein —Q is a radical of the formula

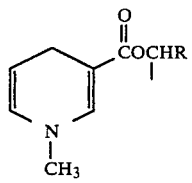

wherein R is as defined above, especially when R is hydrogen, methyl, phenyl or trichloromethyl, and/or when D'' is the residue of a tetracycline antibiotic containing a —$CONH_2$ function. Of particular interest in this general class are those compounds wherein D'' is the residue of cyclophosphamide, ethotoin, phenobarbital, chlortetracycline, glutethimide, uracil mustard, bemegride, aminoglutethimide, phenytoin, butalbital, demeclocycline, minocycline, doxycycline, oxytetracycline, ethyl β-carboline 3-carboxylate, nifedipine, methylphenidate, 3-deazaguanine, PCNU, spiromustine or L-ICRF.

(F) Compounds adapted for the site-specific/sustained delivery of a centrally acting drug species to the brain, said compounds being:

(i) compounds of the formula $$(D'''(—Q'')_{n''} \tag{I'''}$$

wherein D''' is the residue of a centrally acting drug containing at least one —OH or —SH functional group, said residue being formed by removal of a hydrogen atom from at least one of the —OH or —SH functional groups in said drug; n'' is a positive integer equal to the number of said —OH or —SH functional groups from which a hydrogen atom has been removed; and —Q'' is a radical of any one of formulae (a) through (t) inclusive as set forth in the definition of Class (A) above, the structural variables in those formulae also being defined as in (A) above; and (ii) non-toxic pharmaceutically acceptable salts of compounds of formula (I''');

with the proviso that when the compound is other than a salt as defined in (ii) above, when n is 1, when —Q'' is

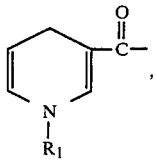

wherein $R_1$ is defined as above, and when the centrally acting drug from which D''' is derived contains only one primary or secondary —OH functional group, no other —OH functional groups and no —$NH_2$, —NH—, —SH or —COOH functional groups, then D''' must be the residue of a centrally acting drug other than a steroid sex hormone or long chain alkanol. Within Class (F), preferred compounds are those in which —Q'' is a radical of any one of formulae (a') through (o') set forth in connection with Class (A) hereinabove. Also preferred are those compounds wherein D''' is a steroid sex hormone, i.e., an androgen, estrogen or progestin. When D''' is the residue of an androgen, it is preferably the residue of testosterone or methyl testosterone or other known 17β-hydroxy-containing analogue of testosterone. When D''' is the residue of an estrogen, it is preferably the residue of a natural estrogen (estradiol, estrone or estriol) or of a known semi-synthetic estrogen having a 17β-hydroxy substituent, such as ethinyl estradiol, mestranol or quinestrol. When D''' is the residue of a progestin, it is preferably the residue of a known semi-synthetic progestin having 17β-hydroxy substituent, such as norethindrone, norgestrel, ethisterone, dimethisterone, allylestrenol, cingestol, ethynerone, lynestrenol, norgesterone, norvinisterone, ethynodiol, oxogestone, tigestol or norethynodrel. Within Class (F), another preferred group of compounds consists of the compounds in which D''' is the residue of an anti-inflammatory steroid, especially a known anti-inflammatory steroid having a 21-hydroxy substituent, such as cortisone, hydrocortisone, betamethasone, dexamethasone, flumethasone, fluprednisolone, methyl prednisolone, meprednisone, prednisolone, prednisone, cortodoxone, fludrocortisone, paramethasone or triamcinolone. Yet another preferred group of Class (F) compounds is the group in which D''' is the residue of a narcotic analgesic, narcotic antagonist or narcotic agonist-antagonist, especially when it is the residue of a known compound of this type bearing at least one hydroxy substituent, such as codeine, pentazocine, naloxone, oxycodone, hydromorphone, oxymorphone, nalorphine, morphine, levorphanol, meptazinol, cyclazocine, phenazocine, profadol, metopon, drocode, myfadol, buprenorphine, nalbuphine, butorphanol, levallorphan, naltrexone, alazocine, oxilorphan or nalmexone. Still another preferred group of Class (F) compounds consists of compounds in which D''' is the residue of an anticancer or antitumor agent; preferably D''' is the residue of a podophyllotoxin derivative (especially etoposide or teniposide) or of Ara-AC, pentostatin, thioguanine, hydroxyurea, dihydro-5-azacytidine, tiazofurin, sangivamycin, Ara-A, 6-MMPR, trimethyl TMM, SR-2555, bisbenzimidazole, SR-2508, aclacinomycin A, phyllanthoside, 6-mercaptopurine, desmethylisonidazole, menogarol, aphidicolin, 5-FUDR, trifluoroacetyl doxorubicin, cytosine arabinoside, 5-azacytidine, Ara-C or streptozotocin. Yet another preferred group of compounds within this general class consists of compounds in which D''' is the residue of an antiviral agent such as ribavirin, acyclovir, syn or anti-6-[[(hydroxyimino)phenyl]methyl]-1-[(1-methylethyl)-sulfonyl]-1H-benzimidazol-2-amine, 5,7-dimethyl-2-β-D-ribofuranosyl-s-triazole(1,5-a)pyrimidine, 2-deoxy-2-fluoro-D-mannose, phenyl-6-chloro-6-deoxy-β-D-glucopyranoside, (S)-9-(2,3-dihydroxypropyl)adenine, idoxuridine, 5,6-dichloro-1-β-D-ribofuranosylbenzimidazole or bisdihydroxyvinyluridine. Another preferred group of compounds in Class (F) consists of compounds in which D''' is the residue of a benzodiazepine or phenothiazine tranquilizer, especially those in which D''' is the residue of a known benzodiazepine such as oxazepam, lorazepam, nitrazepam or temazepam, or of a known phenothiazine such as acetophenazine, carphenazine, fluphenazine, perphenazine or piperacetazine. Other Class (F) compounds of interest are those in which D''' is the residue of thiopental, haloperidol, phenytoin, opipramol, clopenthixol, ethamivan, hydroxyzine, apomorphine, iopydol, clindamycin, lincomycin, benzestrol, diethylstilbestrol, pholcodine or dipyridamole.

(G) Compounds of Class (F) as defined above, wherein the centrally acting drug from which D''' is derived also contains at least one —COOH functional group, and D''' contains, in place of at least one of the —COOH functional groups in said drug, at least one —COOY' group wherein Y' is a hydrolytically or metabolically cleavable carboxyl protective group. Within Class (G), preferred compounds include those in which D''' is the residue of a valproic acid metabolite (such as 5-hydroxy-2-n-propylpentanoic acid, 4-hydroxy-2-n-propylpentanoic acid or 3-hydroxy-2-n-propylpentanoic acid), clorazepate or diflunisal.

(H) Compounds of Class (F) as defined above, wherein —Q'' is a radical of the formula

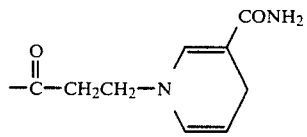

and D''' is the residue of a centrally acting drug containing a hindered tertiary —OH functional group; especially when D''' is the residue of biperiden, cycrimine, procyclidine or trihexyphenidyl.

(I) Compounds adapted for the site-specific/sustained delivery of a centrally acting drug species to the brain, said compounds being:
(i) compounds of the formula $$D^{iv}(-Q''')_{n'''} \quad (I^{iv})$$

wherein $D^{iv}$ is the residue of a centrally acting drug species containing at least one —COOH functional group, said residue being formed by removal of an —OH from at least one of the —COOH functional groups in said drug; n''' is a positive integer equal to the number of said —COOH functional groups from which an —OH has been removed; and —Q''' is a radical of the formula

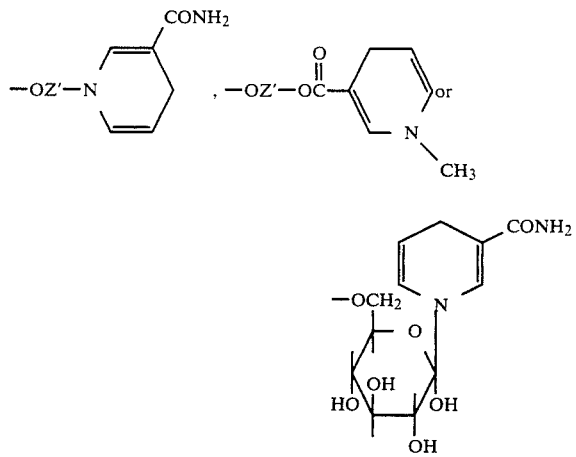

wherein Z' is $C_1-C_8$ straight or branched alkylene;
(ii) compounds of the formula

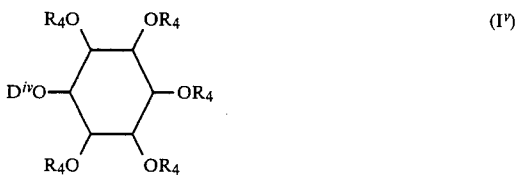

wherein $D^{iv}$ is defined as above and each $R_4$ can independently be hydrogen, $D^{iv}$ or a radical of the formula

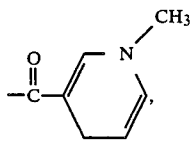

with the proviso that at least one $R_4$ is a radical of the formula

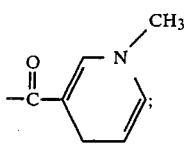

(iii) compounds of the formula

 (I$^{vi}$)

wherein $D^{iv}$ is defined as above, ◯ is the skeleton of a sugar molecule, $n^{iv}$ is a positive integer equal to the total number of —OH functions in the sugar molecule from which said skeleton is derived, and $R_4$ can independently be hydrogen, $D^{iv}$ or a radical of the formula

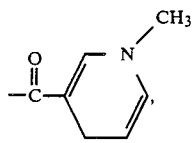

with the proviso that at least one $R_4$ is a radical of the formula

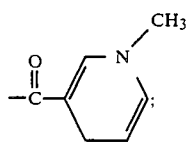

and (iv) non-toxic pharmaceutically acceptable salts of compounds of formula (I$^{iv}$), (I$^{v}$) and (I$^{vi}$). Within this class, preferred compounds are those in which $Z'$ is —CH$_2$CH$_2$— or

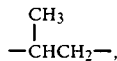

and/or in which ◯ is the skeleton of a pentose or hexose, especially when ◯ is

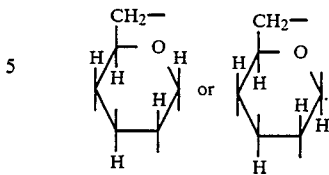

Also preferred Class (I) compounds are those in which $D^{iv}$ is the residue of an antibiotic, a radiodiagnostic, a non-steroidal anti-inflammatory agent or an anticancer or antitumor agent. At the present time, compounds of particular interest within this class are those in which $D^{iv}$ is the residue of cephalothin, valproic acid, cefoxitin, clorazepate, iodopyracet, iodouppurate, iodamide, iopanoic acid, nalidixic acid, amoxicillin, oxolinic acid, chlorambucil, glyoxylic acid sulfonylhydrazone, DACH, methotrexate, aminopterin, 5-methyltetrahydrohomofolic acid, cefazolin, ibuprofin, naproxen, flurbiprofen, zomepirac, mefenamic acid, sulindac, diclofenac, indomethacin, benzylpenicillin, phenoxymethylpenicillin, methicillin, nafcillin, ticarcillin, furosemide, oxacillin, carbenicillin, dicloxacillin, fenbufen, fenoprofen, indoprofen, ketoprofen, fluprofen, bucloxic acid, tolmetin, alclofenac, fenclozic acid, ibufenac, meclofenamic acid, flufenamic acid or flufenisal.

(J) Compounds adapted for the site-specific/sub-stained delivery of a benzodiazepine tranquilizer to the brain, said compounds having the formula

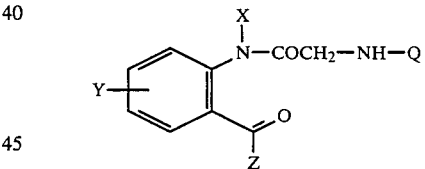

and the nontoxic pharmaceutically acceptable salts thereof, wherein Q is as defined in connection with Class (A) above and X, Y and Z are identical to the corresponding groupings in a known benzodiazepine tranquilizer having the formula

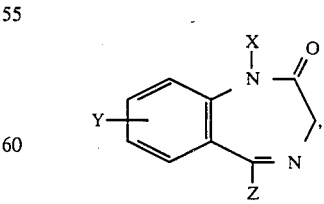

especially when —Q is a radical of any one of formulae (a') through (o') set forth in connection with Class (A) hereinabove. Presently preferred compounds in this class are those having the formula

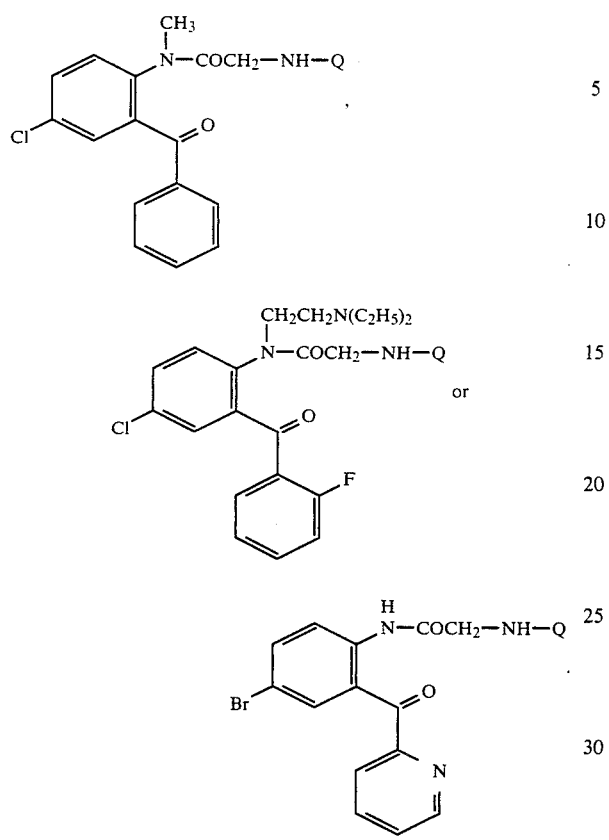

(K) Non-toxic pharmaceutically acceptable quaternary salts having the formula $$D'(—Q^{\oplus})_n Y_n^{\ominus} \quad (II')$$

wherein D' and n are as defined in connection with Class (A), $Y^{\ominus}$ is the anion of a non-toxic pharmaceutically acceptable acid and $—Q^{\oplus}$ has the formula

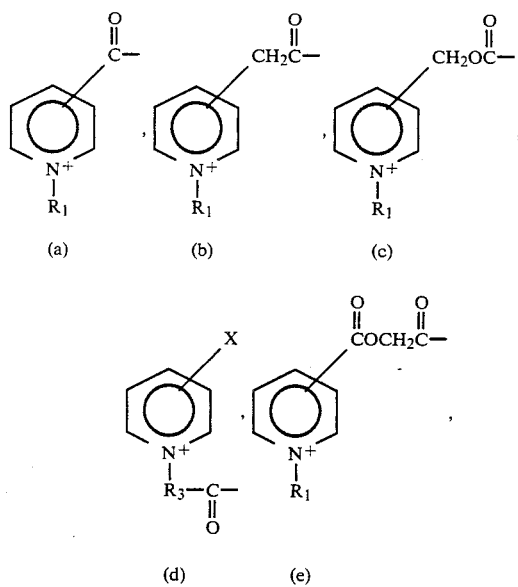

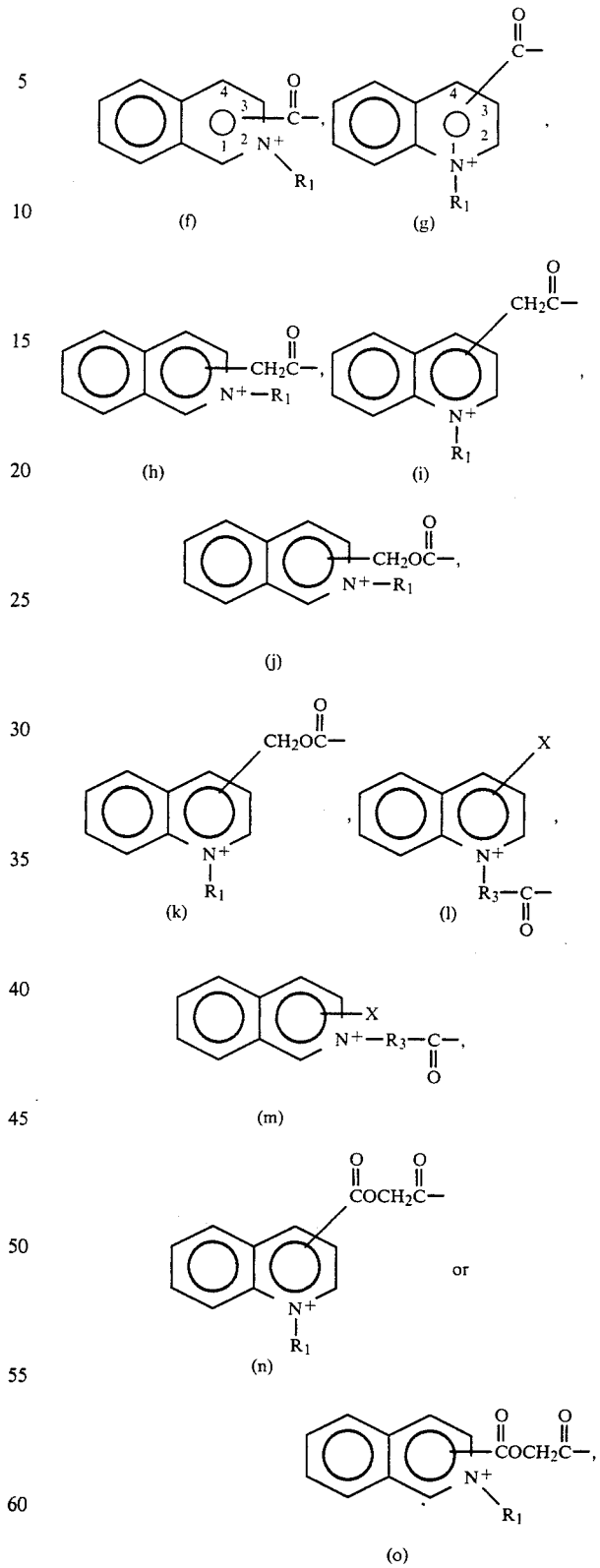

wherein $R_1$ is $C_1$-$C_7$ alkyl or $C_7$-$C_{10}$ aralkyl; $R_3$ is $C_1$ to $C_3$ alkylene; X is —CONR'R" wherein R' and R", which can be the same or different, are each H or $C_1$-$C_7$ alkyl, or X is —CH=NOR''' wherein R''' is H or $C_1$-$C_7$ alkyl; the

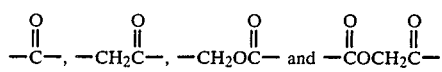

groupings in formulae (a), (b), (c) and (e) and the X substituent in formula (d) can each be attached at the 2, 3 or 4 position of the pyridinium ring; the

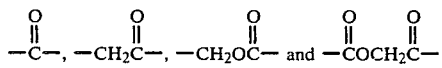

groupings in formulae (g), (i), (k) and (n) and the X substituent in formula (l) can each be attached at the 2, 3 or 4 position of the quinolinium ring; and the

groupings in formulae (f), (h), (j) and (o) and the X substituent in formula (m) can each be attached at the 1, 3 or 4 position of the isoquinolinium ring; with the proviso that when n is 1, when $-Q^{\oplus}$ is

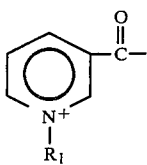

wherein $R_1$ is defined as above, and when the centrally acting drug from which D' is derived contains only one $-NH_2$ functional group and no other functional groups, then D' must be the residue of a centrally acting drug other than a sympathetic stimulant. Within this class of compounds, preferred compounds are those wherein $-Q^{\oplus}$ has the formula

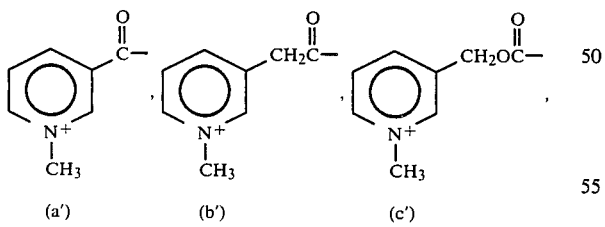

(a')    (b')    (c')

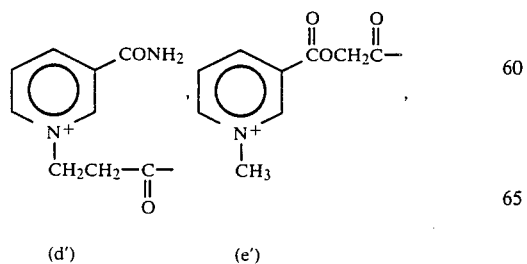

(d')    (e')

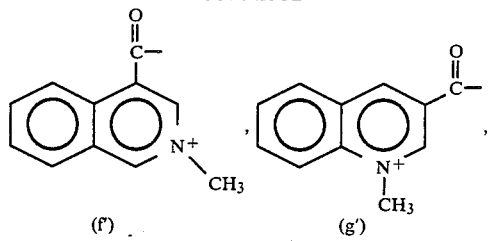

(f')    (g')

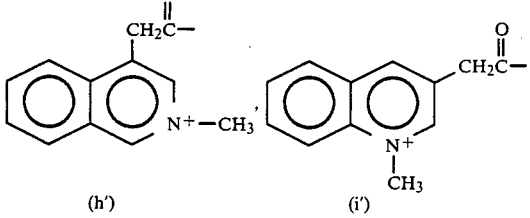

(h')    (i')

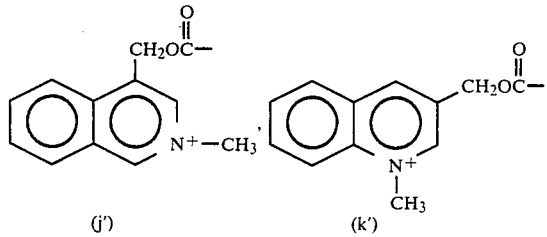

(j')    (k')

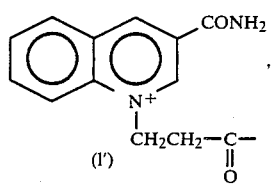

(l')

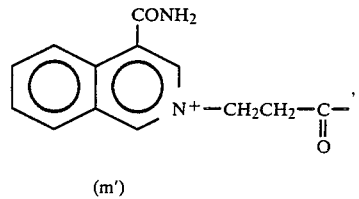

(m')

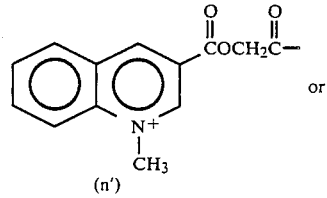

or (n')

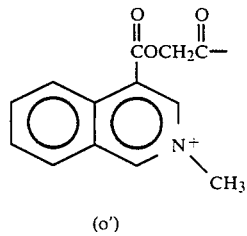

(o')

(L) Non-toxic pharmaceutically acceptable quaternary salts having the formula

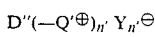 (II″)

wherein D″ and n′ are as defined in connection with Class (E) above, $Y^\ominus$ is the anion of a non-toxic pharmaceutically acceptable acid and —$Q'^\oplus$ has the formula

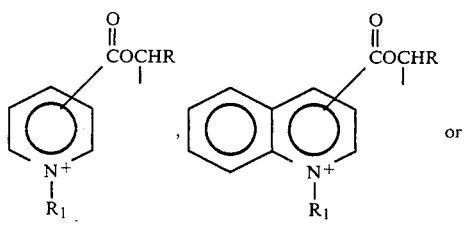

wherein $R_1$ is $C_1$–$C_7$ alkyl or $C_7$–$C_{10}$ aralkyl; R is hydrogen, $C_1$–$C_7$ alkyl, $C_3$–$C_8$ cycloalkyl, $C_1$–$C_7$ alkyl substituted by one or more halogen atoms, pyridyl, furyl, phenyl, or phenyl substituted by one or more halo, lower alkyl, lower alkoxy, carbamoyl, lower alkoxycarbonyl, lower alkanoyloxy, lower haloalkyl, mono(lower alkyl)carbamoyl, di(lower alkyl)carbamoyl, lower alkylthio, lower alkylsulfinyl and lower alkylsulfonyl; and the

grouping can be in the 2, 3 or 4 position of the pyridinium ring, in the 2, 3 or 4 position of the quinolinium ring and in the 1, 3 or 4 position of the isoquinolinium ring.

(M) Non-toxic pharmaceutically acceptable quaternary salts having the formula

 (II‴)

wherein D‴ and n″ are as defined in connection with Class (F) above, $Y^\ominus$ is the anion of a non-toxic pharmaceutically acceptable acid and—$Q''^\oplus$ has any one of formulae (a) through (o) set forth in connection with Class (K) above, wherein the various substituents are defined as in (K) above; with the proviso that when n is 1, when —$Q''^\oplus$ is

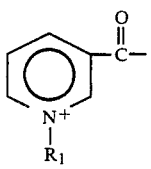

wherein $R_1$ is defined as above, and when the centrally acting drug from which D‴ is derived contains only one primary or secondary —OH functional group, no other —OH functional groups and no —$NH_2$, —NH—, —SH or —COOH functional groups, then D‴ must be the residue of a centrally acting drug other than a steroid sex hormone or long chain alkanol. Within Class (M), preferred compounds are those in which —$Q''^\oplus$ has any one of formulae (a′) through (o′) set forth in connection with Class (K) above.

(N) Non-toxic pharmaceutically acceptable quaternary salts having the formula:

(i)

 (II$^{iv}$)

wherein $D^{iv}$ and n‴ are as defined in connection with Class (I) above, $Y^\ominus$ is the anion of a non-toxic pharmaceutically acceptable acid and —$Q'''^\oplus$ has the formula

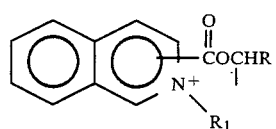 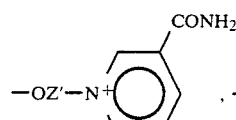

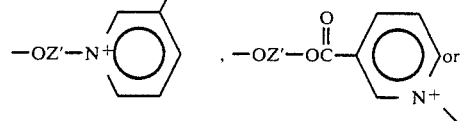

wherein Z′ is $C_1$–$C_8$ straight or branched alkylene;

(ii)

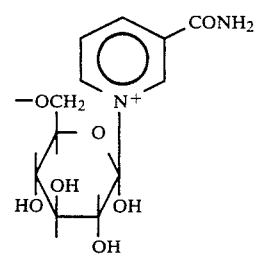 (II$^v$)

wherein $D^{iv}$ is as defined in connection with Class (I) above and each $R_4'$ can independently be hydrogen, $D^{iv}$ or

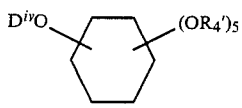

wherein $Y^\ominus$ is defined as above, with the proviso that at least one $R_4'$ is

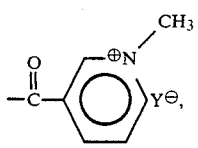; and

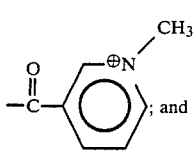

(iii)  (I$^{vi}$)

wherein $D^{iv}$ and ◯ are as defined in connection with Class (I) above, and each $R_4'$ can independently be hydrogen, $D^{iv}$ or

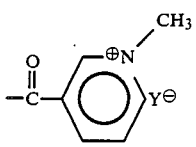

wherein Y⊖ is defined as above, with the proviso that at least one R₄' is

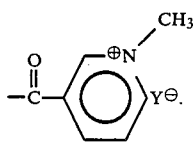

Accordingly, provided hereby are not only a generic method and novel class of pro-prodrugs for the specific and/or target enhanced delivery to the brain of a wide variety of drug species via the bidirectional transport of the drug species into and out of the brain employing dihydropyridine ⇌ pyridinium salt carrier redox systems, but also a system providing insight into the basic transport processes (both active and passive) of, and enzymatic activities in, the blood-brain barrier, as well as into the various processes specific to the function of the brain. Again, another very significant aspect of the bioreversible redox delivery system according to this invention is the toxicity implication, for significantly reduced is systemic toxicity by accelerating the elimination of the drug/quaternary carrier system. And even central toxicity is reduced by providing for low level, sustained release of the active drug species in the brain. Low toxicity is provided both as regards the quaternary carrier and in combination with the drug. Again, the present invention is not based on a simple prodrug concept, as was the case with the earlier work done with 2-PAM. In that case, a hydrophilic compound (2-PAM) was made lipoidal by making its dihydropyridine form (Pro-2-PAM) to enable its penetration through lipoidal barriers. This allowed the compound to get into the brain as well as other organs, but this prodrug manipulation did not and could not result in any brain specificity. And while the possibility of carrying drugs to the brain was also hypothesized earlier, all the experimental evidence reported in the literature negates any possible specificity, for the only compound delivered to the brain (2-PAM via Pro-2-PAM) showed similar efflux properties from the brain as from the other organs. There is no suggestion in the art of the brain-specific delivery which has now been achieved and which is a result of a surprisingly slow in vivo oxidation of the dihydro carrier system compared to the one reported in the earlier 2-PAM ⇌ Pro-2-PAM system. Indeed, a most surprising and unexpected feature of the present delivery system is that it will result in a build-up of the concentration of the intermediate charged species (quaternary form) in the brain even after one single bolus injection of the starting lipophilic chemical delivery system (dihydro form). There is a first portion of the brain level versus time curve which shows a significant increase in the brain (up to doubling or even more) from the starting overall concentration, and this process takes place against the concentration gradient; see, for exsample, FIG. 6 (dopamine) and FIG. 8 (testosterone). The blood levels do simultaneously fall, and after some time (for example, for 1 to 1½ hours) significantly higher concentrations of the precursor, now in its hydrophilic carrier (quaternary) form, will be found in the brain as compared to the rest of the body. This is brain-specific delivery; it is not simply delivery of something which otherwise cannot get to the brain, but is delivery of a given agent in an inactive form specifically to the brain, which then will subsequently lead to a sustained brain-specific delivery of the active specie itself. In the case of testosterone and dopamine, for example, slow enzymatic cleavage of the quaternary form "locked in" the brain provides sustained release of the drug itself.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A compound adapted for the site-specific/sustained delivery of a centrally acting drug species to the brain, said compound being:

(a) a compound of the formula

[D-DHC]     (I)

wherein [D] is a centrally acting drug species, and [DHC] is the reduced, biooxidizable, blood-brain barrier penetrating lipoidal form of a dihydropyridine ⇌ pyridinium salt redox carrier, with the proviso that when [DHC] is

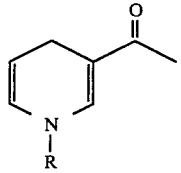

wherein R is lower alkyl or benzyl and [D] is a drug species containing a single NH₂ or OH functional group, the single OH group when present being a primary or secondary OH group, said drug species being linked directly through said NH₂ or OH functional group to the carbonyl function of [DHC], then [D] must be other than a sympathetic stimulant, steroid sex hormone or long chain alkanol; or (b) a non-toxic pharmaceutically acceptable salt of a compound of formula (I) wherein [D] is a centrally acting drug species and [DHC] is the reduced, biooxidizable, blood-brain barrier penetrating lipoidal form of a dihydropyridine ⇌ pyridinium salt redox carrier.

2. A compound according to claim 1, wherein [DHC] comprises the reduced form of a nicotinic acid derivative.

3. A compound according to claim 1, wherein [DHC] comprises the reduced form of a trigonelline.

4. A compound according to claim 1, wherein [DHC] comprises the reduced form of an isoquinoline or of a pyridinium alcohol.

5. A compound according to claim 1, wherein [DHC] is

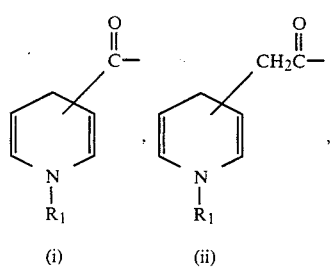
(i) , (ii) ,

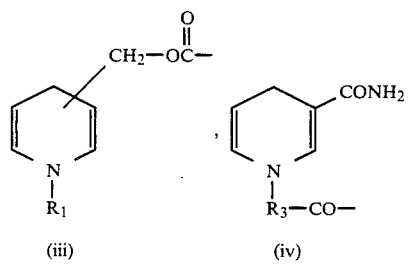
(iii) , (iv)

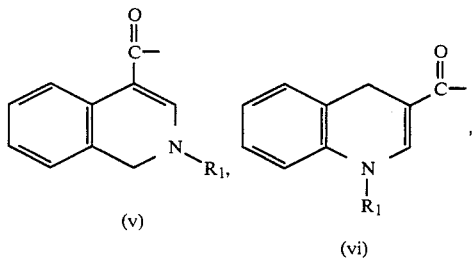
(v) , (vi)

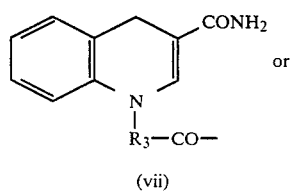
or
(vii)

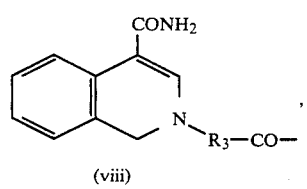
(viii)

wherein the

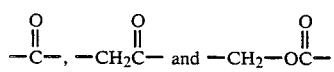

substituents in formulae (i), (ii) and (iii) each can be in the 2-, 3- or 4-position on the ring, $R_1$ is $C_1$–$C_7$ alkyl or $C_7$–$C_{10}$ aralkyl and $R_3$ is $(CH_2)_n$ wherein n is 1, 2 or 3.

6. A compound according to claim 5, wherein [DHC] is

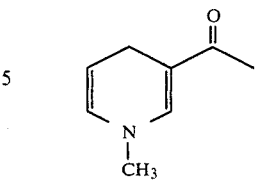

7. A compound of the formula $$[\text{D-QC}]^+ Y^- \qquad (II)$$

wherein $Y^-$ is the anion of a non-toxic pharmaceutically acceptable acid, [D] is a centrally acting drug species and $[QC]^+$ is the hydrophilic, ionic pyridinium salt form of a dihydropyridine ⇌ pyridinium salt redox carrier, with the proviso that when $[QC]^+$ is

wherein R is lower alkyl or benzyl and [D] is a drug species containing a single $NH_2$ or OH functional group, the single OH group when present being a primary or secondary OH group, said drug species being linked directly through said $NH_2$ or OH functional group to the carbonyl function of $[QC]^+$, then [D] must be other than a sympathetic stimulant, steroid sex hormone or long chain alkanol.

8. A compound according to claim 7, wherein $[QC]^+$ comprises the ionic pyridinium salt form of a nicotinic acid derivative; of an isoquinoline; or of a pyridinium alcohol.

9. A compound according to claim 8, wherein $[QC]^+$ compises the ionic pyridinium salt form of a trigonelline.

10. A compound according to claim 7, wherein $[QC]^+$ is

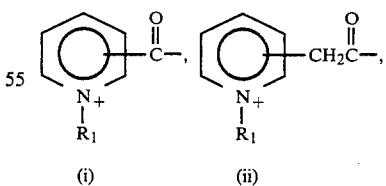
(i) , (ii) ,

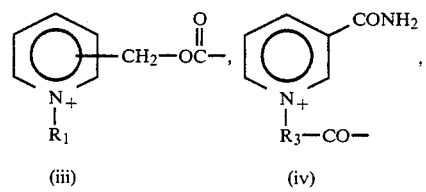
(iii) , (iv)

-continued

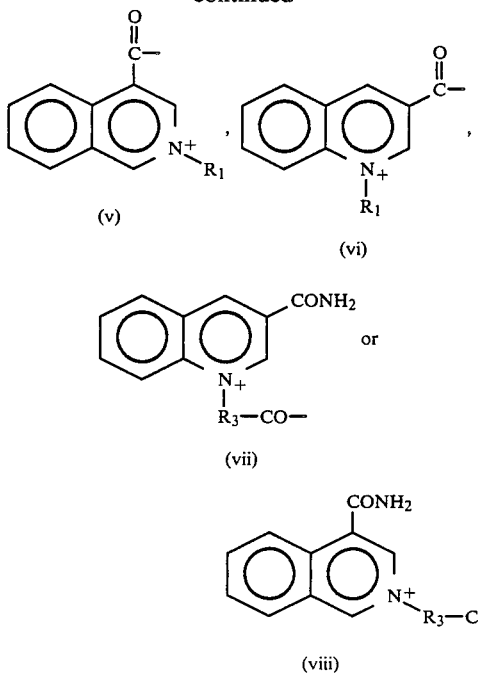

wherein the

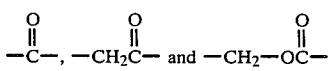

substituents in formulae (i), (ii) and (iii) each can be in the 2-, 3- or 4-position on the ring, $R_1$ is $C_1$-$C_7$ alkyl or $C_7$-$C_{10}$ aralkyl and $R_3$ is $(CH_2)_n$ where n is 1, 2 or 3.

11. A compound as defined by claim 10, wherein [QC]+ is

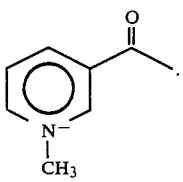

12. A compound according to claim 1, wherein [D] is a steroid residue.

13. A compound according to claim 12, wherein the steroid is a steroid sex hormone.

14. A compound according to claim 13, wherein the steroid sex hormone is an androgen.

15. A compound according to claim 13, wherein the steroid sex hormone is an estrogen.

16. A compound according to claim 13, wherein the steroid sex hormone is a progestin.

17. A compound according to claim 13, wherein the steroid sex hormone is testosterone.

18. A compound according to claim 13, wherein the steroid sex hormone is methyl testosterone.

19. A compound according to claim 13, wherein the steroid sex hormone is ethinyl estradiol.

20. A compound according to claim 13, wherein the steroid sex hormone is norgestrel.

21. A compound according to claim 13, wherein the steroid sex hormone is mestranol.

22. A compound according to claim 13, wherein the steroid sex hormone is norethindrone.

23. A compound according to claim 13, wherein the steroid sex hormone is norethynodrel.

24. A compound according to claim 13, wherein the steroid sex hormone is ethisterone.

25. A compound according to claim 13, wherein the steroid sex hormone is estradiol.

26. A compound according to claim 13, wherein the steroid sex hormone is estriol.

27. A compound according to claim 13, wherein the steroid sex hormone is estrone.

28. A compound according to claim 13, wherein the steroid sex homone is dimethisterone.

29. A compound according to claim 13, wherein the steroid sex hormone is allylestrenol.

30. A compound according to claim 13, wherein the steroid sex hormone is cingestol.

31. A compound according to claim 13, wherein the steroid sex hormone is ethynerone.

32. A compound according to claim 13, wherein the steroid sex hormone is lynestrenol.

33. A compound according to claim 13, wherein the steroid sex hormone is norgesterone.

34. A compound according to claim 13, wherein the steroid sex hormone is norvinisterone.

35. A compound according to claim 13, wherein the steroid sex hormone is ethynodiol.

36. A compound according to claim 13, wherein the steroid sex hormone is oxogestone.

37. A compound according to claim 13, wherein the steroid sex hormone is tigestol.

38. A compound according to claim 13, wherein the steroid sex hormone is quinestrol.

39. A compound according to claim 12, wherein the steroid is an antiinflammatory steroid.

40. A compound according to claim 39, wherein the antiinflammatory steroid is hydrocortisone.

41. A compound according to claim 39, wherein the antiinflammatory steroid is betamethasone.

42. A compound according to claim 39, wherein the antiinflammatory steroid is cortisone.

43. A compound according to claim 39, wherein the antiinflammatory steroid is dexamethasone.

44. A compound according to claim 39, wherein the antiinflammatory steroid is flumethasone.

45. A compound according to claim 39, wherein the antiinflammatory steroid is fluprednisolone.

46. A compound according to claim 39, wherein the antiinflammatory steroid is meprednisone.

47. A compound according to claim 39, wherein the antiinflammatory steroid is methyl prednisolone.

48. A compound according to claim 39, wherein the antiinflammatory steroid is prednisolone.

49. A compound according to claim 39, wherein the antiinflammatory steroid is prednisone.

50. A compound according to claim 39, wherein the antiinflammatory steroid is triamcinolone.

51. A compound according to claim 39, wherein the antiinflammatory steroid is cortodoxone.

52. A compound according to claim 39, wherein the antiinflammatory steroid is fludrocortisone.

53. A compound according to claim 39, wherein the antiinflammatory steroid is flurandrenolone acetonide.

54. A compound according to claim 39, wherein the antiinflammatory steroid is paramethasone.

55. A compound adapted for the site-specific/sustained delivery of a centrally acting drug species to the brain, said compound being:

(i) a compound of the formula $$D'''(-Q'')_n \quad (I''')$$

wherein $D'''$ is the residue of a centrally acting drug containing at least one —OH or —SH functional group, said residue being formed by removal of a hydrogen atom from at least one of the —OH or —SH functional groups in said drug; $n''$ is a positive integer equal to the number of said —OH or —SH functional groups from which a hydrogen atom has been removed; and —Q″ is a radical of the formula (a), (b), (c), (d), (e), (f), (g), (h), (i), (j), (k), (l), (m), (n), (o)

wherein the dotted line in formulae (a), (b), (c), (d) or (e) indicates the presence of a double bond in either the 4 or 5 position of the dihydropyridine ring; the dotted line in formulae (g), (i), (k), (l) and (n) indicates the presence of a double bond in either the 2 or 3 position of the dihydroquinoline ring; $R_1$ is $C_1$-$C_7$ alkyl or $C_7$-$C_{10}$ aralkyl; $R_3$ is $C_1$ to $C_3$ alkylene; X is —CONR'R″ wherein R' and R″, which can be the same or different, are each H or $C_1$-$C_7$ alkyl, or X is —CH=NOR‴ wherein R‴ is H or $C_1$-$C_7$ alkyl, the $$-\overset{O}{\underset{\|}{C}}-, \; -CH_2\overset{O}{\underset{\|}{C}}-, \; -CH_2O\overset{O}{\underset{\|}{C}}- \text{ and } -\overset{O}{\underset{\|}{C}}OCH_2\overset{O}{\underset{\|}{C}}-$$

groupings in formulae (a), (b), (c) and (e) and the X substituent in formula (d) can each be attached at the 2, 3 or 4 position of the dihydropyridine ring; the $$-\overset{O}{\underset{\|}{C}}-, \; -CH_2\overset{O}{\underset{\|}{C}}-, \; -CH_2O\overset{O}{\underset{\|}{C}}- \text{ and } -\overset{O}{\underset{\|}{C}}OCH_2\overset{O}{\underset{\|}{C}}-$$

groupings in formulae (g), (i), (k) and (n) and the X substituent in formula (l) can each be attached at the 2, 3 or 4 position of the dihydroquinoline ring; and the $$-\overset{O}{\underset{\|}{C}}-, \; -CH_2\overset{O}{\underset{\|}{C}}-, \; -CH_2O\overset{O}{\underset{\|}{C}}- \text{ and } -\overset{O}{\underset{\|}{C}}OCH_2\overset{O}{\underset{\|}{C}}-$$

groupings in the formulae (f), (h), (j) and (o) and the X substituent in formula (m) can each be attached at the 1, 3 or 4 position of the dihydroisoquinoline ring; or (ii) a non-toxic pharmaceutically acceptable salt of a compound of formula (I‴);

with the proviso that when the compound is other than a salt as claimed in (ii) above, when n is 1, when —Q″ is

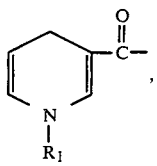

wherein $R_1$ is defined as above, and when the centrally acting drum from which D‴ is derived contains only one primary or secondary —OH functional group, no other —OH functional groups and no —NH$_2$, —NH—, —SH or —COOH functional groups, then D‴ must be the residue of a centrally acting drug other than a steroid sex hormone or long chain alkanol.

56. A compound according to claim 55, wherein D‴ is the residue of a steroid sex hormone.
57. A compound according to claim 56, wherein D‴ is the residue of an androgen.
58. A compound according to claim 56, wherein D‴ is the residue of an estrogen.
59. A compound according to claim 56, wherein D‴ is the residue of a progestin.
60. A compound according to claim 56, wherein D‴ is the residue of testosterone.
61. A compound according to claim 56, wherein D‴ is the residue of methyl testosterone.
62. A compound according to claim 56, wherein D‴ is a residue of estradiol.
63. A compound according to claim 56, wherein D‴ is a residue of estriol or estrone.
64. A compound according to claim 56, wherein D‴ is a residue of ethinyl estradiol.
65. A compound according to claim 56, wherein D‴ is the residue of mestranol.
66. A compound according to claim 56, wherein D‴ is the residue of quinestrol.
67. A compound according to claim 56, wherein D‴ is the residue of norethindrone.
68. A compound according to claim 56, wherein D‴ is the residue of norgestrel.
69. A compound according to claim 56, wherein D‴ is the residue of ethisterone.
70. A compound according to claim 56, wherein D‴ is the residue of dimethisterone.
71. A compound according to claim 56, wherein D‴ is the residue of allylestrenol.
72. A compound according to claim 56, wherein D‴ is the residue of cingestol or ethynerone.
73. A compound according to claim 56, wherein D‴ is the residue of lynestrenol.
74. A compound according to claim 56, wherein D‴ is the residue of norgesterone or norvinisterone.
75. A compound according to claim 56, wherein D‴ is a residue of ethynodiol.
76. A compound according to claim 56, wherein D‴ is the residue of oxogestone or tigestol.
77. A compound according to claim 56, wherein D‴ is the residue of of norethynodrel.
78. A compound according to claim 56, wherein D‴ is the residue of an anti-inflammatory steroid.
79. A compound according to claim 27, wherein D‴ is a residue of cortisone or hydrocortisone.
80. A compound according to claim 27, wherein D‴ is a residue of betamethasone, dexamethasone, flumethasone, fluprednisolone, methyl, prednisolone, meprednisone, prednisolone, prednisone, cortodoxone, fludrocortisone, paramethasone or triamcinolone.

81. A non-toxic pharmaceutically acceptable quaternary salt having the formula

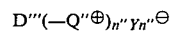 (II‴)

wherein D‴ and n″ are as defined in claim 55, Y$^\ominus$ is the anion of a non-toxic pharmaceutically acceptable acid and —Q″$^\oplus$ has the formula

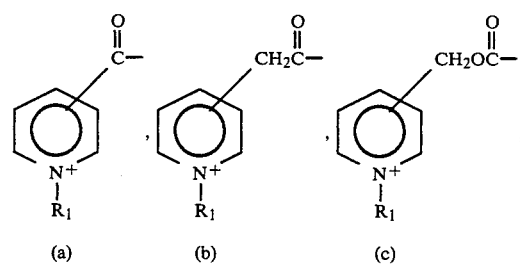

(a)   (b)   (c)

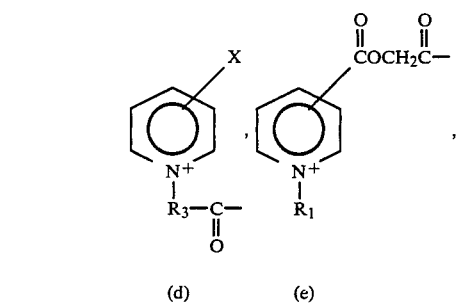

(d)   (e)

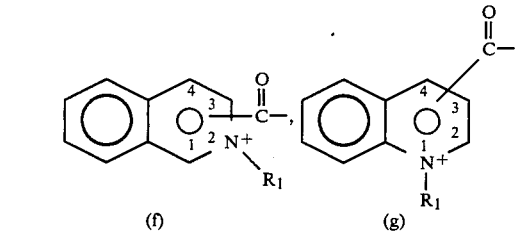

(f)   (g)

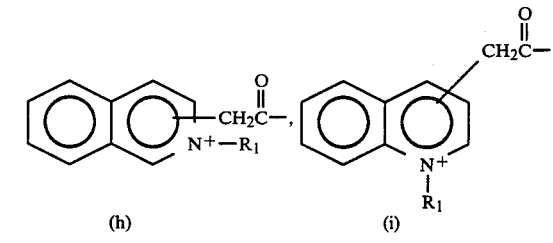

(h)   (i)

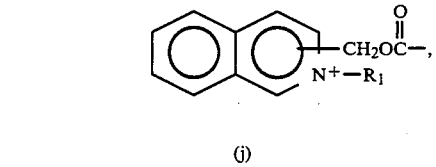

(j)

-continued

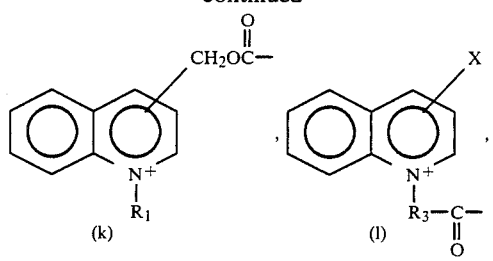

(k) , (l)

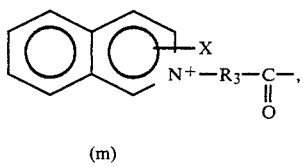

(m)

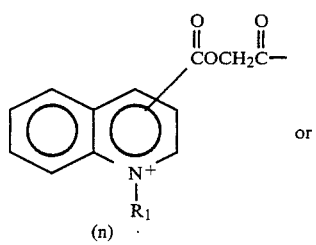

or (n)

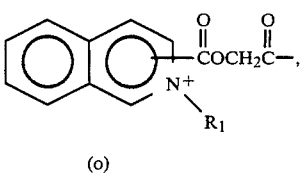

(o)

wherein $R_1$ is $C_1$-$C_7$ alkyl or $C_7$-$C_{10}$ aralkyl; $R_3$ is $C_1$ to $C_3$ alkylene; X is —CONR'R" wherein R' and R", which can be the same or different, are each H or $C_1$-$C_7$ alkyl, or X is —CH=NOR''' wherein R''' is H or $C_1$-$C_7$ alkyl; the

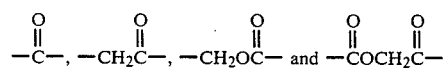

groupings in formulae (a), (b), (c) and (e) and the X substituent in formula (d) can each be attached at the 2, 3 or 4 position of the pyridinium ring; the

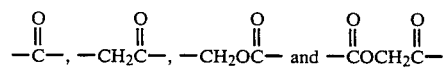

groupings in formulae (g), (i), (k) and (n) and the X substituent in formula (l) can each be attached at the 2, 3 or 4 position of the quinolinium ring; and the

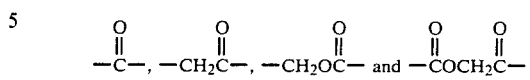

groupings in formulae (f), (h), (j) and (o) and the X substituent in formula (m) can each be attached at the 1, 3 or 4 position of the isoquinolinium ring; with the proviso that when n is 1, when —$Q^\oplus$ is

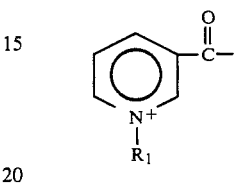

wherein $R_1$ is defined as above, and when the centrally acting drug from which D''' is derived contains only one primary or secondary —OH functional group, no other —OH functional groups and no —$NH_2$, —NH—, —SH or —COOH functional groups, then D''' must be the residue of a centrally acting drug other than a steroid sex hormone or long chain alkanol.

82. A method for site-specifically/sustainedly delivering a centrally acting drug species to the brain, comprising administering to an animal in need of such treatment a quantity of a compound as claimed in claim 1 sufficient to release a pharmacologically effective amount of said centrally acting drug species to the brain.

83. A method according to claim 82, wherein the compound is administered in the form of a pharmaceutically acceptable sustained release composition or wherein the compound is administered via a route of administration capable of slowly releasing the compound into the body.

84. A pharmaceutical composition of matter comprising a compound as claimed in claim 1 and a non-toxic pharmaceutically acceptable carrier thereof.

85. A pharmaceutical composition of matter, in unit dosage form, for use in delivering a pharmacologically effective amount of a centrally acting drug species to the brain, said composition comprising:
 (i) an amount of a compound as claimed in claim 1 sufficient to release a pharmacologically effective amount of a centrally acting drug species to the brain; and
 (ii) a non-toxic pharmaceutically acceptable carrier therefor.

86. A pharmaceutical composition as claimed in claim 85, said composition being a pharmaceutically acceptable sustained release composition.

* * * * *